US008409567B2

(12) United States Patent
Cunningham et al.

(10) Patent No.: US 8,409,567 B2
(45) Date of Patent: Apr. 2, 2013

(54) TOLL-LIKE RECEPTOR 3 ANTAGONISTS

(75) Inventors: Mark Cunningham, Radnor, PA (US);
Yiqing Feng, Radnor, PA (US);
Katharine Heeringa, Radnor, PA (US);
Jinquan Luo, Radnor, PA (US); Robert Rauchenberger, Martinsried (DE);
Mark Rutz, Martinsried (DE); Lani San Mateo, Radnor, PA (US); Robert Sarisky, Yardley, PA (US); Raymond Sweet, Radnor, PA (US); Fang Teng, Radnor, PA (US); Alexey Teplyakov, Radnor, PA (US); Sheng-Jiun Wu, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 425 days.

(21) Appl. No.: 12/609,675

(22) Filed: Oct. 30, 2009

(65) Prior Publication Data

US 2010/0166778 A1    Jul. 1, 2010

Related U.S. Application Data

(60) Provisional application No. 61/109,974, filed on Oct. 31, 2008, provisional application No. 61/161,860, filed on Mar. 20, 2009, provisional application No. 61/165,100, filed on Mar. 31, 2009, provisional application No. 61/173,686, filed on Apr. 29, 2009.

(51) Int. Cl.
*A61K 39/00* (2006.01)
*A61K 39/395* (2006.01)
*C07K 16/00* (2006.01)
*C07K 16/18* (2006.01)
*C07K 16/28* (2006.01)

(52) U.S. Cl. ............... 424/130.1; 424/139.1; 424/141.1; 424/142.1; 424/143.1; 530/387.1; 530/387.9; 530/388.1; 530/388.15; 530/388.22; 530/389.1

(58) Field of Classification Search ................. None
See application file for complete search history.

(56) References Cited

U.S. PATENT DOCUMENTS

| | | | |
|---|---|---|---|
| 7,718,778 B2 * | 5/2010 | Duffy et al. ............... | 530/388.22 |
| 2005/0119273 A1 | 6/2005 | Lipford et al. | |
| 2005/0153910 A1 | 7/2005 | Matsumoto et al. | |
| 2006/0115475 A1 * | 6/2006 | Carton et al. ............... | 424/143.1 |
| 2008/0299138 A1 | 12/2008 | Duffy et al. | |
| 2010/0092462 A1 | 4/2010 | Jordan et al. | |
| 2010/0166778 A1 | 7/2010 | Cunningham et al. | |
| 2011/0212110 A1 | 9/2011 | Chemin et al. | |
| 2012/0034232 A1 * | 2/2012 | Gauthier et al. ........... | 424/143.1 |

FOREIGN PATENT DOCUMENTS

| | | | |
|---|---|---|---|
| WO | WO 2006/035066 A2 | 4/2006 | |
| WO | WO 2006/060513 A2 | 6/2006 | |
| WO | WO 2010/051470 A2 | 5/2010 | |

OTHER PUBLICATIONS

Chemicon International Datasheet, Catalog #AB4217; dated Apr. 19, 2004; 1 page.*
Bell et al. Leucine-rich repeats and pathogen recognition in Toll-like receptors. Trends Immunol 24(10): 528-533, 2003.*
Duffy et al. Down modulation of human TLR3 function by a monoclonal antibody. Cellular Immunol 248: 103-114, 2007.*
Matsumoto et al. Establishment of a monoclonal antibody against human Toll-like receptor 3 that blocks double-stranded RNA-mediated signaling. Biochem Biophys Res Comm 293: 1364-1369, 2002.*
Matsumoto et al. Subcellular localization of Toll-like Receptor 3 in human dendritic cells. J Immunol 171: 3154-3162, 2003.*
Rudikoff et al, 1982 (Proc Natl Acad Sci USA. vol. 79: 1979-1983).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Bergsbaken, et al., "Pyroptosis: host cell death and inflammation," Nature Reviews, 7: 99-109 (2009).
Brentano, et al., "RNA Released From Necrotic Synovial Fluid Cells Activates Rheumatoid Arthritis Synovial Fibroblasts Via Toll-like Receptor 3," Arthritis & Rheumatism, 52(9): 2656-2665 (2005).
Cavassani, et al., "TLR3 is an endogenous sensor of tissue necrosis during acute inflammatory events," Journal of Experimental Medicine, 206(11): 2609-2621 (2008).
Dogusan, et al., "Double-Stranded RNA Induces Pancreatic β-Cell Apoptosis by Activation of the Toll-Like Receptor 3 and Interferon Regulatory Factor 3 Pathways," Diabetes, 57: 1236-1245 (2008).
Fahy, et al., "'Reactive Airway Disease' A Lazy Term of Uncertain Meaning that Should Be Abandoned," American Journal of Respiratory and Critical Care Medicine, 163: 822-823 (2001).
Fransson, et al., "Up-regulation of Toll-like receptors 2, 3 and 4 in allergic rhinitis," Respiratory Research, 6 (100): 1 of 10-10 of 10 (2005).
Gowen, et al., "TLR3 Deletion Limits Mortality and Disease Severity due to Phlebovirus Infection," The Journal of Immunology, 177: 6301-6307 (2006).
Hanauer, et al., "Human Anti-Tumor Necrosis Factor Monoclonal Antibody (Adalimumab) in Crohn's Disease: the CLASSIC-I Trial," Gastroenterology, 130: 323-333 (2006).
Hanauer, et al., "Maintenance infliximab for Crohn's disease: the ACCENT I randomized trial," Lancet, 359: 1541-1549 (2002).
Hessel, et al, "Bronhoconstriction and airway hyperresponsiveness after ovalbumin inhalation in sensitized mice," European Journal of Pharmacology, 293: 401-412 (1995).
Hoffman, et al., "TLR-targeted therapeutics," Nature Reviews, 4: 879-880 (2005).

(Continued)

*Primary Examiner* — Bridget E Bunner
(74) *Attorney, Agent, or Firm* — Kirk Baumeister

(57) ABSTRACT

Toll Like Receptor 3 (TLR3) antibody antagonists, polynucleotides encoding TLR3 antibody antagonists or fragments thereof, and methods of making and using the foregoing are disclosed.

17 Claims, 30 Drawing Sheets

OTHER PUBLICATIONS

Hutchens, et al., "TLR3 Increases Disease Morbidity and Mortality from Vaccinia Infection," The Journal of Immunology, 180: 483-491 (2008).

Kanzler, et al., "Therapeutic targeting of innate immunity with Toll-like receptor agonists and antagonists," Nature Medicine, 13(5): 552-559 (2007).

Kim, et al., "TLR-3 enhances osteoclastogenesis through upregulation of RANKL expression from fibroblast-like synoviocytes in patients with rheumatoid arthritis," Immunology Letters, 124: 9-17 (2009).

Lancaster, et al., "The physiological regulation of toll-like receptor expression and function in humans," Journal of Physiology, 563.3: 945-955 (2005).

Lang, et al. "Immunoprivileged status of the liver is controlled by Toll-like receptor 3 signaling," The Journal of Clinical Investigation, 116(9): 2456-2453 (2006).

LeGoffic, et al., "Detrimental Contribution of the Toll-Like Receptor (TLR)3 to Influenza A Virus-Induced Acute Pneumonia," PLoS Pathogens, 2(6) e53: 0526-0535 (2006).

Lien, et al., "The Role of Toll-Like Receptor Pathways in the Mechanism of Type 1 Diabetes," Current Molecular Medicine, 9: 52-68 (2009).

Linden, et al., "Airway neutrophils and interleukin-17," European Respiratory Journal, 15: 973-977 (2000).

Morikawa, et al., "Identification of Toll-Like Receptor 3 as a Potential Therapeutic Target I Clear Cell Renal Cell Carcinoma," Clinical Cancer Research, 13(19): 5703-5709 (2007).

Morishima, et al., "Ligation of Toll-Like Receptor 3 Differentially Regulates M2 and M3 Muscarinic Receptor Expression and Function in Human Airway Smooth Muscle Cells," International Archives of Allergy and Immunology, 145: 163-174 (2008).

Murray, et al., "Deleterious Role of TLR3 during Hyperoxia-induced Acute Lung Injury," American Journal of Respiratory and Critical Care Medicine, 178: 1227-1237 (2008).

Neurath, et al., "TNBS-Colitis," International Review of Immunology, 19: 51-62 (2000).

Ospelt, et al., "Overexpression of Toll-Like Receptors 3 and 4 in Synovial Tissue From Patients with Early Rheumatoid Arthritis," Arthritis & Rheumatism, 58(12): 3684-3692 (2008).

Pries, et al., Induction of c-Myc-dependent cell proliferation through tol-like receptor 3 in head and neck cancer, International Journal of Molecular Medicine, 21: 209-215 (2008).

Rahman, et al., "IL-17R activation of human airway smooth muscle cells induces CXCL-8 production via a transcriptional-dependent mechanism," Clinical Immunology, 115: 268-276 (2005).

Read, et al., "Induction of Inflammatory Bowel Disease in Immunodeficient Mice by Depletion of Regulatory T Cells," Current Protocols in Immunology, John Wiley & Sons, Inc., 15.13.1-15.13.10 (1999).

Nima Rezaei, et al., "Therapeutic targeting of pattern-recognition receptors," International Immunopharmacology, 6: 863-869 (2006).

Richer, et al., "Toll-Like Receptor 3 Signaling on Macrophages Is Required for Survival Following Coxsackievirus B4 Infection," PLoS one, 4(1): 1-11 (2009).

Stowell, et al., "Long-term activation of TLR3 by Poly(I:C) induces inflammation and impairs lung function in mice," Respiratory Research, 10: 1 of 14-14 of 14 (2009).

Sugiura, et al., "Activation of Toll-Like Receptor 2 Augments Myofibroblast Differentiation," American Journal of Respiratory and Cellular Molecular Biology, 40: 654-662 (2009).

Takii, et al., "Enhanced expression of type 1 interferon and toll-like receptor-3 in primary biliary cirrhosis," Laboratory Investigation, 85: 908-920 (2005).

Van Assche, et al., "Infliximab therapy for patients with inflammatory bowel disease: 10 years on," European Journal of Pharmacology, 623: S17-S25 (2009).

Wang, et al., "Toll-like receptor 3 mediates West Nile virus entry into the brain causing lethal encephalitis," Nature Medicine, 10(12): 1366-1373 (2004).

Ingred Wickelgren, "Targeting the Tolls," Science, 312: 184-187 (2006).

Yang, et al., "Toll-like Receptor 3 and geographic Atrophy in Age-Related Macular Degeneration," New England Journal of Medicine, 359(14): 1456-1463 (2008).

Zhang, et al., "TLR3 Deficiency in Patients with Herpes Simplex Encephalitis," Science, 317: 1522-1527 (2007).

Zhou, et al., "NKG2D recognition mediates Toll-like receptor 3 signaling-induced breakdown of epithelial homeostasis in the small intestines of mice," Proceedings of the National Academy of Science, 104(18): 7512-7515 (2007).

Zhou, et al., "Recognition of Double-Stranded RNA by TLR3 Induces Severe Small Intestinal Injury in Mice," The Journal of Immunology, 178: 4548-4556 (2007).

Mohammad, et al., "Dysregulated Toll-like receptor expression and signaling in bone marrow-derived macrophages at the onset of diabetes in the non-obese diabetic mouse," International Immunology, 18(7): 1101-1112 2006).

PCT International Search Report dated Apr. 17, 2012.

Rothe, et al., "The Human Combinatorial Antibody Library HuCAL GOLD Combines Diversification of All Six CDRs According to the Natural Immune System with a Novel Display Method for Efficient Selection of High-Affinity Antibodies," Journal of Molecular Biology, 376: 1182-1200 (2008).

Supplementary European Search Report dated Sep. 26, 2012.

* cited by examiner

| mAb [ug/ml] | | IL6 | IP-10 | RANTES | MCP-1 | IL8 |
|---|---|---|---|---|---|---|
| #1 | 10 | 36 | 66 | 11 | 23 | 34 |
| | 2 | 30 | 65 | 28 | 19 | 35 |
| | 0.4 | 10 | 34 | 9 | 14 | 20 |
| #2 | 10 | 35 | 52 | 13 | 11 | 35 |
| | 2 | 41 | 76 | 22 | 26 | 33 |
| | 0.4 | 21 | 57 | 19 | 13 | 13 |
| #3 | 10 | 47 | 65 | 23 | 37 | 44 |
| | 2 | 49 | 82 | 26 | 35 | 50 |
| | 0.4 | 26 | 25 | 8 | 19 | 32 |
| #4 | 10 | 98 | 100 | 100 | 83 | 87 |
| | 2 | 46 | 81 | 31 | 29 | 50 |
| | 0.4 | 42 | 54 | 17 | 28 | 45 |
| #5 | 10 | 69 | 87 | 47 | 55 | 63 |
| | 2 | 60 | 82 | 33 | 42 | 55 |
| | 0.4 | 41 | 61 | 7 | 26 | 46 |
| #6 | 10 | 70 | 89 | 49 | 56 | 66 |
| | 2 | 57 | 81 | 29 | 38 | 58 |
| | 0.4 | 58 | 80 | 29 | 35 | 56 |
| #7 | 10 | 71 | 91 | 50 | 60 | 67 |
| | 2 | 67 | 85 | 42 | 50 | 63 |
| | 0.4 | 49 | 72 | 27 | 44 | 50 |
| #8 | 10 | 61 | 78 | 29 | 41 | 41 |
| | 2 | 39 | 37 | 3 | 32 | 34 |
| | 0.4 | 46 | 67 | 14 | 31 | 46 |
| #9 | 10 | 59 | 83 | 37 | 52 | 45 |
| | 2 | 55 | 83 | 33 | 41 | 53 |
| | 0.4 | 48 | 66 | 20 | 40 | 46 |
| #10 | 10 | 75 | 91 | 60 | 60 | 65 |
| | 2 | 62 | 82 | 37 | 48 | 58 |
| | 0.4 | 53 | 73 | 30 | 48 | 51 |

Figure 2B

| mAb [ug/ml] | | IL6 | IP-10 | RANTES | MCP-1 | IL8 |
|---|---|---|---|---|---|---|
| #11 | 10 | 83 | 96 | 74 | 71 | 55 |
| | 2 | 62 | 83 | 32 | 55 | 60 |
| | 0.4 | 61 | 77 | 29 | 46 | 54 |
| #12 | 10 | 74 | 91 | 52 | 57 | 27 |
| | 2 | 69 | 88 | 39 | 53 | 53 |
| | 0.4 | 55 | 79 | 28 | 43 | 51 |
| #13 | 10 | 87 | 97 | 81 | 72 | 80 |
| | 2 | 71 | 88 | 50 | 51 | 68 |
| | 0.4 | 66 | 80 | 24 | 49 | 60 |
| #14 | 10 | 84 | 90 | 59 | 70 | 80 |
| | 2 | 72 | 85 | 40 | 57 | 66 |
| | 0.4 | 61 | 80 | 35 | 46 | 57 |
| #15 | 10 | 84 | 93 | 65 | 70 | 79 |
| | 2 | 69 | 84 | 31 | 55 | 69 |
| | 0.4 | 59 | 66 | 18 | 55 | 56 |
| #16 | 10 | 75 | 84 | 42 | 54 | 65 |
| | 2 | -12 | 4 | -20 | -20 | 5 |
| | 0.4 | 3 | -17 | -3 | -17 | 6 |
| #17 | 10 | 49 | 82 | 34 | 18 | 47 |
| | 2 | 46 | 79 | 27 | 11 | 43 |
| | 0.4 | 26 | 63 | 15 | -1 | 34 |
| #18 | 10 | 37 | 76 | 22 | 11 | 31 |
| | 2 | 34 | 62 | 24 | 9 | 21 |
| | 0.4 | 31 | 33 | 15 | 11 | 26 |
| #19 | 10 | 32 | 41 | 11 | 9 | 39 |
| | 2 | 32 | 59 | 12 | 14 | 36 |
| | 0.4 | 33 | 47 | 5 | -3 | 21 |
| 5465 | 10 | 78 | 94 | 63 | 48 | 68 |
| | 2 | 56 | 79 | 36 | 29 | 55 |
| | 0.4 | 57 | 77 | 25 | 33 | 47 |
| 859 | 10 | 16 | 57 | 3 | 10 | 17 |
| | 2 | 29 | 55 | 10 | 10 | 10 |
| | 0.4 | 1 | 36 | -4 | 2 | -3 |

Figure 5
Figure 5A
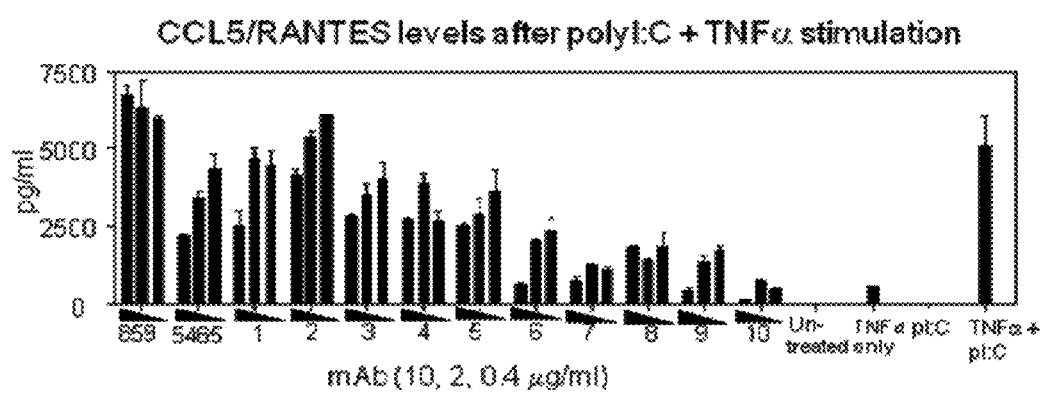
Figure 5B
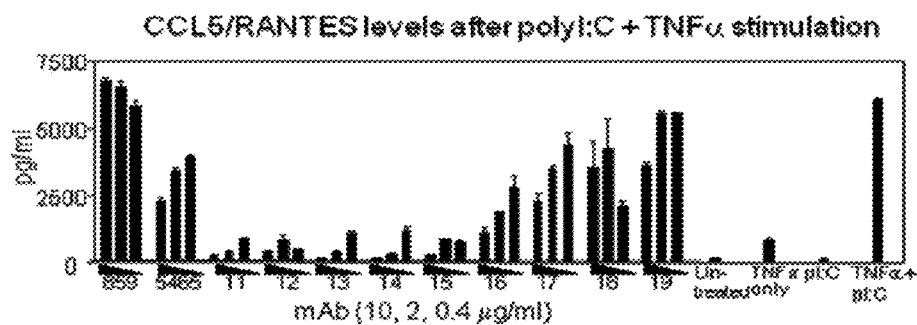

Figure 7B

```
     420        430        440        450        460        470        480        490        500
........LTKNKIS KIESDAFSWL GHLEVLDLGL NEIGQELTGQ EWRGLENIFE IYLSYNKYLQ LTRNSFALVP SLQRLMLRRV ALKNVDSSPS
     510        520        530        540        550        560        570        580        590
PFQPLRNLTI LDLSNKNIAN INDDMLEGLE KLEILDLQHN NLARLWKHAN PGGPIYFLKG LSHLHILNLE SNGFDEIPVE VFKDLFELKI
     600        610        620        630
IDLGLNNINT IPASVFNNQV SLKSLNLQKN LITSVEKKVF GPAFRN........................
```

■ strongly H/D-exchange protected by antibody
▦ weakly H/D-exchange protected by antibody
☐ not protected BLINDED scoring based on: Single cell necrosis, Epithelial ulceration, Epithelial sloughing, Cryptal abscess, Cryptal cell proliferation, LP Granulation tissue Submucosal granulation tissue, Submucosal neutrophils, Submucosal edema Figure 15
Figure 15A
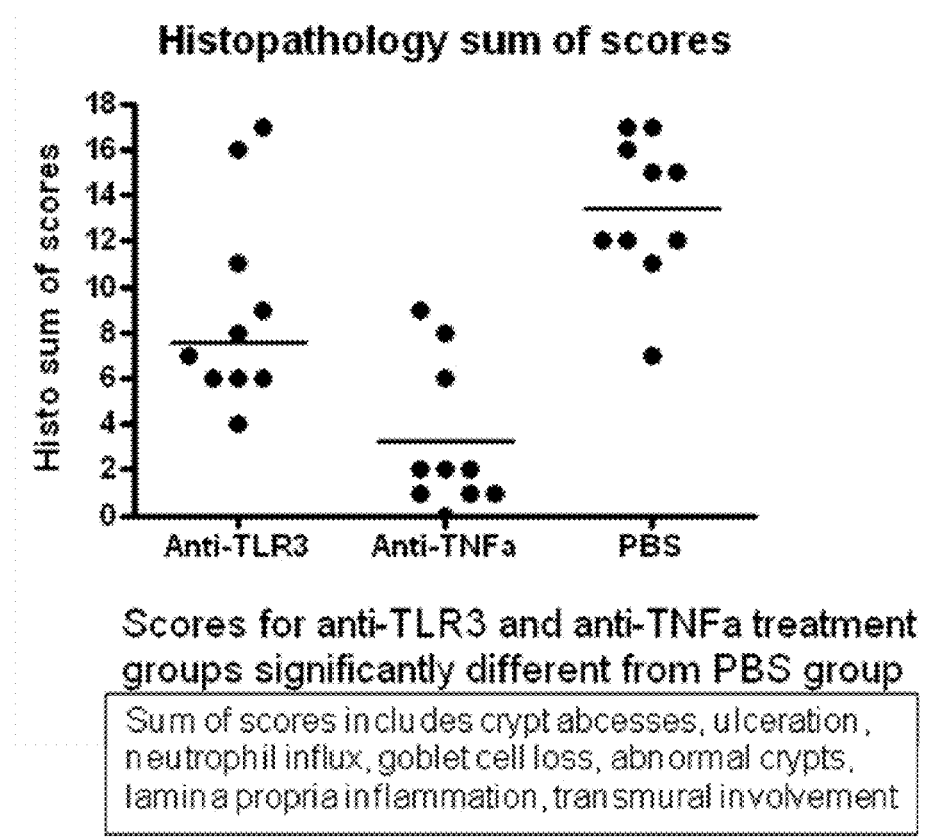
Figure 15B
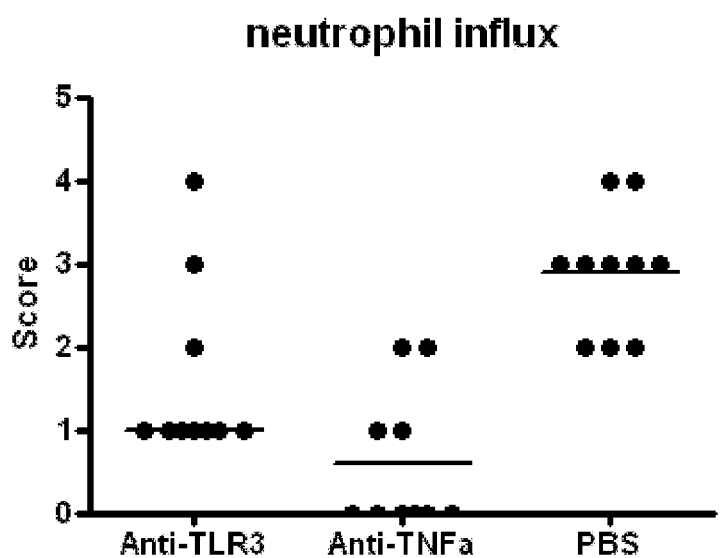

Clinical Score following administration of influenza A/PR/8/34.[3]

Figure 21
Figure 21A
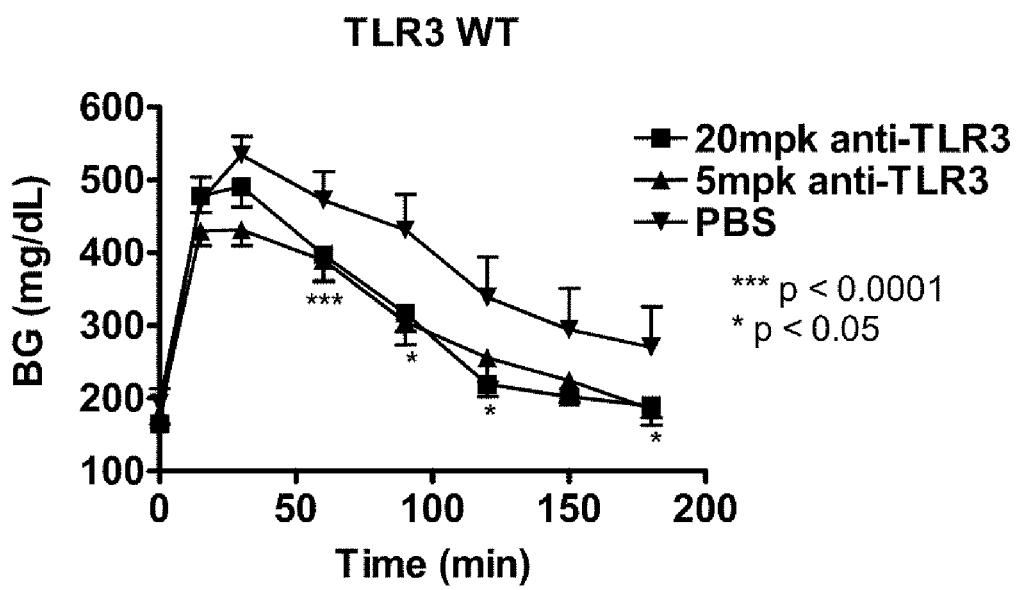
Figure 21B
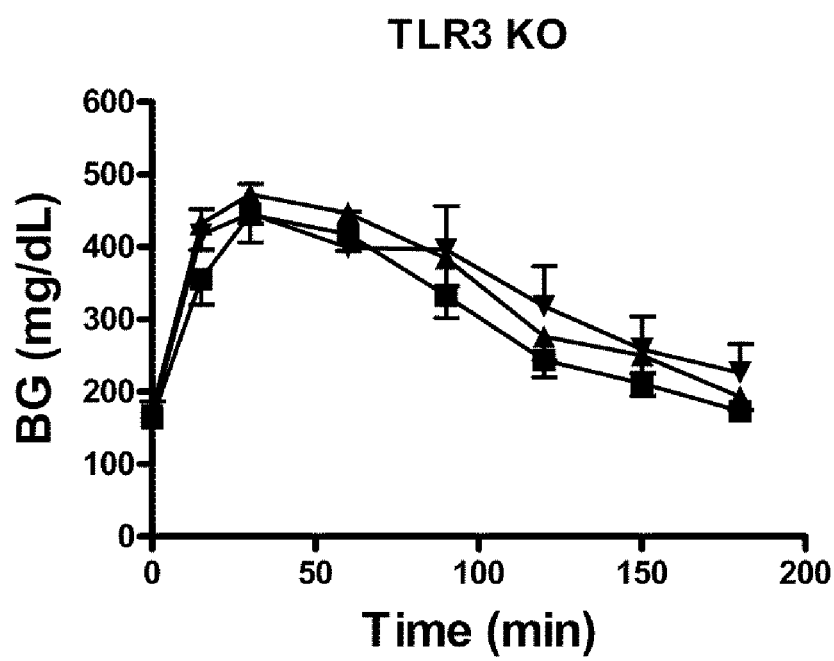

Figure 24
Figure 24A
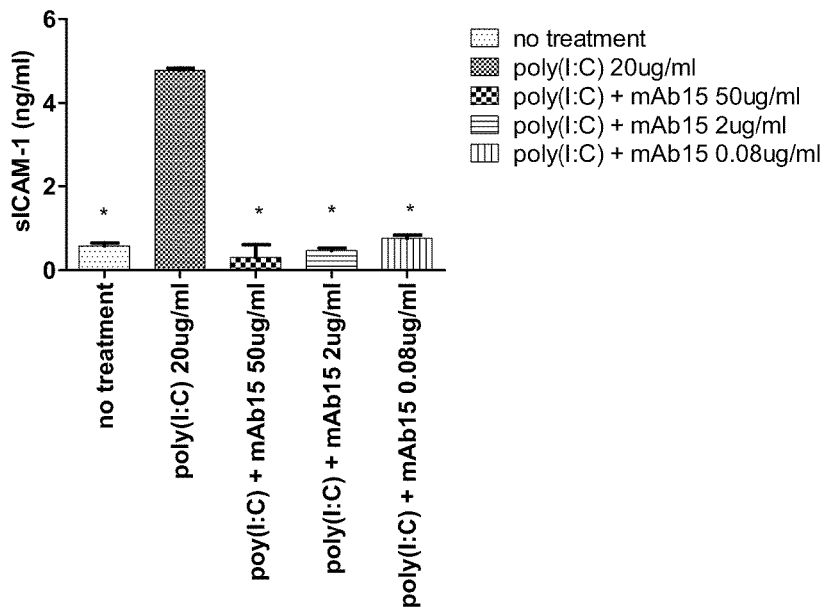
Figure 24B
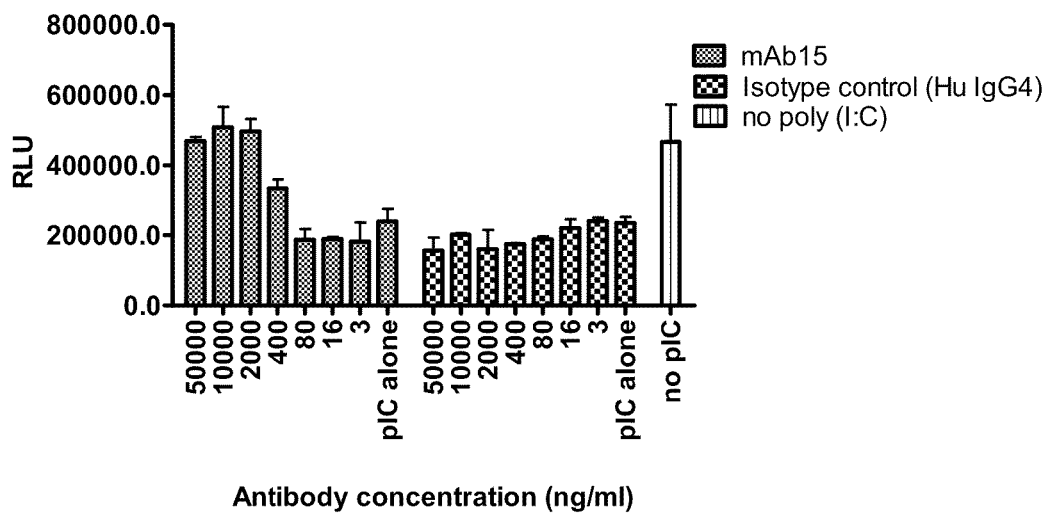

SEQUENCE LISTING

```
<160> NUMBER OF SEQ ID NOS: 220

<210> SEQ ID NO 1
<211> LENGTH: 2712
<212> TYPE: DNA
<213> ORGANISM: Homo sapiens

<400> SEQUENCE: 1
atgagacaga ctttgccttg tatctacttt tgggggggcc ttttgccctt tgggatgctg      60
tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
gatgtaggat ttaacaccat ctcaaaactg gagccagaat tgtgccagaa acttcccatg     300
ttaaaagttt tgaacctcca gcacaatgag ctatctcaac tttctgataa aaccttttgcc     360 ttctgcacga atttgactga actccatctc atgtccaact caatccagaa aattaaaaat     420
```

```
aatcccttttg tcaagcagaa gaatttaatc acattagatc tgtctcataa tggcttgtca    480
tctacaaaat taggaactca ggttcagctg gaaaatctcc aagagcttct attatcaaac    540
aataaaattc aagcgctaaa aagtgaagaa ctggatatct tgccaattc atctttaaaa     600
aaattagagt tgtcatcgaa tcaaattaaa gagttttctc cagggtgttt tcacgcaatt    660
ggaagattat ttggcctctt tctgaacaat gtccagctgg gtcccagcct tacagagaag    720
ctatgtttgg aattagcaaa cacaagcatt cggaatctgt ctctgagtaa cagccagctg    780
tccaccacca gcaatacaac tttcttggga ctaaagtgga caaatctcac tatgctcgat    840
cttcctaca caacttaaa tgtggttggt aacgattcct ttgcttggct tccacaacta      900
gaatatttct tcctagagta taataatata cagcatttgt tttctcactc tttgcacggg    960
cttttcaatg tgaggtacct gaatttgaaa cggtctttta ctaaacaaag tatttccctt   1020
gcctcactcc ccaagattga tgattttcct tttcagtggc taaaatgttt ggagcacctt   1080
aacatggaag ataatgatat ccaggcata aaaagcaata tgttcacagg attgataaac    1140
ctgaaatact taagtctatc caactccttt acaagtttgc gaactttgac aaatgaaaca   1200
tttgtatcac ttgctcattc tcccttacac atactcaacc taaccaagaa taaaatctca   1260
aaaatagaga gtgatgcttt ctcttggttg ggccacctag aagtacttga cctgggcctt   1320
aatgaaattg ggcaagaact cacaggccag gaatggagag gtctagaaaa tattttcgaa   1380
atctatcttt cctacaacaa gtacctgcag ctgactagga actcctttgc cttggtccca   1440
agccttcaac gactgatgct ccgaaggtgt gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct tgacgagat cccagttgag    1740
gtcttcaagg atttatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggttttc gggccagctt tcaggaacct gactgagtta   1920
gatatgcgct ttaatccctt tgattgcacg tgtgaaagta ttgcctggtt tgttaattgg   1980
attaacgaga cccataccaa catccctgag ctgtcaagcc actacctttg caacactcca   2040
cctcactatc atgggttccc agtgagactt tttgatacat catcttgcaa agacagtgcc   2100
cccttgaac tcttttttcat gatcaatacc agtatcctgt tgatttttat ctttattgta   2160
cttctcatcc actttgaggg ctggaggata tcttttttatt ggaatgtttc agtcatcga   2220
gttcttggtt tcaaagaaat agacagacag acagaacagt ttgaatatgc agcatatata   2280
attcatgcct ataagataa ggattgggtc tgggaacatt tctcttcaat ggaaaaggaa    2340
gaccaatctc tcaaattttg tctggaagaa agggactttg aggcgggtgt ttttgaacta   2400
gaagcaattg ttaacagcat caaaagaagc agaaaaatta tttttgttat aacacaccat   2460
ctattaaaag acccattatg caaaagattc aaggtacatc atgcagttca acaagctatt   2520
gaacaaaatc tggattccat tatattggtt ttccttgagg agattccaga ttataaactg   2580
aaccatgcac tctgtttgcg aagaggaatg tttaaatctc actgcatctt gaactggcca   2640
gttcagaaag aacggatagg tgcctttcgt cataaattgc aagtagcact tggatccaaa   2700
aactctgtac at                                                      2712
```

<210> SEQ ID NO 2
<211> LENGTH: 904
<212> TYPE: PRT
<213> ORGANISM: Homo sapiens

<400> SEQUENCE: 2

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr

```
                385                 390                 395                 400
            Phe Val Ser Leu Ala His Ser Pro Leu His Ile Leu Asn Leu Thr Lys
                        405                 410                 415
            Asn Lys Ile Ser Lys Ile Glu Ser Asp Ala Phe Ser Trp Leu Gly His
                        420                 425                 430
            Leu Glu Val Leu Asp Leu Gly Leu Asn Glu Ile Gly Gln Glu Leu Thr
                        435                 440                 445
            Gly Gln Glu Trp Arg Gly Leu Glu Asn Ile Phe Glu Ile Tyr Leu Ser
                        450                 455                 460
            Tyr Asn Lys Tyr Leu Gln Leu Thr Arg Asn Ser Phe Ala Leu Val Pro
            465                 470                 475                 480
            Ser Leu Gln Arg Leu Met Leu Arg Arg Val Ala Leu Lys Asn Val Asp
                        485                 490                 495
            Ser Ser Pro Ser Pro Phe Gln Pro Leu Arg Asn Leu Thr Ile Leu Asp
                        500                 505                 510
            Leu Ser Asn Asn Asn Ile Ala Asn Ile Asn Asp Asp Met Leu Glu Gly
                        515                 520                 525
            Leu Glu Lys Leu Glu Ile Leu Asp Leu Gln His Asn Asn Leu Ala Arg
                        530                 535                 540
            Leu Trp Lys His Ala Asn Pro Gly Gly Pro Ile Tyr Phe Leu Lys Gly
            545                 550                 555                 560
            Leu Ser His Leu His Ile Leu Asn Leu Glu Ser Asn Gly Phe Asp Glu
                        565                 570                 575
            Ile Pro Val Glu Val Phe Lys Asp Leu Phe Glu Leu Lys Ile Ile Asp
                        580                 585                 590
            Leu Gly Leu Asn Asn Leu Asn Thr Leu Pro Ala Ser Val Phe Asn Asn
                        595                 600                 605
            Gln Val Ser Leu Lys Ser Leu Asn Leu Gln Lys Asn Leu Ile Thr Ser
                        610                 615                 620
            Val Glu Lys Lys Val Phe Gly Pro Ala Phe Arg Asn Leu Thr Glu Leu
            625                 630                 635                 640
            Asp Met Arg Phe Asn Pro Phe Asp Cys Thr Cys Glu Ser Ile Ala Trp
                        645                 650                 655
            Phe Val Asn Trp Ile Asn Glu Thr His Thr Asn Ile Pro Glu Leu Ser
                        660                 665                 670
            Ser His Tyr Leu Cys Asn Thr Pro Pro His Tyr His Gly Phe Pro Val
                        675                 680                 685
            Arg Leu Phe Asp Thr Ser Ser Cys Lys Asp Ser Ala Pro Phe Glu Leu
                        690                 695                 700
            Phe Phe Met Ile Asn Thr Ser Ile Leu Leu Ile Phe Ile Phe Ile Val
            705                 710                 715                 720
            Leu Leu Ile His Phe Glu Gly Trp Arg Ile Ser Phe Tyr Trp Asn Val
                        725                 730                 735
            Ser Val His Arg Val Leu Gly Phe Lys Glu Ile Asp Arg Gln Thr Glu
                        740                 745                 750
            Gln Phe Glu Tyr Ala Ala Tyr Ile Ile His Ala Tyr Lys Asp Lys Asp
                        755                 760                 765
            Trp Val Trp Glu His Phe Ser Ser Met Glu Lys Glu Asp Gln Ser Leu
                        770                 775                 780
            Lys Phe Cys Leu Glu Glu Arg Asp Phe Glu Ala Gly Val Phe Glu Leu
            785                 790                 795                 800
            Glu Ala Ile Val Asn Ser Ile Lys Arg Ser Arg Lys Ile Ile Phe Val
                        805                 810                 815
```

```
Ile Thr His His Leu Leu Lys Asp Pro Leu Cys Lys Arg Phe Lys Val
            820                 825                 830

His His Ala Val Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900
```

```
<210> SEQ ID NO 3
<211> LENGTH: 2109
<212> TYPE: DNA
<213> ORGANISM: Homo sapiens

<400> SEQUENCE: 3
```

| | | | | | |
|---|---|---|---|---|---|
| atgagacaga | ctttgccttg | tatctacttt | tggggggggcc | ttttgccctt | tgggatgctg | 60 |
| tgtgcatcct | ccaccaccaa | gtgcactgtt | agccatgaag | ttgctgactg | cagccacctg | 120 |
| aagttgactc | aggtacccga | tgatctaccc | acaaacataa | cagtgttgaa | ccttacccat | 180 |
| aatcaactca | gaagattacc | agccgccaac | ttcacaaggt | atagccagct | aactagcttg | 240 |
| gatgtaggat | ttaacaccat | ctcaaaactg | gagccagaat | tgtgccagaa | acttcccatg | 300 |
| ttaaaagttt | tgaacctcca | gcacaatgag | ctatctcaac | tttctgataa | aaccctttgcc | 360 |
| ttctgcacga | atttgactga | actccatctc | atgtccaact | caatccagaa | aattaaaaat | 420 |
| aatccctttg | tcaagcagaa | gaatttaatc | acattagatc | tgtctcataa | tggcttgtca | 480 |
| tctacaaaat | taggaactca | ggttcagctg | gaaaatctcc | aagagcttct | attatcaaac | 540 |
| aataaaattc | aagcgctaaa | aagtgaagaa | ctggatatct | ttgccaattc | atctttaaaa | 600 |
| aaattagagt | tgtcatcgaa | tcaaattaaa | gagttttctc | agggtgtttt | tcacgcaatt | 660 |
| ggaagattat | ttggcctctt | tctgaacaat | gtccagctgg | gtcccagcct | tacagagaag | 720 |
| ctatgtttgg | aattagcaaa | cacaagcatt | cggaatctgt | ctctgagtaa | cagccagctg | 780 |
| tccaccacca | gcaatacaac | tttcttggga | ctaaagtgga | caaatctcac | tatgctcgat | 840 |
| cttttcctaca | caacttaaa | tgtggttggt | aacgattcct | tgcttggct | tccacaacta | 900 |
| gaatatttct | tcctagagta | taataatata | cagcattgt | tttctcactc | tttgcacggg | 960 |
| cttttcaatg | tgaggtacct | gaatttgaaa | cggtctttta | ctaaacaaag | tatttcccttt | 1020 |
| gcctcactcc | ccaagattga | tgattttctt | tttcagtggc | taaatgtttt | ggagcacctt | 1080 |
| aacatggaag | ataatgatat | tccaggcata | aaaagcaata | tgttcacagg | attgataaac | 1140 |
| ctgaaatact | taagtctatc | caactccttt | acaagtttgc | gaactttgac | aaatgaaaca | 1200 |
| tttgtatcac | ttgctcattc | tcccttacac | atactcaacc | taaccaagaa | taaaatctca | 1260 |
| aaaatagaga | gtgatgcttt | ctcttggttg | ggccacctag | aagtacttga | cctgggcctt | 1320 |
| aatgaaattg | ggcaagaact | cacaggccag | gaatggagag | gtctagaaaa | tattttcgaa | 1380 |
| atctatcttt | cctacaacaa | gtacctgcag | ctgactagga | actcctttgc | cttggtccca | 1440 |
| agccttcaac | gactgatgct | ccgaagggtg | gccttaaaa | atgtggatag | ctctccttca | 1500 |
| ccattccagc | tcttcgtaa | cttgaccatt | ctggatctaa | gcaacaacaa | catagccaac | 1560 |
| ataaatgatg | acatgttgga | gggtcttgag | aaactagaaa | ttctcgattt | gcagcataac | 1620 |

```
aacttagcac ggctctggaa acacgcaaac cctggtggtc ccatttattt cctaaagggt    1680
ctgtctcacc tccacatcct taacttggag tccaacggct tgacgagat  cccagttgag    1740 gtcttcaagg atttatttga actaaagatc atcgatttag gattgaataa tttaaacaca    1800
cttccagcat ctgtctttaa taatcaggtg tctctaaagt cattgaacct tcagaagaat    1860
ctcataacat ccgttgagaa gaaggttttc gggccagctt tcaggaacct gactgagtta    1920
gatatgcgct ttaatccctt tgattgcacg tgtgaaagta ttgcctggtt tgttaattgg    1980
attaacgaga cccataccaa catccctgag ctgtcaagcc actacctttg caacactcca    2040
cctcactatc atgggttccc agtgagactt tttgatacat catcttgcaa agacagtgcc    2100
cccttttgaa                                                          2109
```

<210> SEQ ID NO 4
<211> LENGTH: 703
<212> TYPE: PRT
<213> ORGANISM: Homo sapiens

<400> SEQUENCE: 4

```
Met Arg Gln Thr Leu Pro Cys Ile Tyr Phe Trp Gly Gly Leu Leu Pro
 1               5                  10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285
```

-continued

Val Gly Asn Asp Ser Phe Ala Trp Leu Pro Gln Leu Glu Tyr Phe Phe
290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
            325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
            405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
            530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
            565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
            645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu
690                 695                 700

<210> SEQ ID NO 5

<211> LENGTH: 107
<212> TYPE: PRT
<213> ORGANISM: Artificial Sequence
<220> FEATURE:
<223> OTHER INFORMATION: candidate 16 VL

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asp Asp Phe Ser Ile
                85                  90                  95

Thr Phe Gly Gln Gly Thr Lys Val Glu Ile Lys
            100                 105
```

<210> SEQ ID NO 6
<211> LENGTH: 116
<212> TYPE: PRT
<213> ORGANISM: Artificial Sequence
<220> FEATURE:
<223> OTHER INFORMATION: candidate 16 VH

<400> SEQUENCE: 6

```
Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Gly Trp Val Arg Gln Met Pro Gly Lys Gly Leu Glu Trp Met
        35                  40                  45

Gly Ile Ile Asp Pro Gly Asp Ser Tyr Thr Asn Tyr Ala Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Ile Tyr Glu Phe Asp Tyr Trp Gly Gln Gly Thr Leu Val
            100                 105                 110

Thr Val Ser Ser
        115
```

<210> SEQ ID NO 7
<211> LENGTH: 107
<212> TYPE: PRT
<213> ORGANISM: Artificial Sequence
<220> FEATURE:
<223> OTHER INFORMATION: candidate 17 VL

<400> SEQUENCE: 7

```
Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Gly Tyr Phe Val
            20                  25                  30

Ser Trp Tyr Gln Gln Lys Pro Gly Gln Ala Pro Val Leu Val Ile Tyr
```

```
                35                  40                  45
Asp Asp Asp Asn Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Ala Ser Tyr Asp Gly Asp Glu Phe Thr
                 85                  90                  95
Val Phe Gly Gly Gly Thr Lys Leu Thr Val Leu
                100                 105

<210> SEQ ID NO 8
<211> LENGTH: 122
<212> TYPE: PRT
<213> ORGANISM: Artificial Sequence
<220> FEATURE:
<223> OTHER INFORMATION: candidate 17 VH

<400> SEQUENCE: 8

Gln Val Glu Leu Gln Gln Ser Gly Pro Gly Leu Val Lys Pro Ser Gln
 1                   5                  10                  15
Thr Leu Ser Leu Thr Cys Ala Ile Ser Gly Asp Ser Val Ser Thr Arg
                 20                  25                  30
Ser Ala Ala Trp Gly Trp Ile Arg Gln Ser Pro Gly Arg Gly Leu Glu
                 35                  40                  45
Trp Leu Gly Arg Ile Tyr Met Arg Ser Lys Trp Tyr Asn Asp Tyr Ala
 50                  55                  60
Val Ser Val Lys Ser Arg Ile Thr Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Ala Arg His Thr Tyr Pro Tyr Leu Ser Phe Asp Val Trp
                100                 105                 110
Gly Gln Gly Thr Leu Val Thr Val Ser Ser
                115                 120

<210> SEQ ID NO 9
<211> LENGTH: 108
<212> TYPE: PRT
<213> ORGANISM: Artificial Sequence
<220> FEATURE:
<223> OTHER INFORMATION: candidate 18 VL

<400> SEQUENCE: 9

Asp Ile Glu Leu Thr Gln Pro Pro Ser Val Ser Val Ala Pro Gly Gln
 1                   5                  10                  15
Thr Ala Arg Ile Ser Cys Ser Gly Asp Asn Ile Gly Ser Tyr Tyr Val
                 20                  25                  30
His Trp Tyr Gln Gln Lys Pro Gly Gln Ala Pro Val Leu Val Ile Tyr
                 35                  40                  45
Glu Asp Ser Glu Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Gln Ser Tyr Asp Ser Gln Phe Ser Phe
                 85                  90                  95
Gly Val Phe Gly Gly Gly Thr Lys Leu Thr Val Leu
                100                 105
```

```
<210> SEQ ID NO 10
<211> LENGTH: 122
<212> TYPE: PRT
<213> ORGANISM: Artificial Sequence
<220> FEATURE:
<223> OTHER INFORMATION: candidate 18 VH

<400> SEQUENCE: 10

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Lys Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 11
<211> LENGTH: 107
<212> TYPE: PRT
<213> ORGANISM: Artificial Sequence
<220> FEATURE:
<223> OTHER INFORMATION: candidate 19 VL

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Val Ser Ile
                85                  90                  95

Thr Phe Gly Gln Gly Thr Lys Val Glu Ile Lys
            100                 105

<210> SEQ ID NO 12
<211> LENGTH: 121
<212> TYPE: PRT
<213> ORGANISM: Artificial Sequence
<220> FEATURE:
<223> OTHER INFORMATION: candidate 19 VH

<400> SEQUENCE: 12

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30
```

Trp Val Gly Trp Val Arg Gln Met Pro Gly Lys Gly Leu Glu Trp Met
            35                  40                  45

Gly Phe Ile Asp Pro Ser Asp Ser Tyr Thr Asn Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
            115                 120

<210> SEQ ID NO 13
<211> LENGTH: 108
<212> TYPE: PRT
<213> ORGANISM: Artificial Sequence
<220> FEATURE:
<223> OTHER INFORMATION: candidate 1 VL

<400> SEQUENCE: 13

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Tyr Ile Asp Ile Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Tyr Ser Leu Ser
                85                  90                  95

Ile Thr Phe Gly Gln Gly Thr Lys Val Glu Ile Lys
            100                 105

<210> SEQ ID NO 14
<211> LENGTH: 119
<212> TYPE: PRT
<213> ORGANISM: Artificial Sequence
<220> FEATURE:
<223> OTHER INFORMATION: candidate 1 VH

<400> SEQUENCE: 14

Gly Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Asn
            20                  25                  30

Trp Ile Ser Trp Val Arg Gln Ala Pro Gly Lys Gly Leu Glu Trp Met
        35                  40                  45

Gly Val Ile Asp Pro Ser Asp Ser Tyr Thr Asn Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Trp Gly Ile Gly Met Val Asp Ile Trp Gly Gln Gly
            100                 105                 110

```
Thr Leu Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: candidate 2 VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asp Asp Phe Ser Ile
                85                  90                  95

Thr Phe Gly Gln Gly Thr Lys Val Glu Ile Lys
            100                 105

<210> SEQ ID NO 16
<211> LENGTH: 116
<212> TYPE: PRT
<213> ORGANISM: Artificial Sequence
<220> FEATURE:
<223> OTHER INFORMATION: candidate 2 VH

<400> SEQUENCE: 16

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Gly Trp Val Arg Gln Met Pro Gly Lys Gly Leu Glu Trp Met
        35                  40                  45

Gly Ile Ile Asp Pro Gln Asp Ser Trp Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Ile Tyr Glu Phe Asp Tyr Trp Gly Gln Gly Thr Leu Val
            100                 105                 110

Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: candidate 3 VL

<400> SEQUENCE: 17

Asp Ile Glu Leu Thr Gln Pro Pro Ser Val Ser Val Ala Pro Gly Gln
1               5                   10                  15
```

Thr Ala Arg Ile Ser Cys Ser Gly Asp Ala Leu Gly Gly Tyr Phe Val
            20                  25                  30

Ser Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Tyr Asp Gly Asp Glu Phe Thr
                85                  90                  95

Val Phe Gly Gly Gly Thr Lys Leu Thr Val Leu
            100                 105

<210> SEQ ID NO 18
<211> LENGTH: 122
<212> TYPE: PRT
<213> ORGANISM: Artificial Sequence
<220> FEATURE:
<223> OTHER INFORMATION: candidate 3 VH

<400> SEQUENCE: 18

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Arg Ile His Arg Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: candidate 4 VL

<400> SEQUENCE: 19

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Gly Tyr Phe Val
            20                  25                  30

Ser Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Tyr Asp Gly Asp Glu Phe Thr
                85                  90                  95

Val Phe Gly Gly Gly Thr Lys Leu Thr Val Leu
            100                 105

<210> SEQ ID NO 20
<211> LENGTH: 122
<212> TYPE: PRT
<213> ORGANISM: Artificial Sequence
<220> FEATURE:
<223> OTHER INFORMATION: candidate 4 VH

<400> SEQUENCE: 20

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Lys Ile Ser Tyr Arg Ser Arg Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: candidate 5 VL

<400> SEQUENCE: 21

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Gly Tyr Phe Val
            20                  25                  30

Ser Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Glu Asp Ser Ala Thr
                85                  90                  95

Val Phe Gly Gly Gly Thr Lys Leu Thr Val Leu
            100                 105

<210> SEQ ID NO 22
<211> LENGTH: 122
<212> TYPE: PRT
<213> ORGANISM: Artificial Sequence
<220> FEATURE:
<223> OTHER INFORMATION: candidate 5 VH

<400> SEQUENCE: 22

Gln Val Glu Leu Gln Gln Ser Gly Pro Gly Leu Val Lys Pro Ser Gln
 1               5                  10                  15

```
                1               5                  10                  15
Thr Leu Ser Leu Thr Cys Ala Ile Ser Gly Asp Ser Val Ser Thr Arg
                    20                  25                  30

Ser Ala Ala Trp Gly Trp Ile Arg Gln Ser Pro Gly Arg Gly Leu Glu
                    35                  40                  45

Trp Leu Gly Arg Ile Tyr Met Arg Ser Lys Trp Tyr Asn Asp Tyr Ala
            50                  55                  60

Val Ser Val Lys Ser Arg Ile Thr Ile Asn Pro Asp Thr Ser Lys Asn
 65                 70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
                    100                 105                 110

Gly Gln Gly Thr Leu Val Thr Val Ser Ser
                    115                 120
```

<210> SEQ ID NO 23
<211> LENGTH: 107
<212> TYPE: PRT
<213> ORGANISM: Artificial Sequence
<220> FEATURE:
<223> OTHER INFORMATION: candidate 6 VL

<400> SEQUENCE: 23

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Gly Tyr Phe Val
                    20                  25                  30

Ser Trp Tyr Gln Gln Lys Pro Gly Gln Ala Pro Val Leu Val Ile Tyr
                    35                  40                  45

Asp Asp Asp Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
 65                 70                  75                  80

Asp Glu Ala Asp Tyr Tyr Cys Gly Ser Tyr Asp Ser Asn Ser Leu Thr
                85                  90                  95

Val Phe Gly Gly Gly Thr Lys Leu Thr Val Leu
                    100                 105
```

<210> SEQ ID NO 24
<211> LENGTH: 122
<212> TYPE: PRT
<213> ORGANISM: Artificial Sequence
<220> FEATURE:
<223> OTHER INFORMATION: candidate 6 VH

<400> SEQUENCE: 24

```
Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
                    20                  25                  30

Ser Ala Ala Trp Gly Trp Ile Arg Gln Ser Pro Gly Arg Gly Leu Glu
                    35                  40                  45

Trp Leu Gly Arg Ile Tyr Met Arg Ser Lys Trp Tyr Asn Asp Tyr Ala
            50                  55                  60

Val Ser Val Lys Ser Arg Ile Thr Ile Asn Pro Asp Thr Ser Lys Asn
 65                 70                  75                  80

Gln Phe Ser Leu Gln Leu Asn Ser Val Thr Pro Glu Asp Thr Ala Val
```

-continued

```
                 85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: candidate 7 VL

<400> SEQUENCE: 25

Asp Ile Glu Leu Thr Gln Pro Pro Ser Val Ser Val Ala Pro Gly Gln
1               5                  10                  15

Thr Ala Arg Ile Ser Cys Ser Gly Asp Ala Leu Gly Gly Tyr Phe Val
            20                  25                  30

Ser Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Ser Asp Ser Leu Thr
                85                  90                  95

Val Phe Gly Gly Gly Thr Lys Leu Thr Val Leu
            100                 105

<210> SEQ ID NO 26
<211> LENGTH: 122
<212> TYPE: PRT
<213> ORGANISM: Artificial Sequence
<220> FEATURE:
<223> OTHER INFORMATION: candidate 7 VH

<400> SEQUENCE: 26

Gln Val Glu Leu Gln Gln Ser Gly Pro Gly Leu Val Lys Pro Ser Gln
1               5                  10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Arg Ile Tyr Met Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser
        115                 120

<210> SEQ ID NO 27
<211> LENGTH: 108
<212> TYPE: PRT
<213> ORGANISM: Artificial Sequence
<220> FEATURE:
<223> OTHER INFORMATION: candidate 8 VL
```

```
<400> SEQUENCE: 27

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Gln Phe Ser Phe
                85                  90                  95

Gly Val Phe Gly Gly Gly Thr Lys Leu Thr Val Leu
            100                 105

<210> SEQ ID NO 28
<211> LENGTH: 122
<212> TYPE: PRT
<213> ORGANISM: Artificial Sequence
<220> FEATURE:
<223> OTHER INFORMATION: candidate 8 VH

<400> SEQUENCE: 28

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Thr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 29
<211> LENGTH: 108
<212> TYPE: PRT
<213> ORGANISM: Artificial Sequence
<220> FEATURE:
<223> OTHER INFORMATION: candidate 9 VL

<400> SEQUENCE: 29

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
    50                  55                  60
```

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Gln Phe Ser Phe
                85                  90                  95

Gly Val Phe Gly Gly Gly Thr Lys Leu Thr Val Leu
            100                 105

<210> SEQ ID NO 30
<211> LENGTH: 122
<212> TYPE: PRT
<213> ORGANISM: Artificial Sequence
<220> FEATURE:
<223> OTHER INFORMATION: candidate 9 VH

<400> SEQUENCE: 30

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Ile Arg Ser Lys Trp Tyr Asn Asp Tyr Ala
50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 31
<211> LENGTH: 107
<212> TYPE: PRT
<213> ORGANISM: Artificial Sequence
<220> FEATURE:
<223> OTHER INFORMATION: candidate 10 VL

<400> SEQUENCE: 31

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Thr Pro Val Tyr Ser
                85                  90                  95

Val Phe Gly Gly Gly Thr Lys Leu Thr Val Leu
            100                 105

<210> SEQ ID NO 32
<211> LENGTH: 122
<212> TYPE: PRT
<213> ORGANISM: Artificial Sequence
<220> FEATURE:

<223> OTHER INFORMATION: candidate 10 VH

<400> SEQUENCE: 32

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Lys Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: candidate 11 VL

<400> SEQUENCE: 33

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Glu Pro Asn Phe Asn
                85                  90                  95

Val Phe Gly Gly Gly Thr Lys Leu Thr Val Leu
            100                 105

<210> SEQ ID NO 34
<211> LENGTH: 122
<212> TYPE: PRT
<213> ORGANISM: Artificial Sequence
<220> FEATURE:
<223> OTHER INFORMATION: candidate 11 VH

<400> SEQUENCE: 34

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Lys Arg Ser Lys Trp Tyr Asn Asn Tyr Ala
    50                  55                  60

```
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Ser Tyr Pro Phe Tyr Ser Ile Asp Tyr Trp
                100                 105                 110

Gly Gln Gly Thr Leu Val Thr Val Ser Ser
            115                 120
```

<210> SEQ ID NO 35
<211> LENGTH: 122
<212> TYPE: PRT
<213> ORGANISM: Artificial Sequence
<220> FEATURE:
<223> OTHER INFORMATION: candidate 12 VL

<400> SEQUENCE: 35

```
Asp Ile Glu Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Gly Trp Ile Arg Gln Ser Pro Gly Arg Gly Leu Glu
                35                  40                  45

Trp Leu Gly Ile Ile Gln Lys Ser Lys Trp Tyr Asn Asn Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Ser Tyr Pro Phe Tyr Ser Ile Asp Tyr Trp
                100                 105                 110

Gly Gln Gly Thr Leu Val Thr Val Ser Ser
            115                 120
```

<210> SEQ ID NO 36
<211> LENGTH: 122
<212> TYPE: PRT
<213> ORGANISM: Artificial Sequence
<220> FEATURE:
<223> OTHER INFORMATION: candidate 12 VH

<400> SEQUENCE: 36

```
Gln Val Glu Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Gly Trp Ile Arg Gln Ser Pro Gly Arg Gly Leu Glu
                35                  40                  45

Trp Leu Gly Ile Ile Gln Lys Ser Lys Trp Tyr Asn Asn Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Ser Tyr Pro Phe Tyr Ser Ile Asp Tyr Trp
                100                 105                 110

Gly Gln Gly Thr Leu Val Thr Val Ser Ser
            115                 120
```

```
<210> SEQ ID NO 37
<211> LENGTH: 107
<212> TYPE: PRT
<213> ORGANISM: Artificial Sequence
<220> FEATURE:
<223> OTHER INFORMATION: candidate 13 VL

<400> SEQUENCE: 37

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Glu Ser Ile Leu Ser
                85                  90                  95

Thr Phe Gly Gln Gly Thr Lys Val Glu Ile Lys
            100                 105

<210> SEQ ID NO 38
<211> LENGTH: 121
<212> TYPE: PRT
<213> ORGANISM: Artificial Sequence
<220> FEATURE:
<223> OTHER INFORMATION: candidate 13 VH

<400> SEQUENCE: 38

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Phe Ile Asp Pro Ser Asp Ser Tyr Thr Asn Tyr Ala Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
        115                 120

<210> SEQ ID NO 39
<211> LENGTH: 107
<212> TYPE: PRT
<213> ORGANISM: Artificial Sequence
<220> FEATURE:
<223> OTHER INFORMATION: candidate 14 VL

<400> SEQUENCE: 39

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
```

```
                    20                  25                  30
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Glu Thr Val Ser Pro
                 85                  90                  95

Thr Phe Gly Gln Gly Thr Lys Val Glu Ile Lys
                100                 105

<210> SEQ ID NO 40
<211> LENGTH: 121
<212> TYPE: PRT
<213> ORGANISM: Artificial Sequence
<220> FEATURE:
<223> OTHER INFORMATION: candidate 14 VH

<400> SEQUENCE: 40

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
            35                  40                  45

Gly Phe Ile Asp Pro Ser Asp Ser Tyr Thr Asn Tyr Ala Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
                100                 105                 110

Gln Gly Thr Leu Val Thr Val Ser Ser
            115                 120

<210> SEQ ID NO 41
<211> LENGTH: 107
<212> TYPE: PRT
<213> ORGANISM: Artificial Sequence
<220> FEATURE:
<223> OTHER INFORMATION: candidate 15 VL

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Ser Tyr
                 85                  90                  95

Thr Phe Gly Gln Gly Thr Lys Val Glu Ile Lys
```

```
                         100                 105

<210> SEQ ID NO 42
<211> LENGTH: 121
<212> TYPE: PRT
<213> ORGANISM: Artificial Sequence
<220> FEATURE:
<223> OTHER INFORMATION: candidate 15 VH

<400> SEQUENCE: 42

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Phe Ile Asp Pro Ser Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
        115                 120

<210> SEQ ID NO 43
<211> LENGTH: 7
<212> TYPE: PRT
<213> ORGANISM: Artificial Sequence
<220> FEATURE:
<223> OTHER INFORMATION: candidate 1 LCDR1

<400> SEQUENCE: 43

Gln Tyr Ile Asp Ile Ser Tyr
 1               5

<210> SEQ ID NO 44
<211> LENGTH: 3
<212> TYPE: PRT
<213> ORGANISM: Artificial Sequence
<220> FEATURE:
<223> OTHER INFORMATION: candidate 1 LCDR2

<400> SEQUENCE: 44

Asp Ala Ser
 1

<210> SEQ ID NO 45
<211> LENGTH: 9
<212> TYPE: PRT
<213> ORGANISM: Artificial Sequence
<220> FEATURE:
<223> OTHER INFORMATION: candidate 1 LCDR3

<400> SEQUENCE: 45

Gln Gln Tyr Tyr Ser Leu Ser Ile Thr
 1               5

<210> SEQ ID NO 46
<211> LENGTH: 8
<212> TYPE: PRT
<213> ORGANISM: Artificial Sequence
```

```
<220> FEATURE:
<223> OTHER INFORMATION: candidate 1 HCDR1

<400> SEQUENCE: 46

Gly Tyr Ser Phe Thr Asp Asn Trp
 1               5

<210> SEQ ID NO 47
<211> LENGTH: 8
<212> TYPE: PRT
<213> ORGANISM: Artificial Sequence
<220> FEATURE:
<223> OTHER INFORMATION: candidate 1 HCDR2

<400> SEQUENCE: 47

Ile Asp Pro Ser Asp Ser Gln Thr
 1               5

<210> SEQ ID NO 48
<211> LENGTH: 12
<212> TYPE: PRT
<213> ORGANISM: Artificial Sequence
<220> FEATURE:
<223> OTHER INFORMATION: candidate 1 HCDR3

<400> SEQUENCE: 48

Ala Arg Glu Trp Gly Ile Gly Gly Met Val Asp Ile
 1               5                  10

<210> SEQ ID NO 49
<211> LENGTH: 6
<212> TYPE: PRT
<213> ORGANISM: Artificial Sequence
<220> FEATURE:
<223> OTHER INFORMATION: candidate 2 LCDR1

<400> SEQUENCE: 49

Gln Gly Ile Ser Ser Trp
 1               5

<210> SEQ ID NO 50
<211> LENGTH: 3
<212> TYPE: PRT
<213> ORGANISM: Artificial Sequence
<220> FEATURE:
<223> OTHER INFORMATION: candidate 2 LCDR2

<400> SEQUENCE: 50

Gly Ala Ser
 1

<210> SEQ ID NO 51
<211> LENGTH: 9
<212> TYPE: PRT
<213> ORGANISM: Artificial Sequence
<220> FEATURE:
<223> OTHER INFORMATION: candidate 2 LCDR3

<400> SEQUENCE: 51

Gln Gln Tyr Asp Asp Phe Ser Ile Thr
 1               5

<210> SEQ ID NO 52
<211> LENGTH: 8
<212> TYPE: PRT
<213> ORGANISM: Artificial Sequence
<220> FEATURE:
<223> OTHER INFORMATION: candidate 2 HCDR1
```

```
<400> SEQUENCE: 52

Gly Tyr Ser Phe Asn Asn Tyr Trp
 1               5

<210> SEQ ID NO 53
<211> LENGTH: 8
<212> TYPE: PRT
<213> ORGANISM: Artificial Sequence
<220> FEATURE:
<223> OTHER INFORMATION: candidate 2 HCDR2

<400> SEQUENCE: 53

Ile Asp Pro Gln Asp Ser Trp Thr
 1               5

<210> SEQ ID NO 54
<211> LENGTH: 9
<212> TYPE: PRT
<213> ORGANISM: Artificial Sequence
<220> FEATURE:
<223> OTHER INFORMATION: candidate 2 HCDR3

<400> SEQUENCE: 54

Ala Arg Asn Ile Tyr Glu Phe Asp Tyr
 1               5

<210> SEQ ID NO 55
<211> LENGTH: 6
<212> TYPE: PRT
<213> ORGANISM: Artificial Sequence
<220> FEATURE:
<223> OTHER INFORMATION: Candidates 3,4,5,6, 7 LCDR1

<400> SEQUENCE: 55

Ala Leu Gly Gly Tyr Phe
 1               5

<210> SEQ ID NO 56
<211> LENGTH: 3
<212> TYPE: PRT
<213> ORGANISM: Artificial Sequence
<220> FEATURE:
<223> OTHER INFORMATION: Candidates 3,4,5,6, 7 LCDR2

<400> SEQUENCE: 56

Asp Asp Asp
 1

<210> SEQ ID NO 57
<211> LENGTH: 10
<212> TYPE: PRT
<213> ORGANISM: Artificial Sequence
<220> FEATURE:
<223> OTHER INFORMATION: Candidates 3,4 LCDR3

<400> SEQUENCE: 57

Ala Ser Tyr Asp Gly Asp Glu Phe Thr Val
 1               5                   10

<210> SEQ ID NO 58
<211> LENGTH: 10
<212> TYPE: PRT
<213> ORGANISM: Artificial Sequence
<220> FEATURE:
<223> OTHER INFORMATION: Candidates 3 HCDR1

<400> SEQUENCE: 58
```

Gly Asp Ser Val Ser Thr Arg Ser Ala Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Candidates 3 HCDR2

<400> SEQUENCE: 59

Ile His Arg Arg Ser Lys Tyr Trp Asn Asp
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Candidates 3,4,5,6,7 HCDR3

<400> SEQUENCE: 60

Ala Arg His Thr Tyr Pro Tyr Leu Ser Phe Asp Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Candidates 4,5,6,7 HCDR1

<400> SEQUENCE: 61

Gly Asp Ser Val Ser Thr Arg Ser Ala Ala
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Candidate 4 HCDR2

<400> SEQUENCE: 62

Ile Ser Tyr Arg Ser Arg Trp Tyr Asn Asp
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Candidate 5 LCDR3

<400> SEQUENCE: 63

Gln Ser Tyr Asp Glu Asp Ser Ala Thr Val
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Candidates 5,6,7 HCDR2

<400> SEQUENCE: 64

Ile Tyr Met Arg Ser Lys Trp Tyr Asn

-continued

```
<210> SEQ ID NO 65
<211> LENGTH: 10
<212> TYPE: PRT
<213> ORGANISM: Artificial Sequence
<220> FEATURE:
<223> OTHER INFORMATION: Candidate 6 LCDR3

<400> SEQUENCE: 65

Gly Ser Tyr Asp Ser Asn Ser Leu Thr Val
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Candidate 7 LCDR3

<400> SEQUENCE: 66

Ser Ser Tyr Asp Ser Asp Ser Leu Thr Val
 1               5                  10

<210> SEQ ID NO 67
<211> LENGTH: 6
<212> TYPE: PRT
<213> ORGANISM: Artificial Sequence
<220> FEATURE:
<223> OTHER INFORMATION: Candidate 8,9,10,11,12 LCDR1

<400> SEQUENCE: 67

Asn Ile Gly Ser Tyr Tyr
 1               5

<210> SEQ ID NO 68
<211> LENGTH: 3
<212> TYPE: PRT
<213> ORGANISM: Artificial Sequence
<220> FEATURE:
<223> OTHER INFORMATION: Candidate 8,9,10,11,12 LCDR2

<400> SEQUENCE: 68

Glu Asp Ser
 1

<210> SEQ ID NO 69
<211> LENGTH: 11
<212> TYPE: PRT
<213> ORGANISM: Artificial Sequence
<220> FEATURE:
<223> OTHER INFORMATION: Candidate 8,9 LCDR3

<400> SEQUENCE: 69

Gln Ser Tyr Asp Ser Gln Phe Ser Phe Gly Val
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Candidate 78,9,10,11,12 HCDR1

<400> SEQUENCE: 70

Gly Asp Ser Val Ser Ser Asn Ser Ala Ala
 1               5                  10
```

```
<210> SEQ ID NO 71
<211> LENGTH: 9
<212> TYPE: PRT
<213> ORGANISM: Artificial Sequence
<220> FEATURE:
<223> OTHER INFORMATION: Candidate 8 HCDR2

<400> SEQUENCE: 71

Ile Gln Thr Arg Ser Lys Tyr Trp Asn
1               5

<210> SEQ ID NO 72
<211> LENGTH: 12
<212> TYPE: PRT
<213> ORGANISM: Artificial Sequence
<220> FEATURE:
<223> OTHER INFORMATION: Candidate 8,9,10,11,12 HCDR3

<400> SEQUENCE: 72

Ala Arg Tyr Ser Tyr Pro Phe Tyr Ser Ile Asp Tyr
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Candidate 9 HCDR2

<400> SEQUENCE: 73

Ile Gln Ile Arg Ser Lys Tyr Trp Asn
1               5

<210> SEQ ID NO 74
<211> LENGTH: 10
<212> TYPE: PRT
<213> ORGANISM: Artificial Sequence
<220> FEATURE:
<223> OTHER INFORMATION: Candidate 10 LCDR3

<400> SEQUENCE: 74

Gln Ser Tyr Asp Thr Pro Val Tyr Ser Val
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Candidate 10 HCDR2

<400> SEQUENCE: 75

Ile Gln Lys Arg Ser Lys Tyr Trp Asn
1               5

<210> SEQ ID NO 76
<211> LENGTH: 10
<212> TYPE: PRT
<213> ORGANISM: Artificial Sequence
<220> FEATURE:
<223> OTHER INFORMATION: Candidate 11 LCDR3

<400> SEQUENCE: 76

Ser Ser Tyr Asp Glu Pro Asn Phe Asn Val
1               5                   10

<210> SEQ ID NO 77
```

```
<211> LENGTH: 9
<212> TYPE: PRT
<213> ORGANISM: Artificial Sequence
<220> FEATURE:
<223> OTHER INFORMATION: Candidate 11,12 HCDR2

<400> SEQUENCE: 77

Ile Gln Lys Arg Ser Lys Trp Tyr Asn
1               5

<210> SEQ ID NO 78
<211> LENGTH: 10
<212> TYPE: PRT
<213> ORGANISM: Artificial Sequence
<220> FEATURE:
<223> OTHER INFORMATION: Candidate 12 LCDR3

<400> SEQUENCE: 78

Ser Ser Tyr Asp Asp Pro Asn Phe Gln Val
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Candidate 13, 14, 15 LCDR1

<400> SEQUENCE: 79

Gln Ser Ile Gly Leu Tyr
1               5

<210> SEQ ID NO 80
<211> LENGTH: 3
<212> TYPE: PRT
<213> ORGANISM: Artificial Sequence
<220> FEATURE:
<223> OTHER INFORMATION: Candidate 13, 14, 15 LCDR2

<400> SEQUENCE: 80

Ala Ala Ser
1

<210> SEQ ID NO 81
<211> LENGTH: 9
<212> TYPE: PRT
<213> ORGANISM: Artificial Sequence
<220> FEATURE:
<223> OTHER INFORMATION: Candidate 13 LCDR3

<400> SEQUENCE: 81

Gln Gln Gly Glu Ser Ile Leu Ser Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Candidate 13, 14, 15 HCDR1

<400> SEQUENCE: 82

Gly Tyr Ser Phe Thr Asn Tyr Trp
1               5

<210> SEQ ID NO 83
<211> LENGTH: 8
<212> TYPE: PRT
```

```
<213> ORGANISM: Artificial Sequence
<220> FEATURE:
<223> OTHER INFORMATION: Candidate 13 HCDR2

<400> SEQUENCE: 83

Ile Asp Pro Ser Asp Ser Tyr Thr
1               5

<210> SEQ ID NO 84
<211> LENGTH: 14
<212> TYPE: PRT
<213> ORGANISM: Artificial Sequence
<220> FEATURE:
<223> OTHER INFORMATION: Candidates 13, 14, 15, 15-1, 15-2, 15-3, 15-4,
      15-5, 15-7, 15-8 HCDR3

<400> SEQUENCE: 84

Ala Arg Glu Leu Tyr Gln Gly Tyr Met Asp Thr Phe Asp Ser
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Candidate 14 LCDR3

<400> SEQUENCE: 85

Gln Gln Ala Glu Thr Val Ser Pro Thr
1               5

<210> SEQ ID NO 86
<211> LENGTH: 10
<212> TYPE: PRT
<213> ORGANISM: Artificial Sequence
<220> FEATURE:
<223> OTHER INFORMATION: Candidate 14, 15 HCDR2

<400> SEQUENCE: 86

Ile Asp Pro Ser Asp Ser Tyr Thr Asn Tyr
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Candidate 15 LCDR3

<400> SEQUENCE: 87

Gln Gln Gly Asn Thr Leu Ser Tyr Thr
1               5

<210> SEQ ID NO 88
<211> LENGTH: 8
<212> TYPE: PRT
<213> ORGANISM: Artificial Sequence
<220> FEATURE:
<223> OTHER INFORMATION: Candidate 16 HCDR3

<400> SEQUENCE: 88

Ile Asp Pro Gly Asp Ser Tyr Thr
1               5

<210> SEQ ID NO 89
<211> LENGTH: 9
<212> TYPE: PRT
<213> ORGANISM: Artificial Sequence
```

```
<220> FEATURE:
<223> OTHER INFORMATION: Candidate 10 LCDR3

<400> SEQUENCE: 89

Gln Gln Tyr Gly Ser Val Ser Ile Thr
 1               5

<210> SEQ ID NO 90
<211> LENGTH: 443
<212> TYPE: PRT
<213> ORGANISM: Artificial Sequence
<220> FEATURE:
<223> OTHER INFORMATION: Candidate 16 Full length heavy chain

<400> SEQUENCE: 90

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Asn Asn Tyr
                20                  25                  30

Trp Ile Gly Trp Val Arg Gln Met Pro Gly Lys Gly Leu Glu Trp Met
            35                  40                  45

Gly Ile Ile Asp Pro Gly Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Ile Tyr Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335
```

```
Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 91
<211> LENGTH: 449
<212> TYPE: PRT
<213> ORGANISM: Artificial Sequence
<220> FEATURE:
<223> OTHER INFORMATION: Candidate 17 Full length heavy chain

<400> SEQUENCE: 91

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
            35                  40                  45

Trp Leu Gly Arg Ile Tyr Met Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255
```

```
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Lys

<210> SEQ ID NO 92
<211> LENGTH: 449
<212> TYPE: PRT
<213> ORGANISM: Artificial Sequence
<220> FEATURE:
<223> OTHER INFORMATION: Candidate 18 Full length heavy chain

<400> SEQUENCE: 92

Gln Val Glu Leu Gln Gln Ser Gly Pro Gly Leu Val Lys Pro Ser Gln
  1               5                  10                  15
Thr Leu Ser Leu Thr Cys Ala Ile Ser Gly Asp Ser Val Ser Ser Asn
             20                  25                  30
Ser Ala Ala Trp Gly Trp Ile Arg Gln Ser Pro Gly Arg Gly Leu Glu
         35                  40                  45
Trp Leu Gly Ile Ile Gln Lys Arg Ser Lys Trp Tyr Asn Asn Tyr Ala
 50                  55                  60
Val Ser Val Lys Ser Arg Ile Thr Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Ala Arg Tyr Ser Tyr Pro Phe Tyr Ser Ile Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 93
<211> LENGTH: 448
<212> TYPE: PRT
<213> ORGANISM: Artificial Sequence
<220> FEATURE:
<223> OTHER INFORMATION: Candidate 19 Full length heavy chain

<400> SEQUENCE: 93

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
            35                  40                  45

Gly Phe Ile Asp Pro Ser Asp Ser Tyr Thr Asn Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys

```
                    85                  90                  95
Ala Arg Glu Leu Tyr Gln Gly Tyr Met Asp Thr Phe Asp Ser Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 94
<211> LENGTH: 446
<212> TYPE: PRT
<213> ORGANISM: Artificial Sequence
<220> FEATURE:
<223> OTHER INFORMATION: Candidate 1 Full length heavy chain

<400> SEQUENCE: 94

Gln Val Glu Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Asp Asn
                20                  25                  30

Trp Ile Ser Trp Val Arg Gln Ala Pro Gly Lys Gly Leu Glu Trp Met
            35                  40                  45

Gly Val Ile Asp Pro Ser Asp Ser Tyr Thr Asn Tyr Ala Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Glu Trp Gly Ile Gly Gly Met Val Asp Ile Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
```

<210> SEQ ID NO 95
<211> LENGTH: 443
<212> TYPE: PRT
<213> ORGANISM: Artificial Sequence
<220> FEATURE:
<223> OTHER INFORMATION: Candidate 2 Full length heavy chain

<400> SEQUENCE: 95

```
Gln Val Glu Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Asn Asn Tyr
             20                  25                  30

Trp Ile Gly Trp Val Arg Gln Met Pro Gly Lys Gly Leu Glu Trp Met
         35                  40                  45

Gly Ile Ile Asp Pro Gln Asp Ser Trp Thr Asn Tyr Ala Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asn Ile Tyr Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365
```

```
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 96
<211> LENGTH: 449
<212> TYPE: PRT
<213> ORGANISM: Artificial Sequence
<220> FEATURE:
<223> OTHER INFORMATION: Candidate 3 Full length heavy chain

<400> SEQUENCE: 96

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Arg Ile His Arg Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285
```

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 97
<211> LENGTH: 449
<212> TYPE: PRT
<213> ORGANISM: Artificial Sequence
<220> FEATURE:
<223> OTHER INFORMATION: Candidate 4 Full length heavy chain

<400> SEQUENCE: 97

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Lys Ile Ser Tyr Arg Ser Arg Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 98
<211> LENGTH: 449
<212> TYPE: PRT
<213> ORGANISM: Artificial Sequence
<220> FEATURE:
<223> OTHER INFORMATION: Candidate 5,6,7 Full length heavy chain

<400> SEQUENCE: 98

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Arg
            20                  25                  30

Ser Ala Ala Trp Gly Trp Ile Arg Gln Ser Pro Gly Arg Gly Leu Glu
        35                  40                  45

Trp Leu Gly Arg Ile Tyr Met Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser Ala Ser Thr Lys Gly Pro

```
                115                 120                 125
Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 99
<211> LENGTH: 449
<212> TYPE: PRT
<213> ORGANISM: Artificial Sequence
<220> FEATURE:
<223> OTHER INFORMATION: Candidate 8 Full length heavy chain

<400> SEQUENCE: 99

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

```
Ser Ala Ala Trp Gly Trp Ile Arg Gln Ser Pro Gly Arg Gly Leu Glu
        35                  40                  45

Trp Leu Gly Ile Ile Gln Thr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

```
<210> SEQ ID NO 100
<211> LENGTH: 449
<212> TYPE: PRT
<213> ORGANISM: Artificial Sequence
<220> FEATURE:
<223> OTHER INFORMATION: Candidate 9 Full length heavy chain

<400> SEQUENCE: 100
```

| | | | | | | | | | | | | | | | |
|---|---|---|---|---|---|---|---|---|---|---|---|---|---|---|---|
| Gln | Val | Glu | Leu | Gln | Gln | Ser | Gly | Pro | Gly | Leu | Val | Lys | Pro | Ser | Gln |
| 1 | | | | 5 | | | | | 10 | | | | | 15 | |
| Thr | Leu | Ser | Leu | Thr | Cys | Ala | Ile | Ser | Gly | Asp | Ser | Val | Ser | Ser | Asn |
| | | | 20 | | | | | 25 | | | | | 30 | | |
| Ser | Ala | Ala | Trp | Gly | Trp | Ile | Arg | Gln | Ser | Pro | Gly | Arg | Gly | Leu | Glu |
| | | 35 | | | | | 40 | | | | | 45 | | | |
| Trp | Leu | Gly | Ile | Ile | Gln | Ile | Arg | Ser | Lys | Trp | Tyr | Asn | Asp | Tyr | Ala |
| 50 | | | | | 55 | | | | | 60 | | | | | |
| Leu | Ser | Val | Lys | Ser | Arg | Ile | Thr | Ile | Asn | Pro | Asp | Thr | Ser | Lys | Asn |
| 65 | | | | | 70 | | | | | 75 | | | | | 80 |
| Gln | Phe | Ser | Leu | Gln | Leu | Asn | Ser | Val | Thr | Pro | Glu | Asp | Thr | Ala | Val |
| | | | | 85 | | | | | 90 | | | | | 95 | |
| Tyr | Tyr | Cys | Ala | Arg | Tyr | Ser | Tyr | Pro | Phe | Tyr | Ser | Ile | Asp | Tyr | Trp |
| | | | 100 | | | | | 105 | | | | | 110 | | |
| Gly | Gln | Gly | Thr | Leu | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Cys | Ser | Arg | Ser | Thr | Ser | Glu | Ser | Thr |
| 130 | | | | | 135 | | | | | 140 | | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Lys | Thr | Tyr | Thr | Cys | Asn | Val | Asp |
| | | 195 | | | | | 200 | | | | | 205 | | | |
| His | Lys | Pro | Ser | Asn | Thr | Lys | Val | Asp | Lys | Arg | Val | Glu | Ser | Lys | Tyr |
| 210 | | | | | 215 | | | | | 220 | | | | | |
| Gly | Pro | Pro | Cys | Pro | Pro | Cys | Pro | Ala | Pro | Glu | Phe | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | Gln | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Tyr | Arg | Val |
| 290 | | | | | 295 | | | | | 300 | | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ser | Ser | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Gln | Glu | Glu | Met | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |

```
            370                 375                 380
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 101
<211> LENGTH: 449
<212> TYPE: PRT
<213> ORGANISM: Artificial Sequence
<220> FEATURE:
<223> OTHER INFORMATION: Candidate 10,11, 12 Full length heavy chain

<400> SEQUENCE: 101

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Gly Trp Ile Arg Gln Ser Pro Gly Arg Gly Leu Glu
                35                  40                  45

Trp Leu Gly Ile Ile Gln Lys Arg Ser Lys Trp Tyr Asn Asn Tyr Ala
        50                  55                  60

Val Ser Val Lys Ser Arg Ile Thr Ile Asn Pro Asp Thr Ser Lys Asn
65              70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285
```

```
Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 102
<211> LENGTH: 448
<212> TYPE: PRT
<213> ORGANISM: Artificial Sequence
<220> FEATURE:
<223> OTHER INFORMATION: Candidate 13,14,15,15-7,15-8 Full length heavy
      chain

<400> SEQUENCE: 102

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Phe Ile Asp Pro Ser Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
```

```
                195              200              205
Lys Pro Ser Asn Thr Lys Val Asp Lys Arg Val Glu Ser Lys Tyr Gly
    210              215              220

Pro Pro Cys Pro Pro Cys Pro Ala Pro Glu Phe Leu Gly Gly Pro Ser
225             230              235              240

Val Phe Leu Phe Pro Pro Lys Pro Lys Asp Thr Leu Met Ile Ser Arg
            245              250              255

Thr Pro Glu Val Thr Cys Val Val Val Asp Val Ser Gln Glu Asp Pro
            260              265              270

Glu Val Gln Phe Asn Trp Tyr Val Asp Gly Val Glu Val His Asn Ala
        275              280              285

Lys Thr Lys Pro Arg Glu Glu Gln Phe Asn Ser Thr Tyr Arg Val Val
    290              295              300

Ser Val Leu Thr Val Leu His Gln Asp Trp Leu Asn Gly Lys Glu Tyr
305             310              315              320

Lys Cys Lys Val Ser Asn Lys Gly Leu Pro Ser Ser Ile Glu Lys Thr
            325              330              335

Ile Ser Lys Ala Lys Gly Gln Pro Arg Glu Pro Gln Val Tyr Thr Leu
            340              345              350

Pro Pro Ser Gln Glu Glu Met Thr Lys Asn Gln Val Ser Leu Thr Cys
        355              360              365

Leu Val Lys Gly Phe Tyr Pro Ser Asp Ile Ala Val Glu Trp Glu Ser
    370              375              380

Asn Gly Gln Pro Glu Asn Asn Tyr Lys Thr Thr Pro Pro Val Leu Asp
385             390              395              400

Ser Asp Gly Ser Phe Phe Leu Tyr Ser Arg Leu Thr Val Asp Lys Ser
            405              410              415

Arg Trp Gln Glu Gly Asn Val Phe Ser Cys Ser Val Met His Glu Ala
            420              425              430

Leu His Asn His Tyr Thr Gln Lys Ser Leu Ser Leu Ser Leu Gly Lys
        435              440              445

<210> SEQ ID NO 103
<211> LENGTH: 19
<212> TYPE: PRT
<213> ORGANISM: Artificial Sequence
<220> FEATURE:
<223> OTHER INFORMATION: N-terminal leader sequence for expressing heavy
      chains

<400> SEQUENCE: 103

Met Ala Trp Val Trp Thr Leu Leu Phe Leu Met Ala Ala Gln Ser
  1               5                  10                  15

Ile Gln Ala

<210> SEQ ID NO 104
<211> LENGTH: 1401
<212> TYPE: DNA
<213> ORGANISM: Artificial Sequence
<220> FEATURE:
<223> OTHER INFORMATION: Full length IgG4 Heavy chains of Candidate
      15EVQ with leader sequence

<400> SEQUENCE: 104
atggcttggg tgtggacctt gctattcctg atggcagctg cccaaagtat ccaagcagag     60
gtgcagctgg tgcagagcgg cgccgaggtg aagaagcccg gcgagagcct gaagatcagc    120
tgcaagggca gcggctacag cttcaccaac tactgggtgg gctgggtgcg ccagatgccc    180
```

```
ggcaagggcc tggagtggat gggcttcatc gaccccagcg acagctacac caactacgcg    240
cctagcttcc agggccaggt gaccatcagc gccgacaaga gcatcagcac cgcctacctg    300
cagtggagca gcctgaaggc cagcgacacc gccatgtact actgcgcccg cgagctgtac    360
cagggctaca tggacacgtt cgacagctgg ggccagggca ccctggtgac cgtgagcagc    420
gcttccacca agggcccatc cgtcttcccc ctggcgccct gctccaggag cacctccgag    480
agcacagccg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacgaaaacc    660
tacacctgca acgtagatca caagcccagc aacaccaagg tggacaagag agttgagtcc    720
aaatatggtc cccatgccca ccatgccca gcacctgagg ccgccggggg accatcagtc    780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga tgaccaag    1140 aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca agagcaggtg gcaggagggg   1320
aatgtcttct catgctccgt gatgcatgag gctctgcaca accactacac acagaagagc   1380
ctctccctgt ctctgggtaa a                                              1401

<210> SEQ ID NO 105
<211> LENGTH: 1344
<212> TYPE: DNA
<213> ORGANISM: Artificial Sequence
<220> FEATURE:
<223> OTHER INFORMATION: IgG4 Heavy chains of Candidate 15EVQ without
      leader sequence

<400> SEQUENCE: 105
gaggtgcagc tggtgcagag cggcgccgag gtgaagaagc ccggcgagag cctgaagatc     60
agctgcaagg gcagcggcta cagcttcacc aactactggg tggctgggt gcgccagatg    120 cccggcaagg gcctggagtg gatgggcttc atcgacccca gcgacagcta caccaactac    180
gcgcctagct tccagggcca ggtgaccatc agcgccgaca gagcatcag caccgcctac    240 ctgcagtgga gcagcctgaa ggccagcgac accgccatgt actactgcgc ccgcgagctg    300
taccagggct acatggacac gttcgacagc tggggccagg gcaccctggt gaccgtgagc    360
agcgcttcca ccaagggccc atccgtcttc cccctggcgc cctgctccag gagcacctcc    420
gagagcacag ccgccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacgaaa    600
acctacacct gcaacgtaga tcacaagccc agcaacacca aggtggacaa gagagttgag    660
tccaaatatg gtccccatg cccaccatgc ccagcacctg aggccgccgg gggaccatca    720
gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
```

```
gatggcgtgg aggtgcataa tgccaagaca aagccgcggg aggagcagtt caacagcacg    900
taccgtgtgg tcagcgtcct caccgtcctg caccaggact ggctgaacgg caaggagtac    960
aagtgcaagg tctccaacaa aggcctcccg tcctccatcg agaaaaccat ctccaaagcc   1020
aaagggcagc cccgagagcc acaggtgtac accctgcccc catcccagga ggagatgacc   1080
aagaaccagg tcagcctgac ctgcctggtc aaaggcttct accccagcga catcgccgtg   1140
gagtgggaga gcaatgggca gccggagaac aactacaaga ccacgcctcc cgtgctggac   1200
tccgacggct ccttcttcct ctacagcagg ctaaccgtgg acaagagcag gtggcaggag   1260
gggaatgtct tctcatgctc cgtgatgcat gaggctctgc acaaccacta cacacagaag   1320
agcctctccc tgtctctggg taaa                                          1344
```

<210> SEQ ID NO 106
<211> LENGTH: 20
<212> TYPE: PRT
<213> ORGANISM: Artificial Sequence
<220> FEATURE:
<223> OTHER INFORMATION: N-termina leader sequence for expressing light
      chains

<400> SEQUENCE: 106

Met Gly Val Pro Thr Gln Val Leu Gly Leu Leu Leu Leu Trp Leu Thr
1               5                   10                  15

Asp Ala Arg Cys
            20

<210> SEQ ID NO 107
<211> LENGTH: 702
<212> TYPE: DNA
<213> ORGANISM: Artificial Sequence
<220> FEATURE:
<223> OTHER INFORMATION: Full length light chain of Candidate 15 with
      leader sequence

<400> SEQUENCE: 107

```
atgggtgtgc caactcaggt attaggatta ctgctgctgt ggcttacaga tgcaagatgt     60
gacatccaga tgacccagag ccccagcagc ctgagcgcca gcgtgggcga ccgcgtgacc    120
atcacctgcc gcgccagcca gagcatcggc ctgtacctgg cctggtacca gcagaagccc    180
ggcaaggccc ccaagctgct gatctacgcc gccagcagcc tgcagagcgg cgtgcccagc    240
cgcttcagcg gcagcggcag cggcaccgac ttcaccctga ccatcagcag cctgcagccc    300
gaggacttcg ccacctacta ctgccagcag ggcaacaccc tgagctacac cttcggccag    360
ggcaccaagg tggagatcaa gcgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                      702
```

<210> SEQ ID NO 108
<211> LENGTH: 642
<212> TYPE: DNA
<213> ORGANISM: Artificial Sequence
<220> FEATURE:
<223> OTHER INFORMATION: Light chain of Candidate 15 without leader
      sequence (starts DIQ)

<400> SEQUENCE: 108

```
gacatccaga tgacccagag ccccagcagc ctgagcgcca gcgtgggcga ccgcgtgacc    60
atcacctgcc gcgccagcca gagcatcggc ctgtacctgg cctggtacca gcagaagccc   120
ggcaaggccc ccaagctgct gatctacgcc gccagcagcc tgcagagcgg cgtgcccagc   180
cgcttcagcg gcagcggcag cggcaccgac ttcaccctga ccatcagcag cctgcagccc   240
gaggacttcg ccacctacta ctgccagcag ggcaacaccc tgagctacac cttcggccag   300
ggcaccaagg tggagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 109
<211> LENGTH: 11
<212> TYPE: PRT
<213> ORGANISM: Artificial Sequence
<220> FEATURE:
<223> OTHER INFORMATION: Candidates 15, 15-1, 15-2, 15-3, 15-4, 15-5,
      15-6, 15-9 LCDR1 composite sequence

<400> SEQUENCE: 109

```
Arg Ala Ser Gln Ser Ile Gly Leu Tyr Leu Ala
  1               5                  10
```

<210> SEQ ID NO 110
<211> LENGTH: 7
<212> TYPE: PRT
<213> ORGANISM: Artificial Sequence
<220> FEATURE:
<223> OTHER INFORMATION: Candidates 15, 15-1, 15-9 LCDR2

<400> SEQUENCE: 110

```
Ala Ala Ser Ser Leu Gln Ser
  1               5
```

<210> SEQ ID NO 111
<211> LENGTH: 10
<212> TYPE: PRT
<213> ORGANISM: Artificial Sequence
<220> FEATURE:
<223> OTHER INFORMATION: Candidates 15, 15-1, 15-4, 15-7, 15-8 HCDR1
      composite sequence

<400> SEQUENCE: 111

```
Gly Tyr Ser Phe Thr Asn Tyr Trp Val Gly
  1               5                  10
```

<210> SEQ ID NO 112
<211> LENGTH: 17
<212> TYPE: PRT
<213> ORGANISM: Artificial Sequence
<220> FEATURE:
<223> OTHER INFORMATION: Candidates 15, 15-2, 15-3, 15-6, 15-7, 15-8
      HCDR2 composite sequence

<400> SEQUENCE: 112

```
Phe Ile Asp Pro Ser Asp Ser Tyr Thr Asn Tyr Ala Pro Ser Phe Gln
  1               5                  10                  15

Gly
```

```
<210> SEQ ID NO 113
<211> LENGTH: 9
<212> TYPE: PRT
<213> ORGANISM: Artificial Sequence
<220> FEATURE:
<223> OTHER INFORMATION: Candidates 15, 15-1, 15-9 LCDR3 conmposite
      sequence

<400> SEQUENCE: 113

Gln Gln Gly Asn Thr Leu Ser Tyr Thr
1               5

<210> SEQ ID NO 114
<211> LENGTH: 17
<212> TYPE: PRT
<213> ORGANISM: Artificial Sequence
<220> FEATURE:
<223> OTHER INFORMATION: Candidates 15-1 HCDR2

<400> SEQUENCE: 114

Arg Ile Asp Pro Ser Asp Ser Tyr Thr Asn Tyr Ala Pro Ser Phe Gln
1               5                   10                  15

Gly

<210> SEQ ID NO 115
<211> LENGTH: 10
<212> TYPE: PRT
<213> ORGANISM: Artificial Sequence
<220> FEATURE:
<223> OTHER INFORMATION: Candidates 15-2 HCDR1

<400> SEQUENCE: 115

Gly Tyr Ser Phe Thr Asn Tyr Trp Ile Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Candidates 15-3, 15-5, 15-6, 15-9 HCDR1

<400> SEQUENCE: 116

Gly Tyr Ser Phe Thr Asn Tyr Trp Ile Ser
1               5                   10

<210> SEQ ID NO 117
<211> LENGTH: 17
<212> TYPE: PRT
<213> ORGANISM: Artificial Sequence
<220> FEATURE:
<223> OTHER INFORMATION: Candidates 15-4 HCDR2

<400> SEQUENCE: 117

Phe Ile Asp Pro Ser Asp Ser Tyr Thr Asn Tyr Ser Pro Ser Phe Gln
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Candidates 15-5, 15-9 HCDR2

<400> SEQUENCE: 118
```

Arg Ile Asp Pro Ser Asp Ser Tyr Thr Asn Tyr Ser Pro Ser Phe Gln
1               5                   10                  15

Gly

<210> SEQ ID NO 119
<211> LENGTH: 14
<212> TYPE: PRT
<213> ORGANISM: Artificial Sequence
<220> FEATURE:
<223> OTHER INFORMATION: Candidates 15-6, 15-9 HCDR3

<400> SEQUENCE: 119

Ala Arg Gln Leu Tyr Gln Gly Tyr Met Asp Thr Phe Asp Ser
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Candidates 15-7 LCDR1

<400> SEQUENCE: 120

Arg Ala Ser Gln Ser Ile Ser Ser Tyr Leu Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Candidates 15-8 LCDR1

<400> SEQUENCE: 121

Arg Ala Ser Gln Ser Ile Gly Leu Tyr Leu Asn
1               5                   10

<210> SEQ ID NO 122
<211> LENGTH: 107
<212> TYPE: PRT
<213> ORGANISM: Artificial Sequence
<220> FEATURE:
<223> OTHER INFORMATION: Candidates 15-7 VL

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Ser Tyr
                85                  90                  95

Thr Phe Gly Gln Gly Thr Lys Val Glu Ile Lys
            100                 105

<210> SEQ ID NO 123
<211> LENGTH: 107
<212> TYPE: PRT

```
<213> ORGANISM: Artificial Sequence
<220> FEATURE:
<223> OTHER INFORMATION: Candidates 15-8 VL

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Ser Tyr
                85                  90                  95

Thr Phe Gly Gln Gly Thr Lys Val Glu Ile Lys
            100                 105

<210> SEQ ID NO 124
<211> LENGTH: 121
<212> TYPE: PRT
<213> ORGANISM: Artificial Sequence
<220> FEATURE:
<223> OTHER INFORMATION: Candidates 15-1 VH

<400> SEQUENCE: 124

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Arg Ile Asp Pro Ser Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
            115                 120

<210> SEQ ID NO 125
<211> LENGTH: 121
<212> TYPE: PRT
<213> ORGANISM: Artificial Sequence
<220> FEATURE:
<223> OTHER INFORMATION: Candidate 15-2 VH

<400> SEQUENCE: 125

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45
```

```
Gly Phe Ile Asp Pro Ser Asp Ser Tyr Thr Asn Tyr Ala Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
                100                 105                 110

Gln Gly Thr Leu Val Thr Val Ser Ser
            115                 120

<210> SEQ ID NO 126
<211> LENGTH: 121
<212> TYPE: PRT
<213> ORGANISM: Artificial Sequence
<220> FEATURE:
<223> OTHER INFORMATION: Candidate 15-3 VH

<400> SEQUENCE: 126

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                 20                  25                  30

Trp Ile Ser Trp Val Arg Gln Met Pro Gly Lys Gly Leu Glu Trp Met
             35                  40                  45

Gly Phe Ile Asp Pro Ser Asp Ser Tyr Thr Asn Tyr Ala Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
                100                 105                 110

Gln Gly Thr Leu Val Thr Val Ser Ser
            115                 120

<210> SEQ ID NO 127
<211> LENGTH: 121
<212> TYPE: PRT
<213> ORGANISM: Artificial Sequence
<220> FEATURE:
<223> OTHER INFORMATION: Candidate 15-4 VH

<400> SEQUENCE: 127

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                 20                  25                  30

Trp Val Gly Trp Val Arg Gln Met Pro Gly Lys Gly Leu Glu Trp Met
             35                  40                  45

Gly Phe Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
                100                 105                 110
```

```
Gln Gly Thr Leu Val Thr Val Ser Ser
        115                 120

<210> SEQ ID NO 128
<211> LENGTH: 121
<212> TYPE: PRT
<213> ORGANISM: Artificial Sequence
<220> FEATURE:
<223> OTHER INFORMATION: Candidate 15-5 VH

<400> SEQUENCE: 128

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
                 20                  25                  30

Trp Ile Ser Trp Val Arg Gln Met Pro Gly Lys Gly Leu Glu Trp Met
             35                  40                  45

Gly Arg Ile Asp Pro Ser Asp Ser Tyr Thr Asn Tyr Ser Pro Ser Phe
         50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
        115                 120

<210> SEQ ID NO 129
<211> LENGTH: 121
<212> TYPE: PRT
<213> ORGANISM: Artificial Sequence
<220> FEATURE:
<223> OTHER INFORMATION: Candidate 15-6 VH

<400> SEQUENCE: 129

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
                 20                  25                  30

Trp Ile Ser Trp Val Arg Gln Met Pro Gly Lys Gly Leu Glu Trp Met
             35                  40                  45

Gly Phe Ile Asp Pro Ser Asp Ser Tyr Thr Asn Tyr Ala Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Leu Tyr Gln Gly Tyr Met Asp Thr Phe Asp Ser Trp Gly
            100                 105                 110

Gln Gly Thr Leu Val Thr Val Ser Ser
        115                 120

<210> SEQ ID NO 130
<211> LENGTH: 448
<212> TYPE: PRT
<213> ORGANISM: Artificial Sequence
<220> FEATURE:
<223> OTHER INFORMATION: Candidate 15-1 full length heavy chain

<400> SEQUENCE: 130
```

-continued

```
Glu Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Thr Asn Tyr
             20                  25                  30
Trp Val Gly Trp Val Arg Gln Met Pro Gly Lys Gly Leu Glu Trp Met
         35                  40                  45
Gly Arg Ile Asp Pro Ser Asp Ser Tyr Thr Asn Tyr Ala Pro Ser Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Glu Leu Tyr Gln Gly Tyr Met Asp Thr Phe Asp Ser Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
```

```
                            420                 425                 430
Leu His Asn His Tyr Thr Gln Lys Ser Leu Ser Leu Ser Leu Gly Lys
                435                 440                 445

<210> SEQ ID NO 131
<211> LENGTH: 448
<212> TYPE: PRT
<213> ORGANISM: Artificial Sequence
<220> FEATURE:
<223> OTHER INFORMATION: Candidate 15-2 full length heavy chain

<400> SEQUENCE: 131

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
             20                  25                  30

Trp Ile Gly Trp Val Arg Gln Met Pro Gly Lys Gly Leu Glu Trp Met
         35                  40                  45

Gly Phe Ile Asp Pro Ser Asp Ser Tyr Thr Asn Tyr Ala Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 132
<211> LENGTH: 448
<212> TYPE: PRT
<213> ORGANISM: Artificial Sequence
<220> FEATURE:
<223> OTHER INFORMATION: Candidate 15-3 full length heavy chain

<400> SEQUENCE: 132

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Phe Ile Asp Pro Ser Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 133
<211> LENGTH: 448
<212> TYPE: PRT
<213> ORGANISM: Artificial Sequence
<220> FEATURE:
<223> OTHER INFORMATION: Candidate 15-4 full length heavy chain

<400> SEQUENCE: 133

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
             20                  25                  30

Trp Val Gly Trp Val Arg Gln Met Pro Gly Lys Gly Leu Glu Trp Met
         35                  40                  45

Gly Phe Ile Asp Pro Ser Asp Ser Tyr Thr Asn Tyr Ser Pro Ser Phe
     50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His

```
                195                 200                 205
Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 134
<211> LENGTH: 448
<212> TYPE: PRT
<213> ORGANISM: Artificial Sequence
<220> FEATURE:
<223> OTHER INFORMATION: Candidate 15-5 full length heavy chain

<400> SEQUENCE: 134

Glu Val Gln Leu Val Gln Ser Gly Ala Glu Val Lys Lys Pro Gly Glu
  1               5                   10                  15

Ser Leu Lys Ile Ser Cys Lys Gly Ser Gly Tyr Ser Phe Thr Asn Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125
```

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 135
<211> LENGTH: 448
<212> TYPE: PRT
<213> ORGANISM: Artificial Sequence
<220> FEATURE:
<223> OTHER INFORMATION: Candidate 15-6 full length heavy chain

<400> SEQUENCE: 135

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                20                  25                  30

Trp Ile Ser Trp Val Arg Gln Met Pro Gly Lys Gly Leu Glu Trp Met
            35                  40                  45

```
Gly Phe Ile Asp Pro Ser Asp Ser Tyr Thr Asn Tyr Ala Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 136
<211> LENGTH: 40
<212> TYPE: DNA
<213> ORGANISM: Artificial Sequence
```

```
<220> FEATURE:
<223> OTHER INFORMATION: Primer

<400> SEQUENCE: 136
ccttacccat aatcaactcg agagattacc agccgccaac                    40

<210> SEQ ID NO 137
<211> LENGTH: 49
<212> TYPE: DNA
<213> ORGANISM: Artificial Sequence
<220> FEATURE:
<223> OTHER INFORMATION: Primer

<400> SEQUENCE: 137
caagagcttc tattatcaaa caatgagatt caagcgctaa aaagtgaag          49

<210> SEQ ID NO 138
<211> LENGTH: 45
<212> TYPE: DNA
<213> ORGANISM: Artificial Sequence
<220> FEATURE:
<223> OTHER INFORMATION: Primer

<400> SEQUENCE: 138
ccttacacat actcaaccta accgagaata aaatctcaaa aatag              45

<210> SEQ ID NO 139
<211> LENGTH: 47
<212> TYPE: DNA
<213> ORGANISM: Artificial Sequence
<220> FEATURE:
<223> OTHER INFORMATION: Primer

<400> SEQUENCE: 139
gaaatctatc tttcctacaa cgaggccctg cagctgacta ggaactc            47

<210> SEQ ID NO 140
<211> LENGTH: 58
<212> TYPE: DNA
<213> ORGANISM: Artificial Sequence
<220> FEATURE:
<223> OTHER INFORMATION: Primer

<400> SEQUENCE: 140
gccttcaacg actgatgctc gaggaggtgg cccttgagaa tgtggatagc tctccttc    58

<210> SEQ ID NO 141
<211> LENGTH: 39
<212> TYPE: DNA
<213> ORGANISM: Artificial Sequence
<220> FEATURE:
<223> OTHER INFORMATION: Primer

<400> SEQUENCE: 141
gtacctgcag ctgtctacga gctcctttgc cttggtccc                     39

<210> SEQ ID NO 142
<211> LENGTH: 33
<212> TYPE: DNA
<213> ORGANISM: Artificial Sequence
<220> FEATURE:
<223> OTHER INFORMATION: Primer

<400> SEQUENCE: 142
gcctggagtg gatgggccgg atcgacccca gcg                           33
```

```
<210> SEQ ID NO 143
<211> LENGTH: 33
<212> TYPE: DNA
<213> ORGANISM: Artificial Sequence
<220> FEATURE:
<223> OTHER INFORMATION: Primer

<400> SEQUENCE: 143
cgctggggtc gatccggccc atccactcca ggc                          33

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
agaggtaact cccgttgcgg                                         20

<210> SEQ ID NO 145
<211> LENGTH: 38
<212> TYPE: DNA
<213> ORGANISM: Artificial Sequence
<220> FEATURE:
<223> OTHER INFORMATION: Primer

<400> SEQUENCE: 145
gcatctggcg cacccagccg atccagtagt tggtgaag                     38

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
agaggtaact cccgttgcgg                                         20

<210> SEQ ID NO 147
<211> LENGTH: 38
<212> TYPE: DNA
<213> ORGANISM: Artificial Sequence
<220> FEATURE:
<223> OTHER INFORMATION: Primer

<400> SEQUENCE: 147
gcatctggcg cacccagctg atccagtagt tggtgaag                     38

<210> SEQ ID NO 148
<211> LENGTH: 47
<212> TYPE: DNA
<213> ORGANISM: Artificial Sequence
<220> FEATURE:
<223> OTHER INFORMATION: Primer

<400> SEQUENCE: 148
cgctgatggt cacgtggccc tggaagctag ggctgtagtt ggtgtag            47

<210> SEQ ID NO 149
<211> LENGTH: 38
<212> TYPE: DNA
<213> ORGANISM: Artificial Sequence
<220> FEATURE:
<223> OTHER INFORMATION: Primer

<400> SEQUENCE: 149
```
cttcaccaac tactggatca gctgggtgcg ccagatgc                              38

<210> SEQ ID NO 150
<211> LENGTH: 40
<212> TYPE: DNA
<213> ORGANISM: Artificial Sequence
<220> FEATURE:
<223> OTHER INFORMATION: Primer

<400> SEQUENCE: 150
cgccatgtac tactgcgccc gccagctgta ccagggctac                            40

<210> SEQ ID NO 151
<211> LENGTH: 40
<212> TYPE: DNA
<213> ORGANISM: Artificial Sequence
<220> FEATURE:
<223> OTHER INFORMATION: Primer

<400> SEQUENCE: 151
gtagccctgg tacagctggc gggcgcagta gtacatggcg                            40

<210> SEQ ID NO 152
<211> LENGTH: 40
<212> TYPE: DNA
<213> ORGANISM: Homo sapiens

<400> SEQUENCE: 152
gccagccaga gcatcagcag ctacctggcc tggtaccagc                            40

<210> SEQ ID NO 153
<211> LENGTH: 40
<212> TYPE: DNA
<213> ORGANISM: Artificial Sequence
<220> FEATURE:
<223> OTHER INFORMATION: Primer

<400> SEQUENCE: 153
gctggtacca ggccaggtag ctgctgatgc tctggctggc                            40

<210> SEQ ID NO 154
<211> LENGTH: 43
<212> TYPE: DNA
<213> ORGANISM: Artificial Sequence
<220> FEATURE:
<223> OTHER INFORMATION: Primer

<400> SEQUENCE: 154
cgggcttctg ctggtaccag ttcaggtagc tgctgatgct ctg                        43

<210> SEQ ID NO 155
<211> LENGTH: 214
<212> TYPE: PRT
<213> ORGANISM: Artificial Sequence
<220> FEATURE:
<223> OTHER INFORMATION: Candidate 14 full length light chain

<400> SEQUENCE: 155

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Glu Thr Val Ser Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 156
<211> LENGTH: 214
<212> TYPE: PRT
<213> ORGANISM: Artificial Sequence
<220> FEATURE:
<223> OTHER INFORMATION: Candidate 15, 15-1, 15-2, 15-3, 15-4, 15-5,
      15-6, 15-9 full length light chain

<400> SEQUENCE: 156

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Leu Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Ser Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 157
<211> LENGTH: 214
<212> TYPE: PRT
<213> ORGANISM: Artificial Sequence
<220> FEATURE:
<223> OTHER INFORMATION: Candidate 15-7 full length light cahin

<400> SEQUENCE: 157

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Ser Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 158
<211> LENGTH: 214
<212> TYPE: PRT
<213> ORGANISM: Artificial Sequence
<220> FEATURE:
<223> OTHER INFORMATION: Candidate 15-8 full length light chain

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Ser Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 159
<211> LENGTH: 121
<212> TYPE: PRT
<213> ORGANISM: Artificial Sequence
<220> FEATURE:
<223> OTHER INFORMATION: Candidate 15-9 VH

<400> SEQUENCE: 159

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
             20                  25                  30

Trp Ile Ser Trp Val Arg Gln Met Pro Gly Lys Gly Leu Glu Trp Met
         35                  40                  45

Gly Arg Ile Asp Pro Ser Asp Ser Tyr Thr Asn Tyr Ser Pro Ser Phe
     50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Leu Tyr Gln Gly Tyr Met Asp Thr Phe Asp Ser Trp Gly
            100                 105                 110

Gln Gly Thr Leu Val Thr Val Ser Ser
        115                 120
```

<210> SEQ ID NO 160
<211> LENGTH: 448
<212> TYPE: PRT
<213> ORGANISM: Artificial Sequence
<220> FEATURE:
<223> OTHER INFORMATION: Candidate 15-9 full length heavy chain

<400> SEQUENCE: 160

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
             20                  25                  30
```

```
Trp Ile Ser Trp Val Arg Gln Met Pro Gly Lys Gly Leu Glu Trp Met
         35                  40                  45

Gly Arg Ile Asp Pro Ser Asp Ser Tyr Thr Asn Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 161
```

<211> LENGTH: 2718
<212> TYPE: DNA
<213> ORGANISM: Mus musculus

<400> SEQUENCE: 161

```
atgaaagggt gttcctctta tctaatgtac tcctttgggg gacttttgtc cctatggatt      60
cttctggtgt cttccacaaa ccaatgcact gtgagataca acgtagctga ctgcagccat     120
ttgaagctaa cacacatacc tgatgatctt ccctctaaca taacagtgtt gaatcttact     180
cacaaccaac tcagaagatt accacctacc aactttacaa gatacagcca acttgctatc     240
ttggatgcag gatttaactc catttcaaaa ctggagccag aactgtgcca atactccct      300
ttgttgaaag tattgaacct gcaacataat gagctctctc agatttctga tcaaaccttt     360
gtcttctgca cgaacctgac agaactcgat ctaatgtcta actcaataca caaaattaaa     420
agcaacccct tcaaaaacca gaagaatcta atcaaattag atttgtctca taatggttta     480
tcatctacaa agttgggaac gggggtccaa ctggagaacc tccaagaact gctcttagca     540
aaaaataaaa tccttgcgtt gcgaagtgaa gaacttgagt ttcttggcaa ttcttcttta     600
cgaaagttgg acttgtcatc aaatccactt aaagagttct ccccgggggtg tttccagaca    660
attggcaagt tattcgccct cctcttgaac aacgcccaac tgaaccccca cctcacagag     720
aagctttgct gggaactttc aaacacaagc atccagaatc tctctctggc taacaaccag     780
ctgctggcca ccagcgagag cactttctct gggctgaagt ggacaaatct cacccagctc     840
gatctttcct acaacaacct ccatgatgtc ggcaacggtt ccttctccta tctcccaagc     900
ctgaggtatc tgtctctgga gtacaacaat atacagcgtc tgtcccctcg ctctttttat     960
ggactctcca acctgaggta cctgagtttg aagcgagcat ttactaagca aagtgtttca   1020
cttgcttcac atcccaacat tgacgatttt tcctttcaat ggttaaaata tttggaatat   1080
ctcaacatgg atgacaataa tattccaagt accaaaagca ataccttcac gggattggtg   1140
agtctgaagt acctaagtct ttccaaaact ttcacaagtt tgcaaacttt aacaaatgaa   1200
acatttgtgt cacttgctca ttctcccttg ctcactctca acttaacgaa aaatcacatc   1260
tcaaaaatag caaatggtac tttctcttgg ttaggccaac tcaggatact tgatctcggc   1320
cttaatgaaa ttgaacaaaa actcagcggc caggaatgga gaggtctgag aaatatattt   1380
gagatctacc tatcctataa caaataccctc caactgtcta ccagttcctt tgcattggtc   1440
cccagccttt caaagactgat gctcaggagg gtggccctta aaaatgtgga tatctcccct   1500
tcaccttttcc gccctcttcg taacttgacc attctggact taagcaacaa caacatagcc   1560
aacataaatg aggacttgct ggagggtctt gagaatctag aaatcctgga ttttcagcac   1620
aataacttag ccaggctctg gaaacgcgca accccggtg gtcccgttaa tttcctgaag     1680
gggctgtctc acctccacat cttgaattta gagtccaacg gcttagatga atcccagtc     1740
ggggttttca gaacttatt cgaactaaag agcatcaatc taggactgaa taacttaaac   1800
aaacttgaac cattcatttt tgatgaccag acatctctaa ggtcactgaa cctccagaag   1860
aacctcataa catctgttga aaggatgtt ttcgggccgc cttttcaaaa cctgaacagt     1920
ttagatatgc gcttcaatcc gttcgactgc acgtgtgaaa gtatttcctg gtttgttaac   1980
tggatcaacc agaccacac taatatctct gagctgtcca ctcactacct ctgtaacact   2040
ccacatcatt attatggctt ccccctgaag cttttcgata catcatcctg taaagacagc   2100
gcccccttttg aactcctctt cataatcagc accagtatgc tcctggtttt tatacttgtg   2160
gtactgctca ttcacatcga gggctggagg atctcttttt actggaatgt ttcagtgcat   2220
```

-continued

```
cggattcttg gtttcaagga aatagacaca caggctgagc agtttgaata tacagcctac    2280
ataattcatg cccataaaga cagagactgg gtctgggaac atttctcccc aatggaagaa    2340
caagaccaat ctctcaaatt ttgcctagaa gaaagggact ttgaagcagg cgtccttgga    2400
cttgaagcaa ttgttaatag catcaaaaga agccgaaaaa tcattttcgt tatcacacac    2460
catttattaa aagaccctct gtgcagaaga ttcaaggtac atcacgcagt tcagcaagct    2520
attgagcaaa atctggattc aattatactg attttctcc agaatattcc agattataaa     2580
ctaaaccatg cactctgttt gcgaagagga atgtttaaat ctcattgcat cttgaactgg    2640
ccagttcaga aagaacggat aaatgccttt catcataaat tgcaagtagc acttggatct    2700
cggaattcag cacattaa                                                  2718
```

<210> SEQ ID NO 162
<211> LENGTH: 905
<212> TYPE: PRT
<213> ORGANISM: Mus musculus

<400> SEQUENCE: 162

```
Met Lys Gly Cys Ser Ser Tyr Leu Met Tyr Ser Phe Gly Gly Leu Leu
 1               5                  10                  15

Ser Leu Trp Ile Leu Val Ser Ser Thr Asn Gln Cys Thr Val Arg
             20                  25                  30

Tyr Asn Val Ala Asp Cys Ser His Leu Lys Leu Thr His Ile Pro Asp
         35                  40                  45

Asp Leu Pro Ser Asn Ile Thr Val Leu Asn Leu Thr His Asn Gln Leu
     50                  55                  60

Arg Arg Leu Pro Pro Thr Asn Phe Thr Arg Tyr Ser Gln Leu Ala Ile
 65                  70                  75                  80

Leu Asp Ala Gly Phe Asn Ser Ile Ser Lys Leu Glu Pro Glu Leu Cys
                 85                  90                  95

Gln Ile Leu Pro Leu Leu Lys Val Leu Asn Leu Gln His Asn Glu Leu
            100                 105                 110

Ser Gln Ile Ser Asp Gln Thr Phe Val Phe Cys Thr Asn Leu Thr Glu
        115                 120                 125

Leu Asp Leu Met Ser Asn Ser Ile His Lys Ile Lys Ser Asn Pro Phe
    130                 135                 140

Lys Asn Gln Lys Asn Leu Ile Lys Leu Asp Leu Ser His Asn Gly Leu
145                 150                 155                 160

Ser Ser Thr Lys Leu Gly Thr Gly Val Gln Leu Glu Asn Leu Gln Glu
                165                 170                 175

Leu Leu Leu Ala Lys Asn Lys Ile Leu Ala Leu Arg Ser Glu Glu Leu
            180                 185                 190

Glu Phe Leu Gly Asn Ser Ser Leu Arg Lys Leu Asp Leu Ser Ser Asn
        195                 200                 205

Pro Leu Lys Glu Phe Ser Pro Gly Cys Phe Gln Thr Ile Gly Lys Leu
    210                 215                 220

Phe Ala Leu Leu Leu Asn Asn Ala Gln Leu Asn Pro His Leu Thr Glu
225                 230                 235                 240

Lys Leu Cys Trp Glu Leu Ser Asn Thr Ser Ile Gln Asn Leu Ser Leu
                245                 250                 255

Ala Asn Asn Gln Leu Leu Ala Thr Ser Glu Ser Thr Phe Ser Gly Leu
            260                 265                 270

Lys Trp Thr Asn Leu Thr Gln Leu Asp Leu Ser Tyr Asn Asn Leu His
        275                 280                 285
```

-continued

Asp Val Gly Asn Gly Ser Phe Ser Tyr Leu Pro Ser Leu Arg Tyr Leu
        290                 295                 300

Ser Leu Glu Tyr Asn Asn Ile Gln Arg Leu Ser Pro Arg Ser Phe Tyr
305                 310                 315                 320

Gly Leu Ser Asn Leu Arg Tyr Leu Ser Leu Lys Arg Ala Phe Thr Lys
                325                 330                 335

Gln Ser Val Ser Leu Ala Ser His Pro Asn Ile Asp Asp Phe Ser Phe
        340                 345                 350

Gln Trp Leu Lys Tyr Leu Glu Tyr Leu Asn Met Asp Asp Asn Asn Ile
                355                 360                 365

Pro Ser Thr Lys Ser Asn Thr Phe Thr Gly Leu Val Ser Leu Lys Tyr
        370                 375                 380

Leu Ser Leu Ser Lys Thr Phe Thr Ser Leu Gln Thr Leu Thr Asn Glu
385                 390                 395                 400

Thr Phe Val Ser Leu Ala His Ser Pro Leu Leu Thr Leu Asn Leu Thr
                405                 410                 415

Lys Asn His Ile Ser Lys Ile Ala Asn Gly Thr Phe Ser Trp Leu Gly
                420                 425                 430

Gln Leu Arg Ile Leu Asp Leu Gly Leu Asn Glu Ile Glu Gln Lys Leu
        435                 440                 445

Ser Gly Gln Glu Trp Arg Gly Leu Arg Asn Ile Phe Glu Ile Tyr Leu
450                 455                 460

Ser Tyr Asn Lys Tyr Leu Gln Leu Ser Thr Ser Ser Phe Ala Leu Val
465                 470                 475                 480

Pro Ser Leu Gln Arg Leu Met Leu Arg Arg Val Ala Leu Lys Asn Val
                485                 490                 495

Asp Ile Ser Pro Ser Pro Phe Arg Pro Leu Arg Asn Leu Thr Ile Leu
                500                 505                 510

Asp Leu Ser Asn Asn Asn Ile Ala Asn Ile Asn Glu Asp Leu Leu Glu
        515                 520                 525

Gly Leu Glu Asn Leu Glu Ile Leu Asp Phe Gln His Asn Asn Leu Ala
        530                 535                 540

Arg Leu Trp Lys Arg Ala Asn Pro Gly Gly Pro Val Asn Phe Leu Lys
545                 550                 555                 560

Gly Leu Ser His Leu His Ile Leu Asn Leu Glu Ser Asn Gly Leu Asp
                565                 570                 575

Glu Ile Pro Val Gly Val Phe Lys Asn Leu Phe Glu Leu Lys Ser Ile
                580                 585                 590

Asn Leu Gly Leu Asn Asn Leu Asn Lys Leu Glu Pro Phe Ile Phe Asp
        595                 600                 605

Asp Gln Thr Ser Leu Arg Ser Leu Asn Leu Gln Lys Asn Leu Ile Thr
        610                 615                 620

Ser Val Glu Lys Asp Val Phe Gly Pro Pro Phe Gln Asn Leu Asn Ser
625                 630                 635                 640

Leu Asp Met Arg Phe Asn Pro Phe Asp Cys Thr Cys Glu Ser Ile Ser
                645                 650                 655

Trp Phe Val Asn Trp Ile Asn Gln Thr His Thr Asn Ile Ser Glu Leu
                660                 665                 670

Ser Thr His Tyr Leu Cys Asn Thr Pro His His Tyr Tyr Gly Phe Pro
        675                 680                 685

Leu Lys Leu Phe Asp Thr Ser Ser Cys Lys Asp Ser Ala Pro Phe Glu
        690                 695                 700

Leu Leu Phe Ile Ile Ser Thr Ser Met Leu Leu Val Phe Ile Leu Val
705                 710                 715                 720

```
Val Leu Leu Ile His Ile Glu Gly Trp Arg Ile Ser Phe Tyr Trp Asn
                725                 730                 735

Val Ser Val His Arg Ile Leu Gly Phe Lys Glu Ile Asp Thr Gln Ala
            740                 745                 750

Glu Gln Phe Glu Tyr Thr Ala Tyr Ile Ile His Ala His Lys Asp Arg
            755                 760                 765

Asp Trp Val Trp Glu His Phe Ser Pro Met Glu Gln Asp Gln Ser
    770                 775                 780

Leu Lys Phe Cys Leu Glu Glu Arg Asp Phe Glu Ala Gly Val Leu Gly
785                 790                 795                 800

Leu Glu Ala Ile Val Asn Ser Ile Lys Arg Ser Lys Ile Ile Phe
                805                 810                 815

Val Ile Thr His His Leu Leu Lys Asp Pro Leu Cys Arg Arg Phe Lys
                820                 825                 830

Val His His Ala Val Gln Gln Ala Ile Glu Gln Asn Leu Asp Ser Ile
            835                 840                 845

Ile Leu Ile Phe Leu Gln Asn Ile Pro Asp Tyr Lys Leu Asn His Ala
850                 855                 860

Leu Cys Leu Arg Arg Gly Met Phe Lys Ser His Cys Ile Leu Asn Trp
865                 870                 875                 880

Pro Val Gln Lys Glu Arg Ile Asn Ala Phe His His Lys Leu Gln Val
                885                 890                 895

Ala Leu Gly Ser Arg Asn Ser Ala His
                900                 905

<210> SEQ ID NO 163
<211> LENGTH: 107
<212> TYPE: PRT
<213> ORGANISM: Rattus rattus

<400> SEQUENCE: 163

Asp Ile Gln Met Thr Gln Ser Pro Thr Ser Leu Ser Ala Ser Leu Gly
1               5                   10                  15

Glu Thr Val Thr Ile Glu Cys Arg Ala Ser Glu Asp Ile Tyr Asn Gly
                20                  25                  30

Leu Ala Trp Tyr Gln Gln Lys Pro Gly Lys Ser Pro Gln Leu Leu Ile
            35                  40                  45

Tyr Asp Ser Asn Ser Leu His Thr Gly Val Pro Ser Arg Phe Ser Gly
        50                  55                  60

Arg Gly Ser Gly Thr Gln Tyr Ser Leu Arg Ile Asn Ser Leu Gln Ser
65                  70                  75                  80

Glu Asp Val Ala Ser Tyr Phe Cys Gln Gln Tyr Tyr Asp Tyr Pro Leu
                85                  90                  95

Thr Phe Gly Ser Gly Thr Lys Leu Glu Ile Lys
            100                 105

<210> SEQ ID NO 164
<211> LENGTH: 119
<212> TYPE: PRT
<213> ORGANISM: Rattus rattus

<400> SEQUENCE: 164

Glu Val Gln Leu Val Ala Ser Gly Gly Gly Leu Val Lys Pro Gly Ala
1               5                   10                  15

Ser Leu Lys Leu Ser Cys Val Ala Ser Gly Phe Thr Phe Ser Asp Tyr
                20                  25                  30
```

```
Trp Met Ala Trp Val Arg Gln Thr Pro Gly Lys Pro Met Glu Tyr Ile
             35                  40                  45

Gly Asp Ile Lys Ser Asp Gly Ser Lys Val Asn Tyr Ala Pro Ser Leu
 50                  55                  60

Lys Asn Arg Phe Thr Ile Ser Arg Asp Asn Ala Arg Thr Thr Leu Tyr
 65                  70                  75                  80

Leu Gln Met Ser Asn Val Arg Ser Glu Asp Thr Ala Thr Tyr Tyr Cys
             85                  90                  95

Asn Arg Asp Ile Gly Pro Asp Trp Tyr Phe Asp Phe Trp Gly Pro Gly
            100                 105                 110

Thr Met Val Thr Val Ser Ser
        115

<210> SEQ ID NO 165
<211> LENGTH: 234
<212> TYPE: PRT
<213> ORGANISM: Artificial Sequence
<220> FEATURE:
<223> OTHER INFORMATION: Hybrid of rat variable region and mouse
      constant region

<400> SEQUENCE: 165

Met Gly Val Pro Thr Gln Leu Leu Gly Leu Leu Leu Leu Trp Ile Thr
 1               5                  10                  15

Asp Ala Ile Cys Asp Ile Gln Met Thr Gln Ser Pro Thr Ser Leu Ser
             20                  25                  30

Ala Ser Leu Gly Glu Thr Val Thr Ile Glu Cys Arg Ala Ser Glu Asp
         35                  40                  45

Ile Tyr Asn Gly Leu Ala Trp Tyr Gln Gln Lys Pro Gly Lys Ser Pro
 50                  55                  60

Gln Leu Leu Ile Tyr Asp Ser Asn Ser Leu His Thr Gly Val Pro Ser
 65                  70                  75                  80

Arg Phe Ser Gly Arg Gly Ser Gly Thr Gln Tyr Ser Leu Arg Ile Asn
             85                  90                  95

Ser Leu Gln Ser Glu Asp Val Ala Ser Tyr Phe Cys Gln Gln Tyr Tyr
            100                 105                 110

Asp Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 166
<211> LENGTH: 462
<212> TYPE: PRT
<213> ORGANISM: Artificial Sequence
<220> FEATURE:
```

-continued

<223> OTHER INFORMATION: Hybrid of rat variable region and mouse constant region

<400> SEQUENCE: 166

```
Met Lys Leu Arg Leu Ser Leu Ile Phe Ile Cys Ala Leu Leu Lys Asp
  1               5                  10                  15

Val Gln Cys Glu Val Gln Leu Val Ala Ser Gly Gly Leu Val Lys
             20                  25                  30

Pro Gly Ala Ser Leu Lys Leu Ser Cys Val Ala Ser Gly Phe Thr Phe
             35                  40                  45

Ser Asp Tyr Trp Met Ala Trp Val Arg Gln Thr Pro Gly Lys Pro Met
 50                  55                  60

Glu Tyr Ile Gly Asp Ile Lys Ser Asp Gly Ser Lys Val Asn Tyr Ala
 65                  70                  75                  80

Pro Ser Leu Lys Asn Arg Phe Thr Ile Ser Arg Asp Asn Ala Arg Thr
                 85                  90                  95

Thr Leu Tyr Leu Gln Met Ser Asn Val Arg Ser Glu Thr Ala Thr
                100                 105                 110

Tyr Tyr Cys Asn Arg Asp Ile Gly Pro Asp Trp Tyr Phe Asp Phe Trp
                115                 120                 125

Gly Pro Gly Thr Met Val Thr Val Ser Ser Ala Lys Thr Thr Pro Pro
            130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
                180                 185                 190

Ala Val Leu Glu Ser Asp Leu Tyr Thr Leu Ser Ser Ser Val Thr Val
            195                 200                 205

Pro Ser Ser Pro Arg Pro Ser Glu Thr Val Thr Cys Asn Val Ala His
        210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
        290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400
```

-continued

```
Gln Pro Ala Glu Asn Tyr Lys Asn Thr Gln Pro Ile Met Asn Thr Asn
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 167
<211> LENGTH: 234
<212> TYPE: PRT
<213> ORGANISM: Rattus rattus

<400> SEQUENCE: 167

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Thr Ser Leu Ser
            20                  25                  30

Ala Ser Leu Gly Glu Thr Val Thr Ile Glu Cys Arg Ala Ser Glu Asp
        35                  40                  45

Ile Tyr Asn Gly Leu Ala Trp Tyr Gln Gln Lys Pro Gly Lys Ser Pro
    50                  55                  60

Gln Leu Leu Ile Tyr Asp Ser Asn Ser Leu His Thr Gly Val Pro Ser
65                  70                  75                  80

Arg Phe Ser Gly Arg Gly Ser Gly Thr Gln Tyr Ser Leu Arg Ile Asn
                85                  90                  95

Ser Leu Gln Ser Glu Asp Val Ala Ser Tyr Phe Cys Gln Gln Tyr Tyr
            100                 105                 110

Asp Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 168
<211> LENGTH: 462
<212> TYPE: PRT
<213> ORGANISM: Rattus rattus

<400> SEQUENCE: 168

Met Lys Leu Arg Leu Ser Leu Ile Phe Ile Cys Ala Leu Leu Lys Asp
1               5                   10                  15

Val Gln Cys Glu Val Gln Leu Val Ala Ser Gly Gly Gly Leu Val Lys
            20                  25                  30

Pro Gly Ala Ser Leu Lys Leu Ser Cys Val Ala Ser Gly Phe Thr Phe
```

-continued

```
                35                  40                  45
Ser Asp Tyr Trp Met Ala Trp Val Arg Gln Thr Pro Gly Lys Pro Met
 50                  55                  60
Glu Tyr Ile Gly Asp Ile Lys Ser Asp Gly Ser Lys Val Asn Tyr Ala
 65                  70                  75                  80
Pro Ser Leu Lys Asn Arg Phe Thr Ile Ser Arg Asp Asn Ala Arg Thr
                 85                  90                  95
Thr Leu Tyr Leu Gln Met Ser Asn Val Arg Ser Glu Thr Ala Thr
                100                 105                 110
Tyr Tyr Cys Asn Arg Asp Ile Gly Pro Asp Trp Tyr Phe Asp Phe Trp
            115                 120                 125
Gly Pro Gly Thr Met Val Thr Val Ser Ser Ala Lys Thr Thr Pro Pro
            130                 135                 140
Ser Val Tyr Pro Leu Ala Pro Gly Ser Ala Ala Gln Thr Asn Ser Met
145                 150                 155                 160
Val Thr Leu Gly Cys Leu Val Lys Gly Tyr Phe Pro Glu Pro Val Thr
                165                 170                 175
Val Thr Trp Asn Ser Gly Ser Leu Ser Ser Gly Val His Thr Phe Pro
            180                 185                 190
Ala Val Leu Glu Ser Asp Leu Tyr Thr Leu Ser Ser Ser Val Thr Val
            195                 200                 205
Pro Ser Ser Pro Arg Pro Ser Glu Thr Val Thr Cys Asn Val Ala His
210                 215                 220
Pro Ala Ser Ser Thr Lys Val Asp Lys Lys Ile Val Pro Arg Asp Cys
225                 230                 235                 240
Gly Cys Lys Pro Cys Ile Cys Thr Val Pro Glu Val Ser Ser Val Phe
                245                 250                 255
Ile Phe Pro Pro Lys Pro Lys Asp Val Leu Thr Ile Thr Leu Thr Pro
            260                 265                 270
Lys Val Thr Cys Val Val Val Asp Ile Ser Lys Asp Asp Pro Glu Val
            275                 280                 285
Gln Phe Ser Trp Phe Val Asp Asp Val Glu Val His Thr Ala Gln Thr
290                 295                 300
Gln Pro Arg Glu Glu Gln Phe Asn Ser Thr Phe Arg Ser Val Ser Glu
305                 310                 315                 320
Leu Pro Ile Met His Gln Asp Trp Leu Asn Gly Lys Glu Phe Lys Cys
                325                 330                 335
Arg Val Asn Ser Ala Ala Phe Pro Ala Pro Ile Glu Lys Thr Ile Ser
            340                 345                 350
Lys Thr Lys Gly Arg Pro Lys Ala Pro Gln Val Tyr Thr Ile Pro Pro
            355                 360                 365
Pro Lys Glu Gln Met Ala Lys Asp Lys Val Ser Leu Thr Cys Met Ile
370                 375                 380
Thr Asp Phe Phe Pro Glu Asp Ile Thr Val Glu Trp Gln Trp Asn Gly
385                 390                 395                 400
Gln Pro Ala Glu Asn Tyr Lys Asn Thr Gln Pro Ile Met Asn Thr Asn
                405                 410                 415
Gly Ser Tyr Phe Val Tyr Ser Lys Leu Asn Val Gln Lys Ser Asn Trp
            420                 425                 430
Glu Ala Gly Asn Thr Phe Thr Cys Ser Val Leu His Glu Gly Leu His
            435                 440                 445
Asn His His Thr Glu Lys Ser Leu Ser His Ser Pro Gly Lys
450                 455                 460
```

<210> SEQ ID NO 169
<211> LENGTH: 48
<212> TYPE: DNA
<213> ORGANISM: Artificial Sequence
<220> FEATURE:
<223> OTHER INFORMATION: Oligonucleotide for mutagenesis for TLR3

<400> SEQUENCE: 169
gaagaactgg atatctttgc cgcttcatct ttaaaaaaat tagagttg            48

<210> SEQ ID NO 170
<211> LENGTH: 44
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 170
gtcatctaca aaattaggaa ctgcggttca gctggaaaat ctcc                44

<210> SEQ ID NO 171
<211> LENGTH: 45
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 171
ctcataatgg cttgtcatct acagaattag gaactcaggt tcagc               45

<210> SEQ ID NO 172
<211> LENGTH: 57
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 172
gaaaattaaa aataatccct ttgtcaagca ggagaattta atcacattag atctgtc   57

<210> SEQ ID NO 173
<211> LENGTH: 50
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 173
gaaaattaaa aataatccct ttgtcgagca gaagaattta atcacattag          50

<210> SEQ ID NO 174
<211> LENGTH: 52
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 174
cagaaaatta aaaataatcc ctttgcaaag cagaagaatt taatcacatt ag       52

<210> SEQ ID NO 175
<211> LENGTH: 47

```
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 175
ccaactcaat ccagaaaatt aaagctaatc cctttgtcaa gcagaag            47

<210> SEQ ID NO 176
<211> LENGTH: 45
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 176
caatgagcta tctcaacttt ctcgtaaaac ctttgccttc tgcac              45

<210> SEQ ID NO 177
<211> LENGTH: 48
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 177
gtcttgagaa actagaaatt ctcaagttgc agcataacaa cttagcac            48

<210> SEQ ID NO 178
<211> LENGTH: 46
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 178
cttgagaaac tagaaattct cgcattgcag cataacaact tagcac              46

<210> SEQ ID NO 179
<211> LENGTH: 43
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 179
ctaaagtcat tgaaccttca ggagaatctc ataacatccg ttg                 43

<210> SEQ ID NO 180
<211> LENGTH: 47
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 180
ctctaaagtc attgaacctt caggcgaatc tcataacatc cgttgag             47

<210> SEQ ID NO 181
<211> LENGTH: 37
<212> TYPE: DNA
<213> ORGANISM: Artificial Sequence
```

```
<220> FEATURE:
<223> OTHER INFORMATION: Oligonucleotide for mutagenesis for TLR3
      variant

<400> SEQUENCE: 181
ccacatcctt aacttgaggt ccaacggctt tgacgag                              37

<210> SEQ ID NO 182
<211> LENGTH: 46
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 182
gaaattctcg atttgcagca taacgcctta gcacggctct ggaaac                    46

<210> SEQ ID NO 183
<211> LENGTH: 46
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 183
gagaaactag aaattctcga tttggcgcat aacaacttag cacggc                    46

<210> SEQ ID NO 184
<211> LENGTH: 44
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 184
ctagaaattc tcgatttgca ggaaaacaac ttagcacggc tctg                      44

<210> SEQ ID NO 185
<211> LENGTH: 44
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 185
ctagaaattc tcgatttgca ggctaacaac ttagcacggc tctg                      44

<210> SEQ ID NO 186
<211> LENGTH: 46
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 186
cattctggat ctaagcaaca acgccatagc caacataaat gatgac                    46

<210> SEQ ID NO 187
<211> LENGTH: 50
<212> TYPE: DNA
<213> ORGANISM: Artificial Sequence
<220> FEATURE:
<223> OTHER INFORMATION: Oligonucleotide for mutagenesis for TLR3
``` variant

<400> SEQUENCE: 187
gaaatatttt tcgaaatcta tctttccgcc aacaagtacc tgcagctgac                50

<210> SEQ ID NO 188
<211> LENGTH: 41
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 188
gccttcaacg actgatgctg aaagggtggc ccttaaaaat g                         41

<210> SEQ ID NO 189
<211> LENGTH: 43
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 189
cttcaacgac tgatgctccg agaggtggcc cttaaaaatg tgg                       43

<210> SEQ ID NO 190
<211> LENGTH: 42
<212> TYPE: DNA
<213> ORGANISM: Artificial Sequence
<220> FEATURE:
<223> OTHER INFORMATION: Oligonucleotide for mutagenesis for TLR3
      variant

<400> SEQUENCE: 190
cgaaatctat ctttcctaca acgagtacct gcagctgact ag                        42

<210> SEQ ID NO 191
<211> LENGTH: 10
<212> TYPE: PRT
<213> ORGANISM: Artificial Sequence
<220> FEATURE:
<223> OTHER INFORMATION: Consensus sequence for family 17 LCDR3
<220> FEATURE:
<221> NAME/KEY: misc_feature
<222> LOCATION: (1)
<223> OTHER INFORMATION: Wherein Xaa can be Ala, Gln, Gly or Ser
<220> FEATURE:
<221> NAME/KEY: misc_feature
<222> LOCATION: (5)
<223> OTHER INFORMATION: Wherein Xaa can be Gly, Glu or Ser
<220> FEATURE:
<221> NAME/KEY: misc_feature
<222> LOCATION: (6)
<223> OTHER INFORMATION: Wherein Xaa can be Asp or Asn
<220> FEATURE:
<221> NAME/KEY: misc_feature
<222> LOCATION: (7)
<223> OTHER INFORMATION: Wherein Xaa can be Glu or Ser
<220> FEATURE:
<221> NAME/KEY: misc_feature
<222> LOCATION: (8)
<223> OTHER INFORMATION: Wherein Xaa can be Phe, Ala or Leu

<400> SEQUENCE: 191

Xaa Ser Tyr Asp Xaa Xaa Xaa Xaa Thr Val
 1               5                  10

<210> SEQ ID NO 192

```
<211> LENGTH: 18
<212> TYPE: PRT
<213> ORGANISM: Artificial Sequence
<220> FEATURE:
<223> OTHER INFORMATION: Consensus sequence for family 17 HCDR2
<220> FEATURE:
<221> NAME/KEY: misc_feature
<222> LOCATION: (1)
<223> OTHER INFORMATION: Wherein Xaa can be Arg or Lys
<220> FEATURE:
<221> NAME/KEY: misc_feature
<222> LOCATION: (3)
<223> OTHER INFORMATION: Wherein Xaa can be Tyr, His or Ser
<220> FEATURE:
<221> NAME/KEY: misc_feature
<222> LOCATION: (4)
<223> OTHER INFORMATION: Wherein Xaa can be Met, Arg or Tyr
<220> FEATURE:
<221> NAME/KEY: misc_feature
<222> LOCATION: (7)
<223> OTHER INFORMATION: Wherein Xaa can be Lys or Arg

<400> SEQUENCE: 192

Xaa Ile Xaa Xaa Arg Ser Xaa Trp Tyr Asn Asp Tyr Ala Val Ser Val
 1               5                  10                  15

Lys Ser

<210> SEQ ID NO 193
<211> LENGTH: 10
<212> TYPE: PRT
<213> ORGANISM: Artificial Sequence
<220> FEATURE:
<223> OTHER INFORMATION: Consensus sequence for family 18B LCDR3
<220> FEATURE:
<221> NAME/KEY: misc_feature
<222> LOCATION: (1)
<223> OTHER INFORMATION: Wherein Xaa can be Gln or Ser
<220> FEATURE:
<221> NAME/KEY: misc_feature
<222> LOCATION: (5)
<223> OTHER INFORMATION: Wherein Xaa can be Thr, Glu or Asp
<220> FEATURE:
<221> NAME/KEY: misc_feature
<222> LOCATION: (7)
<223> OTHER INFORMATION: Wherein Xaa can be Val or Asn
<220> FEATURE:
<221> NAME/KEY: misc_feature
<222> LOCATION: (8)
<223> OTHER INFORMATION: Wherein Xaa can be Tyr or Phe
<220> FEATURE:
<221> NAME/KEY: misc_feature
<222> LOCATION: (9)
<223> OTHER INFORMATION: Wherein Xaa can be Ser, Asn or Gln

<400> SEQUENCE: 193

Xaa Ser Tyr Asp Xaa Pro Xaa Xaa Xaa Val
 1               5                  10

<210> SEQ ID NO 194
<211> LENGTH: 18
<212> TYPE: PRT
<213> ORGANISM: Artificial Sequence
<220> FEATURE:
<223> OTHER INFORMATION: Consensus sequence for family 18B HCDR3
<220> FEATURE:
<221> NAME/KEY: misc_feature
<222> LOCATION: (4)
<223> OTHER INFORMATION: Wherein Xaa can be Lys, Thr or Ile
<220> FEATURE:
<221> NAME/KEY: misc_feature
<222> LOCATION: (11)
<223> OTHER INFORMATION: Wherein Xaa can be Asn or Asp
<220> FEATURE:
<221> NAME/KEY: misc_feature
<222> LOCATION: (14)
```

<223> OTHER INFORMATION: Wherein Xaa can be Val or Leu

<400> SEQUENCE: 194

Ile Ile Gln Xaa Arg Ser Lys Trp Tyr Asn Xaa Tyr Ala Xaa Ser Val
1               5                   10                  15
Lys Ser

<210> SEQ ID NO 195
<211> LENGTH: 9
<212> TYPE: PRT
<213> ORGANISM: Artificial Sequence
<220> FEATURE:
<223> OTHER INFORMATION: Consensus sequence for family 19 LCDR3
<220> FEATURE:
<221> NAME/KEY: misc_feature
<222> LOCATION: (3)
<223> OTHER INFORMATION: Wherein Xaa can be Tyr, Gly or Ala
<220> FEATURE:
<221> NAME/KEY: misc_feature
<222> LOCATION: (4)
<223> OTHER INFORMATION: Wherein Xaa can be Gly, Glu or Asn
<220> FEATURE:
<221> NAME/KEY: misc_feature
<222> LOCATION: (5)
<223> OTHER INFORMATION: Wherein Xaa can be Ser or Thr
<220> FEATURE:
<221> NAME/KEY: misc_feature
<222> LOCATION: (6)
<223> OTHER INFORMATION: Wherein Xaa can be Val, Ile or Leu
<220> FEATURE:
<221> NAME/KEY: misc_feature
<222> LOCATION: (7)
<223> OTHER INFORMATION: Wherein Xaa can be Ser or Leu
<220> FEATURE:
<221> NAME/KEY: misc_feature
<222> LOCATION: (8)
<223> OTHER INFORMATION: Wherein Xaa can be Ile, Ser, Pro or Tyr

<400> SEQUENCE: 195

Gln Gln Xaa Xaa Xaa Xaa Xaa Xaa Thr
1               5

<210> SEQ ID NO 196
<211> LENGTH: 17
<212> TYPE: PRT
<213> ORGANISM: Artificial Sequence
<220> FEATURE:
<223> OTHER INFORMATION: Consensus sequence for family 19 HCDR2
<220> FEATURE:
<221> NAME/KEY: misc_feature
<222> LOCATION: (1)
<223> OTHER INFORMATION: Wherein Xaa can be Phe or Arg
<220> FEATURE:
<221> NAME/KEY: misc_feature
<222> LOCATION: (12)
<223> OTHER INFORMATION: Wherein Xaa can be Ala or Ser

<400> SEQUENCE: 196

Xaa Ile Asp Pro Ser Asp Ser Tyr Thr Asn Tyr Xaa Pro Ser Phe Gln
1               5                   10                  15
Gly

<210> SEQ ID NO 197
<211> LENGTH: 107
<212> TYPE: PRT
<213> ORGANISM: Artificial Sequence
<220> FEATURE:
<223> OTHER INFORMATION: Consensus variable light chain family 17
<220> FEATURE:
<221> NAME/KEY: misc_feature
<222> LOCATION: (88)
<223> OTHER INFORMATION: Wherein Xaa can be Ala, Gln, Gly or Ser

```
<220> FEATURE:
<221> NAME/KEY: misc_feature
<222> LOCATION: (92)
<223> OTHER INFORMATION: Wherein Xaa can be Gly, Glu or Ser
<220> FEATURE:
<221> NAME/KEY: misc_feature
<222> LOCATION: (93)
<223> OTHER INFORMATION: Wherein Xaa can be Asp or Asn
<220> FEATURE:
<221> NAME/KEY: misc_feature
<222> LOCATION: (94)
<223> OTHER INFORMATION: Wherein Xaa can be Glu or Ser
<220> FEATURE:
<221> NAME/KEY: misc_feature
<222> LOCATION: (95)
<223> OTHER INFORMATION: Wherein Xaa can be Phe, Ala or Leu

<400> SEQUENCE: 197

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Gly Tyr Phe Val
             20                  25                  30

Ser Trp Tyr Gln Gln Lys Pro Gly Gln Ala Pro Val Leu Val Ile Tyr
         35                  40                  45

Asp Asp Asp Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Ser Tyr Asp Xaa Xaa Xaa Xaa Thr
                 85                  90                  95

Val Phe Gly Gly Gly Thr Lys Leu Thr Val Leu
            100                 105

<210> SEQ ID NO 198
<211> LENGTH: 122
<212> TYPE: PRT
<213> ORGANISM: Artificial Sequence
<220> FEATURE:
<223> OTHER INFORMATION: Consensus variable heavy chain family 17
<220> FEATURE:
<221> NAME/KEY: misc_feature
<222> LOCATION: (52)
<223> OTHER INFORMATION: Wherein Xaa can be Arg or Lys
<220> FEATURE:
<221> NAME/KEY: misc_feature
<222> LOCATION: (54)
<223> OTHER INFORMATION: Wherein Xaa can be Tyr, His or Ser
<220> FEATURE:
<221> NAME/KEY: misc_feature
<222> LOCATION: (55)
<223> OTHER INFORMATION: Wherein Xaa can be Met, Arg or Tyr
<220> FEATURE:
<221> NAME/KEY: misc_feature
<222> LOCATION: (58)
<223> OTHER INFORMATION: Wherein Xaa can be Lys or Arg

<400> SEQUENCE: 198

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
             20                  25                  30

Ser Ala Ala Trp Gly Trp Ile Arg Gln Ser Pro Gly Arg Gly Leu Glu
         35                  40                  45

Trp Leu Gly Xaa Ile Xaa Xaa Arg Ser Xaa Trp Tyr Asn Asp Tyr Ala
 50                  55                  60

Val Ser Val Lys Ser Arg Ile Thr Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95

Tyr Tyr Cys Ala Arg His Thr Tyr Pro Tyr Leu Ser Phe Asp Val Trp
            100                 105                 110

Gly Gln Gly Thr Leu Val Thr Val Ser Ser
        115                 120

<210> SEQ ID NO 199
<211> LENGTH: 107
<212> TYPE: PRT
<213> ORGANISM: Artificial Sequence
<220> FEATURE:
<223> OTHER INFORMATION: Consensus variable light chain family 18B
<220> FEATURE:
<221> NAME/KEY: misc_feature
<222> LOCATION: (88)
<223> OTHER INFORMATION: Wherein Xaa can be Gln or Ser
<220> FEATURE:
<221> NAME/KEY: misc_feature
<222> LOCATION: (92)
<223> OTHER INFORMATION: Wherein Xaa can be Thr, Glu or Asp
<220> FEATURE:
<221> NAME/KEY: misc_feature
<222> LOCATION: (94)
<223> OTHER INFORMATION: Wherein Xaa can be Val or Asn
<220> FEATURE:
<221> NAME/KEY: misc_feature
<222> LOCATION: (95)
<223> OTHER INFORMATION: Wherein Xaa can be Tyr or Phe
<220> FEATURE:
<221> NAME/KEY: misc_feature
<222> LOCATION: (96)
<223> OTHER INFORMATION: Wherein Xaa can be Ser, Asn or Gln

<400> SEQUENCE: 199

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Ile Gly Ser Tyr Tyr Val
             20                  25                  30

His Trp Tyr Gln Gln Lys Pro Gly Gln Ala Pro Val Leu Val Ile Tyr
         35                  40                  45

Glu Asp Ser Glu Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Ser Tyr Asp Xaa Pro Xaa Xaa Xaa
                85                  90                  95

Val Phe Gly Gly Gly Thr Lys Leu Thr Val Leu
            100                 105

<210> SEQ ID NO 200
<211> LENGTH: 122
<212> TYPE: PRT
<213> ORGANISM: Artificial Sequence
<220> FEATURE:
<223> OTHER INFORMATION: Consensus variable heavy chain family 18A and
      18B
<220> FEATURE:
<221> NAME/KEY: misc_feature
<222> LOCATION: (55)
<223> OTHER INFORMATION: Wherein Xaa can be Lys, Thr or Ile
<220> FEATURE:
<221> NAME/KEY: misc_feature
<222> LOCATION: (62)
<223> OTHER INFORMATION: Wherein Xaa can be Asn or Asp
<220> FEATURE:
<221> NAME/KEY: misc_feature
<222> LOCATION: (65)
```

<223> OTHER INFORMATION: Wherein Xaa can be Val or Leu

<400> SEQUENCE: 200

```
Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Xaa Arg Ser Lys Trp Tyr Asn Xaa Tyr Ala
 50                  55                  60

Xaa Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
            115                 120
```

<210> SEQ ID NO 201
<211> LENGTH: 107
<212> TYPE: PRT
<213> ORGANISM: Artificial Sequence
<220> FEATURE:
<223> OTHER INFORMATION: Consensus variable light chain family 19
<220> FEATURE:
<221> NAME/KEY: misc_feature
<222> LOCATION: (91)
<223> OTHER INFORMATION: Wherein Xaa can be Tyr, Gly or Ala
<220> FEATURE:
<221> NAME/KEY: misc_feature
<222> LOCATION: (92)
<223> OTHER INFORMATION: Wherein Xaa can be Gly, Glu or Asn
<220> FEATURE:
<221> NAME/KEY: misc_feature
<222> LOCATION: (93)
<223> OTHER INFORMATION: Wherein Xaa can be Ser or Thr
<220> FEATURE:
<221> NAME/KEY: misc_feature
<222> LOCATION: (94)
<223> OTHER INFORMATION: Wherein Xaa can be Val, Ile or Leu
<220> FEATURE:
<221> NAME/KEY: misc_feature
<222> LOCATION: (95)
<223> OTHER INFORMATION: Wherein Xaa can be Ser or Leu
<220> FEATURE:
<221> NAME/KEY: misc_feature
<222> LOCATION: (96)
<223> OTHER INFORMATION: Wherein Xaa can be Ile, Ser, Pro or Tyr

<400> SEQUENCE: 201

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Xaa Xaa Xaa Xaa Xaa Xaa
                85                  90                  95
```

```
Thr Phe Gly Gln Gly Thr Lys Val Glu Ile Lys
            100                 105

<210> SEQ ID NO 202
<211> LENGTH: 121
<212> TYPE: PRT
<213> ORGANISM: Artificial Sequence
<220> FEATURE:
<223> OTHER INFORMATION: Consensus variable heavy chain family 19
<220> FEATURE:
<221> NAME/KEY: misc_feature
<222> LOCATION: (50)
<223> OTHER INFORMATION: Wherein Xaa can be Phe or Arg
<220> FEATURE:
<221> NAME/KEY: misc_feature
<222> LOCATION: (61)
<223> OTHER INFORMATION: Wherein Xaa can be Ala or Ser

<400> SEQUENCE: 202

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Xaa Ile Asp Pro Ser Asp Ser Tyr Thr Asn Tyr Xaa Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser
        115                 120

<210> SEQ ID NO 203
<211> LENGTH: 214
<212> TYPE: PRT
<213> ORGANISM: Artificial Sequence
<220> FEATURE:
<223> OTHER INFORMATION: Full length consensus light chain, family 17
<220> FEATURE:
<221> NAME/KEY: misc_feature
<222> LOCATION: (88)
<223> OTHER INFORMATION: Wherein Xaa can be Ala, Gln, Gly or Ser
<220> FEATURE:
<221> NAME/KEY: misc_feature
<222> LOCATION: (92)
<223> OTHER INFORMATION: Wherein Xaa can be Gly, Glu or Ser
<220> FEATURE:
<221> NAME/KEY: misc_feature
<222> LOCATION: (93)
<223> OTHER INFORMATION: Wherein Xaa can be Asp or Asn
<220> FEATURE:
<221> NAME/KEY: misc_feature
<222> LOCATION: (94)
<223> OTHER INFORMATION: Wherein Xaa can be Glu or Ser
<220> FEATURE:
<221> NAME/KEY: misc_feature
<222> LOCATION: (95)
<223> OTHER INFORMATION: Wherein Xaa can be Phe, Ala or Leu

<400> SEQUENCE: 203

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Gly Tyr Phe Val
            20                  25                  30
```

```
Ser Trp Tyr Gln Gln Lys Pro Gly Gln Ala Pro Val Leu Val Ile Tyr
         35                  40                  45

Asp Asp Asp Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Xaa Ser Tyr Asp Xaa Xaa Xaa Xaa Thr
                 85                  90                  95

Val Phe Gly Gly Gly Thr Lys Leu Thr Val Leu Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 204
<211> LENGTH: 449
<212> TYPE: PRT
<213> ORGANISM: Artificial Sequence
<220> FEATURE:
<223> OTHER INFORMATION: Full length consensus heavy chain, family 17
<220> FEATURE:
<221> NAME/KEY: misc_feature
<222> LOCATION: (52)
<223> OTHER INFORMATION: Wherein Xaa can be Arg or Lys
<220> FEATURE:
<221> NAME/KEY: misc_feature
<222> LOCATION: (54)
<223> OTHER INFORMATION: Wherein Xaa can be Tyr, His or Ser
<220> FEATURE:
<221> NAME/KEY: misc_feature
<222> LOCATION: (55)
<223> OTHER INFORMATION: Wherein Xaa can be Met, Arg or Tyr
<220> FEATURE:
<221> NAME/KEY: misc_feature
<222> LOCATION: (58)
<223> OTHER INFORMATION: Wherein Xaa can be Lys or Arg

<400> SEQUENCE: 204

Gln Val Glu Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr Arg
                 20                  25                  30

Ser Ala Ala Trp Gly Trp Ile Arg Gln Ser Pro Gly Arg Gly Leu Glu
             35                  40                  45

Trp Leu Gly Xaa Ile Xaa Xaa Arg Ser Xaa Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95
```

```
Tyr Tyr Cys Ala Arg His Thr Tyr Pro Tyr Leu Ser Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 205
<211> LENGTH: 214
<212> TYPE: PRT
<213> ORGANISM: Artificial Sequence
<220> FEATURE:
<223> OTHER INFORMATION: Full length consensus light chain family 18B
<220> FEATURE:
<221> NAME/KEY: misc_feature
<222> LOCATION: (88)
<223> OTHER INFORMATION: Wherein Xaa can be Gln or Ser
```

<220> FEATURE:
<221> NAME/KEY: misc_feature
<222> LOCATION: (92)
<223> OTHER INFORMATION: Wherein Xaa can be Thr, Glu or Asp
<220> FEATURE:
<221> NAME/KEY: misc_feature
<222> LOCATION: (94)
<223> OTHER INFORMATION: Wherein Xaa can be Val or Asn
<220> FEATURE:
<221> NAME/KEY: misc_feature
<222> LOCATION: (95)
<223> OTHER INFORMATION: Wherein Xaa can be Tyr or Phe
<220> FEATURE:
<221> NAME/KEY: misc_feature
<222> LOCATION: (96)
<223> OTHER INFORMATION: Wherein Xaa can be Ser, Asn or Gln

<400> SEQUENCE: 205

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Ser Tyr Asp Xaa Pro Xaa Xaa Xaa
                85                  90                  95

Val Phe Gly Gly Gly Thr Lys Leu Thr Val Leu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 206
<211> LENGTH: 449
<212> TYPE: PRT
<213> ORGANISM: Artificial Sequence
<220> FEATURE:
<223> OTHER INFORMATION: Full length consensus heavy chain family 18A
      and 18B
<220> FEATURE:
<221> NAME/KEY: misc_feature
<222> LOCATION: (55)
<223> OTHER INFORMATION: Wherein Xaa can be Lys, Thr or Ile
<220> FEATURE:
<221> NAME/KEY: misc_feature
<222> LOCATION: (62)
<223> OTHER INFORMATION: Wherein Xaa can be Asn or Asp
<220> FEATURE:
<221> NAME/KEY: misc_feature
<222> LOCATION: (65)

<223> OTHER INFORMATION: Wherein Xaa can be Val or Leu

<400> SEQUENCE: 206

Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Xaa Arg Ser Lys Trp Tyr Asn Xaa Tyr Ala
    50                  55                  60

Xaa Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys

```
                    405                 410                 415
Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 207
<211> LENGTH: 214
<212> TYPE: PRT
<213> ORGANISM: Artificial Sequence
<220> FEATURE:
<223> OTHER INFORMATION: Full length consensus light chain family 19
<220> FEATURE:
<221> NAME/KEY: misc_feature
<222> LOCATION: (91)
<223> OTHER INFORMATION: Wherein Xaa can be Tyr, Gly or Ala
<220> FEATURE:
<221> NAME/KEY: misc_feature
<222> LOCATION: (92)
<223> OTHER INFORMATION: Wherien Xaa can be Gly, Glu or Asn
<220> FEATURE:
<221> NAME/KEY: misc_feature
<222> LOCATION: (93)
<223> OTHER INFORMATION: Wherein Xaa can be Ser or Thr
<220> FEATURE:
<221> NAME/KEY: misc_feature
<222> LOCATION: (94)
<223> OTHER INFORMATION: Wherein Xaa can be Val, Ile or Leu
<220> FEATURE:
<221> NAME/KEY: misc_feature
<222> LOCATION: (95)
<223> OTHER INFORMATION: Wherein Xaa can be Ser or Leu
<220> FEATURE:
<221> NAME/KEY: misc_feature
<222> LOCATION: (96)
<223> OTHER INFORMATION: Wherein Xaa can be Ile, Ser, Pro or Tyr

<400> SEQUENCE: 207

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Leu Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa Xaa
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 208
<211> LENGTH: 448
<212> TYPE: PRT
<213> ORGANISM: Artificial Sequence
<220> FEATURE:
<223> OTHER INFORMATION: Full length consensus heavy chain family 19
<220> FEATURE:
<221> NAME/KEY: misc_feature
<222> LOCATION: (50)
<223> OTHER INFORMATION: Wherein Xaa can be Phe or Arg
<220> FEATURE:
<221> NAME/KEY: misc_feature
<222> LOCATION: (61)
<223> OTHER INFORMATION: Wherein Xaa can be Ala or Ser

<400> SEQUENCE: 208

Gln Val Glu Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
         20                  25                  30

Trp Val Gly Trp Val Arg Gln Met Pro Gly Lys Gly Leu Glu Trp Met
     35                  40                  45

Gly Xaa Ile Asp Pro Ser Asp Ser Tyr Thr Asn Tyr Xaa Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300
```

-continued

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 209
<211> LENGTH: 108
<212> TYPE: PRT
<213> ORGANISM: Artificial Sequence
<220> FEATURE:
<223> OTHER INFORMATION: QSV Variant of candidate 9 variable light chain

<400> SEQUENCE: 209

Gln Ser Val Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Gln Phe Ser Phe
                85                  90                  95

Gly Val Phe Gly Gly Gly Thr Lys Leu Thr Val Leu
            100                 105

<210> SEQ ID NO 210
<211> LENGTH: 107
<212> TYPE: PRT
<213> ORGANISM: Artificial Sequence
<220> FEATURE:
<223> OTHER INFORMATION: QSV variant of candidate 10 variable light
      chain

<400> SEQUENCE: 210

Gln Ser Val Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

His Trp Tyr Gln Gln Lys Pro Gly Gln Ala Pro Val Leu Val Ile Tyr
        35                  40                  45

Glu Asp Ser Glu Arg Pro Ser Gly Ile Pro Glu Arg Phe Ser Gly Ser
```

```
                  50                  55                  60
Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Thr Pro Val Tyr Ser
                 85                  90                  95

Val Phe Gly Gly Gly Thr Lys Leu Thr Val Leu
                100                 105

<210> SEQ ID NO 211
<211> LENGTH: 107
<212> TYPE: PRT
<213> ORGANISM: Artificial Sequence
<220> FEATURE:
<223> OTHER INFORMATION: QSV variant of candidate 12 variable light
      chain

<400> SEQUENCE: 211

Gln Ser Val Leu Thr Gln Pro Pro Ser Val Ser Val Ala Pro Gly Gln
  1               5                  10                  15

Thr Ala Arg Ile Ser Cys Ser Gly Asp Asn Ile Gly Ser Tyr Tyr Val
                 20                  25                  30

His Trp Tyr Gln Gln Lys Pro Gly Gln Ala Pro Val Leu Val Ile Tyr
                 35                  40                  45

Glu Asp Ser Glu Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Asp Asp Pro Asn Phe Gln
                 85                  90                  95

Val Phe Gly Gly Gly Thr Lys Leu Thr Val Leu
                100                 105

<210> SEQ ID NO 212
<211> LENGTH: 122
<212> TYPE: PRT
<213> ORGANISM: Artificial Sequence
<220> FEATURE:
<223> OTHER INFORMATION: QVQ variant of candidate 9 variable heavy chain

<400> SEQUENCE: 212

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Gly Trp Ile Arg Gln Ser Pro Gly Arg Gly Leu Glu
                 35                  40                  45

Trp Leu Gly Ile Ile Gln Ile Arg Ser Lys Trp Tyr Asn Asp Tyr Ala
 50                  55                  60

Leu Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Ser Tyr Pro Phe Tyr Ser Ile Asp Tyr Trp
                100                 105                 110

Gly Gln Gly Thr Leu Val Thr Val Ser Ser
                115                 120

<210> SEQ ID NO 213
<211> LENGTH: 122
```

```
<212> TYPE: PRT
<213> ORGANISM: Artificial Sequence
<220> FEATURE:
<223> OTHER INFORMATION: QVQ variant of candidate 10 variable heavy
      chain

<400> SEQUENCE: 213

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Lys Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 214
<211> LENGTH: 122
<212> TYPE: PRT
<213> ORGANISM: Artificial Sequence
<220> FEATURE:
<223> OTHER INFORMATION: QVQ variant of candidate 12 variable heavy
      chain

<400> SEQUENCE: 214

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Lys Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser
        115                 120

<210> SEQ ID NO 215
<211> LENGTH: 121
<212> TYPE: PRT
<213> ORGANISM: Artificial Sequence
<220> FEATURE:
<223> OTHER INFORMATION: EVQ variant of candidate 14

<400> SEQUENCE: 215

Glu Val Gln Leu Val Gln Ser Gly Ala Glu Val Lys Lys Pro Gly Glu
1               5                   10                  15
```

-continued

Ser Leu Lys Ile Ser Cys Lys Gly Ser Gly Tyr Ser Phe Thr Asn Tyr
           20                  25                  30

Trp Val Gly Trp Val Arg Gln Met Pro Gly Lys Gly Leu Glu Trp Met
       35                  40                  45

Gly Phe Ile Asp Pro Ser Asp Ser Tyr Thr Asn Tyr Ala Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
               85                  90                  95

Ala Arg Glu Leu Tyr Gln Gly Tyr Met Asp Thr Phe Asp Ser Trp Gly
           100                 105                 110

Gln Gly Thr Leu Val Thr Val Ser Ser
       115                 120

<210> SEQ ID NO 216
<211> LENGTH: 121
<212> TYPE: PRT
<213> ORGANISM: Artificial Sequence
<220> FEATURE:
<223> OTHER INFORMATION: EVQ variant of candidate 15

<400> SEQUENCE: 216

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
           20                  25                  30

Trp Val Gly Trp Val Arg Gln Met Pro Gly Lys Gly Leu Glu Trp Met
       35                  40                  45

Gly Phe Ile Asp Pro Ser Asp Ser Tyr Thr Asn Tyr Ala Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
               85                  90                  95

Ala Arg Glu Leu Tyr Gln Gly Tyr Met Asp Thr Phe Asp Ser Trp Gly
           100                 105                 110

Gln Gly Thr Leu Val Thr Val Ser Ser
       115                 120

<210> SEQ ID NO 217
<211> LENGTH: 2712
<212> TYPE: DNA
<213> ORGANISM: Macaca fascicularis

<400> SEQUENCE: 217
atgagacaga ctttgcctta tacctacttt tggtggggac ttttgccctt tgggatgctg      60
tgtgcatcct ccaccaacaa atgcactgtt agccaagaag ttgctgactg cagccacctg    120
aagttaactc aggtacccga tgatctcccc acaaacataa cagtgttgaa tcttacccat    180
aatcaactca gaagattacc agctgccaat tttacaagat atagccaact aactatcttg    240
gatgtaggat taactccat ctcaaaactg gagccagaat gtgccaaaa acttcccatg      300 ttaaagttt tgaacctcca gcacaatgag ctatctcaac tttctgataa acttttgcc      360 ttctgcacga atttgacgga actccatctc atgtccaact caatccagaa aattaaaaat    420
aatccctttg taaagcagaa gaatttaatc acattagatc tgtctcataa tggcttgtca    480
tctacaaaat taggaactca ggttcagctg gaaaatctcc aagagcttct attatcaaac    540

```
aataaaatcc aagcgctaaa aagtgaagaa cttggtatcc ttgccaattc atctttaaaa    600
aagttagagt tgtcatcgaa tcaaattaaa gagttttctc cagggtgttt tcacgcaatt    660
ggaagattat tgggcctctt tctgaacaat gtccagctgg gtccccgcct cacagagaag    720
ctatgtttgg aattagcaaa cacaagcgtt cggaatctgt ctctgagtaa cagccagctg    780
tccaccacca gcaatacaac tttcttggga ctaaagtgga caaacctcac tatgctcgat    840 cttcccaca acaacttaaa tgtgattggt aacgattcct ttgtttggct tccacatcta     900
gaatatttct tcctggagta taataatata cagcatttgc tctctcactc tttgcacggg    960
cttttcaatg tgcggtacct gaatttgaaa cggtctttta ctaaacaaag tatttccctt   1020
gcttcgctcc ccaagattga tgattttcct tttcggtggc taacatgttt ggagcacctt   1080
aacatggaag ataatgatat ttcaggcata aaaagcaata tgttcacagg attgataaac   1140
ctgaaatact taagtctatc caactccttt acaagtttgc aaactttgac aaatgaaaca   1200
tttgtatcac ttgctcattc tcccttacac atactcaacc taaccaagaa taaaatctca   1260
aaaatagaga gtggtgcctt ctcttggttg ggccacctag aagtacttga cttgggcctt   1320
aatgaaattg gcaagaact cacaggccag gaatggagtg gtctagaaaa tattttcgaa    1380
atctatcttt cctacaacaa gtacctgcaa ctgactaaga actcctttgc cttggtccga   1440
agccttcaac gactgatgct ccgaagggtg gcccttaaaa atgtggattg ctctccttca   1500
ccattccagc ctcttggtaa cctgaccatt ctggatctaa gcaacaacaa catagccaac   1560
ataaatgatg acatgttgga aggtcttgag aaactagaaa ttctggattt gcagcataac   1620
aacttagcac ggctctggaa acacgcaaac cctggtggtc ctgtttattt cctaaagggt   1680
ctgtctcacc tccacatcct taacttggag tctaatggct ttgacgagat cccagttgag   1740
gtcttcaagg atttatctga actaaagatc attgatttag gattgaataa tttaaacaca   1800
cttccagcgt ctgtctttga taatcaggtg tctctaaagt cattgaacct tcagaagaat   1860
ctcataacat cagttgagaa gaaggttttc gggccagctt tcaggaacct gagtaactta   1920
gatatgcgct ttaatccctt tgattgcaca tgtgaaagta ttgcctggtt tgttaattgg   1980
attaacaaga cccacgccaa catccctgag ctgtcaagcc actacctttg caacactcca   2040
ccccactatc atgggttccc agtgagactt tttgatacat catcctgcaa agacagtgcc   2100 cccttgaac tctttttcat gatcaatacc agtatcctgt tgattttat ctttgttgta    2160 cttctcatcc actttgaggg ctggaggata tctttttact ggaatgtttc agtacatcga   2220
gttcttggtt tcaaagaaat agacagacag acagaacagt ttgaatatgc agcatatata   2280
attcacgccc ataaagataa ggattgggtc tgggaacatt tctcttcaat ggaaaaggaa   2340
gaccaatctc tcaaattttg tctggaagaa agggactttg aggcaggtgt ttttgaactg   2400
gaagcaattg ttaacagcat caaaagaagc agaaaaatta tttttattat aacacaccat   2460
ctattaaaag acccattatg caaaagattc aaggtacatc atgccgttca acaagctatt   2520
gaacaaaatc tggattccat tatattgatt ttccttgagg agattccaga ttataaactg   2580
aaccatgcac tctgtttgcg aagaggaatg tttaaatctc actgcatctt gaactggcca   2640
gttcagaaag aacggatagg tgcctttcat cataaactgc aagtagcact tggatccaaa   2700
aactcagtac at                                                       2712
```

<210> SEQ ID NO 218
<211> LENGTH: 449
<212> TYPE: PRT
<213> ORGANISM: Artificial Sequence -continued
<220> FEATURE:
<223> OTHER INFORMATION: Candidate 9EVQ full length heavy chain with
     S229P, F235A/L236A

<400> SEQUENCE: 218

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Ile Ile Gln Ile Arg Ser Lys Trp Tyr Asn Asp Tyr Ala
50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Ser Tyr Pro Phe Tyr Ser Ile Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

<210> SEQ ID NO 219
<211> LENGTH: 449
<212> TYPE: PRT
<213> ORGANISM: Artificial Sequence
<220> FEATURE:
<223> OTHER INFORMATION: Candidates 10EVQ, 12EVQ heavy chain with S229P, F235A/L236A

<400> SEQUENCE: 219

```
Asp Ser Asp Gly Ser Phe Phe Leu Tyr Ser Arg Leu Thr Val Asp Lys
            405                 410                 415
Ser Arg Trp Gln Glu Gly Asn Val Phe Ser Cys Ser Val Met His Glu
        420                 425                 430
Ala Leu His Asn His Tyr Thr Gln Lys Ser Leu Ser Leu Ser Leu Gly
    435                 440                 445
Lys

Glu Val Gln Leu Gln Gln Ser Gly Pro Gly Leu Val Lys Pro Ser Gln
  1               5                  10                  15
Thr Leu Ser Leu Thr Cys Ala Ile Ser Gly Asp Ser Val Ser Ser Asn
             20                  25                  30
Ser Ala Ala Trp Gly Trp Ile Arg Gln Ser Pro Gly Arg Gly Leu Glu
         35                  40                  45
Trp Leu Gly Ile Ile Gln Lys Arg Ser Lys Trp Tyr Asn Asn Tyr Ala
 50                  55                  60
Val Ser Val Lys Ser Arg Ile Thr Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Ala Arg Tyr Ser Tyr Pro Phe Tyr Ser Ile Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 220
<211> LENGTH: 448
<212> TYPE: PRT
<213> ORGANISM: Artificial Sequence
<220> FEATURE:
<223> OTHER INFORMATION: EVQ variant mAb14 and mAb15 full length heavy
      Chain S229P, F235A/L236A

<400> SEQUENCE: 220

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Phe Ile Asp Pro Ser Asp Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Tyr Gln Gly Tyr Met Asp Thr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
```

-continued

```
                  210                 215                 220
Pro Pro Cys Pro Pro Cys Pro Ala Pro Glu Ala Ala Gly Gly Pro Ser
225             230             235                 240

Val Phe Leu Phe Pro Pro Lys Pro Lys Asp Thr Leu Met Ile Ser Arg
                245             250                 255

Thr Pro Glu Val Thr Cys Val Val Asp Val Ser Gln Glu Asp Pro
                260             265             270

Glu Val Gln Phe Asn Trp Tyr Val Asp Gly Val Glu Val His Asn Ala
                275             280             285

Lys Thr Lys Pro Arg Glu Glu Gln Phe Asn Ser Thr Tyr Arg Val Val
            290             295             300

Ser Val Leu Thr Val Leu His Gln Asp Trp Leu Asn Gly Lys Glu Tyr
305             310             315                 320

Lys Cys Lys Val Ser Asn Lys Gly Leu Pro Ser Ser Ile Glu Lys Thr
                325             330             335

Ile Ser Lys Ala Lys Gly Gln Pro Arg Glu Pro Gln Val Tyr Thr Leu
                340             345             350

Pro Pro Ser Gln Glu Glu Met Thr Lys Asn Gln Val Ser Leu Thr Cys
            355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395                 400

Ser Asp Gly Ser Phe Phe Leu Tyr Ser Arg Leu Thr Val Asp Lys Ser
                405             410             415

Arg Trp Gln Glu Gly Asn Val Phe Ser Cys Ser Val Met His Glu Ala
            420             425             430

Leu His Asn His Tyr Thr Gln Lys Ser Leu Ser Leu Ser Leu Gly Lys
            435             440             445
```

TOLL-LIKE RECEPTOR 3 ANTAGONISTS

This application claims the benefit of U.S. Provisional Application No. 61/109,974, filed 31 Oct. 2008 and U.S. Provisional Application No. 61/161,860, filed 20 Mar. 2009 and U.S. Provisional Application No. 61/165,100, filed 31 Mar. 2009 and U.S. Provisional Application No. 61/173,686, filed 29 Apr. 2009, the entire contents of which are incorporated herein by reference.

FIELD OF THE INVENTION

The present invention relates to Toll-Like Receptor 3 (TLR3) antibody antagonists, polynucleotides encoding TLR3 antibody antagonists or fragments thereof, and methods of making and using the foregoing.

BACKGROUND OF THE INVENTION

Toll-like receptors (TLRs) regulate activation of the innate immune response and influence the development of adaptive immunity by initiating signal transduction cascades in response to bacterial, viral, parasitic, and in some cases, host-derived ligands (Lancaster et al., J. Physiol. 563:945-955, 2005). The plasma membrane localized TLRs, TLR1, TLR2, TLR4 and TLR6 recognize ligands including protein or lipid components of bacteria and fungi. The predominantly intracellular TLRs, TLR3, TLR7 and TLR9 respond to dsRNA, ssRNA and unmethylated CpG DNA, respectively. Dysregulation of TLR signaling is believed to cause a multitude of problems, and therapeutic strategies are in development towards this axis (Hoffman et al., Nat. Rev. Drug Discov. 4:879-880, 2005; Rezaei, Int. Immunopharmacol. 6:863-869, 2006; Wickelgren, Science 312:184-187, 2006). For example, antagonists of TLR4 and TLRs 7 and 9 are in clinical development for severe sepsis and lupus, respectively (Kanzler et al., Nat. Med. 13:552-559, 2007).

TLR3 signaling is activated by dsRNA, mRNA or RNA released from necrotic cells during inflammation or virus infection. TLR3 activation induces secretion of interferons and pro-inflammatory cytokines and triggers immune cell activation and recruitement that are protective during certain microbial infections. For example, a dominant-negative TLR3 allele has been associated with increased susceptibility to Herpes Simplex encephalitis upon primary infection with HSV-1 in childhood (Zheng et al., Science 317:1522-1527 2007). In mice, TLR3 deficiency is associated with decreased survival upon coxsackie virus challenge (Richer et al., PLoS One 4:e4127, 2009). However, uncontrolled or dysregulated TLR3 signaling has been shown to contribute to morbidity and mortality in certain viral infection models including West Nile, phlebovirus, vaccinia, and influenza A (Wang et al., Nat. Med. 10:1366-1373, 2004; Gowen et al., J. Immunol. 177: 6301-6307, 2006; Hutchens et al., J. Immunol. 180:483-491, 2008; Le Goffic et al., PloS Pathog. 2:E53, 2006).

TLR3 has also been shown to drive pathogenic mechanisms in a spectrum of inflammatory, immune-mediated and autoimmune diseases including, for example, septic shock (Cavassani et al., J. Exp. Med. 205:2609-2621, 2008), acute lung injury (Murray et al., Am. J. Respir. Crit. Care Med. 178:1227-1237, 2008), rheumatoid arthritis (Kim et al., Immunol. Lett. 124:9-17, 2009; Brentano et al., Arth. Rheum. 52:2656-2665, 2005), asthma (Sugiura et al., Am. J. Resp. Cell Mol. Biol. 40:654-662, 2009; Morishima et al., Int. Arch. Allergy Immunol. 145:163-174, 2008; Stowell et al., Respir. Res. 10:43, 2009), inflammatory bowel disease such as Crohn's disease and ulcerative colitis (Zhou et al., J. Immunol. 178:4548-4556, 2007; Zhou et al., Proc. Natl. Acad. Sci. (USA) 104:7512-7515, 2007), autoimmune liver disease (Lang et al., J. Clin. Invest. 116:2456-2463, 2006) and type I diabetes (Dogusan et al. Diabetes 57:1236-1245, 2008; Lien and Zipris, Curr. Mol. Med. 9:52-68, 2009). Furthermore, organ-specific increases in TLR3 expression have been shown to correlate with a number of pathological conditions driven by dysregulated local inflammatory responses such as primary biliary cirrhosis of liver tissues (Takii et al., Lab Invest. 85:908-920, 2005), rheumatoid arthritis joints (Ospelt et al., Arthritis Rheum. 58:3684-3692, 2008), and nasal mucosa of allergic rhinitis patients (Fransson et al., Respir. Res. 6:100, 2005).

In necrotic conditions, the release of intracellular content including endogenous mRNA triggers secretion of cytokines, chemokines and other factors that induce local inflammation, facilitate clearance of dead cell remnants and repair the damage. Necrosis often perpetuates inflammatory processes, contributing to chronic or exaggerated inflammation (Bergsbaken et al., Nature Reviews 7:99-109, 2009). Activation of TLR3 at the site of necrosis may contribute to these aberrant inflammatory processes and generate a further pro-inflammatory positive feedback loop via the released TLR3 ligands. Thus, TLR3 antagonism may be beneficial in a variety of disorders involving chronic or exaggerated inflammation and/or necrosis.

Down-modulation of TLR3 activation may also represent a novel treatment strategy for oncologic indications including renal cell carcinomas and head and neck squamous cell carcinomas (Morikawa et al., Clin. Cancer Res. 13:5703-5709, 2007; Pries et al., Int. J. Mol. Med. 21: 209-215, 2008). Furthermore, the $TLR3^{L423F}$ allele encoding a protein with reduced activity has been associated with protection against advanced "dry" age-related macular degeneration (Yang et al., N. Engl. J. Med. 359:1456-1463, 2008), indicating that TLR3 antagonists may be beneficial in this disease.

Pathologies associated with inflammatory conditions and others, such as those associated with infections, have significant health and economic impacts. Yet, despite advances in many areas of medicine, comparatively few treatment options and therapies are available for many of these conditions.

Thus, a need exists to suppress TLR3 activity to treat TLR3-associated conditions.

BRIEF DESCRIPTION OF THE DRAWINGS

FIGS. 2A and 2B show the effect (% inhibition) or anti-huTLR3 mAbs in a BEAS-2B assay.

FIGS. 5A and 5B show the effect of anti-huTLR3 mAbs in a HASM assay.

FIG. 7B shows localized H/D/ exchange perturbation map of TLR3 ECD protein complexed with mAb 15EVQ. Residue numbering of TLR3 ECD is according to SEQ ID NO: 2

FIG. 15 shows effect of the surrogate mAb on A) histopathology scores and B) neutrophil influx in a T-cell transfer model.

FIG. 21 shows effect of the surrogate mAbs on blood glucose levels in (A) WT DIO and (B) TLR3KO DIO animals after glucose challenge.

FIG. 24 shows effect of mAb 15EVQ on (A) sICAM-1 levels and (B) viability in HUVEC cells.

SUMMARY OF THE INVENTION

Figure 1:
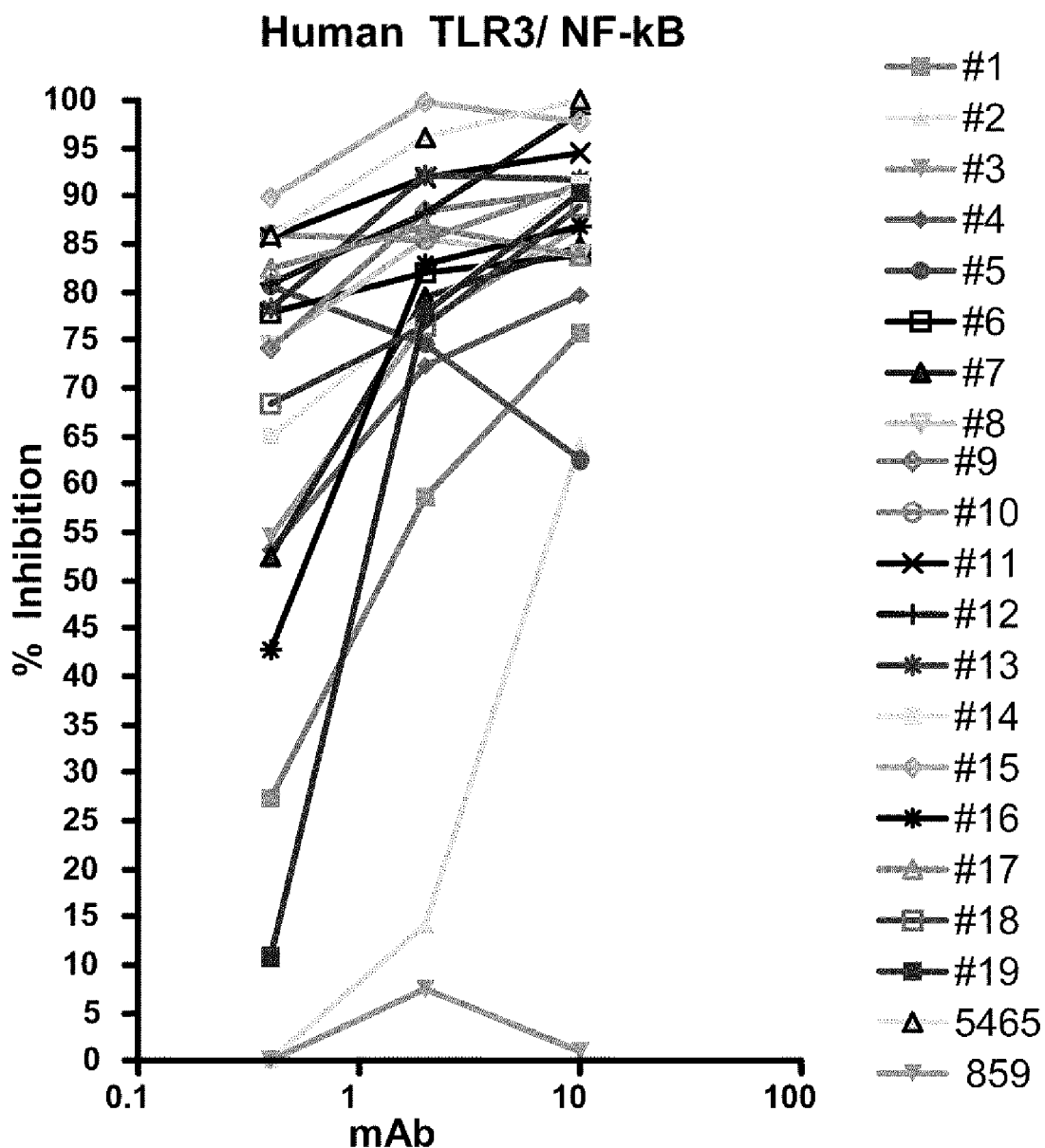
FIG. 1 shows the effect of anti-human TLR3 (huTLR3) mAbs in an NF-κB reporter gene assay.

One aspect of the invention is an isolated antibody or antigen binding fragment thereof, wherein the antibody binds at least one TLR3 amino acid residue selected from a group consisting of residues K467, R488, or R489 of SEQ ID NO: 2.

Another aspect of the invention is an isolated antibody or antigen binding fragment thereof, wherein the antibody binds at least one TLR3 amino acid residue selected from a group consisting of residues D116 or K145 of SEQ ID NO: 2. Another aspect of the invention is an isolated antibody reactive with TLR3, wherein the antibody has at least one of the following properties:
  a. reduces human TLR3 biological activity in an in vitro poly(I:C) NF-kB reporter gene assay >50% at <1 μg/ml;
  b. inhibits >60% of IL-6 or CXCL10/IP-10 production from BEAS-2B cells stimulated with <100 ng/ml poly (I:C) at <10 μg/ml;
  c. inhibits >50% of IL-6 or CXCL10/IP-10 production from BEAS-2B cells stimulated with <100 ng/ml poly (I:C) at <0.4 μg/ml;
  d. inhibits >50% of IL-6 production from NHBE cells stimulated with 62.5 ng/ml poly(I:C) at <5 μg/ml;
  e. inhibits >50% of IL-6 production from NHBE cells stimulated with 62.5 ng/ml poly(I:C) at <1 μg/ml;
  f. inhibits >20% of poly(I:C)-induced IFN-γ, IL-6 or IL-12 production by PBMC cells at <1 μg/ml;
  g. inhibits cynomologus TLR3 biological activity in an in vitro NF-kB reporter gene assay with IC50<10 μg/ml; or
  h. inhibits cynomologus TLR3 biological activity in an in vitro ISRE reporter gene assay with IC50 <5 1 μg/ml.

Another aspect of the invention is an isolated antibody reactive with TLR3 that competes for TLR3 binding with a monoclonal antibody, wherein the monoclonal antibody comprises the amino acid sequences of certain heavy chain complementarity determining regions (CDRs) 1, 2 and 3, the amino acid sequences of certain light chain CDRs 1, 2 and 3, the amino acid sequences of certain heavy chain variable regions (VH) or the amino acid sequence of certain light chain variable regions (VL).

Another aspect of the invention is an isolated antibody reactive with TLR3 comprising both a heavy chain and a light chain variable region and wherein the antibody comprises certain heavy chain complementarity determining regions (CDRs) 1, 2 and 3 and the amino acid sequences of certain light chain CDRs 1, 2 and 3.

Another aspect of the invention is an isolated antibody reactive with TLR3 comprising both a heavy chain and a light chain variable region and wherein the antibody comprises the amino acid sequences of certain heavy chain variable regions (VH) and the amino acid sequences of certain light chain variable regions (VL).

Another aspect of the invention is an isolated antibody reactive with TLR3 comprising both a heavy chain and a light chain variable region and wherein the antibody comprises the amino acid sequence of certain heavy chain and the amino acid sequence of certain light chain.

Another aspect of the invention is an isolated antibody heavy chain comprising the amino acid sequence shown in SEQ ID NO: 6, 8, 10, 12, 14, 16, 18, 20, 22, 24, 26, 28, 30, 32, 34, 36, 38, 40, 42, 124, 125, 126, 127, 128, 129, 159, 198, 200, 202, 164, 212, 213, 214, 215 or 216.

Another aspect of the invention is an isolated antibody light chain comprising the amino acid sequence shown in SEQ ID NO: 5, 7, 9, 11, 13, 15, 17, 19, 21, 23, 25, 27, 29, 31, 33, 35, 37, 39, 41, 122, 123, 197, 199, 201, 163, 209, 210 or 211.

Another aspect of the invention is an isolated antibody heavy chain comprising the amino acid sequence shown in SEQ ID NO: 102, 130, 131, 132, 133, 134, 135, 160, 204, 206, 208, 220, 166 or 168.

Another aspect of the invention is an isolated antibody light chain comprising the amino acid sequence shown in SEQ ID NO: 155, 156, 157, 158, 203, 205, 207, 165 or 167.

Another aspect of the invention is an isolated polynucleotide encoding an antibody heavy chain comprising the amino acid sequence shown in SEQ ID NO: 6, 8, 10, 12, 14, 16, 18, 20, 22, 24, 26, 28, 30, 32, 34, 36, 38, 40, 42, 124, 125, 126, 127, 128, 129, 159, 198, 200, 202, 164, 212, 213, 214, 215 or 216.

Another aspect of the invention is an isolated polynucleotide encoding an antibody light chain comprising the amino acid sequence shown in SEQ ID NO: 5, 7, 9, 11, 13, 15, 17, 19, 21, 23, 25, 27, 29, 31, 33, 35, 37, 39, 41, 122, 123, 197, 199, 201, 163, 209, 210 or 211.

Another aspect of the invention is an isolated polynucleotide encoding an antibody heavy chain comprising the amino acid sequence shown in SEQ ID NO: 102, 130, 131, 132, 133, 134, 135, 160, 204, 206, 208, 220, 166 or 168.

Another aspect of the invention is an isolated polynucleotide encoding an antibody light chain comprising the amino acid sequence shown in SEQ ID NO: 155, 156, 157, 158, 203, 205, 207, 165 or 167.

Another aspect of the invention is a pharmaceutical composition comprising the isolated antibody of the invention and a pharmaceutically acceptable carrier.

Another aspect of the invention is a vector comprising at least one polynucleotide of the invention.

Another aspect of the invention is a host cell comprising the vector of the invention.

Another aspect of the invention is a method of making an antibody reactive with TLR3 comprising culturing the host cell of the invention and recovering the antibody produced by the host cell.

Another aspect of the invention is a method of treating or preventing an inflammatory condition comprising administering a therapeutically effective amount of the isolated antibody of the invention to a patient in need thereof for a time sufficient to treat or prevent the inflammatory condition.

Another aspect of the invention is method of treating or preventing a systemic inflammatory condition comprising administering a therapeutically effective amount of the isolated antibody of the invention to a patient in need thereof for a time sufficient to treat or prevent the systemic inflammatory condition.

Another aspect of the invention is a method of treating type II diabetes comprising administering a therapeutically effective amount of the isolated antibody of the invention to a patient in need thereof for a time sufficient to treat type II diabetes.

Another aspect of the invention is a method of treating hyperglycemia comprising administering a therapeutically effective amount of the isolated antibody of the invention to a patient in need thereof for a time sufficient to treat the hyperglycemia.

Another aspect of the invention is a method of treating hyperinsulinemia comprising administering a therapeutically effective amount of the isolated antibody of the invention to a patient in need thereof for a time sufficient to treat the insulin resistance.

Another aspect of the invention is a method of treating or preventing viral infections comprising administering a therapeutically effective amount of the isolated antibody of the invention to a patient in need thereof for a time sufficient to treat or prevent viral infections.

DETAILED DESCRIPTION OF THE INVENTION

All publications, including but not limited to patents and patent applications, cited in this specification are herein incorporated by reference as though fully set forth.

The term "antagonist" as used herein means a molecule that partially or completely inhibits, by any mechanism, an effect of another molecule such as a receptor or intracellular mediator.

As used herein, a "TRL3 antibody antagonist" or an antibody "reactive with TLR3" describes an antibody that is capable of, directly or indirectly, substantially counteracting, reducing or inhibiting TLR3 biological activity or TLR3 receptor activation. For example, an antibody reactive with TLR3 can bind directly to TLR3 and neutralize TLR3 activity, i.e, block TLR3 signaling to reduce cytokine and chemokine release or NF-κB activation.

The term "antibodies" as used herein is meant in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragments" means a portion of an intact antibody, generally the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies.

An immunoglobulin light or heavy chain variable region consists of a "framework" region interrupted by three "antigen-binding sites". The antigen-binding sites are defined using various terms as follows: (i) the term Complementarity Determining Regions (CDRs) is based on sequence variability (Wu and Kabat, J. Exp. Med. 132:211-250, 1970). Generally, the antigen-binding site has six CDRs; three in the VH (HCDR1, HCDR2, HCDR3), and three in the VL (LCDR1, LCDR2, LCDR3) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hypervariable in structure as defined by Chothia and Lesk (Chothia and Lesk, Mol. Biol. 196:901-917, 1987). Generally, the antigen-binding site has six hypervariable regions, three in VH (H1, H2, H3) and three in VL (L1, L2, L3). Chothia and Lesk refer to structurally conserved HVs as "canonical structures". (iii) The "IMGT-CDRs" as proposed by Lefranc (Lefranc et al., Dev. Comparat. Immunol. 27:55-77, 2003) are based on the comparison of V domains from immunoglobulins and T-cell receptors. The International ImMunoGeneTics (IMGT) database (http://www_imgt_org) provides a standardized numbering and definition of these regions. The correspondence between CDRs, HVs and IMGT delineations is described in Lefranc et al., Dev. Comparat. Immunol. 27:55-77, 2003. (iv) The antigen-binding site can also be delineated based on Specificity Determining Residue Usage (SDRU), according to Almagro (Almagro, Mol. Recognit. 17:132-143, 2004), where Specificity Determining Residues (SDR), refers to amino acid residues of an immunoglobulin that are directly involved in antigen contact. SDRU as defined by Almargo is a precise measure of a number and distribution of SDR for different types of antigens as defined by analyses of crystal structures of antigen-antibody complexes.

The term "composite sequences" as used herein means an antigen-binding site defined to include all amino acid residues delineated individually by Kabat, Chothia or IMGT, or any other suitable antigen-binding region delineation.

"Framework" or "framework sequences" are the remaining sequences of a variable region other than those defined to be antigen-binding site. Because the antigen-binding site can be defined by various terms as described above, the exact amino acid sequence of a framework depends on how the antigen-binding site was defined.

The term "antigen" as used herein means any molecule that has the ability to generate antibodies either directly or indirectly. Included within the definition of "antigen" is a protein-encoding nucleic acid.

The term "homolog" means protein sequences having between 40% and 100% sequence identity to a reference sequence. Homologs of human TLR3 include polypeptides from other species that have between 40% and 100% sequence identity to a known human TLR3 sequence. Percent identity between two peptide chains can be determined by pairwise alignment using the default settings of the AlignX module of Vector NTI v.9.0.0 (Invitrogen, Carslbad, Calif.). By "TLR3" is meant human TLR3 (huTLR3) and its homologs. The nucleotide and amino acid sequences of the full length huTLR3 are shown in SEQ ID NOs: 1 and 2, respectively. The nucleotide and amino acid sequences of the huTLR3 extracellular domain (ECD) are shown in SEQ ID NOs: 3 and 4, respectively.

The term "substantially identical" as used herein means that the two antibody or antibody fragment amino acid sequences being compared are identical or have "insubstantial differences". Insubstantial differences are substitutions of 1, 2, 3, 4, 5 or 6 amino acids in an antibody or antibody fragment amino acid sequence. Amino acid sequences substantially identical to the sequences disclosed herein are also part of this application. In some embodiments, the sequence identity can be about 90%, 91%, 92%, 93%, 94%, 95%, 96%, 97%, 98%, 99% or higher. Percent identity can be determined as described above. Exemplary peptide chains being compared are heavy or light chain variable regions.

The term "in combination with" as used herein means that the described agents can be administered to an animal together in a mixture, concurrently as single agents or sequentially as single agents in any order.

The term "inflammatory condition" as used herein means a localized response to cellular injury that is mediated in part by the activity of cytokines, chemokines, or inflammatory cells (e.g., neutrophils, monocytes, lymphocytes, macrophages) which is characterized in most instances by pain, redness, swelling, and loss of tissue function. The term "inflammatory pulmonary condition" as used herein means an inflammatory condition affecting or associated with the lungs.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., Nature 256: 495-497, 1975. Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Human-adapted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Human framework sequences useful for human-adaptation can be selected from relevant databases by those skilled in the art. Optionally, human-adapted mAbs can be further modified by incorporating altered framework support residues to preserve binding affinity by techniques such as those disclosed in Queen et al., Proc. Natl. Acad. Sci. (USA), 86:10029-10032, 1989 and Hodgson et al., Bio/Technology, 9:421, 1991.

Fully human mAbs lacking any non-human sequences can be prepared from human immunoglobulin transgenic mice by techniques referenced in, e.g., Lonberg et al., Nature 368: 856-859, 1994; Fishwild et al., Nature Biotechnology 14:845-851, 1996; and Mendez et al., Nature Genetics 15:146-156, 1997. Human mAbs can also be prepared and optimized from phage display libraries by techniques referenced in, e.g., Knappik et al., J. Mol. Biol. 296:57-86, 2000; and Krebs et al., J. Immunol. Meth. 254:67-84 2001.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be linear in nature or can be a discontinous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space.

The term "specific binding" as used herein refers to antibody binding to a predetermined antigen with greater affinity than for other antigens or proteins. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen" or "an antigen specific antibody" e.g. a TLR3 specific antibody. The dissociation constant can be measured using standard procedures as described below.

The term "TLR3 biological activity" or "TLR3 activation" as used herein refers to any activity occurring as a result of ligand binding to TLR3. TLR3 ligands include dsRNA, poly (I:C), and endogenous mRNA, e.g., engodenous mRNA released from necrotic cells. An exemplary TLR3 activation results in activation of NF-κB in response to the TLR3 ligand. NF-κB activation can be assayed using a reporter-gene assay upon induction of the receptor with poly(I:C) (Alexopoulou et al., Nature 413:732-738, 2001; Hacker et al., EMBO J. 18:6973-6982, 1999). Another exemplary TLR3 activation results in activation of interferon response factors (IRF-3, IRF-7) in response to TLR3 ligand. TLR3-mediated IRF activation can be assayed using a reporter gene driven by an interferon-stimulated response element (ISRE). Another exemplary TLR3 activation results in secretion of pro-inflammatory cytokines and chemokines, for example TNF-α, IL-6, IL-8, IL-12, CXCL5/IP-10 and RANTES. The release of cytokines and chemokines from cells, tissues or in circulation can be measured using well-known immunoassays, such as an ELISA immunoassay.

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention provides antibody antagonists capable of inhibiting TLR3 biological activity and uses of such antibodies. Such TLR3 antagonists may have the properties of binding TLR3 and inhibiting TLR3 activation. Exemplary mechanisms by which TLR3 activation may be inhibited by such antibodies include in vitro, in vivo or in situ inhibition of ligand binding to TLR3, inhibition of receptor dimerization, inhibition of TLR3 localization to the endosomal compartment, inhibition of kinase activity of downstream signaling pathways, or inhibition of TLR3 mRNA transcription. Other antibody antagonists capable of inhibiting TLR3 activation by other mechanisms are also within the scope of the various aspects and embodiments of the invention. These antagonists are useful as research reagents, diagnostic reagents and therapeutic agents.

Antibody diversity is created by use of multiple germline genes encoding variable regions and a variety of somatic events. The somatic events include recombination of variable (V) gene segments and diversity (D) and joining (J) gene segments to make a complete VH region and the recombination of variable and joining gene segments to make a complete VL region. Antibodies and compositions having identical or similar CDR sequence to those disclosed herein are not likely to have been independently generated. The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, Calif., 1995).

The invention provides novel antigen-binding sites derived from human immunoglobulin gene libraries. The structure for carrying an antigen-binding site is generally an antibody heavy or light chain or portion thereof, where the antigen-binding site is located to a naturally occurring antigen-binding site as determined as described above.

The invention provides an isolated antibody or fragment thereof reactive with TLR3 comprising both a heavy chain and a light chain variable region and wherein the antibody comprises the heavy chain complementarity determining regions (CDR) amino acid sequences 1, 2 and 3 (HCDR1, HCDR2 and HCDR3) and the light chain complementarity determining regions (CDR) amino acid sequences 1, 2 and 3 (LCDR1, LCDR2 and LCDR3) as shown in Table 1a.

TABLE 1a

| mAb | HCDR1 | HCDR2 | HCDR3 | LCDR1 | LCDR2 | LCDR3 |
|---|---|---|---|---|---|---|
| 16 | 52 | 88 | 54 | 49 | 50 | 51 |
| 17 | 58 | 64 | 60 | 55 | 56 | 57 |
| 18 | 70 | 77 | 72 | 67 | 68 | 69 |
| 19 | 82 | 83 | 84 | 79 | 80 | 89 |
| 1 | 46 | 47 | 48 | 43 | 44 | 45 |
| 2 | 52 | 53 | 54 | 49 | 50 | 51 |
| 3 | 58 | 59 | 60 | 55 | 56 | 57 |
| 4 | 61 | 62 | 60 | 55 | 56 | 57 |
| 5 | 61 | 64 | 60 | 55 | 56 | 63 |
| 6 | 61 | 64 | 60 | 55 | 56 | 65 |
| 7 | 61 | 64 | 60 | 55 | 56 | 66 |
| 8 | 70 | 71 | 72 | 67 | 68 | 69 |
| 9 | 70 | 73 | 72 | 67 | 68 | 69 |
| 10 | 70 | 75 | 72 | 67 | 68 | 74 |
| 11 | 70 | 77 | 72 | 67 | 68 | 76 |
| 12 | 70 | 77 | 72 | 67 | 68 | 78 |
| 13 | 82 | 83 | 84 | 79 | 80 | 81 |
| 14 | 82 | 86 | 84 | 79 | 80 | 85 |
| 15* | 82 | 86 | 84 | 79 | 80 | 87 |
| 15** | 111 | 112 | 84 | 109 | 110 | 113 |
| 15-1 | 111 | 114 | 84 | 109 | 110 | 113 |
| 15-2 | 115 | 112 | 84 | 109 | 110 | 113 |
| 15-3 | 116 | 112 | 84 | 109 | 110 | 113 |
| 15-4 | 111 | 117 | 84 | 109 | 110 | 113 |
| 15-5 | 116 | 118 | 84 | 109 | 110 | 113 |
| 15-6 | 116 | 112 | 119 | 109 | 110 | 113 |
| 15-7 | 111 | 112 | 84 | 120 | 110 | 113 |
| 15-8 | 111 | 112 | 84 | 121 | 110 | 113 |
| 15-9 | 116 | 118 | 119 | 109 | 110 | 113 |
| F17 | 61 | 192 | 60 | 55 | 56 | 191 |
| F18 | 70 | 194 | 72 | 67 | 68 | 193 |
| F19 | 82 | 196 | 84 | 79 | 80 | 195 |

In certain embodiments the invention provides an isolated antibody or fragment reactive with TLR3 comprising both a heavy chain and a light chain variable region and wherein the antibody comprises a HCDR2 amino acid sequence as shown in SEQ ID NO: 192, wherein the HCDR2 of SEQ ID NO: 192 is defined as shown in Formula (I):

$$Xaa_6\text{-I-}Xaa_7\text{-}Xaa_8\text{-R-S-}Xaa_9\text{-W-Y-N-D-Y-A-V-S-V-K-S,} \quad (I)$$

wherein

Xaa$_6$ may be Arg or Lys;

Xaa$_7$ may be Tyr, His or Ser;

Xaa$_8$ may be Met, Arg or Tyr; and

Xaa$_8$ may be Lys or Arg.

In other embodiments, the invention provides an isolated antibody or fragment reactive with TLR3 comprising both a heavy chain and a light chain variable region and wherein the antibody comprises a HCDR2 amino acid sequence as shown in SEQ ID NO: 194, wherein the HCDR2 of SEQ ID NO: 194 is defined as shown in Formula (III):

$$\text{I-I-Q-}Xaa_{15}\text{-R-S-K-W-Y-N-}Xaa_{16}\text{-Y-A-}Xaa_{17}\text{-S-V-K-S,} \quad (III)$$

wherein

Xaa$_{15}$ may be Lys, Thr or Ile;

Xaa$_{16}$ may be Asn or Asp; and

Xaa$_{17}$ may be Val or Leu.

In other embodiments, the invention provides an isolated antibody or fragment reactive with TLR3 comprising both a heavy chain and a light chain variable region and wherein the antibody comprises a HCDR2 amino acid sequence as shown in SEQ ID NO: 196, wherein the HCDR2 of SEQ ID NO: 196 is defined as shown in Formula (V):

$$Xaa_{24}\text{-I-D-P-S-D-S-Y-T-N-Y-}Xaa_{25}\text{-P-S-F-Q-G,} \qquad (V)$$

wherein
$Xaa_{24}$ may be Phe or Arg; and
$Xaa_{25}$ may be Ala or Ser.

In other embodiments, the invention provides an isolated antibody or fragment reactive with TLR3 comprising both a heavy chain and a light chain variable region and wherein the antibody comprises a LCDR3 amino acid sequence as shown in SEQ ID NO: 191, wherein the LCDR3 of SEQ ID NO: 191 is defined as shown in Formula (II):

$$Xaa_1\text{-S-Y-D-}Xaa_2\text{-}Xaa_3\text{-}Xaa_4\text{-}Xaa_5\text{-T-V,} \qquad (II)$$

wherein
$Xaa_1$ may be Ala, Gln, Gly or Ser;
$Xaa_2$ may be Gly, Glu or Ser;
$Xaa_3$ may be Asp or Asn;
$Xaa_4$ may be Glu or Ser; and
$Xaa_5$ may be Phe, Ala or Leu.

In other embodiments, the invention provides an isolated antibody or fragment reactive with TLR3 comprising both a heavy chain and a light chain variable region and wherein the antibody comprises a LCDR3 amino acid sequence as shown in SEQ ID NO: 193, wherein the LCDR3 of SEQ ID NO: 193 is defined as shown in Formula (IV):

$$Xaa_{10}\text{-S-Y-D-}Xaa_{11}\text{-P-}Xaa_{12}\text{-}Xaa_{13}\text{-}Xaa_{14}\text{-V,} \qquad (IV)$$

wherein
$Xaa_{10}$ may be Gln or Ser;
$Xaa_{11}$ may be Thr, Glu or Asp;
$Xaa_{12}$ may be Val or Asn;
$Xaa_{13}$ may be Tyr or Phe; and
$Xaa_{14}$ may be Ser, Asn or Gln.

In other embodiments, the invention provides an isolated antibody or fragment reactive with TLR3 comprising both a heavy chain and a light chain variable region and wherein the antibody comprises a LCDR3 amino acid sequence as shown in SEQ ID NO: 195, wherein the LCDR3 of SEQ ID NO: 195 is defined as shown in Formula (VI):

$$Q\text{-}Q\text{-}Xaa_{18}\text{-}Xaa_{19}\text{-}Xaa_{20}\text{-}Xaa_{21\text{-}Xaa22}\text{-}Xaa_{23}\text{-T,} \qquad (VI)$$

wherein
$Xaa_{18}$ may be Tyr, Gly or Ala;
$Xaa_{19}$ may be Gly, Glu or Asn;
$Xaa_{20}$ may be Ser or Thr;
$Xaa_{21}$ may be Val, Ile or Leu;
$Xaa_{22}$ may be Ser or Leu; and
$Xaa_{23}$ may be Ile, Ser, Pro or Tyr.

The invention also provides an isolated antibody or fragment reactive with TLR3 having the heavy chain complementarity determining regions (CDR) amino acid sequences 1,2 and 3 (HCDR1, HCDR2 and HCDR3) and light chain complementarity determining regions (CDR) amino acid sequences 1, 2 and 3 (LCDR1, LCDR2 and LCDR3) as shown in Table 1a.

Antibodies whose antigen-binding site amino acid sequences differ insubstantially from those shown in Table 1a (SEQ ID NOs: 49-121 and 191-196) are encompassed within the scope of the invention. Typically, this involves one or more amino acid substitutions with an amino acid having similar charge, hydrophobic, or stereochemical characteristics. Additional substitutions in the framework regions, in contrast to antigen-binding sites may also be made as long as they do not adversely affect the properties of the antibody. Substitutions may be made to improve antibody properties, for example stability or affinity. One, two, three, four, five or six substitutions can be made to the antigen binding site.

Conservative modifications will produce molecules having functional and chemical characteristics similar to those of the molecule from which such modifications are made. Substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, or (3) the size of the molecule. For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998). Desired amino acid substitutions (whether conservative or non-conservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions are shown in Table 1b.

TABLE 1b

| Original residue | Exemplary substitutions | More Conservative substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems. Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (ACDE-GKNRSYW), and screening the libararies for variants with desired properties, as shown in Example 1. Table 1c shows substitutions made to three parent TLR3 antibody antagonists within the LCDR3 and HCDR2 regions to improve antibody properties.

Depending on delineation of the antigen-binding sites, the antigen-binding site residues of the antibodies of the invention and subsequently the framework residues may vary slightly for each heavy and light chain. Table 2a and 2b shows the antigen-binding site residues of exemplary antibodies of the invention delineated according to Kabat, Chothia and IMGT, and their composite sequences.

TABLE 1c

| Family 17 mAb | | | | LCDR3 | | | | | | | SEQ ID NO: |
|---|---|---|---|---|---|---|---|---|---|---|---|
| 17 | A | S | Y | D | G | D | E | F | T | V | |
| 3 | | | | | | | | | | | |
| 4 | | | | | | | | | | | |
| 5 | Q | | | | E | | S | A | | | |
| 6 | G | | | | S | N | S | L | | | |
| 7 | S | | | | S | | S | L | | | |
| consensus | A, Q, G, S | S | Y | D | G, E, S | D, N | E, S | F, A, L | T | V | 191 |

| Family 17 mAb | | | | | HCDR2 | | | | | | | | | | | SEQ ID NO: |
|---|---|---|---|---|---|---|---|---|---|---|---|---|---|---|---|---|
| 17 | R | I | Y | M | R | S | K | W | Y | N | D | Y | A | V | S | V K S |
| 3 | | | H | R | | | | | | | | | | | | |
| 4 | K | | S | Y | | | R | | | | | | | | | |
| 5 | | | | | | | | | | | | | | | | |
| 6 | | | | | | | | | | | | | | | | |
| 7 | | | | | | | | | | | | | | | | |
| consensus | R, K | I | Y, H, S | M, R, Y | R | S | K, R | W | Y | N | D | Y | A | V | S | V K S | 192 |

| mAb | | | | LCDR3 | | | | | | | SEQ ID NO: |
|---|---|---|---|---|---|---|---|---|---|---|---|
| Family 18A | | | | | | | | | | | |
| 18 | Q | S | Y | D | S | Q | F | S | F | G | V |
| 8 | | | | | | | | | | | |
| 9 | | | | | | | | | | | |
| Family 18B | | | | | | | | | | | |
| 10 | Q | S | Y | D | T | P | V | Y | S | | V |
| 11 | S | | | | E | | N | | F | N | |
| 12 | S | | | | D | | N | | F | Q | |
| consensus | Q, S | S | Y | D | T, E, D | P | V, N | Y, F | S, N, Q | | V | 193 |

| Family 18A, 18B mAb | | | | | HCDR2 | | | | | | | | | SEQ ID NO: |
|---|---|---|---|---|---|---|---|---|---|---|---|---|---|---|
| 18 | I | I | Q | K | R | S | K | W | Y | N | N | Y | A | V | S V K S |
| 8 | | | | T | | | | | | | D | | | | |
| 9 | | | | I | | | | | | | D | | | L | |
| 10 | | | | | | | | | | | | | | | |
| 11 | | | | | | | | | | | | | | | |
| 12 | | | | | | | | | | | | | | | |
| consensus | I | I | Q | K, T, I | R | S | K | W | Y | N | N, D | Y | A | V, L | S V K S | 194 |

| Family 19 mAb | | | | LCDR2 | | | | | SEQ ID NO: |
|---|---|---|---|---|---|---|---|---|---|
| 19 | Q | Q | Y | G | S | V | S | I | T |
| 13 | | | G | E | S | I | L | S | |
| 14 | | | A | E | T | | | P | |
| 15 | | | G | N | T | L | | Y | |
| 15-1 | | | G | N | T | L | | Y | |
| 15-2 | | | G | N | T | L | | Y | |
| 15-3 | | | G | N | T | L | | Y | |
| 15-4 | | | G | N | T | L | | Y | |
| 15-5 | | | G | N | T | L | | Y | |
| 15-6 | | | G | N | T | L | | Y | |
| 15-7 | | | G | N | T | L | | Y | |
| 15-8 | | | G | N | T | L | | Y | |
| 15-9 | | | G | N | T | L | | Y | |
| consensus | Q | Q | Y, G, A | G, E, N | S, T | V, I, L | S, L | I, S, P, Y | T | 195 |

TABLE 1c-continued

| Family 19 mAb | HCDR2 | | | | | | | | | | | | | | SEQ ID NO: |
|---|---|---|---|---|---|---|---|---|---|---|---|---|---|---|---|
| 19 | F | I | D | P | S | D | S | Y | T | N | Y | A | P | S | F | Q | G | |
| 13 | | | | | | | | | | | | | | | | | | |
| 14 | | | | | | | | | | | | | | | | | | |
| 15 | | | | | | | | | | | | | | | | | | |
| 15.1 | R | | | | | | | | | | | | | | | | | |
| 15.2 | | | | | | | | | | | | | | | | | | |
| 15.3 | | | | | | | | | | | | | | | | | | |
| 15.4 | | | | | | | | | | | | | S | | | | | |
| 15.5 | R | | | | | | | | | | | | S | | | | | |
| 15.6 | | | | | | | | | | | | | | | | | | |
| 15.7 | | | | | | | | | | | | | | | | | | |
| 15-8 | | | | | | | | | | | | | | | | | | |
| 15-9 | R | | | | | | | | | | | | S | | | | | |
| consensus | F,R | I | D | P | S | D | S | Y | T | N | Y | A,S | P | S | F | Q | G | 196 |

*consensus based on mAbs 10, 11, 12

TABLE 2a

| mAb | CDR definition | HCDR1 SEQ ID | Sequence | HCDR2 SEQ ID | Sequence | HCDR3 SEQ ID | Sequence |
|---|---|---|---|---|---|---|---|
| 14 | IMGT | 82 | GYSFTNYW | 86 | IDPSDSYTNY | 84 | ARELYQGYMDTFDS |
| 14 | Kabat | | NYWVG | | FIDPSDSYTNYAPSFQ | | ELYQGYMDTFDS |
| 14 | Chothia | | GYSFT | | PSDSYT | | LYQGYMDTFD |
| 14 | Consensus | 111 | GYSFTNYWVG | 112 | FIDPSDSYTNYAPSFQ | 84 | ARELYQGYMDTFDS |
| 15 | IMGT | 82 | GYSFTNYW | 86 | IDPSDSYTNY | 84 | ARELYQGYMDTFDS |
| 15 | Kabat | | NYWVG | | FIDPSDSYTNYAPSFQ | | ELYQGYMDTFDS |
| 15 | Chothia | | GYSFT | | PSDSYT | | LYQGYMDTFD |
| 15 | Consensus | 111 | GYSFTNYWVG | 112 | FIDPSDSYTNYAPSFQ | 84 | ARELYQGYMDTFDS |
| 15-1 | IMGT | 82 | GYSFTNYW | 86 | IDPSDSYTNY | 84 | ARELYQGYMDTFDS |
| 15-1 | Kabat | | NYWVG | | RIDPSDSYTNYAPSFQ | | ELYQGYMDTFDS |
| 15-1 | Chothia | | GYSFT | | PSDSYT | | LYQGYMDTFD |
| 15-1 | Consensus | 111 | GYSFTNYWVG | 114 | RIDPSDSYTNYAPSFQ | 84 | ARELYQGYMDTFDS |
| 15-2 | IMGT | 82 | GYSFTNYW | 86 | IDPSDSYTNY | 84 | ARELYQGYMDTFDS |
| 15-2 | Kabat | | NYWIG | | FIDPSDSYTNYAPSFQ | | ELYQGYMDTFDS |
| 15-2 | Chothia | | GYSFT | | PSDSYT | | LYQGYMDTFD |
| 15-2 | Consensus | 115 | GYSFTNYWIG | 112 | FIDPSDSYTNYAPSFQ | 84 | ARELYQGYMDTFDS |
| 15-3 | IMGT | 82 | GYSFTNYW | 86 | IDPSDSYTNY | 84 | ARELYQGYMDTFDS |
| 15-3 | Kabat | | NYWIS | 86 | FIDPSDSYTNYAPSFQ | 84 | ELYQGYMDTFDS |
| 15-3 | Chothia | | GYSFT | | PSDSYT | | LYQGYMDTFD |
| 15-3 | Consensus | 116 | GYSFTNYWIS | 112 | FIDPSDSYTNYAPSFQ | 84 | ARELYQGYMDTFDS |
| 15-4 | IMGT | 82 | GYSFTNYW | 86 | IDPSDSYTNY | 84 | ARELYQGYMDTFDS |
| 15-4 | Kabat | | NYWVG | | FIDPSDSYTNYSPSFQ | | ELYQGYMDTFDS |
| 15-4 | Chothia | | GYSFT | | PSDSYT | | LYQGYMDTFD |
| 15-4 | Consensus | 111 | GYSFTNYWVG | 117 | FIDPSDSYTNYSPSFQ | 84 | ARELYQGYMDTFDS |
| 15-5 | IMGT | 82 | GYSFTNYW | 86 | IDPSDSYTNY | 84 | ARELYQGYMDTFDS |

TABLE 2a-continued

| mAb | CDR definition | HCDR1 SEQ ID | Sequence | HCDR2 SEQ ID | Sequence | HCDR3 SEQ ID | Sequence |
|---|---|---|---|---|---|---|---|
| 15-5 | Kabat | | NYWIS | | RIDPSDSYTNYSPSFQ | | ELYQGYMDTFDS |
| 15-5 | Chothia | | GYSFT | | PSDSYT | | LYQGYMDTFD |
| 15-5 | Consensus | 116 | GYSFTNYWIS | 118 | RIDPSDSYTNYSPSFQ | 84 | ARELYQGYMDTFDS |
| 15-6 | IMGT | 82 | GYSFTNYW | 86 | IDPSDSYTNY | | ARQLYQGYMDTFDS |
| 15-6 | Kabat | | NYWIS | | FIDPSDSYTNYAPSFQ | | QLYQGYMDTFDS |
| 15-6 | Chothia | | GYSFT | | PSDSYT | | LYQGYMDTFD |
| 15-6 | Consensus | 116 | GYSFTNYWIS | 112 | FIDPSDSYTNYAPSFQ | 119 | ARQLYQGYMDTFDS |
| 15-7 | IMGT | 82 | GYSFTNYW | 86 | IDPSDSYTNY | 84 | ARELYQGYMDTFDS |
| 15-7 | Kabat | | NYWVG | | FIDPSDSYTNYAPSFQ | | ELYQGYMDTFDS |
| 15-7 | Chothia | | GYSFT | | PSDSYT | | LYQGYMDTFD |
| 15-7 | Consensus | 111 | GYSFTNYWVG | 112 | FIDPSDSYTNYAPSFQ | 84 | ARELYQGYMDTFDS |
| 15-8 | IMGT | 82 | GYSFTNYW | 86 | IDPSDSYTNY | 84 | ARELYQGYMDTFDS |
| 15-8 | Kabat | | NYWVG | | FIDPSDSYTNYAPSFQ | | ELYQGYMDTFDS |
| 15-8 | Chothia | | GYSFT | | PSDSYT | | LYQGYMDTFD |
| 15-8 | Consensus | 111 | GYSFTNYWVG | 112 | FIDPSDSYTNYAPSFQ | 84 | ARELYQGYMDTFDS |
| 15-9 | IMGT | 82 | GYSFTNYW | 86 | IDPSDSYTNY | 119 | ARQLYQGYMDTFDS |
| 15-9 | Kabat | | NYWIS | | RIDPSDSYTNYSPSFQG | | QLYQGYMDTFDS |
| 15-9 | Chothia | | GYSFT | | PSDSYT | | LYQGYMDTFD |
| 15-9 | Consensus | 116 | GYSFTNYWIS | 118 | RIDPSDSYTNYSPSFQG | 119 | ARQLYQGYMDTFDS |

In other embodiments, the invention provides an isolated antibody or fragment reactive with TLR3 comprising both a heavy chain and a light chain variable region and wherein the antibody comprises the amino acid sequences of the heavy chain variable (VH) and the light chain variable (VL) regions and also provides for each isolated heavy chain variable and light chain variable region as shown in Table 3a. F17, F18 and F19 represent antibody variants comprising consensus amino acid sequences for families 17, 18 and 19, respectively (see Example 1).

TABLE 2b

| mAb | CDR definition | LCDR1 SEQ ID NO: | Sequence | LCDR2 SEQ ID NO: | Sequence | LCDR3 SEQ ID NO: | Sequence |
|---|---|---|---|---|---|---|---|
| 14 | IMGT | 79 | QSIGLY | 80 | AAS | 85 | QQAETVSPT |
| 14 | Kabat | | RASQSIGLYLA | | AASSLQS | | QQAETVSPT |
| 14 | Chothia | | SQSIGLY | | AAS | | AETVSP |
| 14 | Consensus | 109 | RASQSIGLYLA | 110 | AASSLQS | 85 | QQAETVSPT |
| 15 | IMGT | 79 | QSIGLY | 80 | AAS | 87 | QQGNTLSYT |
| 15 | Kabat | | RASQSIGLYLA | | AASSLQS | | QQGNTLSYT |
| 15 | Chothia | | SQSIGLY | | AAS | | GNTLSY |
| 15 | Consensus | 109 | RASQSIGLYLA | 110 | AASSLQS | 113 | QQGNTLSYT |
| 15-1 | IMGT | 79 | QSIGLY | 80 | AAS | 87 | QQGNTLSYT |

TABLE 2b-continued

| mAb | CDR definition | LCDR1 SEQ ID NO: | LCDR1 Sequence | LCDR2 SEQ ID NO: | LCDR2 Sequence | LCDR3 SEQ ID NO: | LCDR3 Sequence |
|---|---|---|---|---|---|---|---|
| 15-1 | Kabat | | RASQSIGLYLA | | AASSLQS | | QQGNTLSYT |
| 15-1 | Chothia | | SQSIGLY | | AAS | | GNTLSY |
| 15-1 | Consensus | 109 | RASQSIGLYLA | 110 | AASSLQS | 113 | QQGNTLSYT |
| 15-2 | IMGT | 79 | QSIGLY | 80 | AAS | 87 | QQGNTLSYT |
| 15-2 | Kabat | | RASQSIGLYLA | | AASSLQS | | QQGNTLSYT |
| 15-2 | Chothia | | SQSIGLY | | AAS | | GNTLSY |
| 15-2 | Consensus | 109 | RASQSIGLYLA | 110 | AASSLQS | 113 | QQGNTLSYT |
| 15-3 | IMGT | 79 | QSIGLY | 80 | AAS | 87 | QQGNTLSYT |
| 15-3 | Kabat | | RASQSIGLYLA | | AASSLQS | | QQGNTLSYT |
| 15-3 | Chothia | | SQSIGLY | | AAS | | GNTLSY |
| 15-3 | Consensus | 109 | RASQSIGLYLA | 110 | AASSLQS | 113 | QQGNTLSYT |
| 15-4 | IMGT | 79 | QSIGLY | 80 | AAS | 87 | QQGNTLSYT |
| 15-4 | Kabat | | RASQSIGLYLA | | AASSLQS | | QQGNTLSYT |
| 15-4 | Chothia | | SQSIGLY | | AAS | | GNTLSY |
| 15-4 | Consensus | 109 | RASQSIGLYLA | 110 | AASSLQS | 113 | QQGNTLSYT |
| 15-5 | IMGT | 79 | QSIGLY | 80 | AAS | 87 | QQGNTLSYT |
| 15-5 | Kabat | | RASQSIGLYLA | | AASSLQS | | QQGNTLSYT |
| 15-5 | Chothia | | SQSIGLY | | AAS | | GNTLSY |
| 15-5 | Consensus | 109 | RASQSIGLYLA | 110 | AASSLQS | 113 | QQGNTLSYT |
| 15-6 | IMGT | 79 | QSIGLY | 80 | AAS | 87 | QQGNTLSYT |
| 15-6 | Kabat | | RASQSIGLYLA | | AASSLQS | | QQGNTLSYT |
| 15-6 | Chothia | | SQSIGLY | | AAS | | GNTLSY |
| 15-6 | Consensus | 109 | RASQSIGLYLA | 110 | AASSLQS | 113 | QQGNTLSYT |
| 15-7 | IMGT | | QSISSY | 80 | AAS | 87 | QQGNTLSYT |
| 15-7 | Kabat | | RASQSISSYLA | | AASSLQS | | QQGNTLSYT |
| 15-7 | Chothia | | SQSISSY | | AAS | | GNTLSY |
| 15-7 | Consensus | 120 | RASQSISSYLA | 110 | AASSLQS | 113 | QQGNTLSYT |
| 15-8 | IMGT | 79 | QSIGLY | 80 | AAS | 87 | QQGNTLSYT |
| 15-8 | Kabat | | RASQSIGLYLN | | AASSLQS | | QQGNTLSYT |
| 15-8 | Chothia | | SQSIGLY | | AAS | | GNTLSY |
| 15-8 | Consensus | 121 | RASQSIGLYLN | 110 | AASSLQS | 113 | QQGNTLSYT |
| 15-9 | IMGT | 79 | QSIGLY | 80 | AAS | 87 | QQGNTLSYT |
| 15-9 | Kabat | | RASQSIGLYLA | | AASSLQS | | QQGNTLSYT |
| 15-9 | Chothia | | SQSIGLY | | AAS | | GNTLSY |
| 15-9 | Consensus | 109 | RASQSIGLYLA | 110 | AASSLQS | 113 | QQGNTLSYT |

TABLE 3a

| mAb | VH (SEQ ID NO:) | VL (SEQ ID NO:) |
|---|---|---|
| 16 | 6 | 5 |
| 17 | 8 | 7 |
| 18 | 10 | 9 |
| 19 | 12 | 11 |
| 1 | 14 | 13 |
| 2 | 16 | 15 |
| 3 | 18 | 17 |
| 4 | 20 | 19 |
| 5 | 22 | 21 |
| 6 | 24 | 23 |
| 7 | 26 | 25 |
| 8 | 28 | 27 |
| 9 | 30 | 29 |
| 10 | 32 | 31 |
| 11 | 34 | 33 |
| 12 | 36 | 35 |
| 13 | 38 | 37 |
| 14 | 40 | 39 |
| 15 | 42 | 41 |
| 15-1 | 124 | 41 |
| 15-2 | 125 | 41 |
| 15-3 | 126 | 41 |
| 15-4 | 127 | 41 |
| 15-5 | 128 | 41 |
| 15-6 | 129 | 41 |
| 15-7 | 42 | 122 |
| 15-8 | 42 | 123 |
| 15-9 | 159 | 41 |
| F17 | 198 | 197 |
| F18 | 200 | 199 |
| F19 | 202 | 201 |
| c1811 | 164 | 163 |
| 9QVQ/QSV | 212 | 209 |
| 10QVQ/QSV | 213 | 210 |
| 12QVQ/QSV | 214 | 211 |
| 14EVQ | 215 | 39 |
| 15EVQ | 216 | 41 |

Although the embodiments illustrated in the Examples comprise pairs of variable regions, one from a heavy and one from a light chain, a skilled artisan will recognize that alternative embodiments may comprise single heavy or light chain variable regions. The single variable region can be used to screen for variable domains capable of forming a two-domain specific antigen-binding fragment capable of, for example, binding to TLR3. The screening may be accomplished by phage display screening methods using for example hierarchical dual combinatorial approach disclosed in PCT Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described.

In other embodiments, the invention provides an isolated antibody or fragment reactive with TLR3 comprising both a heavy chain and a light chain variable regions having amino acid sequences at least 95% identical to the variable region amino acid sequence as shown in Table 3a.

In another aspect, the invention provides an isolated antibody having certain heavy chain and light chain amino acid sequences as shown in Table 3b.

Another aspect of the invention is isolated polynucleotides encoding any of the antibodies of the invention or their complement. Certain exemplary polynucleotides are disclosed herein, however, other polynucleotides which, given the degeneracy of the genetic code or codon preferences in a given expression system, encode the antibody antagonists of the invention are also within the scope of the invention.

Exemplary antibody antagonists may be antibodies of the IgG, IgD, IgG, IgA or IgM isotypes. Additionally, such antibody antagonists can be post-translationally modified by processes such as glycosylation, isomerization, deglycosylation or non-naturally occurring covalent modification such as the addition of polyethylene glycol (PEG) moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function. See Deckert et al., Int. J. Cancer 87:382-390, 2000; Knight et al., Platelets 15:409-418, 2004; Leong et al., Cytokine 16:106-119, 2001; and Yang et al., Protein Eng. 16:761-770, 2003.

TABLE 3b

| mAb | Heavy chain SEQ ID NO: | Light chain SEQ ID NO: |
|---|---|---|
| 14 | 102 | 155 |
| 15 | 102 | 156 |
| 15-1 | 130 | 156 |
| 15-2 | 131 | 156 |
| 15-3 | 132 | 156 |
| 15-4 | 133 | 156 |
| 15-5 | 134 | 156 |
| 15-6 | 135 | 156 |
| 15-7 | 102 | 157 |
| 15-8 | 102 | 158 |
| 15-9 | 160 | 156 |
| F17 | 204 | 203 |
| F18 | 206 | 205 |
| F19 | 208 | 207 |
| 14EVQ | 220 | 155 |
| 15EVQ | 220 | 156 |
| 5429 | 166 | 165 |
| c1811 | 168 | 167 |

Pharmacokinetic properties of the antibodies of the invention could also be enhanced through Fc modifications by techniques known to those skilled in the art. For example, IgG4 isotype heavy chains contain a Cys-Pro-Ser-Cys (CPSC) motif in the hinge region capable of forming either inter- or intra-heavy chain disulfide bonds, i.e., the two Cys residues in the CPSC motif may disulfide bond with the corresponding Cys residues in the other heavy chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, Immunology 105: 9-19, 2002). Accordingly, since the heavy:light chain (H:L) pairs in those IgG4 molecules with intra-heavy chain bonds in the hinge region are not covalently associated with each other, they may dissociate into H:L monomers that then reassociate with H:L monomers derived from other IgG4 molecules forming bispecific, heterodimeric IgG4 molecules. In a bispecific IgG antibody the two Fabs of the antibody molecule differ in the epitopes that they bind. Substituting the Ser residue in the hinge region CPSC motif of IgG4 with Pro results in "IgG1-like behavior," i.e., the molecules form stable disulfide bonds between heavy chains and therefore, are not susceptible to H:L exchange with other IgG4 molecules. In one embodiment, the antibodies of the invention will comprise an IgG4 Fc domain with a S to P mutation in the CPSC motif. The location of the CPSC motif is typically found at residue 228 of a mature heavy chain but can change depending on CDR lengths.

Further, sites can be removed that affect binding to Fc receptors other than an FcRn salvage receptor in the antibodies of the invention. For example, the Fc receptor binding regions involved in ADCC activity can be removed in the antibodies of the invention. For example, mutation of Leu234/Leu235 in the hinge region of IgG1 to L234A/L235A or Phe235/Leu236 in the hinge region of IgG4 to P235A/L236A minimizes FcR binding and reduces the ability of the immunoglobulin to mediate complement dependent cytotoxicity and ADCC. In one embodiment, the antibodies of the invention will comprise an IgG4 Fc domain with P235A/L236A mutations. The location of these residues identified above is typical in a mature heavy chain but can change depending on CDR lengths. Exemplary antibodies having P235A/L236A mutations are antibodies having heavy chains encoded by sequence shown in SEQ ID NOs: 218, 219 or 220.

Fully human, human-adapted, humanized and affinity-matured antibody molecules or antibody fragments are within the scope of the invention as are fusion proteins and chimeric proteins. Antibody affinity towards an antigen may be improved by rational design or random affinity maturation using well-known methods such as random or directed mutagenesis, or employing phage display libraries. For example, variation of Vernier Zone residues that mostly reside in the framework region can be employed to modulate affinity of an antibody as described in U.S. Pat. No. 6,639,055. Recently, Almagro et al. defined "Affinity Determining Residues", ADRs, that reside in the CDRs, and whose engineering can increase affinity (Cobaugh et al., J Mol. Biol. 378: 622-633, 2008).

Fully human, human-adapted, humanized, affinity-matured antibody molecules or antibody fragments modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., J. Mol. Biol., 305:989-1010, 2001). Potential structure destabilizing residues may be identified based upon the crystal structure of the antibody or by molecular modeling in certain cases, and the effect of the residues on antibody stability can be tested by generating and evaluating variants harboring mutations in the identified residues. One of the ways to increase antibody stability is to raise the thermal transition midpoint (Tm) as measured by differential scanning calorimetry (DSC). In general, the protein Tm is correlated with its stability and inversely correlated with its susceptibility to unfolding and denaturation in solution and the degradation processes that depend on the tendency of the protein to unfold (Remmele et al., Biopharm., 13:36-46, 2000). A number of studies have found correlation between the ranking of the physical stability of formulations measured as thermal stability by DSC and physical stability measured by other methods (Gupta et al., AAPS PharmSci. 5E8, 2003; Zhang et al., J. Pharm. Sci. 93:3076-3089, 2004; Maa et al., Int. J. Pharm., 140:155-168, 1996; Bedu-Addo et al., Pharm. Res., 21:1353-1361, 2004; Remmele et al., Pharm. Res., 15:200-208, 1997). Formulation studies suggest that a Fab Tm has implication for long-term physical stability of a corresponding mAb. Differences in amino acids in either framework or within the CDRs could have significant effects on the thermal stability of the Fab domain (Yasui, et al., FEBS Lett. 353:143-146, 1994).

The antibody antagonists of the invention may bind TLR3 with a $K_d$ less than or equal to about $10^{-7}$, $10^{-8}$, $10^{-9}$, $10^{-10}$, $10^{-11}$ or $10^{-12}$ M. The affinity of a given molecule for TLR3, such as an antibody can be determined experimentally using any suitable method. Such methods may utilize Biacore or KinExA instrumentation, ELISA or competitive binding assays known to those skilled in the art.

Antibody antagonists binding a given TLR3 homolog with a desired affinity can be selected from libraries of variants or fragments by techniques including antibody affinity maturation. Antibody antagonists can be identified based on their inhibition of TLR3 biological activity using any suitable method. Such methods may utilize reporter-gene assays or assays measuring cytokine production using well known methods and as described in the application.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means.

Another embodiment of the invention is a host cell comprising any of the polynucleotides of the invention such as a polynucleotide encoding a polypeptide comprising an immunoglobulin heavy chain variable region having the amino acid sequence shown in SEQ ID NO: 6, 8, 10, 12, 14, 16, 18, 20, 22, 24, 26, 28, 30, 32, 34, 36, 38, 40, 42, 124, 125, 126, 127, 128, 129, 159, 198, 200, 202, 164, 212, 213, 214, 215 or 216 or an immunoglobulin light chain variable region having the amino acid sequence shown in SEQ ID NO: 5, 7, 9, 11, 13, 15, 17, 19, 21, 23, 25, 27, 29, 31, 33, 35, 37, 39, 41, 122, 123, 197, 199, 201, 163, 209 or 210.

Another embodiment of the invention is a host cell comprising a polynucleotide encoding a polypeptide comprising an immunoglobulin heavy chain having the amino acid sequence shown in SEQ ID NO: 102, 130, 131, 132, 133, 134, 135, 160, 204, 206, 208, 220, 166 or 168, or an immunoglobulin light chain having the amino acid sequence shown in SEQ ID NO: 155, 156, 157, 158, 203, 205, 207, 165 or 167. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of making an antibody reactive with TLR3 comprising culturing a host cell of the invention and recovering the antibody produced by the host cell. Methods of making antibodies and purifying them are well known in the art.

Another embodiment of the invention is a hybridoma cell line that produces an antibody of the invention.

Another embodiment of the invention is an isolated antibody or fragment thereof that is reactive with TLR3, wherein the antibody binds at least one TLR3 amino acid residue selected from a group consisting of (a) residues K467, R488, or R489 of SEQ ID NO: 2; (b) residue K467 of SEQ ID NO: 2; (c) residue R489 of SEQ ID NO: 2; (d) residues K467 and R489 of SEQ ID NO: 2; and (e) residues K467, R488, and R489 of SEQ ID NO: 2. The isolated antibody may further bind at least one TLR3 amino acid residue selected from the residues Y465, Y468, N517, D536, Q538, H539, N541, E570 or K619 of SEQ ID NO:2.

Another embodiment of the invention is isolated antibody or fragment thereof, wherein the antibody binds at least on TLR3 amino acid residue selected from a group consisting of residues D116 or K145 of SEQ ID NO: 2.

Several well known methodologies can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding. For large proteins such as TLR3, point mutagenesis mapping is simplified when the binding site is first localized to a region on the protein, such as by docking, segment mutagenesis or H/D exchange.

Another aspect of the invention is an isolated antibody or fragment thereof reactive with TLR3 that competes for TLR3 binding with a monoclonal antibody, wherein the monoclonal antibody comprises the amino acid sequences of certain heavy chain complementarity determining regions (CDRs) 1, 2 and 3, the amino acid sequences of certain light chain CDRs 1, 2 and 3, the amino acid sequences of certain heavy chain variable regions (VH) or the amino acid sequence of certain light chain variable regions (VL). Exemplary monoclonal antibodies of the invention are an isolated antibody comprising a heavy chain variable region having an amino acid sequence shown in SEQ ID NO: 216 and a light chain variable region amino acid sequence shown in SEQ ID NO: 41, and an antibody comprising a heavy chain variable region having an amino acid sequence shown in SEQ ID NO: 214 and a light chain variable region amino acid sequence shown in SEQ ID NO: 211.

Competition between binding to TLR3 can be assayed in vitro using well known methods. For example, binding of MSD Sulfo-Tag™NHS-ester -labeled antibody to TLR3 in the presence of an unlableled antibody can be assessed by ELISA. Exemplary antibodies of the invention are mAb 12, mAb 15 and mAb c1811 (see Table 3a). Previously described anti-TLR3 antibodies c1068 and its derivatives (described in PCT Publ. No. WO06/060513A2), TLR3.7 (eBiosciences, cat no 14-9039) and Imgenex IMG-315A (Imgenex IMG-315A; generated against human TLR3 amino acids amino acids 55-70, VLNLTHNQLRRLPAAN, residues 55-70 of SEQ ID NO: 2) do not compete with binding to TLR3with mAbs 12, 15 or c1811 as shown in Example 5.

Another aspect of the invention is an isolated antibody reactive with TLR3, wherein the antibody has at least one of the following properties:
a. reduces human TLR3 biological activity in an in vitro poly(I:C) NF-kB reporter gene assay >50% at <1 μg/ml;
b. inhibits >60% of IL-6 or CXCL5/IP-10 production from BEAS-2B cells stimulated with <100 ng/ml poly(I:C) at <10 μg/ml;
c. inhibits >50% of IL-6 or CXCL5/IP-10 production from BEAS-2B cells stimulated with <100 ng/ml poly(I:C) at <0.4 μg/ml;
d. inhibits >50% of IL-6 production from NHBE cells stimulated with 62.5 ng/ml poly(I:C) at <5 μg/ml;
e. inhibits >50% of IL-6 production from NHBE cells stimulated with 62.5 ng/ml poly(I:C) at <1 μg/ml;
f. inhibits >20% of poly(I:C)-induced IFN-γ, IL-6 or IL-12 production by PBMC cells at <1 μg/ml.
g. inhibits cynomologus TLR3 biological activity in an in vitro NF-kB reporter gene assay with IC50<10 μg/ml; or
h. inhibits cynomologus TLR3 biological activity in an in vitro ISRE reporter gene assay with IC50<5 μg/ml.

Methods of Treatment

TLR3 antagonists of the invention, for example TLR3 antibody antagonists, can be used to modulate the immune system. While not wishing to be bound by any particular theory, the antagonists of the invention may modulate the immune system by preventing or reducing ligand binding to TLR3, dimerization of TLR3, TLR3 internalization or TLR3 trafficking. The methods of the invention may be used to treat an animal patient belonging to any classification. Examples of such animals include mammals such as humans, rodents, dogs, cats and farm animals. For example, the antibodies of the invention are useful in antagonizing TLR3 activity, in the treatment of inflammation, inflammatory and metabolic diseases and are also useful in the preparation of a medicament for such treatment wherein the medicament is prepared for administration in dosages defined herein.

Generally, inflammatory conditions, infection-associated conditions or immune-mediated inflammatory disorders that may be prevented or treated by administration of the TLR3 antibody antagonists of the invention include those mediated by cytokines or chemokines and those conditions which result wholly or partially from activation of TLR3 or signaling through the TLR3 pathway. Examples of such inflammatory conditions include sepsis-associated conditions, inflammatory bowel diseases, autoimmune disorders, inflammatory disorders and infection-associated conditions. It is also thought that cancers, cardiovascular and metabolic conditions, neurologic and fibrotic conditions can be prevented or treated by administration of the TLR3 antibody antagonists of the invention. Inflammation may affect a tissue or be systemic. Exemplary affected tissues are the respiratory tract, lung, the gastrointestinal tract, small intestine, large intestine, colon, rectum, the cardiovascular system, cardiac tissue, blood vessels, joint, bone and synovial tissue, cartilage, epithelium, endothelium, hepatic or adipose tissue. Exemplary systemic inflammatory conditions are cytokine storm or hypercytokinemia, systemic inflammatory response syndrome (SIRS), graft versus host disease (GVHD), acute respiratory distress syndrome (ARDS), severe acute respiratory distress syndrome (SARS), catastrophic anti-phospholipid syndrome, severe viral infections, influenza, pneumonia, shock, or sepsis.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g. asthma, psoriasis, arthritis, rheumatoid arthritis, multiple sclerosis, inflammatory bowel disease and the like), septic shock and multiple organ failure. Importantly, these diverse disease states share common inflammatory mediators, such as cytokines, chemokines, inflammatory cells and other mediators secreted by these cells.

TLR3 activation by its ligands poly(I:C), dsRNA or endogenous mRNA leads to activation of signaling pathways resulting in synthesis and secretion of pro-inflammatory cytokines, activation and recruitment of inflammatory cells, such as macrophages, granulocytes, neutrophils and eosinophils, cell death, and tissue destruction. TLR3 induces secretion of IL-6, IL-8, IL-12, TNF-α, MIP-1, CXCL5/IP-10 and RANTES, and other pro-inflammatory cytokines and chemokines implicated in immune cell recruitment and activation, thus contributing to tissue destruction in autoimmune and other inflammatory diseases. TLR3 ligand endogenous mRNA is released from necrotic cells during inflammation, and may result in a positive feedback loop to activate TLR3 and perpetuate inflammation and further tissue damage. TLR3 antagonists, such as TLR3 antibody antagonists, may normalize cytokine secretion, reduce recruitment of inflammatory cells, and reduce tissue damage and cell death. Therefore, TLR3 antagonists have therapeutic potential to treat inflammation and a spectrum of inflammatory conditions.

One example of an inflammatory condition is sepsis-associated condition that may include systemic inflammatory response syndrome (SIRS), septic shock or multiple organ dysfunction syndrome (MODS). dsRNA released by viral, bacterial, fungal, or parasitic infection and by necrotic cells can contribute to the onset of sepsis. While not wishing to be bound by any particular theory, it is believed that treatment with TLR3 antagonists can provide a therapeutic benefit by extending survival times in patients suffering from sepsis-associated inflammatory conditions or prevent a local inflammatory event (e.g., in the lung) from spreading to become a systemic condition, by potentiating innate antimicrobial activity, by demonstrating synergistic activity when combined with antimicrobial agents, by minimizing the local inflammatory state contributing to the pathology, or any combination of the foregoing. Such intervention may be sufficient to permit additional treatment (e.g., treatment of underlying infection or reduction of cytokine levels) necessary to ensure patient survival. Sepsis can be modeled in animals, such as mice, by the administration of D-galactosamine and poly(I:C). In such models, D-galactosamine is a hepatotoxin which functions as a sepsis sensitizer and poly(I:C) is a sepsis-inducing molecule that mimics dsRNA and activates TLR3. TLR3 antagonist treatment may increase animal survival rates in a murine model of sepsis, and thus TLR3 antagonists may be useful in the treatment of sepsis.

Gastrointestinal inflammation is inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Mucosal layer may be mucosa of the bowel (including the small intestine and large intestine), rectum, stomach (gastric) lining, or oral cavity. Exemplary chronic gastrointestinal inflammatory conditions are inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), infections colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., *Helicobacter pylori*-infected chronic active gastritis) and other forms of gastrointestinal inflammation caused by an infectious agent.

Inflammatory bowel disease (IBD) includes a group of chronic inflammatory disorders of generally unknown etiology, e.g., ulcerative colitis (UC) and Crohn's disease (CD). Clinical and experimental evidence suggest that the pathogenesis of IBD is multifactorial involving susceptibility genes and environmental factors. In inflammatory bowel disease, the tissue damage results from an inappropriate or exaggerated immune response to antigens of the gut microflora. Several animal models for inflammatory bowel diseases exist. Some of the most widely used models are the 2,4,6-trinitrobenesulfonic acid/ethanol (TNBS)-induced colitis model or the oxazalone model, which induce chronic inflammation and ulceration in the colon (Neurath et al., Intern. Rev. Immunol 19:51-62, 2000). Another model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration (Hendrickson et al., Clinical Microbiology Reviews 15:79-94, 2002). Another model involves the adoptive transfer of naïve $CD45RB^{high}$ CD4 T cells to RAG or SCID mice. In this model, donor naïve T cells attack the recipient gut causing chronic bowel inflammation and symptoms similar to human inflammatory bowel diseases (Read and Powrie, Curr. Protoc. Immunol. Chapter 15 unit 15.13, 2001). The administration of antagonists of the present invention in any of these models can be used to evaluate the potential efficacy of those antagonists to ameliorate symptoms and alter the course of diseases associated with inflammation in the gut, such as inflammatory bowel disease. Several treatment options for IBD are available, for example anti-TNF-α antibody therapies have been used for a decade to treat Crohn's disease (Van Assche et al., Eur. J. Pharmacol. Epub October 2009). However, a significant percentage of patients are refractory to the current treatments (Hanauer et al., Lancet 359:1541-1549, 2002; Hanauer et al., Gastroenterology 130:323-333, 2006), and thus new therapies targeting refractory patient populations are needed.

Another example of an inflammatory condition is an inflammatory pulmonary condition. Exemplary inflammatory pulmonary conditions include infection-induced pulmonary conditions including those associated with viral, bacterial, fungal, parasite or prion infections; allergen-induced pulmonary conditions; pollutant-induced pulmonary conditions such as asbestosis, silicosis, or berylliosis; gastric aspiration-induced pulmonary conditions, immune dysregulation, inflammatory conditions with genetic predisposition such as as cystic fibrosis, and physical trauma-induced pulmonary conditions, such as ventilator injury. These inflammatory conditions also include asthma, emphysema, bronchitis, chronic obstructive pulmonary disease (COPD), sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, rotavirus infection, human metapneumovirus infection, respiratory syncitial virus infection and *aspergillus* or other fungal infections. Exemplary infection-associated inflammatory diseases may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection.

Asthma is an inflammatory disease of the lung that is characterized by airway hyperresponsiveness ("AHR"), bronchoconstriction, wheezing, eosinophilic or neutrophilic inflammation, mucus hypersecretion, subepithelial fibrosis, and elevated IgE levels. Patients with asthma experience "exacerbations", a worsening of symptoms, most commonly due to microbial infections of the respiratory tract (e.g. rhinovirus, influenza virus, *Haemophilus influenza*, etc.). Asthmatic attacks can be triggered by environmental factors (e.g. ascarids, insects, animals (e.g., cats, dogs, rabbits, mice, rats, hamsters, guinea pigs and birds), fungi, air pollutants (e.g., tobacco smoke), irritant gases, fumes, vapors, aerosols, chemicals, pollen, exercise, or cold air. Apart from asthma, several chronic inflammatory diseases affecting the lung are characterized by neutrophil infiltration to the airways, for example chronic obstructive pulmonary disease (COPD), bacterial pneumonia and cystic fibrosis (Linden et al., Eur. Respir. J. 15:973-977, 2000; Rahman et al., Clin. Immunol. 115:268-276, 2005), and diseases such as COPD, allergic rhinitis, and cystic fibrosis are characterized by airway hyperresponsiveness (Fahy and O'Byrne, Am. J. Respir. Crit. Care Med. 163:822-823, 2001). Commonly used animal models for asthma and airway inflammation include the ovalbumin challenge model and methacholine sensitization models (Hessel et al., Eur. J. Pharmacol. 293:401-412, 1995). Inhibition of cytokine and chemokine production from cultured human bronchial epithelial cells, bronchial fibroblasts or airway smooth muscle cells can also be used as in vitro models. The administration of antagonists of the present invention to any of these models can be used to evaluate the use of those antagonists to ameliorate symptoms and alter the course of asthma, airway inflammation, COPD and the like.

Other inflammatory conditions and neuropathies, which may be prevented or treated by the methods of the invention are those caused by autoimmune diseases. These conditions and neuropathies include multiple sclerosis, systemic lupus erythematous, and neurodegenerative and central nervous system (CNS) disorders including Alzheimer's disease, Parkinson's disease, Huntington's disease, bipolar disorder and Amyotrophic Lateral Sclerosis (ALS), liver diseases including primary biliary cirrhosis, primary sclerosing cholangitis, non-alcoholic fatty liver disease/steatohepatitis, fibrosis, hepatitis C virus (HCV) and hepatitis B virus (HBV), diabetes and insulin resistance, cardiovascular disorders including atherosclerosis, cerebral hemorrhage, stroke and myocardial infarction, arthritis, rheumatoid arthritis, psoriatic arthritis and juvenile rheumatoid arthritis (JRA), osteoporosis, osteoarthritis, pancreatitis, fibrosis, encephalitis, psoriasis, Giant cell arteritis, ankylosing spondolytis, autoimmune hepatitis, human immunodeficiency virus (HIV), inflammatory skin conditions, transplant, cancer, allergies, endocrine diseases, wound repair, other autoimmune disorders, airway hyperresponsiveness and cell, virus, or prion-mediated infections or disorders.

Arthritis, including osteoarthritis, rheumatoid arthritis, arthritic joints as a result of injury, and the like, are common inflammatory conditions which would benefit from the therapeutic use of anti-inflammatory proteins, such as the antagonists of the present invention. For example, rheumatoid arthritis (RA) is a systemic disease that affects the entire body and is one of the most common forms of arthritis. Since rheumatoid arthritis results in tissue damage, TLR3 ligands could be present at the site of the inflammation. Activation of TLR3 signaling may perpetuate inflammation and further tissue damage in the inflamed joint. Several animal models for rheumatoid arthritis are known in the art. For example, in the collagen-induced arthritis (CIA) model, mice develop chronic inflammatory arthritis that closely resembles human rheumatoid arthritis. Administration of the TLR3 antagonists of the present invention to the CIA model mice can be used to evaluate the use of these antagonists to ameliorate symptoms and alter the course of diseases.

Diabetes mellitus, diabetes, refers to a disease process derived from multiple causative factors and characterized by hyperglycemia (LeRoith et al., (eds.), Diabetes Mellitus, Lippincott-Raven Publishers, Philadelphia, Pa. U.S.A. 1996), and all references cited therein. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is a critically important approach for the treatment of diabetes.

Underlying defects lead to a classification of diabetes into two major groups: type I diabetes (insulin dependent diabetes mellitus, IDDM), which arises when patients lack insulin-producing beta-cells in their pancreatic glands, and type 2 diabetes (non-insulin dependent diabetes mellitus, NIDDM), which occurs in patients with an impaired beta-cell insulin secretion and/or resistance to insulin action.

Type 2 diabetes is characterized by insulin resistance accompanied by relative, rather than absolute, insulin deficiency. In insulin resistant individuals, the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Adipocity-associated inflammation has been stronly implicated in the development of insulin resistance, type 2 diabetes, dyslipidemia and cardiovascular disease. Obese adipose recruits and retains macrophages and can produce excessive pro-inflammatory cytokines including TNF-α and IL-6, free fatty acids and adipokines, which can interfere with insulin signaling and induce insulin resistance. TLR3 activation on macrophages may contribute to the pro-inflammatory status of the adipose. Several animal modes of insulin resistance are known. For example, in a diet-induced obesity model (DIO) animals develop hyperglycemia and insulin resistance accompanied by weight gain. Administration of TLR3 antagonists of the present invention to the DIO model can be used to evaluate the use of the antagonists to ameliorate complications associated with type 2 diabetes and alter the course of the disease.

Exemplary cancers may include at least one malignant disease in a cell, tissue, organ, animal or patient, including, but not limited to leukemia, acute leukemia, acute lymphoblastic leukemia (ALL), B-cell or T-cell ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption and cancer related bone pain.

Exemplary cardiovascular diseases may include cardiovascular disease in a cell, tissue, organ, animal, or patient, including, but not limited to, cardiac stun syndrome, myocardial infarction, congestive heart failure, stroke, ischemic stroke, hemorrhage, arteriosclerosis, atherosclerosis, restenosis, diabetic atherosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrhythmias, ventricular fibrillation, His bundle arrhythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneurysms, aortic dissection, inflammation of the aorta, occulsion of the abdominal aorta and its branches, peripheral vascular disorders, occulsive arterial disorders, peripheral atherosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome and ischemia-reperfusion injury.

Exemplary neurological diseases may include neurologic disease in a cell, tissue, organ, animal or patient, including, but not limited to neurodegenerative diseases, multiple sclerosis, migraine headache, AIDS dementia complex, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multisystem disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease and Dementia pugilistica.

Exemplary fibrotic conditions may include liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular nehpritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures. In such a method, the fibrosis can be organ specific fibrosis or systemic fibrosis. The organ specific fibrosis can be associated with at least one of lung fibrosis, liver fibrosis, kidney fibrosis, heart fibrosis, vascular fibrosis, skin fibrosis, eye fibrosis, bone marrow fibrosis or other fibrosis. The lung fibrosis can be associated with at least one of idiopathic pulmonary fibrosis, drug induced pulmonary fibrosis, asthma, sarcoidosis or chronic obstructive pulmonary disease. The liver fibrosis can be associated with at least one of cirrhosis, schistomasomiasis or cholangitis. The cirrhosis can be selected from alcoholic cirrhosis, post-hepatitis C cirrhosis, primary biliary cirrhosis. The cholangitis is sclerosing cholangitis. The kidney fibrosis can be associated with diabetic nephropathy or lupus glomeruloschelerosis. The heart fibrosis can be associated with myocardial infarction. The vascular fibrosis can be associated with postangioplasty arterial restenosis or atherosclerosis. The skin fibrosis can be associated with burn scarring, hypertrophic scarring, keloid, or nephrogenic fibrosing dermatopathy. The eye fibrosis can be associated with retro-orbital fibrosis, postcataract surgery or proliferative vitreoretinopathy. The bone marrow fibrosis can be associated with idiopathic myelofibrosis or drug induced myelofibrosis. The other fibrosis can be selected from Peyronie's disease, Dupuytren's contracture or dermatomyositis. The systemic fibrosis can be systemic sclerosis or graft versus host disease.

Administration/Pharmaceutical Compositions

The "therapeutically effective amount" of the agent effective in the treatment or prevention of conditions where suppression of TLR3 activity is desirable can be determined by standard research techniques. For example, the dosage of the agent that will be effective in the treatment or prevention of inflammatory condition such as asthma, Crohn's Disease, ulcerative colitis or rheumatoid arthritis can be determined by administering the agent to relevant animal models, such as the models described herein.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

In the methods of the invention, the TLR3 antagonist may be administered singly or in combination with at least one other molecule. Such additional molecules may be other TLR3 antagonist molecules or molecules with a therapeutic benefit not mediated by TLR3 receptor signaling. Antibiotics, antivirals, palliatives and other compounds that reduce cytokine levels or activity are examples of such additional molecules.

The mode of administration for therapeutic use of the agent of the invention may be any suitable route that delivers the agent to the host. Pharmaceutical compositions of these agents are particularly useful for parenteral administration, e.g., intradermal, intramuscular, intraperitoneal, intravenous, subcutaneous or intranasal.

The agent of the invention may be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of a TLR3 antibody antagonist of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known or are described in more detail in, for example, "Remington's Pharmaceutical Science", 15th ed., Mack Publishing Company, Easton, Pa.

The antibody antagonists of the invention can be lyophilized for storage and reconstituted in a suitable carrier prior to use. This technique has been shown to be effective with conventional immunoglobulins and protein preparations and art-known lyophilization and reconstitution techniques can be employed.

The present invention will now be described with reference to the following specific, non-limiting examples.

EXAMPLE 1

Identification and Derivation of Anti-huTLR3 Antagonist mAbs

The MorphoSys Human Combinatorial Antibody Library (HuCAL®) Gold phage display library (Morphosys AG, Martinsried, Germany) was used as a source of human antibody fragments and was panned against a purified TLR3 antigen generated from the expression of amino acids 1-703 of human TLR3 (huTLR3) (SEQ ID NO: 4) with a C-terminal poly-histidine tag and purified by immobilized metal affinity chromatography. Amino acids 1-703 correspond to the predicted extracellular domain (ECD) of huTLR3. Fab fragments (Fabs) that bound specifically to huTRL3 ECD were selected by presenting the TLR3 protein in a variety of ways so that a diverse set of antibody fragments could be identified, sequenced and confirmed as unique. From different panning strategies, 62 candidates (different V-region sequences) were identified as unique hTLR3 ECD binders.

The 62 candidates identified as huTLR3 ECD binders were screened for neutralizing activity in a range of cell-based assays relevant to identifying anti-inflammatory activity. Using preliminary activity data (see Example 2 below), four candidates (Fabs 16-19) defining families 16-19 were selected from the 62 as parents for CDR maturation of heavy chain CDR2 (HCDR2) and light chain CDR3 (LCDR3). One of the parental candidates (candidate 19) exhibited an N-linked glycosylation site in HCDR2; a Ser to Ala (S to A) mutation was made in this candidate to delete the site. Following CDR maturation of the four parental candidates, a total of 15 progeny candidates (candidates 1-15) were identified for further characterization as described in Example 2 below. A listing of the light and heavy chain variable regions present in each of the 19 candidates is shown in Table 3 above. The candidates are herein referred to as mAbs 1-19 or Fabs 1-19, depending whether they were Fabs or cloned as full length antibody chains (Example 3). Due to expression vector design, the mature amino termini of the variable regions for all candidates were QVE for heavy chain and DI for the light chain. The preferred sequences at these termini are those in the respective germline genes with high identity to the candidate sequences. For families 17 and 18 the germline sequences are QVQ for VH and SY for VL. For family 19, the sequences are EVQ for VH and DI for VL. The SY sequence is unique to the lambda subgroup 3 and there are reports of heterogeneity with either S or Y as the amino terminal residue. Thus, the QSV consensus terminus from the prominent lambda subgroup 1 was considered a more suitable replacement for DIE for VL of families 17 and 18. These changes were introduced into candidates 9, 10 and 12 from family 18 and candidates 14 and 15 from family 19. In this process, both the VH and VL regions of these antibodies were codon optimized. The amino acid sequences of the light chain variable region N-terminal germline variants of candidates 9, and 11 are shown in SEQ ID NO:s 209-211, and the amino acid sequences of the heavy chain variable region N-terminal germline variants for candidates 9, 10, 12, 14, and 15 are shown in SEQ ID NO:s 212-216, respectively. The N-terminal variants of the candidates are herein referred to as candidate/mAb/Fab 9QVQ/QSV, 10QVQ/QSV, 12QVQ/QSV, 14EVQ or 15EVQ. The N-terminal germline variants were expressed as mAbs and showed no effect on binding to TLR3 or in their ability to inhibit TLR3 biological activity when compared to their parent counterparts (data not shown).

EXAMPLE 2

Determination of TLR3 Antagonist Activity in Vitro

The 15 CDR-matured candidates described above were selected as potential human therapeutics and a range of binding and neutralizing activities were determined. The activity assays and results for the four parental Fabs, Fabs 16-19 and 15 CDR-matured Fabs, Fabs 1-15 or their non-germline V-region variants are described below.

Inhibition of NF-κB and ISRE Signaling Cascasde 293T cells were grown in DMEM and GlutaMax media (Invitrogen, Carlsbad, Calif.) supplemented with heat-inactivated FBS and transfected with 30 ng pNF-κB or ISRE firefly luciferase reporter plasmids, 13.5 ng pcDNA3.1 vector, 5 ng phRL-TK, and 1.5 ng pcDNA encoding FL TLR3 (SEQ ID NO: 2). The phRL-TK plasmid contains the *Renilla* luciferase gene driven by the HSV-1 thymidine kinase promoter (Promega, Madion, Wis.). TLR3 antibodies were incubated 30-60 min. before addition of poly(I:C) (GE Healthcare, Piscataway, N.J.). The plates were incubated 6 h or 24 h at 37° C. before the addition of the Dual-Glo luciferase reagent, and the plates were read on a FLUOstar plate reader. Normalized values (luciferase ratios) were obtained by dividing the firefly RLUs by the *Renilla* RLUs. Upon stimulation with the TLR3 agonist poly (I:C) (1 µg/ml), the NF-κB or ISRE signaling cascade stimulated firefly luciferase production was specifically inhibited by incubation of the cells with anti-TLR3 antibodies (0.4, 2.0 and 10 µg/ml) prior to stimulation. The results for the NF-κB assays are shown in FIG. 1 and are expressed as % inhibition of the Firefly/Renilla ratio with 5465 as the positive control (neutralizing anti-human TLR3 Mab) and an anti-human tissue factor mAb (859) as the human IgG4 isotype control. >50% inhibition was achieved with mAb concentrations 0.4-10 µg/ml. c1068 and TLR3.7 inhibited about 38% and 8% of TLR3 biological activity at 10 µg/ml. Similar results were obtained with the ISRE reporter gene assay (data not shown).

Cytokine Release in BEAS-2B Cells

BEAS-2B cells (SV-40 transformed normal human bronchial epithelial cell line) were seeded in a collagen type I coated dishes and incubated with or without anti-human TLR3 antibodies prior to addition of poly (I:C). Twenty-four hours after treatments, supernatants were collected and assayed for cytokine and chemokine levels using a custom multi-plex bead assay for detection of IL-6, IL-8, CCL-2/MCP-1, CCL5/RANTES, and CXCL10/IP-10. Results are shown in FIG. 2 as % inhibition of the individual cytokine/chemokine following mAb treatment at 0.4, 2.0 and 10 µg/ml. 5465 is a positive control; 859 is an isotype control.

Cytokine Release in NHBE Cells

Figures 3, 3A:
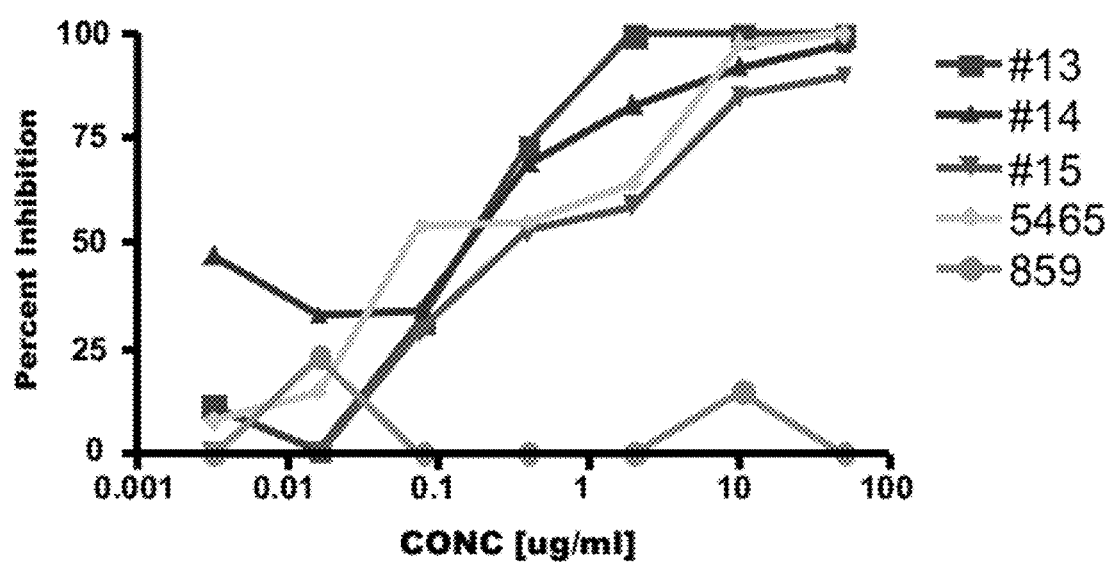
FIGS. 3A and 3B show the effect of anti-huTLR3 mAbs in a NHBE assay.
Figure 3B:
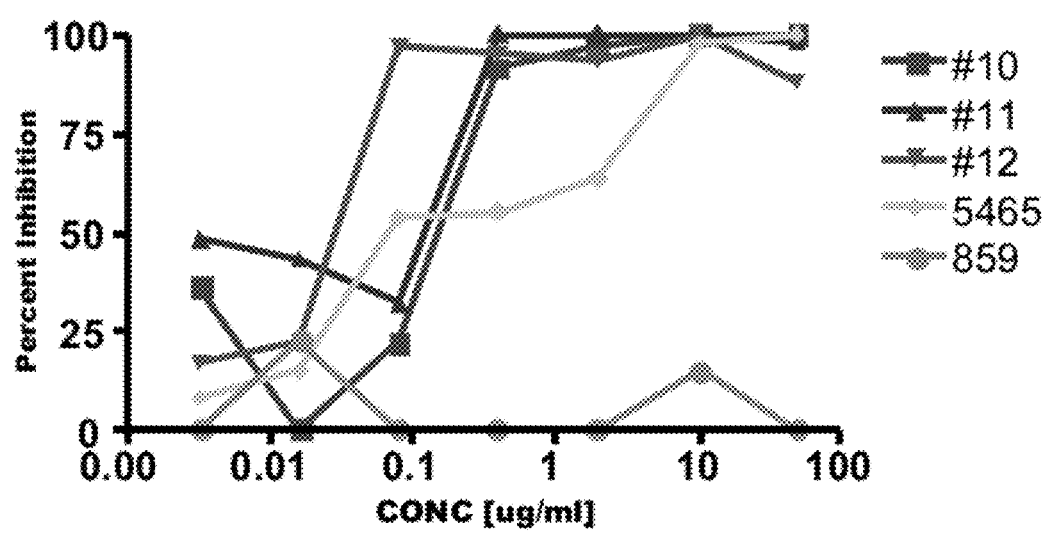

Cytokine release was also assayed in normal human bronchial epithelial (NHBE) cells (Lonza, Walkersville, Md.). NHBE cells were expanded and transferred to collagen-coated dishes and incubated for 48 hours after which the media was removed and replenished with 0.2 ml of fresh media. The cells were then incubated with or without anti-human TLR3 mAbs 60 minutes prior to the addition of poly (I:C). Supernatants were collected after 24 hours and stored at −20° C. or assayed immediately for IL-6 levels. Results are graphed in FIG. 3 as % inhibition of IL-6 secretion following mAb treatment using doses between 0.001 and 50 µg/ml. 5465 is a positive control, 859 is an isotype control. Most mAbs inhibited at least 50% of IL-6 production at <1 µg/ml, and achieved 75% inhibition at <5 µg/ml.

Cytokine Release in PBMC Cells

Figure 4:
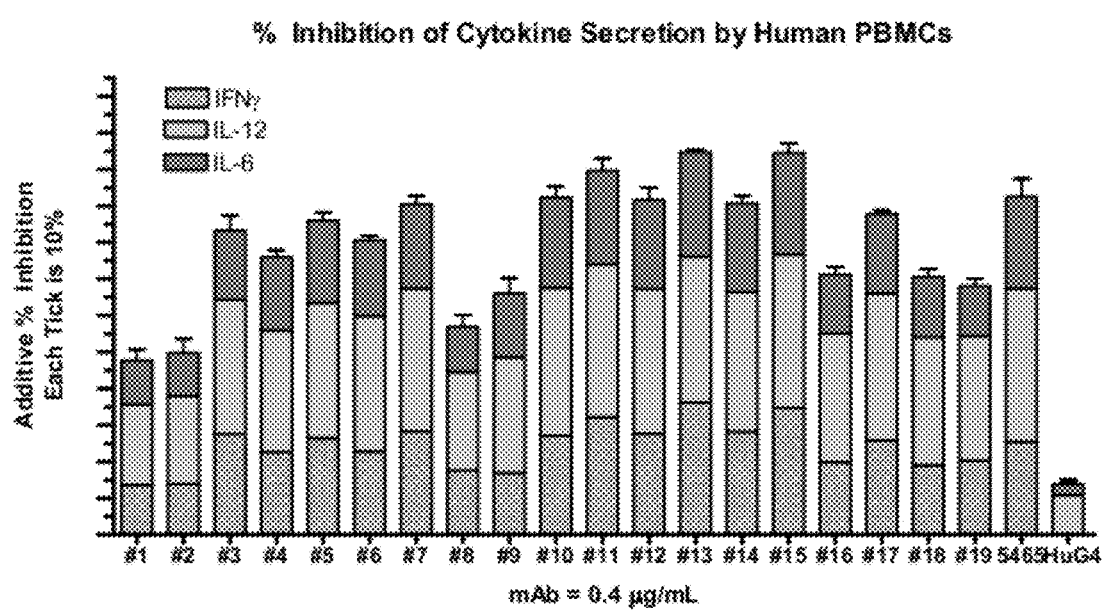
FIG. 4 shows the effect of anti-huTLR3 mAbs in a PBMC assay.
Figures 6, 6A:
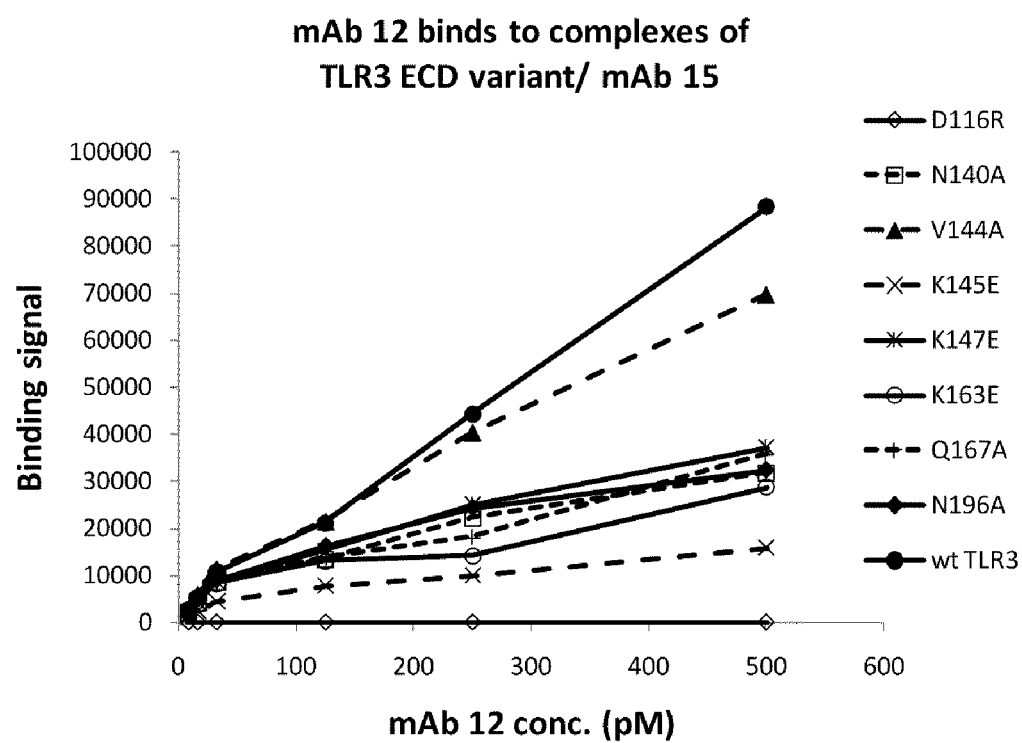
FIGS. 6A, 6B and 6C show the binding of anti-huTLR3 mAbs to TLR3 mutants.
Figure 6B:
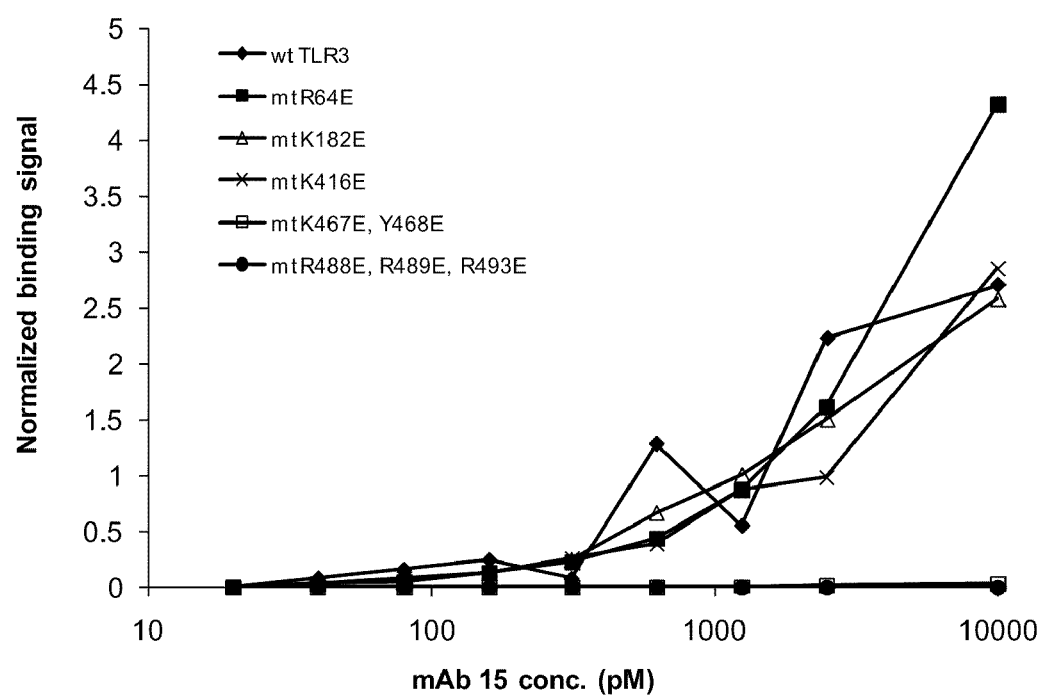
Figure 6C:
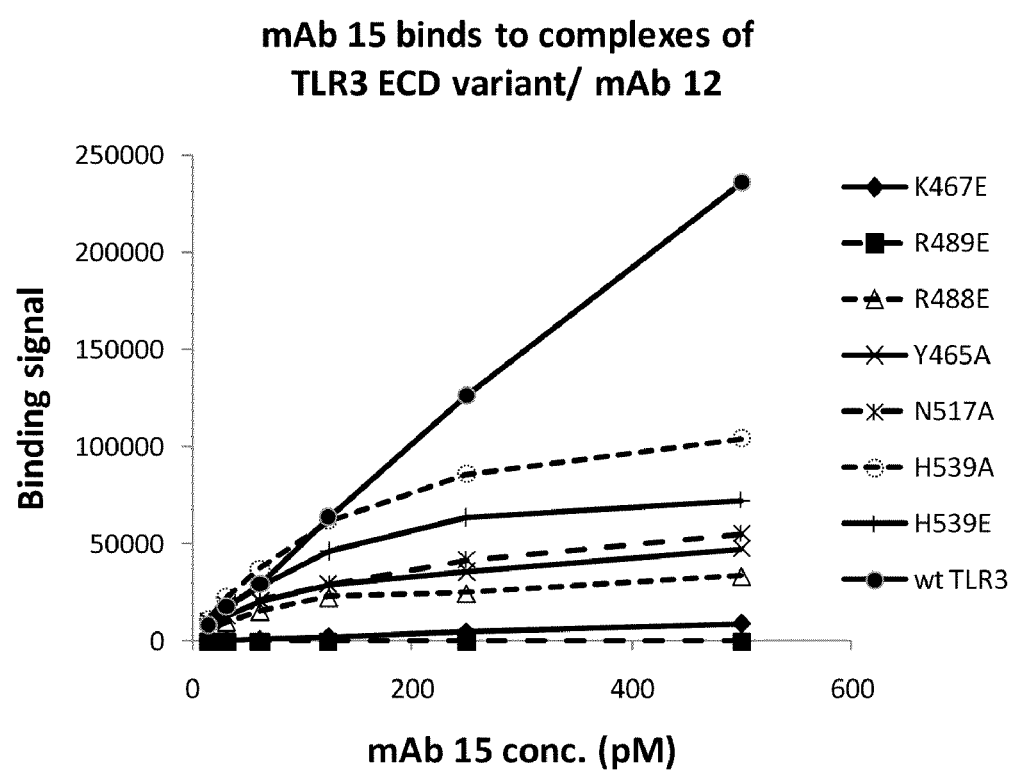

Cytokine release was also assayed in human peripheral blood mononuclear cells (PBMC). Whole blood was collected from human donors into heparin collection tubes to which a Ficoll-Paque Plus solution was slowly layered underneath. The tubes were centrifuged and the PBMCs, that formed a white layer just above the Ficoll, were recovered and plated. The PBMCs were then incubated with or without anti-human TLR3 mAbs prior to the addition of 25 µg/ml poly(I:C). After 24 hrs, supernatants were collected and cytokine levels were determined using Luminex technology. Results are graphed in FIG. 4 as cumulative percentage inhibition of IFN-γ, IL-12 and IL-6 using a single dose of mAb (0.4 µg/ml) with 5465 is a positive control; hIgG4 is an isotype control.

Cytokine Release in HASM Cells

Briefly, human airway smooth muscle (HASM) cells were incubated with or without anti-human TLR3 mAbs prior to the addition of a synergistic combination of 500 ng/ml poly (I:C) and 10 ng/ml TNF-α. After 24 hrs, supernatants were collected and cytokine levels were determined using Luminex technology. Results are graphed in FIG. 5 as levels of the chemokine CCL5/RANTES using three doses of mAb (0.4, 2 and 10 µg/ml). 5465 is a positive control; hIgG4 is an isotype control.

The results from the in vitro assays in human cells confirm the ability of the antibodies of the invention to reduce cytokine and chemokines release as a result of binding to huTLR3.

EXAMPLE 3

Full-Length Antibody Constructs

The four parental Fabs (candidate nos. 16-19) and 15 progeny Fabs (candidate nos. 1-15) heavy chains were cloned onto a human IgG4 background with a S229P Fc mutation. Candidates 9QVQ/QSV, 10QVQ/QSV, 12QVQ/QSV, 14EVQ or 15EVQ were cloned onto a human IgG4 background with F235A/L236A and S229P Fc mutations.

The mature full-length heavy chain amino acid sequences are shown in SEQ ID NOs: 90-102 and 218-220 as follows:

| Candidate | SEQ ID NO: |
|---|---|
| 16 | 90 |
| 17 | 91 |
| 18 | 92 |
| 19 | 93 |
| 1 | 94 |
| 2 | 95 |
| 3 | 96 |
| 4 | 97 |
| 5, 6, 7 | 98 |
| 8 | 99 |
| 9 | 100 |
| 10, 11, 12 | 101 |
| 13, 14, 15 | 102 |
| 9EVQ | 218 |
| 10EVQ, 12EVQ | 219 |
| 14EVQ, 15EVQ | 220 |

For expression, these heavy chain sequences can include an N-terminal leader sequence such as MAWVWTLLFL-MAAAQSIQA (SEQ ID NO: 103). Exemplary nucleotide sequences encoding the heavy chain of candidates 14EVQ and 15EVQ with a leader sequence and the mature form (without a leader sequence) are shown in SEQ ID NOs: 104 and 105, respectively. Likewise, for expression, the light chain sequences of the antibodies of the invention can include an N-terminal leader sequence such as MGVPTQV-LGLLLLWLTDARC (SEQ ID NO: 106). Exemplary nucleotide sequences encoding the light chain of codon optimized candidate 15 with a leader sequence and the mature form (without a leader sequence) are shown in SEQ ID NOs: 107 and 108, respectively.

EXAMPLE 4

Characterization of Anti-TLR3 mAb Binding

EC50 values for the binding of the mAbs to human TLR3 extracellular domain (ECD) were determined by ELISA. Human TLR3 ECD protein was diluted to 2 µg/ml in PBS and 100 aliquots were dispensed to each well of a 96-well plate (Corning Inc., Acton, Mass.). After overnight incubation at 4° C., the plate was washed 3 times in wash buffer consisting of 0.05% Tween-20 (Sigma-Aldrich) in PBS. The wells were blocked with 200 µl blocking solution consisting of 2% I-Block (Applied Biosystems, Foster City, Calif.) and 0.05% Tween-20 in PBS. After blocking for 2 hours at room temperature the plate was washed 3 times followed by addition of serial dilutions of the anti-TLR3 mAb candidates 1 to 19 in blocking buffer. The anti-TLR3 mAbs were incubated for 2 hours at room temperature and washed 3 times. This was followed by addition of a peroxidase-conjugated sheep anti-human IgG (GE Healthcare, Piscataway, N.J.) diluted 1:4000 in blocking buffer, incubated for 1 hour at room temperature followed by 3 washes in wash buffer. Binding was detected by 10-15 minute incubation in TMB-S (Fitzgerald Industries International, Inc., Concord, Mass.). The reaction was stopped with 25 µl 2N $H_2SO_4$ and absorbance read at 450 nm with subtraction at 650 nm using a SPECTRA Max spectrophotometer (Molecular Devices Corp., Sunnyvale, Calif.).

EC50 values were determined by non-linear regression using GraphPad Prism software (GraphPad Software, Inc., San Diego, Calif.).

EC50 values were determined for binding to huTLR3 (Table 4) by incubating with 100 µl of 4-fold serial dilutions of mAbs from 2.5 µg/ml to 0.6 pg/ml. An anti-human tissue factor mAb 859 and hu IgG4κ were included as negative controls.

TABLE 4

| Candidate no. | EC50 (ng/ml) |
|---|---|
| 1 | 17.18 |
| 2 | 53.12 |
| 3 | 23.42 |
| 4 | 12.77 |
| 5 | 19.94 |
| 6 | 19 |
| 7 | 16.13 |
| 8 | 18.58 |
| 9 | 22.61 |
| 10 | 15.84 |
| 11 | 26.33 |
| 12 | 25.59 |
| 13 | 23.51 |
| 14 | 33.59 |
| 15 | 32.64 |
| 16 | 43.66 |
| 17 | 13.8 |
| 18 | 9.68 |
| 19 | 66.54 |

Binding affinity for huTLR3 ECD was also determined by Biacore analysis. The data (not shown) indicated that the mAbs 1-19 had a Kd for huTLR3 ECD of less than $10^{-8}$ M.

EXAMPLE 5

Competitive Epitope Binding

Epitope binding experiments were performed to determine the anti-TLR3 antibody competition groups or "epitope bins".

For competitive ELISA, 5 µl (20 µg/ml) of purified human TLR3 ECD protein generated as described in Example 1 was coated on MSD HighBind plate (Meso Scale Discovery, Gaithersburg, Md.) per well for 2 hr at room temperature. 150 µl of 5% MSD Blocker A buffer (Meso Scale Discovery) was added to each well and incubated for 2 hr at room temperature. Plates were washed three times with 0.1 M HEPES buffer, pH 7.4, followed by the addition of the mixture of labeled anti-TLR3 mAb with different competitors. Labeled antibodies (10 nM) were incubated with increasing concentrations (1 nM to 2 µM) of unlabeled anti-TLR3 antibodies, and then added to the designated wells in a volume of 25 µl mixture. After 2-hour incubation with gentle shaking at room temperature, plates were washed 3 times with 0.1 M HEPES buffer (pH 7.4). MSD Read Buffer T was diluted with distilled water (4-fold) and dispensed at a volume of 150 µl/well and analyzed with a SECTOR Imager 6000. Antibodies were labeled with MSD Sulfo-Tag™ NHS-ester according to manufacturer's instructions (Meso Scale Discovery).

The following anti-TLR3 antibodies were evaluated: mAbs 1-19 obtained from MorphoSys Human Combinatorial Antibody Library (shown in Table 3a); c1068 (described in WO06/060513A2), c1811 (rat anti-mouse TLR3 mAb produced by a hybridoma generated from rats immunized with mouse TLR3 protein), TLR3.7 (eBiosciences, San Diego, CA, cat no 14-9039) and IMG-315A (generated against human TLR3 amino acids amino acids 55-70 (VLNLTH-NQLRRLPAAN) (residues 55-70 of SEQ ID NO: 2) from Imgenex, San Diego, CA). For mAbs 9, 10, 12, 14 and 15, variants 9QVQ/QSV, 10QVQ/QSV, 12QVQ/QSV, 14EVQ or 15EVQ were used in this study.

Based on competition assays, anti-TLR3 antibodies were assigned to five distinct bins. Bin A: mAbs 1, 2, 13, 14EVQ, 15EVQ, 16, 19; Bin B: mAbs 3, 4, 5, 6, 7, 8, 9QVQ/QSV, 10QVQ/Q3v, 11, 12QVQ/QSV, 17, 18; Bin C: antibody Imgenex IMG-315A; Bin D: antibodies TLR3.7, c1068; and Bin E: antibody c1811.

EXAMPLE 6

Epitope Mapping

Representative antibodies from distinct epitope bins as described in Example 5 were selected for further epitope mapping. Epitope mapping was performed using various approaches, including TLR3 segment swapping experiments, mutagenesis, H/D exchange and in silico protein-protein docking (The Epitope Mapping Protocols, Methods in Molecular Biology, Volume 6, Glen E. Morris ed., 1996).

TLR3 segment swapping. TLR3 human-mouse chimeric proteins were used to locate gross antibody binding domains on TLR3. The human TLR3 protein extracellular domain was divided into three segments (aa 1-209, aa 210-436, aa 437-708 according to amino acid numbering based on human TLR3 amino acid sequence, GenBank Acc. No. NP_003256). MT5420 chimeric protein was generated by replacing human TLR3 amino acids 210-436 and 437-708 by corresponding mouse amino acids (mouse TLR3, GenBank Acc. No. NP_569054, amino acids 211-437 and 438-709). The MT6251 chimera was generated by replacing human amino acids at positions 437-708 by mouse TLR3 amino acids (mouse TLR3, GenBank Acc. No. NP_569054, amino acids 438-709). All constructs were generated in the pCEP4 vector (Life Technologies, Carslbad, Calif.) using standard cloning procedures. The proteins were transiently expressed in HEK293 cells as V5-His6 C-terminal fusion proteins, and purified as described in Example 1.

mAb c1068. mAb c1068 bound human TLR3 ECD with high affinity but did not bind well to murine TLR3. c1068 lost its ability to bind to both MT5420 and MT6251, demonstrating that the binding site was located within the amino acids 437-708 of the WT human TLR3 protein.

mAb 12QVQ/QSV. mAb 12QVQ/QSV bound both chimeras, indicating that the binding site for mAb 12QVQ/QSV was located within the amino acids 1-209 of the human TLR3 protein having a sequence shown in SEQ ID NO:2.

In silico protein-protein docking. The crystal structure of mAb 15EVQ (see below) and the published human TLR3 structure (Bell et al., J. Endotoxin Res. 12:375-378, 2006) were energy minimized in CHARMm (Brooks et al., J. Computat. Chem. 4:187-217, 1983) for use as the starting models for docking. Protein docking was carried out with ZDOCK-pro 1.0 (Accelrys, San Diego, Calif.), which is equivalent to ZDOCK 2.1 (Chen and Weng, Proteins 51: 397-408, 2003) with an angular grid of 6 degrees. Known N-linked glycosylation site Asn residues in human TLR3 (Asn 52, 70, 196, 252, 265, 275, 291, 398, 413, 507 and 636) (Sun et al., J. Biol. Chem. 281:11144-11151, 2006) were blocked from participating in the antibody-antigen complex interface by an energy term in the ZDOCK algorithm. 2000 initial poses were output and clustered and the docking poses were refined and rescored in RDOCK (Li et al., Proteins 53:693-707, 2003). The 200 poses with the highest initial ZDOCK scores and 200 top RDOCK poses were visually inspected.

Crystallization of mAb 15EVQ was carried out by the vapor-diffusion method at 20° C. (Benvenuti and Mangani, Nature Protocols 2:1633-51, 2007). The initial screening was set up using a Hydra robot in 96-well plates. The experiments were composed of droplets of 0.5 μl of protein solution mixed with 0.5 μl of reservoir solution. The droplets were equilibrated against 90 μl of reservoir solution. The Fab solution in 20 mM Tris buffer, pH 7.4, containing 50 mM NaCl was concentrated to 14.3 mg/ml using Amicon Ultra-5 kDa cells. The screening was performed with the Wizard I & II (Emerald BioSystems, Bainbridge Island, Wash.) and in-house crystallization screens.

X-ray diffraction data were collected and processed using the Rigaku MicroMax™-007HF microfocus X-ray generator equipped with an Osmic™ VariMax™ confocal optics, Saturn 944 CCD detector, and an X-stream™ 2000 cryocooling system (Rigaku, Woodlands, Tex.). Diffraction intensities were detected over a 270° crystal rotation with the exposure time of 120 s per half-degree image. The X-ray data were processed with the program D*TREK (Rigaku). The structure was determined by the molecular replacement method using the program Phaser or CNX (Accelrys, San Diego, Calif.). Atomic positions and temperature factors were refined with REFMAC using all data in the resolution range 15-2.2 Å for mAb 15 and 50-1.9 Å for mAb 12. Water molecules were added at the ($F_o$-$F_c$) electron density peaks using the cut-off level of 3σ. All crystallographic calculations were performed with the CCP4 suite of programs (Collaborative Computational Project, Number 4. 1994. The CCP4 suite: programs for protein crystallography. Acta Crystallogr. D50: 760-763). Model adjustments were carried out using the program COOT (Emsley et al., Acta Crystallogr. D60:2126-2132, 2004).

The resolved crystal structure of mAb 15EVQ showed that the antibody combining site was characterized by a number of negatively charged residues in the heavy chain (D52, D55, E99, D106 and D109). Thus, recognition between mAb 15EVQ and TLR3 most likely involved positively charged residues. The protein-protein docking simulations performed suggested that two large patches on TLR3 involving multiple positive charge residues showed good complementarity to the antibody. The residues on TLR3 in the interface of the TLR3-anti-TLR3 antibody simulated complexes were R64, K182, K416, K467, Y468, R488, R489 and K493.

Mutagenesis studies. Single and combination point mutations were introduced into surface residues of TLR3 ECD in the regions identified above to contain the epitopes of mAb 12 and mAb 15EVQ and the mutant proteins were tested for antibody binding.

The nucleotide sequence encoding human TLR3 amino acids 1-703 (the ECD), (SEQ ID NO: 4; GenBank accession number NP_003256), was cloned using standard protocols. All mutants were generated by site directed mutagenesis using the Strategene Quickchange II XL kit (Stratagene, San Diego, Calif.) according to the manufacturer's protocol, using the oligonucleotides shown in Table 5a. Mutations were verified by DNA sequencing. The proteins were expressed under a CMV promoter as C-terminal His-tag fusions in HEK293 cells, and purified as described in Example 1.

TABLE 5a

Oligonucleotides used for site-directed mutagenesis. Sequences of the sense oligonucleiotides are shown. The anti-sense oligonucleotides with complementary sequences were used in the mutagenesis reaction.

| Variant | Oligo | SeqID NO: |
|---|---|---|
| R64E | 5' CCTTACCCATAATCAACTCGAGAGATTACCAGCCGCCAAC 3' | 136 |
| K182E | 5' CAAGAGCTTCTATTATCAAACAATGAGATTCAAGCGCTAAAAAGTGAAG 3' | 137 |
| K416E | 5' CCTTACACATACTCAACCTAACCGAGAATAAAATCTCAAAAATAG 3' | 138 |
| K467E/Y468A | 5' GAAATCTATCTTTCCTACAACGAGGCCCTGCAGCTGACTAGGAACTC 3' | 139 |
| R488/R489/K493E | 5' GCCTTCAACGACTGATGCTCGAGGAGGTGGCCCTTGAGAATGTGGATAGCTCTCCTTC 3' | 140 |
| T472S/R473T/N474S | 5' GTACCTGCAGCTGTCTACGAGCTCCTTTGCCTTGGTCCC 3' | 141 |
| N196A | 5' GAAGAACTGGATATCTTTGCCGCTTCATCTTTAAAAAAATTAGAGTTG 3' | 169 |
| Q167A | 5' GTCATCTACAAAATTAGGAACTGCGGTTCAGCTGGAAAATCTCC 3' | 170 |
| K163E | 5' CTCATAATGGCTTGTCATCTACAGAATTAGGAACTCAGGTTCAGC 3' | 171 |
| K147E | 5' GAAAATTAAAAATAATCCCTTTGTCAAGCAGGAGAATTTAATCACATTAGATCTGTC 3' | 172 |
| K145E | 5' GAAAATTAAAAATAATCCCTTTGTCGAGCAGAAGAATTTAATCACATTAG 3' | 173 |
| V144A | 5' CAGAAAATTAAAAATAATCCCTTTGCAAAGCAGAAGAATTTAATCACATTAG 3' | 174 |
| N140A | 5' CCAACTCAATCCAGAAAATTAAAGCTAATCCCTTTGTCAAGCAGAAG 3' | 175 |
| D116R | 5' CAATGAGCTATCTCAACTTTCTCGTAAAACCTTTGCCTTCTGCAC 3' | 176 |
| D536K | 5' GTCTTGAGAAACTAGAAATTCTCAAGTTGCAGCATAACAACTTAGCAC 3' | 177 |
| D536A | 5' CTTGAGAAACTAGAAATTCTCGCATTGCAGCATAACAACTTAGCAC 3' | 178 |
| K619E | 5' CTAAAGTCATTGAACCTTCAGGAGAATCTCATAACATCCGTTG 3' | 179 |

TABLE 5a-continued

Oligonucleotides used for site-directed mutagenesis. Sequences of the sense oligonucleiotides are shown. The anti-sense oligonucleotides with complementary sequences were used in the mutagenesis reaction.

| Variant | Oligo | SeqID NO: |
|---|---|---|
| K619A | 5' CTCTAAAGTCATTGAACCTTCAGGCGAATCTCATAACATCCGTTGAG 3' | 180 |
| E570R | 5' CCACATCCTTAACTTGAGGTCCAACGGCTTTGACGAG 3' | 181 |
| N541A | 5' GAAATTCTCGATTTGCAGCATAACGCCTTAGCACGGCTCTGGAAAC 3' | 182 |
| Q538A | 5' GAGAAACTAGAAATTCTCGATTTGGCGCATAACAACTTAGCACGGC 3' | 183 |
| H539E | 5' CTAGAAATTCTCGATTTGCAGGAAAACAACTTAGCACGGCTCTG 3' | 184 |
| H539A | 5' CTAGAAATTCTCGATTTGCAGGCTAACAACTTAGCACGGCTCTG 3' | 185 |
| N517A | 5' CATTCTGGATCTAAGCAACAACGCCATAGCCAACATAAATGATGAC 3' | 186 |
| Y465A | 5' GAAAATATTTTCGAAATCTATCTTTCCGCCAACAAGTACCTGCAGCTGAC 3' | 187 |
| R488E | 5' GCCTTCAACGACTGATGCTCGAAAGGGTGGCCCTTAAAAATG 3' | 188 |
| R489E | 5' CTTCAACGACTGATGCTCCGAGAGGTGGCCCTTAAAAATGTGG 3' | 189 |
| K467E | 5' CGAAATCTATCTTTCCTACAACGAGTACCTGCAGCTGACTAG 3' | 190 |

Binding assays. The binding activity of mAb 12QVQ/QSV and mAb 15EVQ to human TLR3 and generated variants was evaluated by ELISA. To expedite the process, mutants in the predicted mAb 15EVQ binding site were co-expressed in HEK cells by co-transfection of TLR3 ECD mutant containing a C-terminal His tag with mAb 12QVQ/QSV, followed by purification by metal affinity chromatography. The recovered sample was a complex of the TLR3 mutant with mAb 12. This approach was feasible because the mAb 12QVQ/QSV and mAb 15EVQ binding sites are distant from one another; and thus, point mutations at one site are unlikely to affect the epitope at the other site. These complexes were used in the ELISA binding assays. 5 μl per well of 20 μg/ml wild type TLR3 ECD or mutant proteins in PBS were coated on an MSD HighBind plate (Meso Scale Discovery, Gaithersburg, Md.). The plates were incubated at room temperature for 60 min and blocked overnight in MSD Blocker A buffer (Meso Scale Discovery, Gaithersburg, Md.) at 4° C. The following day the plates were washed and the MSD Sulfo-tag labeled mAb 15EVQ added at concentrations from 500 pM to 1 pM for 1.5 hours. After washes the labeled antibody was detected using MSD Read Buffer T and the plates were read using a SECTOR Imager 6000. To evaluate the binding activity of mAb 12QVQ/QSV to human TLR3 and variants, co-expression was carried out with mAb 15EVQ and binding ELISAs were performed as described for mAb 15EVQ, except that the detecting antibody was labeled mAb 12QVQ/QSV.

mAb 12QVQ/QSV: The binding site for mAb 12QVQ/QSV was located within the amino acids 1-209 of the human TLR3 protein as determined in the segment swap studies. The following TLR3 mutants were evaluated: D116R, N196A, N140A, V144A, K145E, K147E, K163E, and Q167A. The wild type TLR3 and V144A mutant showed comparable binding to mAb 12QVQ/QSV (FIG. 6A). The antibody did not bind to TLR3D116R mutant and had significantly reduced binding affinity to the K145E mutant. Thus, residues D116 and K145 which are closely apposed on the surface of TLR3 were identified as key epitope sites for mAb 12QVQ/QSV (FIG. 7A).

The two critical residues of the mAb 12QVQ/QSV binding epitope were located near the face of the dsRNA binding site at the N-terminal segment of the TLR3 ectodomain (Pirher, et al., Nature Struct. & Mol. Biol., 15:761-763, 2008). The complete epitope will contain other residues in the neighboring regions, which were not revealed by mutational analyses performed. Not wishing to be bound to any particular theory, it is believed that binding of mAb 12QVQ/QSV on its TLR3 epitope may directly or indirectly interfere with dsRNA binding on TLR3 ectodomain, thereby disrupting receptor dimerization and activation of downstream signaling pathways.

mAb 15EVQ: The following TLR3 mutants were evaluated: R64E, K182E, K416E, Y465A, K467E, R488E, R489E, N517A, D536A, D536K, Q538A, H539A, H539E, N541A, E570R, K619A, K619E, a double mutant K467E/Y468A, a triple mutant T472S/R473T/N474S, and a triple mutant R488E/R489E/K493E. The wild type TLR3, the R64E, K182E, K416E mutants and the triple mutant T472S/R473T/N474S showed comparable binding to mAb 15EVQ (FIG. 6B and Table 5b). The antibody did not bind to TLR3 mutants K467E, R489E, K467E/Y468A and R488E/R489E/K493E (FIGS. 6B and 6C). The remaining variants showed intermediate binding with the R488E having the greatest effect. All of these mutants bound to mAb 12QVQ/QSV. These results showed that resides K467 and R489 were critical determinants of the mAb 15EVQ epitope. Residue R488 also contributed to the epitope. These residues were closely apposed on the same surface of TLR3 (FIG. 7A). The results also showed that residues Y465, Y468, N517, D536, Q538, H539, N541, E570, and K619, all on the same surface as K467, R488 and R489, contributed to the epitope. This conclusion was further supported by the H/D exchange studies with mAb 15EVQ. FIG. 7A shows binding epitope sites for mAbs 12QVQ/QSV and 15EVQ (black) and C1068 mAb (grey) superimposed on the structure of human TLR3. The epitope for mAb 15EVQ covers residues Y465, K467, Y468, R488, R489, N517, D536, Q538, H539, N541, E570, and K619.

H/D Exchange studies. For H/D exchange, the procedures used to analyze the antibody perturbation were similar to that described previously (Hamuro et al., J. Biomol. Techniques 14:171-182, 2003; Horn et al., Biochemistry 45:8488-8498, 2006) with some modifications. Recombinant TLR3 ECD (expressed from Sf9 cells with C-terminal His-tag and purified) was incubated in a deuterated water solution for predetermined times resulting in deuterium incorporation at exchangeable hydrogen atoms. The deuterated TLR3 ECD was captured on a column containing immobilized mAb 15EVQ and then washed with aqueous buffer. The back-exchanged TLR3 ECD protein was eluted from the column and localization of deuterium containing fragments was determined by protease digestion and mass spec analysis. As a reference control, TLR3 ECD sample was processed similarly except it was exposed to deuterated water only after capture on the antibody column and then washed and eluted in the same manner as the experimental sample. Regions bound to the antibody were inferred to be those sites relatively protected from exchange and thus contain a higher fraction of deuterium than the reference TLR3 ECD sample. About 80% of the protein could be mapped to specific peptides. Maps of H/D exchange perturbation of TLR3 ECD by mAb 15EVQ are shown in FIG. 7B. Only the segment of TLR3 around the portion affected by mAb 15EVQ is shown for clarity. The remainder of the protein extending to the amino and carboxyl termini of TLR3 ECD was not affected appreciably.

Figures 7, 7A:
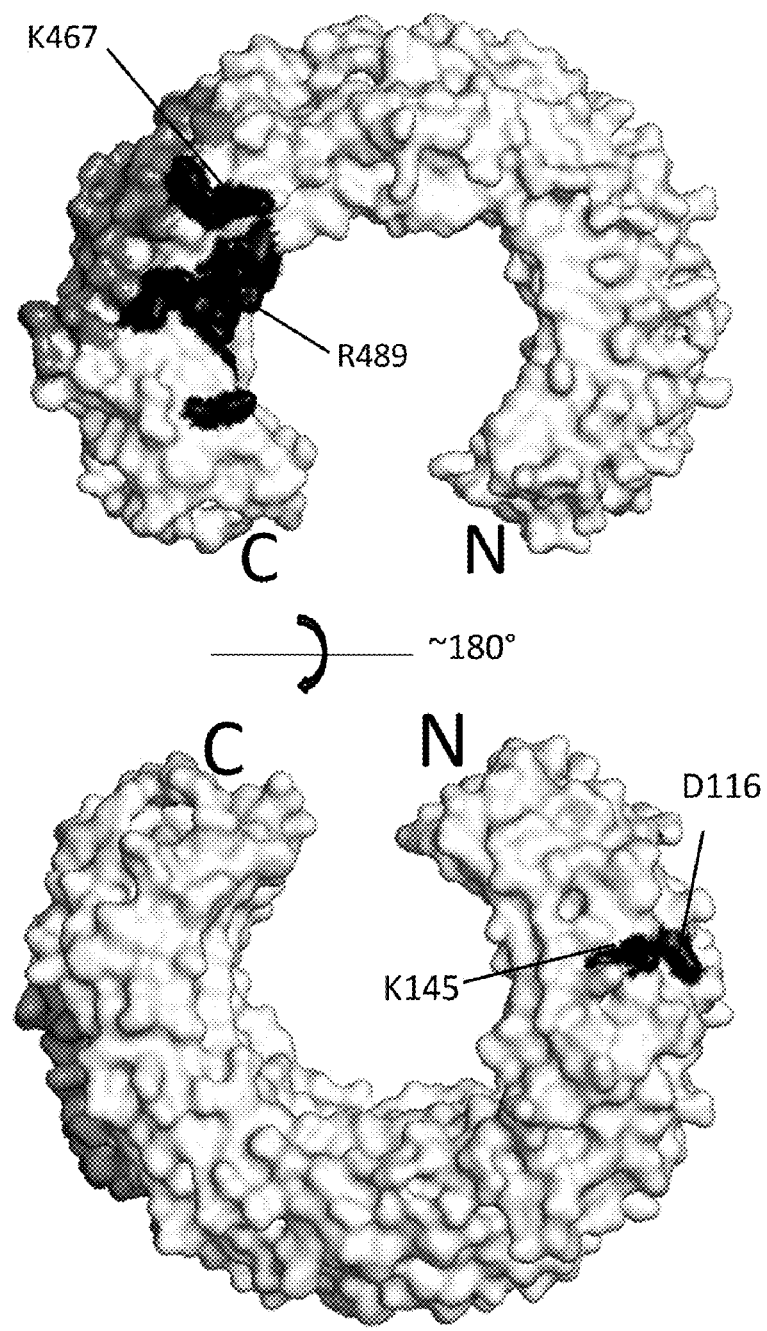
FIG. 7A shows epitopes for mAb 15EVQ (black) and C1068 mAb (grey) (top image) and epitope for mAb 12QVQ/QS (black, bottom image) superimposed on the structure of human TLR3 ECD.

The H/D exchange studies identified peptide segments $_{465}$YNKYLQL$_{471}$, $_{514}$SNNNIANINDDML$_{526}$ and $_{529}$LEKL$_{532}$ of SEQ ID NO: 2 as regions where exchange on TLR3 was particularly altered by binding to mAb 15EVQ. By its nature, H/D exchange is a linear mapping method and usually cannot define which residues within the peptide segment are most affected by antibody binding. However, the extensive overlap between the H/D exchange and mutational results gives added confidence that the surface shown in FIG. 7A is the binding site for mAb 15. This binding site was in same linear amino acid sequence region as previously described for mAb c1068 (PCT Publ. no. WO06/060513A2) but it was found to be located on a completely non-overlapping surface (FIG. 7A) in agreement with the lack of cross-competition between these antibodies.

The mAb 15EVQ binding epitope was spatially proximal to the dsRNA binding site at the C-terminal segment on TLR3 (Bell et al., Proc. Natl. Acad. Sci. (USA) 103: 8792-8797, 2006; Ranjith-Kumar et al., J Biol Chem, 282: 7668-7678, 2007; Liu et al., Science, 320: 379-381, 2008). Not wishing to be bound to any particular theory, it is believed that binding of mAb 15EVQ on its TLR3 epitope causes steric clashes with a ligand dsRNA molecule and/or the dimer partner, preventing ligand binding and ligand-induced receptor dimerization.

TABLE 5b

| Variant | mAb 15 | Variant | mAb 12 |
| --- | --- | --- | --- |
| wt TLR3 ECD | +++ | wt TLR3 ECD | +++ |
| R64E | +++ | D116R | − |
| K182E | +++ | N140A | ++ |
| K416E | +++ | V144A | +++ |
| Y465A | ++ | K145E | + |
| K467E | − | K147E | ++ |
| R488E | + | K163E | ++ |
| R489E | − | Q167A | ++ |
| N517A | ++ | N196A | ++ |
| D536K | ++ | | |
| D536A | ++ | | |
| Q538A | ++ | | |
| H539E | ++ | | |
| H539A | ++ | | |
| N541A | ++ | | |

TABLE 5b-continued

| Variant | mAb 15 | Variant | mAb 12 |
| --- | --- | --- | --- |
| E570R | ++ | | |
| K619E | ++ | | |
| K619A | ++ | | |
| K467E/Y468A | − | | |
| R488/R489/K493E | − | | |
| T472S/R473T/N474S | +++ | | |

EXAMPLE 7

Generation of Variants with Enhanced Thermal Stability

Structure-based engineering was conducted to generate antibody variants with increased thermal stability, with simultaneous efforts to maintain the biological activity and minimize immunogenicity.

mAb 15EVQ was selected for engineering. To minimize immunogenicity, only germline mutations predicted to be beneficial based upon structural considerations were pursued. The VL and VH sequences of mAb 15EVQ (SEQ ID NO: 41 and SEQ ID NO: 216, respectively) were aligned with the human germline genes using BLAST searches. The closest germline sequences identified were GenBank Acc. No. AAC09093 and X59318 for VH and VL, respectively. The following differences were identified between the germline VH, VL and those of the mAb 15EVQ VH and VL sequences: (VH) V34I, G35S, F50R, A61S, and Q67H; (VL) G30S, L31S, and A34N. The identified sequence differences were mapped onto the crystal structure of the mAb 15EVQ, and residues predicted to alter packing and interface interactions were selected for engineering. Based upon the crystal structure of the antibody (see Example 6), potential structure destabilizing residues were identified. (1) A small enclosed cavity was identified in the core of VH near V34. This cavity was large enough to accommodate a slightly larger sidechain such as Ile. (2) E99 of VH CDR3 was buried at the VH/VL interface without a H-bonding network. The negatively charged carboxylate group of E99 was in a generally hydrophobic environment with mostly van der Waals (vdw) contacts to neighboring residues. Burying a charge group is usually energetically unfavorable and thus has destabilizing effect. (3) F50 of VH is a VH/VL interface residue. Its aromatic sidechain is bulky and thus may have negative impact upon the pairing. H-bonding and vdw packing networks for the Fv were calculated and visually inspected in Pymol (www://_pymol_org). Buried cavities in the VH and VL domains were computed by Caver (Petrek et al., BMC Bioinformatics, 7:316, 2006). All molecular graphics figures were prepared in Pymol. Mutations were made to the expression vectors encoding Fab fragments or IgG4 full human antibodies generated as described in Example 3 using standard cloning techniques using Quick Change II XL Site Directed Mutagenesis Kit (Stratagene, San Diego, Calif.), Change-IT Multiple Mutation Site Directed Mutagenesis Kit (USB Corporation, Cleveland, Ohio) or Quick Change II Site Directed Mutagenesis Kit (Stratagene, San Diego, Calif.). The reactions were performed according to each manufacturer's recommendations. The obtained clones were sequenced for verification, and the resulting engineered variants were named mAbs 15-1-15-9. A listing of the SEQ ID NOs: for the CDRs, variable regions of light and heavy chains and full length heavy and light chains for mAb 15EVQ and its engineered variants is shown in Table 6. Table 7 shows primers for generation of each variant.

TABLE 6

| | SEQ ID NO: | | | | | | | | | |
|---|---|---|---|---|---|---|---|---|---|---|
| Candidate no: | HCDR1 | HCDR2 | HCDR3 | LCDR1 | LCDR2 | LCDR3 | LV | HV | Heavy IgG4 | Light chain |
| 15 | 111 | 112 | 84 | 109 | 110 | 113 | 41 | 216 | 220 | 156 |
| 15-1 | 111 | 114 | 84 | 109 | 110 | 113 | 41 | 124 | 130 | 156 |
| 15-2 | 115 | 112 | 84 | 109 | 110 | 113 | 41 | 125 | 131 | 156 |
| 15-3 | 116 | 112 | 84 | 109 | 110 | 113 | 41 | 126 | 132 | 156 |
| 15-4 | 111 | 117 | 84 | 109 | 110 | 113 | 41 | 127 | 133 | 156 |
| 15-5 | 116 | 118 | 84 | 109 | 110 | 113 | 41 | 128 | 134 | 156 |
| 15-6 | 116 | 112 | 119 | 109 | 110 | 113 | 41 | 129 | 135 | 156 |
| 15-7 | 111 | 112 | 84 | 120 | 110 | 113 | 122 | 42 | 102 | 157 |
| 15-8 | 111 | 112 | 84 | 121 | 110 | 113 | 123 | 42 | 102 | 158 |
| 15-9 | 116 | 118 | 119 | 109 | 110 | 113 | 41 | 159 | 160 | 156 |

Binding of mAbs 15-1-15-9 to TLR3 was evaluated by ELISA immunoassay. Human TLR3 ECD (100 µl of 2 µg/ml TLR3-ECD) was bound to a black Maxisorb plate (eBioscience) overnight at 4° C. The plates were washed and blocked, and diluted antibodies were aliquoted at 50 µl per well in duplicate onto the wells. The plate was incubated at RT for 2 hours shaking gently. Binding was detected using luminescence POD substrate (Roche Applied Science, Mannheim, Germany, Cat. No. 11 582 950 001) and goat anti-human Fc:HRP (Jackson ImmunoResearch, West Grove, Pa., Cat. No. 109-035-098) and the plate was read in a SpectraMax plate reader (Molecular Devices, Sunnyvale, Calif.).

TABLE 7

| Candidate no: | Mutants | Primers | Seq ID NO: | Resulting palsmid # | Mutagenesis template palsmid # |
|---|---|---|---|---|---|
| 15-1 | HC: F50R | GCCTGGAGTGGATGGGCCGGATCGACCCCAGCG | 142 | 5042 | p4595 |
| | | CGCTGGGGTCGATCCGGCCCATCCACTCCAGGC | 143 | | |
| 15-2 | HC: V34I | AGAGGTAACTCCCGTTGCGG | 144 | 5046 | p4584 |
| | | GCATCTGGCGCACCCAGCCGATCCAGTAGTTGGTGAAG | 145 | | |
| 15-3 | HC: V34I/G35S | AGAGGTAACTCCCGTTGCGG | 146 | 5045 | p4584 |
| | | GCATCTGGCGCACCCAGCTGATCCAGTAGTTGGTGAAG | 147 | | |
| 15-4 | HC: A61S/Q67H | AGAGGTAACTCCCGTTGCGG | 144 | 5048 | p4584 |
| | | CGCTGATGGTCACGTGGCCCTGGAAGCTAGGGCTGTAGTTGGTGTAG | 148 | | |
| 15-5 | HC: F50R/V34I/G35S/A61S/Q67H | CTTCACCAACTACTGGATCAGCTGGGTGCGCCAGATGC | 149 | 5069 | p5042 |
| | | CGCTGATGGTCACGTGGCCCTGGAAGCTAGGGCTGTAGTTGGTGTAG | 148 | | |
| 15-6 | HC: V34I/G35S/E99Q | CGCCATGTACTACTGCGCCCGCCAGCTGTACCAGGGCTAC | 150 | 5070 | p5045 |
| | | GTAGCCCTGGTACAGCTGGCGGGCGCAGTAGTACATGGCG | 151 | | |
| 15-7 | LC: G30S/L31S | GCCAGCCAGAGCATCAGCAGCTACCTGGCCTGGTACCAGC | 152 | 5043 | p4595 |
| | | GCTGGTACCAGGCCAGGTAGCTGCTGATGCTCTGGCTGGC | 153 | | |
| 15-8 | LC: A34N | AGAGGTAACTCCCGTTGCGG | 144 | 5047 | p4588 |
| | | CGGGCTTCTGCTGGTACCAGTTCAGGTAGCTGCTGATGCTCTG | 154 | | |
| 15-9 | HC: F50R/V34I/G35S/A61S/Q67H/E99Q | CGCCATGTACTACTGCGCCCGCCAGCTGTACCAGGGCTAC | 150 | 5097 | p5069* |
| | | GTAGCCCTGGTACAGCTGGCGGGCGCAGTAGTACATGGCG | 151 | | |

*p5069 as a single gene for heavy chain. Variable reagion of p5069 swaped to p5070 backbone DSC experiments were performed on a MicroCal's Auto VP-capillary DSC system (MicroCal, LLC, Northampton, Mass.) in which temperature differences between the reference and sample cells were continuously measured, and calibrated to power units. Samples were heated from 10° C. to 95° C. at a heating rate of 60° C./hour. The pre-scan time was 15 minutes and the filtering period was 10 seconds. The concentration used in the DSC experiments was about 0.5 mg/ml. Analysis of the resulting thermograms was performed using MicroCal Origin 7 software (MicroCal, LLC).

The thermal stability (Tm) of the generated variants was measured by DSC (Table 8). Binding of the antibody variants to TLR3 was comparable to that of the parental antibody.

mAb c1811 secreted by the hybridoma. Cloned heavy chain and light chain variable region genes were then respectively inserted into plasmid expression vectors that provided coding sequences for generating a chimeric Rat/Balb C muIgG1/κ mAb designated as mAb 5429 using routine methods. The antibodies were expressed as described in Example 3. The amino acid sequences of the mAb 5429 heavy and light chain variable regions are shown in SEQ ID NO:164 and SEQ ID NO: 163, respectively, and the heavy and light chain full length sequences are shown in SEQ ID NO:166 and SEQ ID NO: 165, respectively. The heavy and light chain full length sequences of mAb c1811 are shown in SEQ ID NO: 168 and SEQ ID NO: 167, respectively.

TABLE 8

Summary of melting temperatures ($T_M$) of the variants and rationale for making them.

| Candidate no: | | Mutations | Rationale | TM (° C.) | ΔTM (° C.) |
|---|---|---|---|---|---|
| 15EVQ | | WT | | 64.7 | 0 |
| 15-1 | HV | F50R | VH/VL interface | 69.3 | 4.6 |
| 15-2 | HV | V34I | VH core packing | 66.9 | 2.2 |
| 15-3 | HV | V34I/G35S | H-bonding, VH core packing | 71.2 | 6.5 |
| 15-4 | HV | A61S/Q67H | VH/VL packing, VH surface charge distribution | 65.4 | 0.7 |
| 15-5 | HV | F50R/V34I/G35S/A61S/Q67H | VH/VL interface, H-bonding, VH core packing, VH/VL packing, VH surface charge distribution | 76.2 | 11.5 |
| 15-6 | HV | V34I/G34S/E99Q | H-bonding, VH core packing, removal of buried charge | 75 | 10.3 |
| 15-7 | LV | G30S/L31S | L-CDR1 surface polar residues | 63.1 | −1.6 |
| 15-8 | LV | A34N | VL/VH interface | 64 | −0.7 |
| 15-9 | HV | F50R/V34I/G35S/A61S/Q67H/E99Q | VH/VL interface, H-bonding, VH core packing, VH/VL packing, VH surface charge distribution, removal of buried charge | 76 | 11.3 |

EXAMPLE 8

Generation of a Surrogate Anti-TLR3 Antibody

A chimeric antagonistic rat/mouse anti-mouse TLR3 antibody, herein named mAb 5429 was generated to evaluate effects of inhibiting TLR3 signaling in various in vivo models, as the humanized antibodies generated in Example 1 did not have sufficient specificity or antagonist activity for mouse TLR3. The surrogate chimeric mAb 5429 as well as its parent rat anti-mouse TLR3 antibody c1811 inhibited mouse TLR3 signaling in vitro, and in vivo, and ameliorated pathogenic mechanisms in several disease models in the mouse.

Data discussed below suggests a role for TLR3 in the induction and perpetuation of detrimental inflammation, and contribute to the rationale for the therapeutic use of TLR3 antagonists and TLR3 antibody antagonists, for example acute and chronic inflammatory conditions including hypercytokinemia, asthma and airway inflammation, inflammatory bowel diseases and rheumatoid arthritis, viral infections, and type II diabetes.

Generation of the Surrogate mAb 5429

CD rats were immunized with recombinant murine TLR3 ectodomain (amino acids 1-703 of seq ID NO: 162, GenBank Acc. No. NP_569054) generated using routine methods. Lymphocytes from two rats demonstrating antibody titers specific to murine TLR3 were fused to FO myeloma cells. A panel of monoclonal antibodies reactive to murine TLR3 were identified and tested for in vitro antagonist activity in the murine luciferase reporter and murine embryonic fibroblast assays. The hybridoma line C1811A was selected for further work. Functional variable region genes were sequenced from Characterization of mAb 5429 mAb 5429 was characterized in a panel of in vitro assays for its neutralizing ability on TLR3 signaling. The activity assays and results are described below.

Murine Luciferase Reporter Gene Assay

Figures 8, 8A:
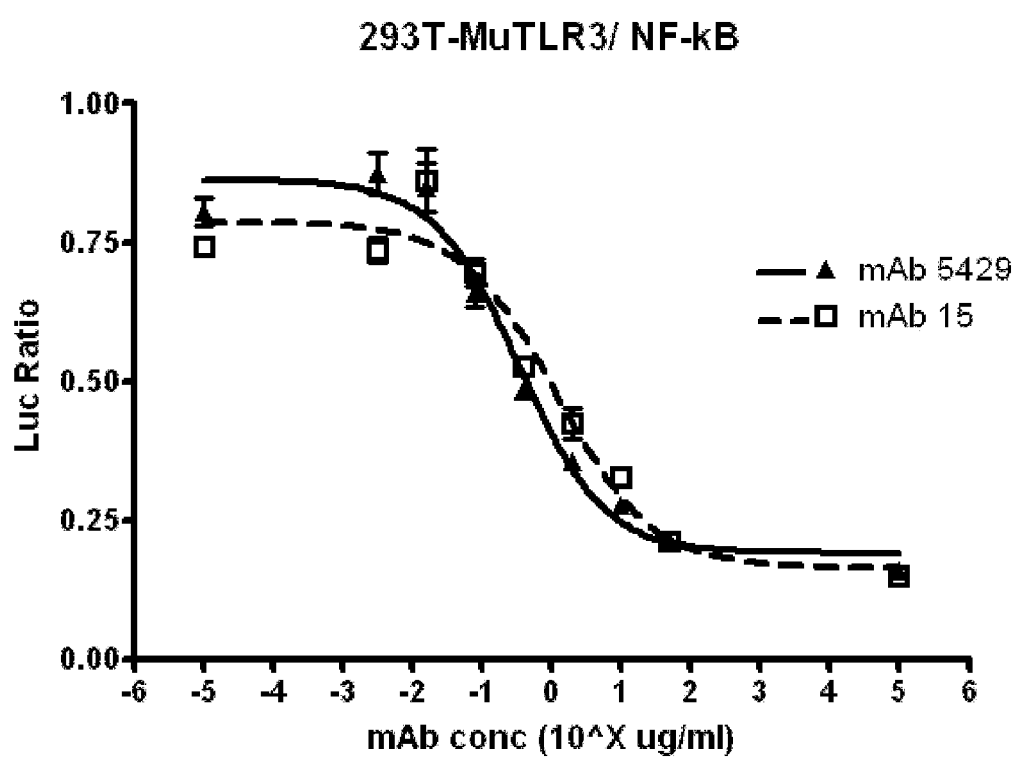
FIGS. 8A and 8B show the effect of rat/mouse anti-mouse TLR3 mAb mAb 5429 (surrogate) in A) NF-κB and B) ISRE reporter gene assays.
Figure 8B:
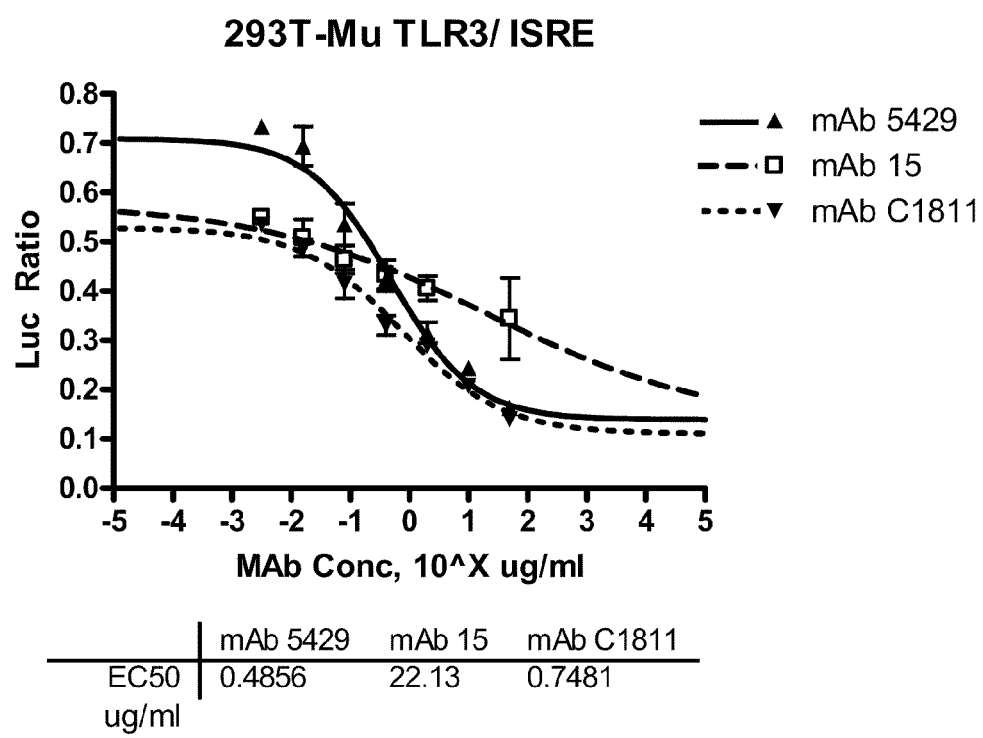

The murine TLR3 cDNA (SEQ ID NO: 161, GenBank Acc. No: NM_126166) was amplified by PCR from murine spleen cDNA (BD Biosciences, Bedford, Mass.), and cloned into the pCEP4 vector (Life Technologies, Carslbad, Calif.) using standard methods. 200 µl HEK293T cells were plated in 96 well white clear-bottom plates at a concentration of $4 \times 10^4$ cells/well in complete DMEM, and used the following day for transfections using Lipofectamine 2000 (Invitrogen Corp., Carslbad, Calif.) using 30 ng pNF-κB firefly luciferase (Stratagene, San Diego, Calif.) or 30 ng pISRE firefly luciferase (BD Biosciences, Bedford, Mass.), 5 ng phRL-TK control Renilla luciferase (Promega Corp., Madison, Wis.) reporter plasmids, 1.5 ng pCEP4 encoding the full-length murine TLR3, and 13.5 ng empty pcDNA3.1 vector (Life Technologies, Carslbad, Calif.) to bring the total DNA amount to 50 ng/well. 24 hours post-transfection, the cells were incubated for 30 minutes to 1 hour at 37° C. with the anti-murine TLR3 antibodies in fresh serum-free DMEM before the addition of 0.1 or 1 µg/µl poly(I:C). The plates were harvested after 24 hours using the Dual-Glo Luciferase Assay System (Promega, Madison, Wis.). The relative light units were measured using a FLUOstar OPTIMA multi-detection reader with OPTIMA software (BMG Labtech GmbH, Germany). Normalized values (luciferase ratios) were obtained by dividing the firefly relative light units (RLUs) by the Renilla RLUs. mAb 5429 as well as its parent mAb c1811 and mAb 15 (Table 3a) reduced poly(I:C)-induced NF-kB and ISRE activation in a dose-dependent fashion (FIGS. 8A and 8B), demonstrating their abilities to antagonize the activity of TLR3. IC50s measured in the ISRE assay were 0.5, 22, and 0.7 µg/ml for mAb 5249, mAb 15 and mAb c1811, respectively.

Murine Embryonic Fibroblast (MEF) Assay

Figure 9:
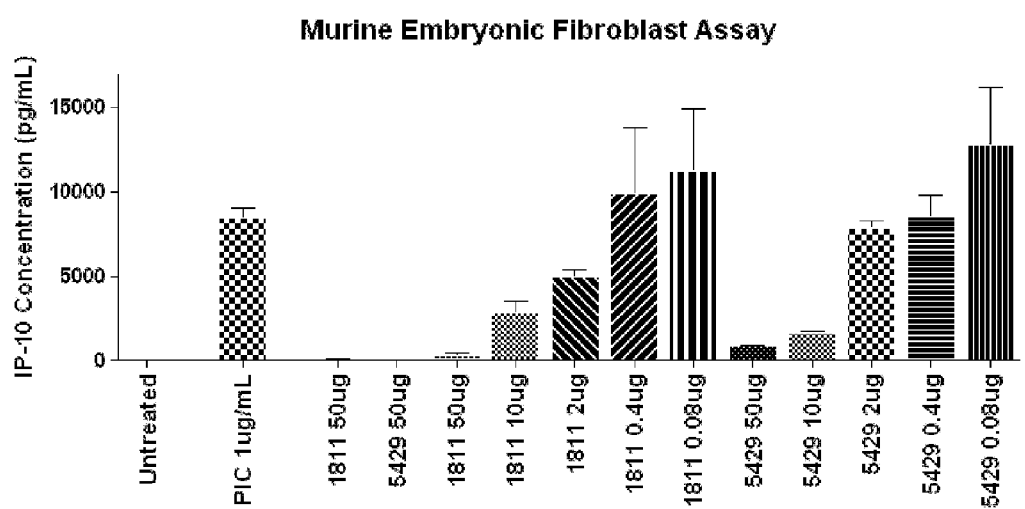
FIG. 9 shows the effect of the surrogate mAbs (mAb 5429, mAb c1811) in the MEF CXCL10/IP-10 assay.

C57BL/6 MEF cells were obtained from Artis Optimus (Opti-MEF™ C57BL/6-0001). The cells were plated in 96-well flat bottom plates (BD Falcon) at 20,000 cells/well in 200 µl MEF media (DMEM with glutamax, 10% heat inactivated-FBS, 1×NEAA, and 10 µg/ml gentamycin). All incubations were done at 37° C./5% $CO_2$. 24 hours after plating, mAb 5429 or mAb c1811 were added into wells. The plates were incubated with the mAbs for 1 hr, after which Poly(I:C) was added at 1 µg/ml in each well. The supernatants were collected after a 24-hour incubation. Cytokine levels were determined using a bead kit (Invitrogen Corp., Carslbad, Calif.) to detect CXCL10/IP-10 following manufacturer's protocol. The results were graphed using GraphPad Prism Software. Both antibodies reduced poly(I:C)-induced CXCL10/IP-10 levels in a dose-dependent manner, demonstrating the abilities of these antibodies to antagonize endogenous TLR3 and inhibit TLR3 signaling (FIG. 9).

Flow Cytometry—Surface Staining

C57BL/6 and TLR3 knockout (TLR3KO) (C57BL/6 background; female, 8-12 weeks of age, Ace Animals, Inc.), 10 per group, were dosed intraperitoneally with 1 ml of 3% Thioglycollate medium (Sigma) and 96 hrs later, the mice were euthanized and the peritoneum from each mouse was lavaged with 10 ml sterile PBS. Thioglycollate-elicited peritoneal macrophages were resuspended in PBS and cell viability was assessed using Trypan Blue staining. Cells were pelleted by centrifugation and resuspended in 250 µl FACS Buffer (PBS-$Ca^{2+}$—$Mg^{2+}$, 1% heat-inactivated FBS, 0.09% Sodium Azide) and were kept on wet ice. The CD16/32 reagent (eBioscience) was used at 10 µg/$10^6$ cells for 10 minutes to block Fc Receptors on the macrophages. The cells were distributed at $10^6$ cells in 100 µl/well for surface staining. Alexa-Fluor 647 (Molecular Probes)-conjugated mAb c1811 and mAb 1679 (rat anti-mouse TLR3 antibody that had no TLR3 specificity, and thus used as an isotype control) were added at 0.25 µg/$10^6$ cells and incubated on ice in the dark for 30 minutes. The cells were washed and resuspended in 250 µl of FACS Buffer. The viability stain, 7-AAD (BD Biosciences, Bedford, Mass.), was added at 5 µl/well no more than 30 minutes before acquisition of samples on FACS Calibur to detect a dead cell population. Samples were collected by the FACS Calibur using Cell Quest Pro Software. FCS Express was used to analyze the collected data by forming histograms.

Figure 10:
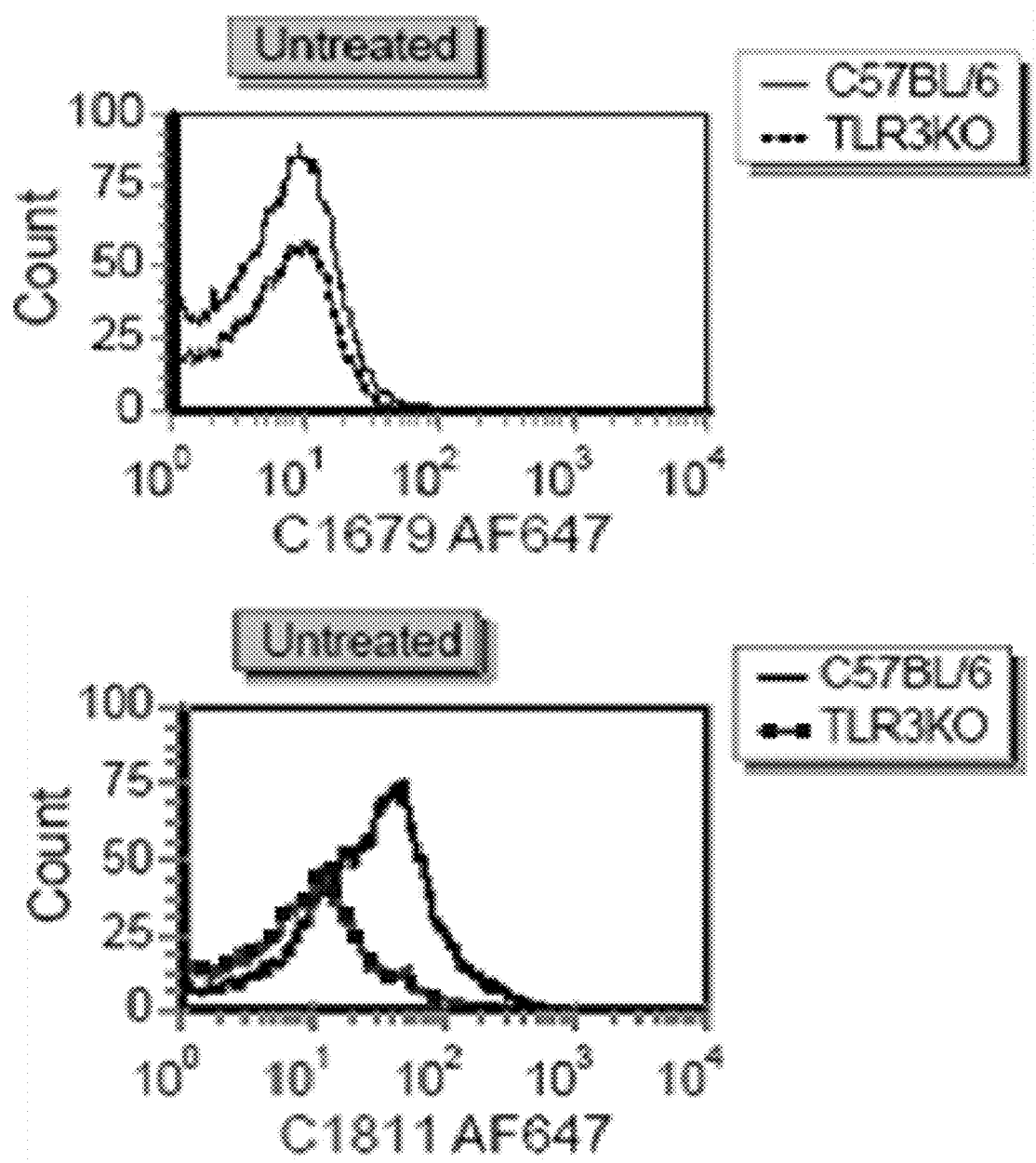
FIG. 10 shows specificity of binding of the surrogate mAb to TLR3. Top panel: isotype control; bottom panel: mAb c1811.

The binding of mAb c1811 to murine thioglycollate-elicited peritoneal macrophages from C57BL/6 and TLR3KO mice were evaluated by flow cytometry to determine binding specificity. mAb 5429 was not used in this assay since the mouse Fc region of this chimeric antibody was expected to contribute to non-specific binding. mAb c1811 exhibited no binding to TLR3KO macrophages, and increased binding to the cell surfaces of C57BL/6 peritoneal macrophages, suggesting a specificity of the mAb for TLR3 (FIG. 10). mAb 5429, having the same binding regions as mAb c1811, is assumed to have the same binding specificity as mAb c1811.

EXAMPLE 9

TLR3 Antibody Antagonists Protect from TLR3-mediated Systemic Inflammation

Model

The Poly(I:C)-induced systemic cytokine/chemokine model was used as a model of TLR3-mediated systemic inflammation. In this model, poly(I:C) (PIC) delivered intraperitoneally induced a systemic cytokine and chemokine response that was partially TLR3-mediated.

Female C57BL/6 mice (8-10 weeks old) or female TLR3KO mice (C57BL/6 background; 8-10 weeks old, Ace Animals, Inc.) were given mAb 5429 at 10, 20 or 50 mg/kg in 0.5 ml PBS, mAb c1811 at 2, 10 or 20 mg/kg in 0.5 ml PBS or 0.5 ml PBS alone (vehicle control) subcutaneously. 24 hours after antibody dosing, mice were given 50 µg poly(I:C) (Amersham Cat. No. 26-4732 Lot no. IH0156) in 0.1 ml PBS intraperitoneally. Retro-orbital blood was collected 1 and 4 hours after the poly(I:C) challenge. Serum was prepared from whole blood and analyzed for cytokine and chemokine concentrations by Luminex.

Results

Poly(I:C) delivered intraperitoneally induced a systemic cytokine and chemokine response that was partially TLR3-mediated, as evidenced by the significantly reduced production of a panel of chemokines and cytokines in the TLR3KO animals (Table 9A). The TLR3-dependent poly(I:C)-induced mediators were IL-6, KC, CCL2/MCP-1 and TNF-α at 1 hr post-poly(I:C) challenge, and IL-1α, CCL5/RANTES and TNF-α at 4 hr post-poly(I:C) challenge. Both mAb c1811 and mAb 5429 significantly reduced levels of these TLR3-dependent mediators, demonstrating the ability of the antibodies to reduce TLR3 signaling in vivo (Table 9B). Values in Table 9 are shown as mean cytokine or chemokine concentrations in pg/ml of six animals/group±SEM. These data suggest that TLR3 antagonism can be beneficial in reducing excess TLR3-mediated cytokine and chemokine levels in conditions such as cytokine storm or lethal shock.

TABLE 9A

|  | C57BL/6 | | TLR3KO | |
| --- | --- | --- | --- | --- |
| PIC | − | + | − | + |
| mAb 5429 (mg/kg) | − | − | − | − |
| mAb c1811 (mg/kg) | − | − | − | − |
| | 1 h PIC challenge | | | |
| TNFα | 6.005 ± 0.32 | 319.4 ± 34.1* | 9.13 ± 4.41 | 43.80 ± 10.13** |
| KC | 129.3 ± 9.83 | 2357 ± 491.5* | 152.0 ± 21.34 | 432.3 ± 90.66** |
| IL-6 | 40.91 ± 5.66 | 5317 ± 856.7* | 120.1 ± 99.99 | 1214 ± 294.9** |
| MCP-1 | 84.67 ± 18.45 | 694.6 ± 127.8* | 67.85 ± 34.16 | 249.9 ± 55.60** |

TABLE 9A-continued

|  | C57BL/6 | | TLR3KO | |
| --- | --- | --- | --- | --- |
|  | 4 h PIC challenge | | | |
| IL-1α | 28.21 ± 17.78 | 796.7 ± 45.0* | 13.94 ± 13.84 | 408.5 ± 29.91** |
| RANTES | 20.87 ± 1.738 | 4511 ± 783.4* | 36.01 ± 4.484 | 706.3 ± 84.36** |
| TNFα | 0.10 ± 0 | 561.7 ± 81.84* | 3.215 ± 3.115 | 305.8 ± 53.63** |

*p < 0.001 One Way ANOVA to C57BL/6 PBS
**p < 0.001 One Way ANOVA to C57BL/6 PIC

TABLE 9B

| | C57BL/6 | | | | | |
| --- | --- | --- | --- | --- | --- | --- |
| PIC | + | + | + | + | + | + |
| mAb 5429 (mg/kg) | 50 | 20 | 10 | – | – | – |
| mAb c1811 (mg/kg) | – | – | – | 20 | 10 | 2 |
| | | | 1 h PIC challenge | | | |
| TNF-α | 29.33 ± 3.78*** | 31.05 ± 1.59*** | 59.55 ± 12.71*** | 32.54 ± 3.89*** | 42.22 ± 7.04*** | 42.61 ± 10.58*** |
| KC | 466.3 ± 92.35*** | 440.3 ± 10.01*** | 744.6 ± 103.1** | 637.3 ± 151.0*** | 944.2 ± 130.9** | 919.3 ± 231.2** |
| IL-6 | 480.2 ± 62.88*** | 375.9 ± 46.14*** | 705.2 ± 149.8*** | 739.2 ± 113.3*** | 1047 ± 222*** | 1229 ± 378.4*** |
| MCP-1 | 168.5 ± 15.04** | 321.6 ± 206.7 | 219.2 ± 70.58* | 184.0 ± 14.92** | 278.3 ± 53.57 | 414.9 ± 97.17 |
| | | | 4 h PIC challenge | | | |
| IL-1α | 343.0 ± 33.01*** | 452.6 ± 94.86** | 481.1 ± 121.0* | 354.8 ± 45.43*** | 351.7 ± 68.85*** | 352.4 ± 39.60*** |
| RANTES | 1381 ± 169.7*** | 2439 ± 308.7** | 1601 ± 398.9*** | 1303 ± 168.0*** | 1365 ± 474.1*** | 2209 ± 402.5** |
| TNF-α | 100.1 ± 8.5*** | 205.1 ± 41.85*** | 226.1 ± 64.72*** | 138.9 ± 26.0*** | 121.6 ± 38.85*** | 223.8 ± 47.74*** |

***p < 0.001,
**p < 0.01,
*p < 0.05: One Way ANOVA statistics were compared to the C57BL/6 + PIC group

EXAMPLE 10

TLR3 Antibody Antagonists Reduce Airway Hyperresponsiveness

Model

Airway hyperresponsiveness was induced by Poly(I:C).

Female C57BL/6 mice (12 weeks old) or female TLR3KO mice (C57BL/6 background; 12 weeks old, Ace Animals, Inc.) were anesthetized with isoflurane and several doses (10-100 μg) of poly(I:C) in 50 μl sterile PBS were administered intranasally. Mice received three administrations of poly(I:C) (or PBS) with a 24 hour rest period between each administration. 24 hours following the last poly(I:C) (or PBS) administration, lung function and airway hyperresponsiveness to methacholine were measured using whole body plethysmography (BUXCO system). The mice were placed into the whole body plethysmograph chamber and allowed to acclimate for at least 5 minutes. Following baseline readings, mice were exposed to increasing doses of nebulized methacholine (Sigma, St. Louis, Mo.). The nebulized methacholine was administered for 2 minutes, followed by a 5-minute data collection period, followed by a 10-minute rest period before subsequent increasing-dose methacholine challenges. The increased airflow resistance was measured as Enhanced Pause (Penh) and is represented as the average Penh value over the 5-minute recording period (BUXCO system). Following lung function measurements, mice were euthanized and the lungs were cannulated. Bronchoalveolar lavages (BAL) were performed by injecting 1 ml of PBS into the lungs and retrieving the effluent. The lung tissues were removed and frozen. BAL fluids were centrifuged (1200 rpm, 10 min.) and the cell-free supernatants were collected and stored at −80° C. until analysis. Cell pellets were resuspended in 200 μl PBS for total and differential cell counts. The multiplex assay was performed following the manufacturer's protocol and the Multiplex Immunoassay Kit (Millipore, Billercia, Mass.).

Results

Previous observations demonstrated that the intranasal administration of poly(I:C) induced a TLR3-mediated impairment in lung function in mice with increased enhanced pause (PenH) measurement in whole body plethysmography (Buxco) at baseline and an increased responsiveness to aerosolized methacholine (an indicator of airway hyperesponsiveness) (PCT Publ. No. WO06/060513A2). This impairment in the lung function was associated with neutrophil recruitment into the lung, and increased levels of pro-inflammatory cytokines/chemokines in the lung. In this study, the effect of mAb 1811 and mAb 5429 was evaluated in poly(I:C)-induced impairment in lung function by administering each antibody at 50 mg/kg subcutaneously prior to poly(I:C) challenge.

Figure 11:
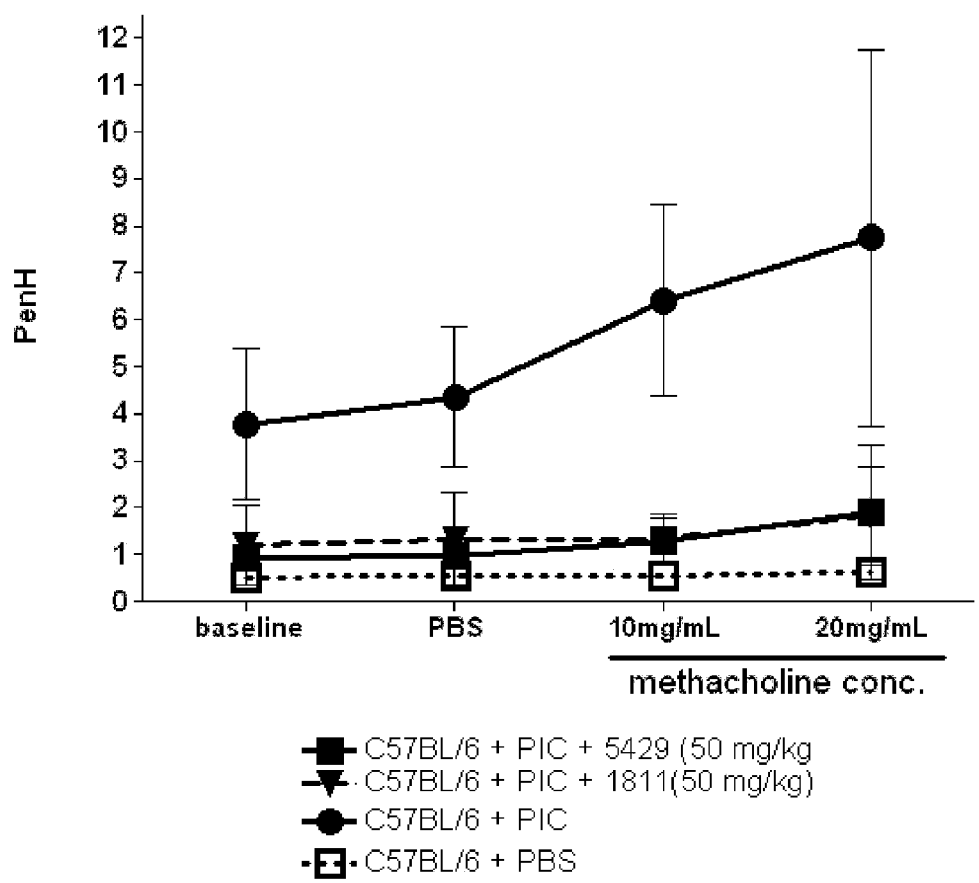
FIG. 11 shows effect of the surrogate mAbs on penH level in an AHR model.
Figure 12:
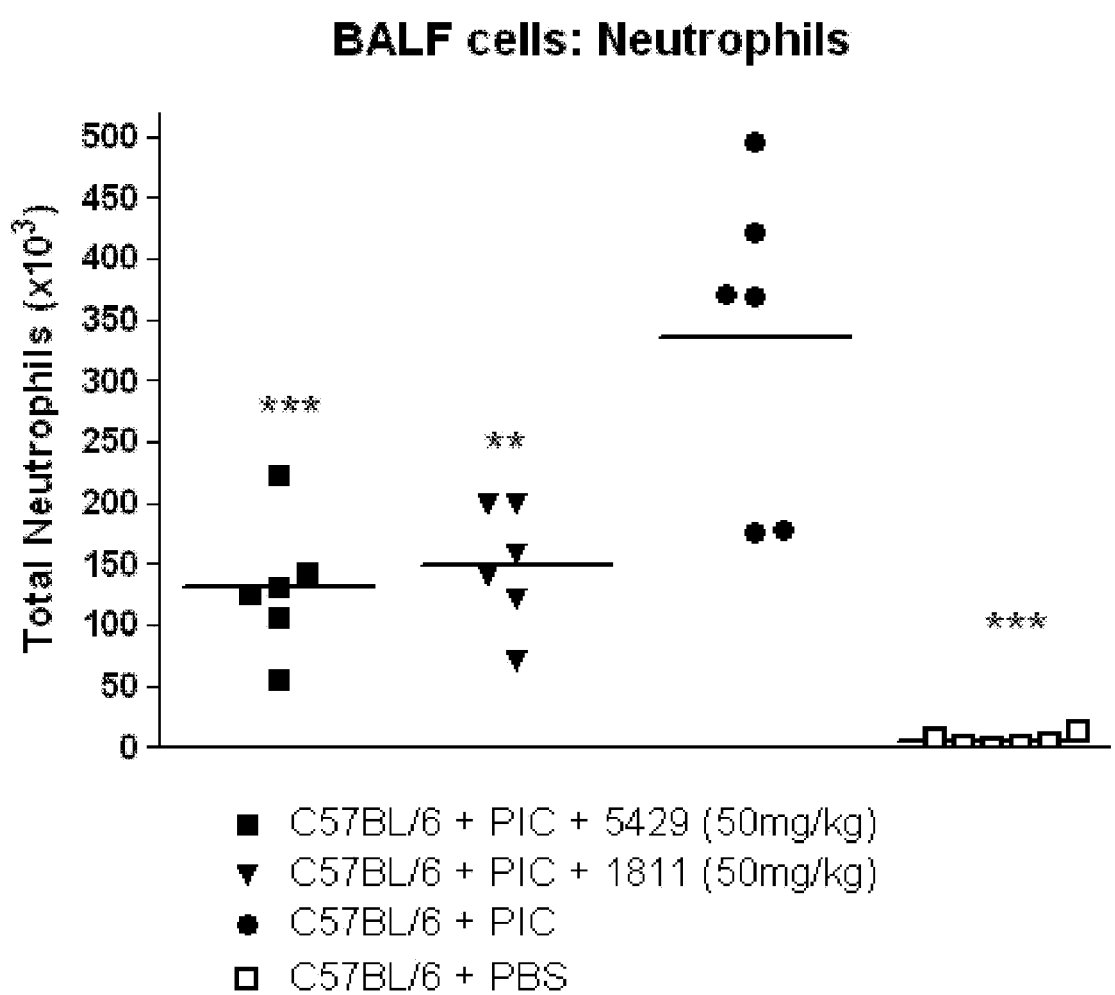
FIG. 12 shows effect of the surrogate mAbs on total neutrophil numbers in BAL fluid in an AHR model.
Figure 13:
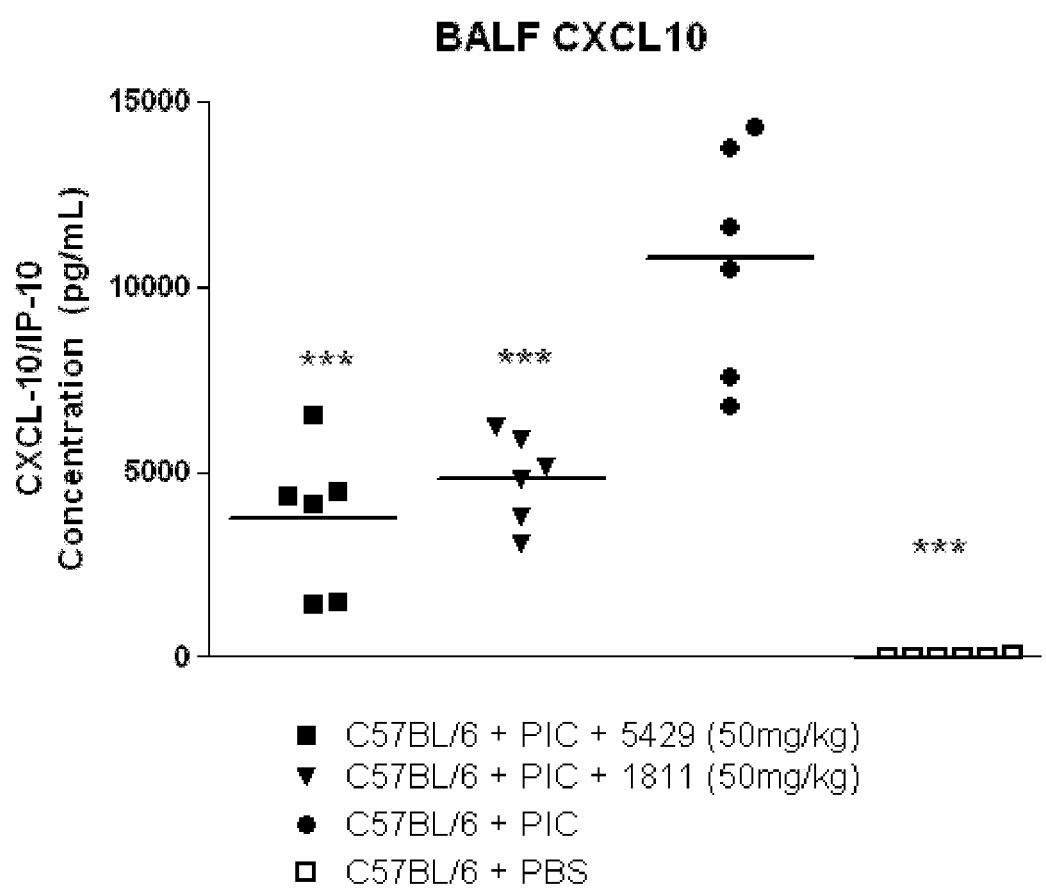
FIG. 13 shows effect of the surrogate mAbs on CXCL10/IP-levels in BAL fluid in an AHR model.

TLR3-mediated impairment of lung function was significantly reduced by treatment of animals with TLR3 antibody antagonists prior to the poly(I:C) challenge. TLR3-mediated increases in baseline PenH and airway sensitivity to methacholine were prevented in the anti-TLR3 antibody-treated animals (FIG. 11). Further, TLR3-mediated recruitment of neutrophils into the mouse lung and generation of chemokines in the airways were reduced in the anti-TLR3 antibody-treated animals. The neutrophil numbers (FIG. 12) and the CXCL10/IP-10 levels (FIG. 13) were measured from the collected bronchoalveolar lavage fluid (BALF). The studies were repeated at least three times with similar results. Data shown in FIGS. 11, 12 and 13 are from one representative study. Each symbol represents a data point from one mouse, and the horizontal bars show group means. The study demonstrated that systemically-administer TLR3 antibody antagonists reached the lung, reduced TLR3-mediated impairment of lung function, neutrophil infiltration into the airway, chemokine generation and respiratory tract inflammation in the used model. Thus, TLR3 antagonists may be beneficial in the treatment or prevention of respiratory diseases characterized by airway hyperresponsiveness, such as asthma, allergic rhinitis, chronic obstructive pulmonary disease (COPD), and cystic fibrosis.

EXAMPLE 11

TLR3 Antibody Antagonists Protect from Inflammatory Bowel Disease

Model

The DSS colitis Model was used as a model of inflammatory bowel disease.

Female C57BL/6 mice (<8 weeks old) or female TLR3KO mice (C57BL/6 background; <8 weeks old weighing between 16.5 g and 18 g, Ace Animals, Inc.) were fed gamma-irradiated food starting on day −1. DSS (Dextran sulfate) (MP Biomedicals, Aurora, Ohio, Catalog no: 160110; 35-50 kDa; 18-20% Sulfur, Lot no. 8247J) was diluted in autoclaved acidified drinking water to a final concentration of 5%. The DSS-water was administered for 5 days, after which it was replaced with plain water. Mice were allowed to drink water ad libitum throughout the study. All water bottles were weighed every day to record water consumption. On days 0, 2, and 4 mice were dosed intraperitoneally with 5 mg/kg (0.1 mg in 0.1 ml PBS) mAb 5429, mouse anti-TNF-α antibody, or PBS as a control. Mice were monitored daily throughout the study and were weighed on days 0 through 4 and day 7. Mice were euthanized on days 2 and 7 of the study. Abdominal cavities were opened and the ascending colons cut where they join the cecum. Colons were collected and fixed in 10% neutral buffered formalin. Colons were paraffin-embedded, sectioned and H&E stained (Qualtek Molecular Labs, Santa Barbara, Calif.). Colonic histopathological assessments were done in a blinded fashion by a veterinary pathologist as described below (PathoMetrix, San Jose, Calif.).

Histopathologic Evaluation

Two segments of large intestine, colon and rectum were evaluated and scored for the following changes: (i) single cell necrosis; (ii) epithelial ulceration; (iii) epithelial sloughing; (iv) cryptal abscess; (v) cell proliferation; (vi) cryptal cell proliferation; (vii) granulation tissue formation in the lamina propria; (viii) granulation tissue in the submucosa; (ix) submucosal inflammatory cell infiltrate, neutrophil predominant; and (x) submucosal edema.

A single, overall score of severity was given based on the following standards:
- 0—non-existent
- 1—mild, focal or occasionally found
- 2—mild, multifocal
- 3—moderate, frequently found but in limited areas
- 4—severe, frequently found in many areas or extensions of the tissue submitted
- 5—very severe, extends to large portions of the tissue submitted Results Previous observations demonstrated that TLR3KO animals showed significantly reduced histopathology compared with wild type mice in a model of inflammatory bowel disease induced by DSS ingestion (PCT Publ. No. WO06/60513A2), thus suggesting that TLR3 signaling plays a role in the pathogenesis in this model. It has been reported that commensal bacterial RNA or mammalian RNA released from necrotic cells can act as endogenous ligands to stimulate TLR3 signaling (Kariko et al., Immunity 23165-231175 2005; Kariko et al., J. Biol. Chem. 279:12542-12550 2004), and therefore TLR3 stimulation by endogenous ligands in the gut may enhance and perpetuate inflammation in the DSS colitis model.

Figure 14:
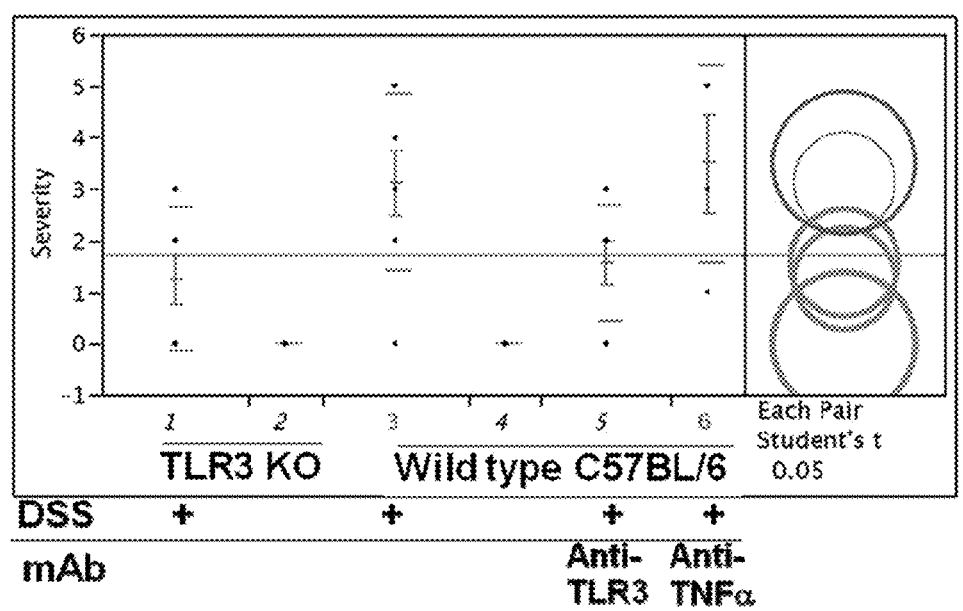
FIG. 14 shows effect of the surrogate mAb on histopathology scores in a DSS model.

Disease severity was ameliorated in DSS-exposed animals upon treatment with anti-TLR3 antibodies, as assessed by compound histopathology scores (FIG. 14). FIG. 14 shows means, standard deviations and 95% confidence intervals for disease severity scores as horizontal bars. Significant reduction in the scores were observed in the wild type DSS-exposed animals treated with anti-TLR3 antibodies ($p<0.05$) when compared to untreated wild type animals. DSS-exposed TLR3KO animals were protected from DSS-induced changes. DSS-exposed animals receiving anti-mouse TNF-α mAb demonstrated no improvement in histopathology in the DSS model. Therefore, the DSS model may be useful in evaluating therapeutics that may target the human patient population that is non-responsive to anti-TNF-α therapies, and neutralizing anti-TLR3 antibodies may have the potential to provide benefit to patients with inflammatory bowel disease who do not respond to anti-TNF-α therapies.

Model

The T cell Transfer Model was used as a model of inflammatory bowel disease. In this model, gut inflammation was induced in SCID mice by the transfer of a population of regulatory T cell-devoid naïve T cells from immune-competent mice, which attack antigen-presenting cells in the gut mucosa.

Naïve T-cells (CD4+CD45RB$^{high}$ T cells) were injected intraperitoneally into SCID recipients to induce chronic colitis. Mice were given either PBS (500 µl/mouse intraperitoneally; vehicle control), mAb 5429 (0.1 mg/mouse intraperitoneally), or anti-TNF-α antibody (0.05 mg/mouse intraperitoneally; positive control) beginning 48 hours following transfer of T-cells and then twice weekly throughout the 8 week study. At 8 weeks following T-cell transfer (or when mice lost >15% of their original body weight) animals were euthanized and colons removed. Colons were fixed, paraffin-embedded and H&E stained. Histopathology (cell infiltration, crypt abscesses, epithelial erosion, goblet cell loss, and bowel wall thickening) was assessed quantitatively in a blinded fashion.

Results

Disease severity was ameliorated in animals that received T-cell transfer upon treatment with anti-TLR3 antibodies, as assessed by significant reduction in the histopathology sum of scores when compared to the control animals ($p<0.05$) (FIG. 15A). For the sum of scores, crypt abscesses, ulceration, neutrophil influx, goblet cell loss, abnormal crypts, lamina propria inflammation and transmural involvement was assessed. Significant reduction was observed with crypt abscesses, ulceration and neutrophil influx (for all $p<0.05$) (FIG. 15B). Anti-TNF-α antibody was used as a positive control at doses known to provide optimal benefit.

Studies using two well known models of inflammatory bowel diseases, the DSS and the T-cell transfer model, demonstrated that systemically delivered TLR3 antibody antagonists reached the gut mucosa and reduced gastrointestinal tract inflammation induced through two different pathogenic mechanisms. Thus, TLR3 antagonists may be beneficial for the treatment of inflammatory bowel diseases, including anti-TNF-α-refractory cases, and other immune-mediated pathologies in the gastrointestinal tract.

EXAMPLE 12

TLR3 Antibody Antagonists Protect from Collagen-Induced Arthritis

Model

The collagen-induced arthritis (CIA) model was used as a model of rheumatoid arthritis.

Male B10RIII mice (6-8 weeks old, Jackson Labs) were divided into groups of 15 per group (arthritis groups) or 4 per group (control mice). Arthritis groups were anesthetized with Isoflurane and given injections of Type II collagen (Elastin Products) and Freund's complete adjuvant supplemented with M. tuberculosis (Difco) on days 0 and 15. On day 12, mice with developing type II collagen arthritis were randomized by body weight into treatment groups and were dosed subcutaneously (SC) on days 12, 17, and 22 (d12, d17, 2d2) with mAb 5429 (25 mg/kg), the negative control antibody CVAM (a recombinant mAb of no known specificity in the mouse) (5 mg/kg) or anti-TNF-α antibody (5 mg/kg, positive control). In addition, control groups of mice were treated with vehicle (PBS) or dexamethasone (0.5 mg/kg, Dex, reference compound) subcutaneously (SC) daily (QD) on days 12-25. Animals were observed daily from days 12 through 26. Fore and Hind paws were evaluated by a clinical scoring system (shown below). Animals were euthanized on study day 26 and histopathology was assessed in a blinded fashion (scoring system described below). Efficacy evaluation was based on animal body weights, and clinical arthritis scores. All animals survived to study termination.

Clinical Scoring Criteria for Fore and Hind Paws
- 0— normal
- 1—hind or fore paw joint affected or minimal diffuse erythema and swelling
- 2—hind or fore paw joints affected or mild diffuse erythema and swelling
- 3—hind or fore paw joints affected or moderate diffuse erythema and swelling
- 4—marked diffuse erythema and swelling, or =4 digit joints affected)
- 5—severe diffuse erythema and severe swelling entire paw, unable to flex digits)

Histopathologic Scoring Methods for Mouse Joints with Type II Collagen Arthritis When scoring paws or ankles from mice with lesions of type II collagen arthritis, severity of changes as well as number of individual joints affected were considered. When only 1-3 joints of the paws or ankles out of a possibility of numerous metacarpal/metatarsal/digit or tarsal/tibiotarsal joints were affected, an arbitrary assignment of a maximum score of 1, 2 or 3 for parameters below was given depending on severity of changes. If more than 2 joints were involved, the criteria below were applied to the most severely affected/majority of joints.

Clinical data for paw scores were analyzed using AUC for days 1-15, and % inhibition from controls were calculated.

Figure 16:
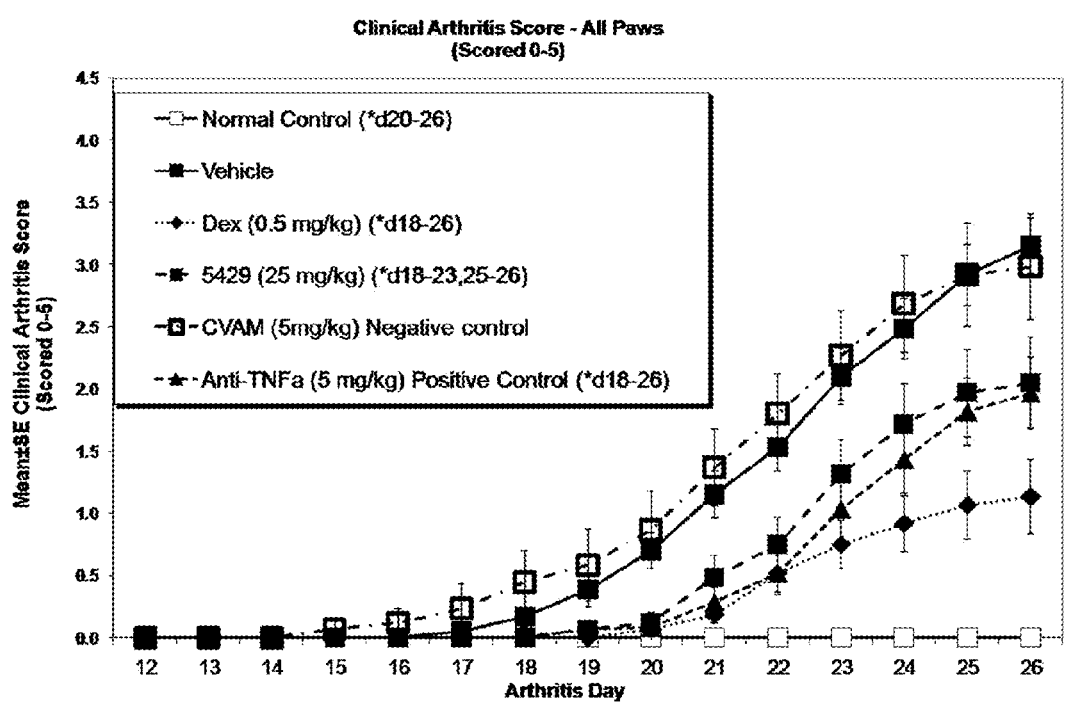
FIG. 16 shows effect of the surrogate mAb on clinical scores in a CIA model.
Figure 17:
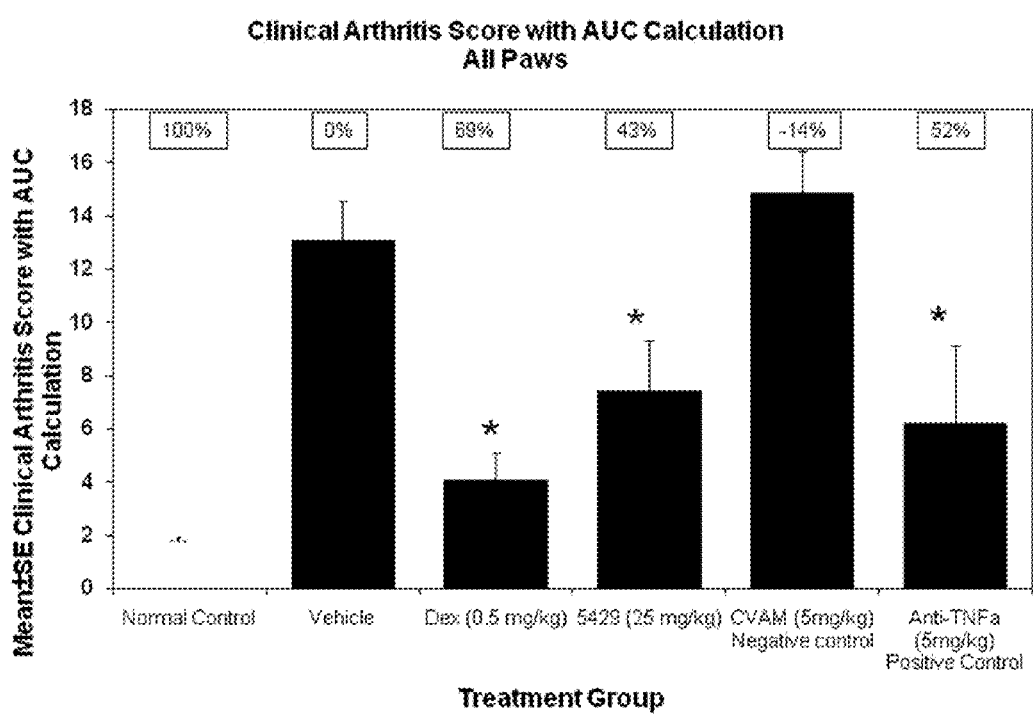
FIG. 17 shows effect of the surrogate mAb on the clinical AUC scores in a CIA model.

Inflammation
- 0— normal
- 1—minimal infiltration of inflammatory cells in synovium and periarticular tissue of affected joints
- 2—mild infiltration, if paws, restricted to affected joints
- 3—moderate infiltration with moderate edema, if paws, restricted to affected joints
- 4—marked infiltration affecting most areas with marked edema
- 5—severe diffuse infiltration with severe edema Pannus
- 0— normal
- 1—minimal infiltration of pannus in cartilage and subchondral bone
- 2—mild infiltration with marginal zone destruction of hard tissue in affected joints
- 3—moderate infiltration with moderate hard tissue destruction in affected joints
- 4—marked infiltration with marked destruction of joint architecture, most joints
- 5—severe infiltration associated with total or near total destruction of joint architecture, affects all joints Cartilage Damage
- 0— normal
- 1—minimal to mild loss of toluidine blue staining with no obvious chondrocyte loss or collagen disruption in affected joints
- 2—mild loss of toluidine blue staining with focal mild (superficial) chondrocyte loss and/or collagen disruption in affected joints
- 3—moderate loss of toluidine blue staining with multifocal moderate (depth to middle zone) chondrocyte loss and/or collagen disruption in affected joints
- 4—marked loss of toluidine blue staining with multifocal marked (depth to deep zone) chondrocyte loss and/or collagen disruption in most joints
- 5—severe diffuse loss of toluidine blue staining with multifocal severe (depth to tide mark) chondrocyte loss and/or collagen disruption in all joints Bone Resorption
- 0— normal
- 1—minimal with small areas of resorption, not readily apparent on low magnification, rare osteoclasts in affected joints
- 2—mild with more numerous areas of, not readily apparent on low magnification, osteoclasts more numerous in affected joints
- 3—moderate with obvious resorption of medullary trabecular and cortical bone without full thickness defects in cortex, loss of some medullary trabeculae, lesion apparent on low magnification, osteoclasts more numerous in affected joints
- 4—marked with full thickness defects in cortical bone, often with distortion of profile of remaining cortical surface, marked loss of medullary bone, numerous osteoclasts, affects most joints
- 5—severe with full thickness defects in cortical bone and destruction of joint architecture of all joints Results Dexamethasone (Dex) and anti-mouse TNF-α antibody was used as a positive control, PBS was used as vehicle control, and CVAM was used as a negative control antibody. All treatments were initiated on day 12 of the study, during the development of joint disease. Disease incidence for vehicle-treated disease control animals was 100% by study day 22. Negative control groups treated with vehicle or CVAM antibody had the highest clinical scores. Significantly reduced clinical scores were observed for the groups treated with Dex ($p<0.05$ for d18-d26), 5 mg/kg anti-TNF-α antibody ($p<0.05$ for d18-26), or 25 mg/kg mAb 5429 ($p<0.05$ for d18-d23 and d25-d26) (FIG. 16). Clinical arthritis scores expressed as area under the curve (AUC) were significantly reduced by treatment with 25 mg/kg mAb 5429 (43% reduction), 5 mg/kg anti-TNF-α antibody (52%), or Dex (69%) as compared to vehicle controls. FIG. 17 shows means and standard deviations for AUC for each group.

Histopathological effects of the treatments were also assessed. Paw bone resorption was significantly decreased by treatment with 25 mg/kg mAb 5429 (47% decrease) as compared to vehicle controls. Positive control mice treated with 5 mg/kg anti-TNF-α antibody had significantly decreased paw inflammation (33%), cartilage damage (38%), and summed paw scores (37%). Treatment with Dex significantly reduced all paw histopathology parameters (73% reduction of summed scores).

These data demonstrate that TLR3 antibody antagonists improve clinical and histopathological disease symptoms in the CIA model, and suggest the use of TLR3 antagonists for treatment of rheumatoid arthritis.

EXAMPLE 14

TLR3 Antibody Antagonists Protect from Acute Lethal Viral Infections

Model

An influenza A virus challenge model was used as a model of acute lethal viral infection.

On Day −1, 4, 8, and 12, female C57BL/6 mice (12 weeks old) or female TLR3KO mice (C57BL/6 background; 12 weeks old, ACE Animals, inc., 15 mice per group) were dosed subcutaneously 20 mg/kg mAb 5429, or PBS alone. On day 0, the mice were anesthetized by isoflurane and were intranasally administered Influenza A/PR/8/34 virus (ATCC, Rockland, Md., Lot no. 218171), in 25 μl PBS (equivalent to $10^{5.55}$CEID50). Animals were observed two times a day for changes in body weight and survival over the period of 14 days. A clinical scoring system was used to evaluate the level of disease progression and subtle improvements in response to Influenza A virus treatment.

Clinical Scores

Figure 18:
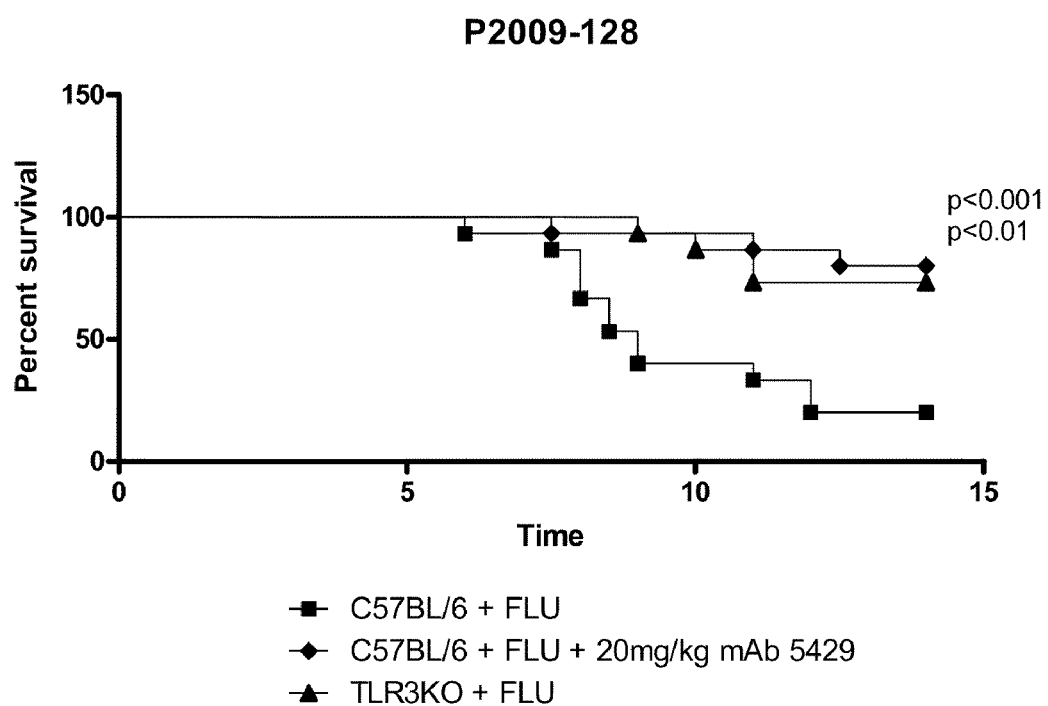
FIG. 18 shows effect of the surrogate mAb on the survival of C57BL/6 mice following intranasal administration of influenza A/PR/8/34.
Figure 19:
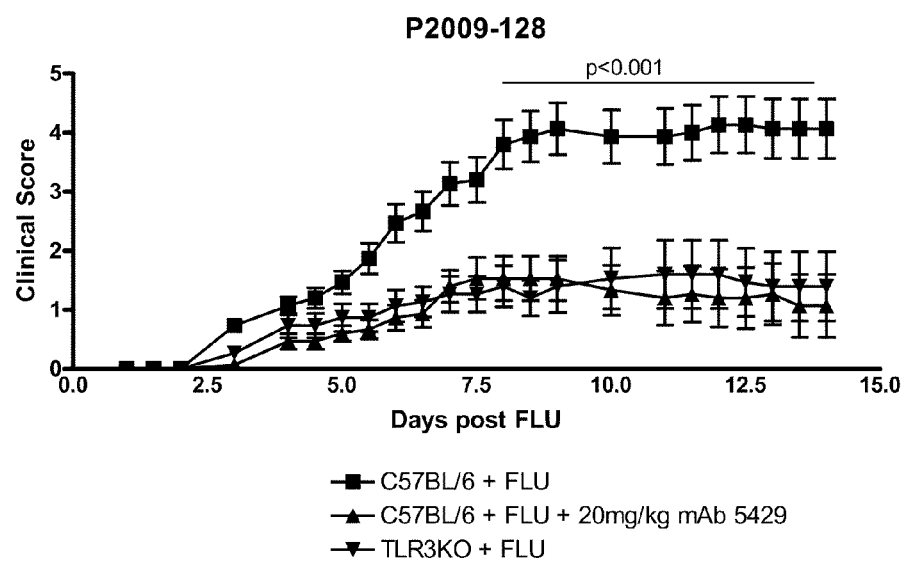
FIG. 19 shows effect of the surrogate mAb on clinical scores following influenza A/PR/8/34 administration.
Figure 20:
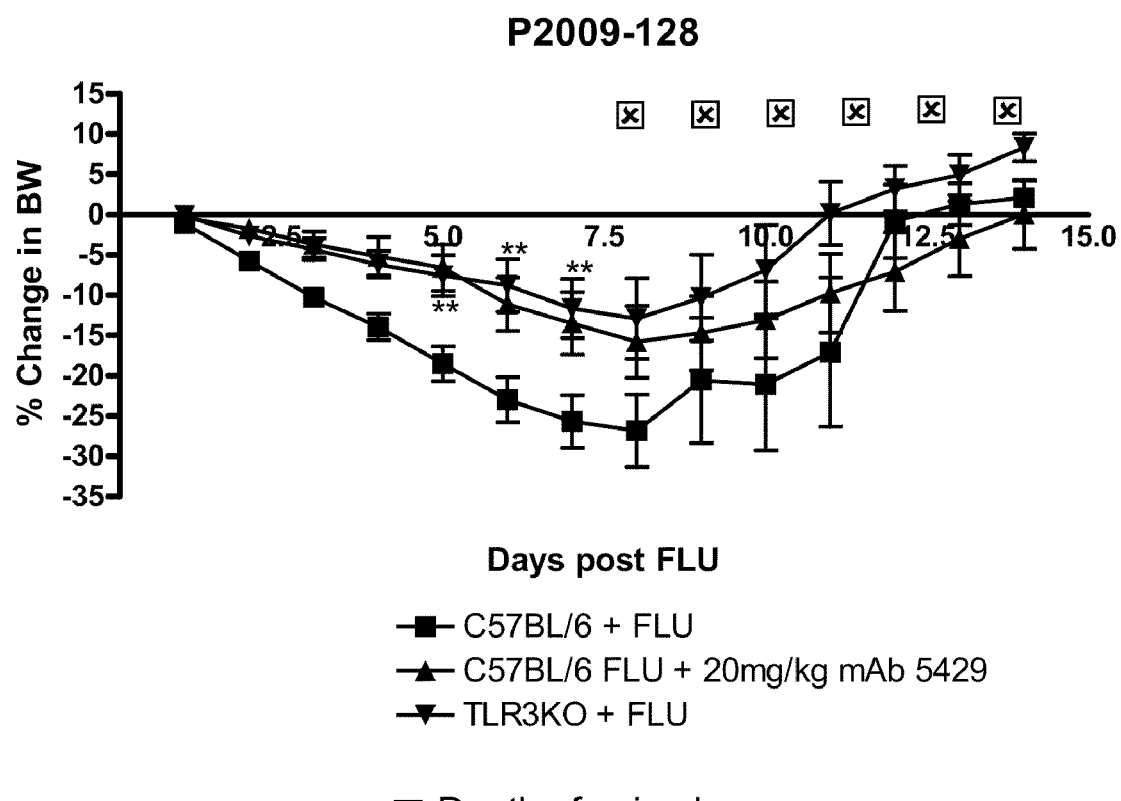
FIG. 20 shows effect of the surrogate mAb on body weight over 14 days after administration of influenza A/PR/8/34.

0—normal, alert and reactive, no visible signs of illness
1—ruffled coat, with or without slightly reduced ambulation
2—ruffled coat, hunched posture when walking, reluctant ambulation, labored breathing
3—ruffled coat, labored breathing, ataxia, tremor
4—ruffled coat, inability to ambulate with gentle prodding, unconsciousness, feels cold to the touch
5—found dead Results Survival, daily clinical scores, and changes in body weight were evaluated in the study. Both influenza A infected WT mice administered mAb 5429 (20 mg/kg) and influenza A infected TLR3KO not receiving mAb 5429 demonstrated a statistically significant increase in survival (p<0.001 and p<0.01, respectively) when compared to C57BL/6 mice inoculated with the Influenza virus, indicating that antagonism or deficiency of TLR3 can prevent influenza-induced mortality (FIG. 18). Clinical scores were significantly reduced in the group receiving 20 mg/kg mAb 5429, as well as in the TLR3KO group (FIG. 19). The body weight of the mice was observed over a period of 14 days after influenza virus administration. Body weight decreased steadily in C57BL/6 mice dosed with Influenza A virus. However, both the C57BL/6 mice dosed with 20 mg/kg mAb 5429 and the TLR3KO mice demonstrated significantly greater body weight relative to the WT C57BL/6 mice inoculated with Influenza virus (FIG. 20). These results demonstrated that TLR3 antibody antagonists reduced clinical symptoms and mortality in an acute lethal influenza viral infection model, and suggested that TLR3 antagonists may provide protection for humans in acute infectious states.

EXAMPLE 15

TLR3 Antibody Antagonists Improve Hyperglycemia and Reduce Plasma Insulin

Model

The Diet-induced obesity (DIO) model was used as a model of hyperglycemia and insulin resistance, and obesity.

C57BL/6 WT animals (about 3 weeks old, Jackson Labs) and TLR3KO animals (C57BL/6 background; about 3 weeks old, Ace Animals, Inc.) were maintained on a high fat diet for 12 to 16 weeks. Both TLR3KO and WT C57BL/6 mice were fed either with normal chow or high-fat diet (Purina TestDiet cat. no. 58126) consisting of 60.9% kcal fat and 20.8% kcal carbohydrates. Mice were maintained on a 12:12-h light-dark cycle, with water and food ad libitum. The weight of each mouse within each group was measured weekly. mAb 5429 was given intraperitoneally twice a week for the first week followed by once a week dosing for total of 7 weeks. Fasting retro-orbital blood serum samples were used for insulin measurements at the time points indicated. Glucose tolerance tests were performed by i.p administration of glucose at 1.0 mg/g body weight after overnight fast at week 7. In addition, fasting insulin and glucose levels were measured.

HOMA-IR was determined from the equation based on the levels of fasting glucose and insulin levels (12) using following equation: HOMA-IR=((fasting glucose (mmol/l)×fasting insulin (mU/l))/22.5 (Wallace et al., Diabetes Care 27:1487-1495-2004). Fasting blood glucose (BG) was determined using glucose oxidase assay. Fasting insulin levels were determined using the insulin rat/mouse ELISA kit (Crystal Chem, cat. No. 90060).

Results

Figure 22:
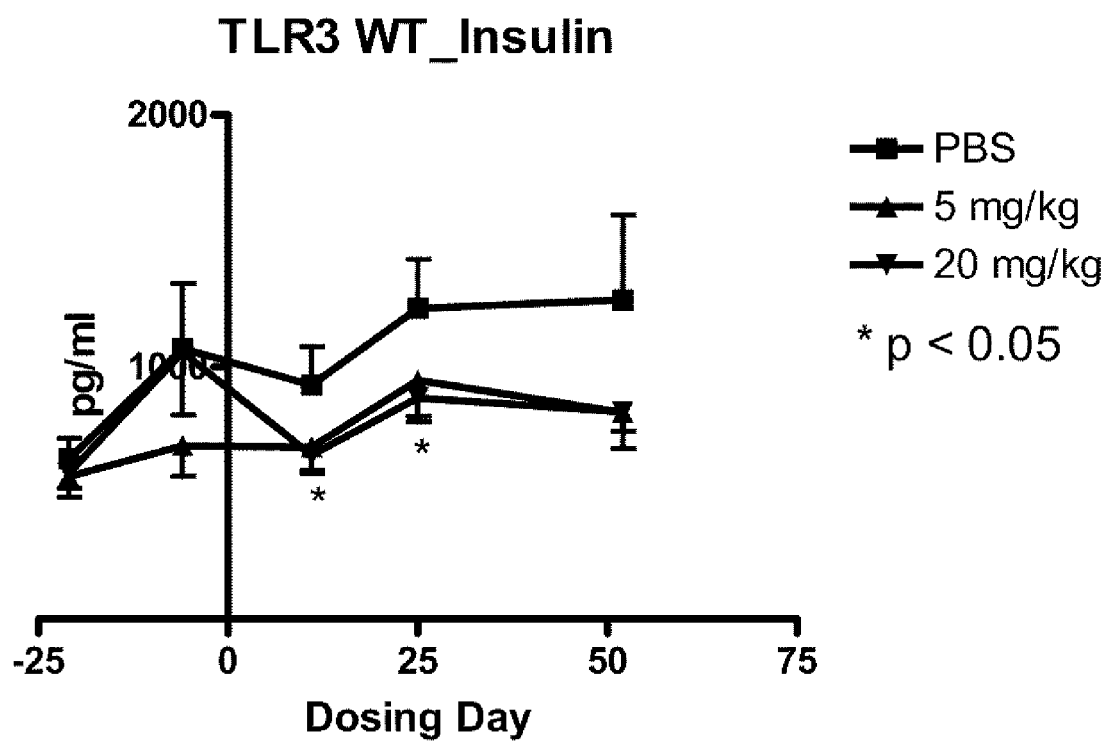
FIG. 22 shows effect of the surrogate mAb on insulin levels in WT DIO animals.

After 12-16 weeks on high fat diet, the WT DIO animals were hyperglycemic and hyperinsulinemic. Glucose tolerance was improved in the WT DIO animals but not in the TLR3KO DIO animals upon treatment with mAb 5429. Significantly reduced blood glucose levels were observed in mAb 5429 treated animals post glucose challenge at 60, 90, 120, and 180 min when compared to control (PBS only) (FIG. 21A). About 21% reduction in AUC was observed in the mAb 5429 treated WT DIO animals when compared to the WT DIO mice not receiving the mAb. Fasting insulin levels were also reduced in the WT DIO animals treated with mAb 5429 (FIG. 22). TLR3KO DIO animals showed no improvement in fasting insulin upon mAb 5429 treatment. Homeostatic model assessment (HOMA) analysis indicated improved insulin sensitivity in the WT DIO animals treated with mAb 5429, but not in the TLR3KO DIO animals. The HOMA-IR values were 14.0±9.8, 8.7±4.9, 9.0±3.0 for WT DIO, 5 mg/kg of WT DIO mAb 5429, and 20 mg/kg of WT DIO mAb 5429 animals, respectively. No effect was observed in TLR3KO DIO animals.

The study demonstrated that TLR3 antibody antagonists improved insulin resistance and reduced fasting glucose in the DIO model without weight loss, suggesting that TLR3 antagonists may be beneficial for the treatment of hyperglycemia, insulin resistance, and type II diabetes.

EXAMPLE 16

TLR3 Antibody Antagonists Protect from Bacteria and Virus-Induced Inflammatory Responses Reagents Nontypeable *Haemophilus influenza* (NTHi) strains 35, isolated from a COPD patient with bacterial exacerbations, was obtained from Dr. T. F. Murphy (Buffalo VA Medical Center, Buffalo, N.Y.). Human rhinovirus 16 was obtained from the American Type Culture Collection (ATCC) with TCID(50)=$2.8 \times 10^7$/ml.

NTHi Stimulation Assays

NHBE cells (Lonza, Wakersville, Md.) were seeded in Microtest 96-well tissue culture plates (BD Biosciences, Bedford, Mass.) at $1 \times 10^5$/well. NTHi grown on agar plates for 16-20 hr were resuspended in growth medium at ~$2 \times 10^8$ cfu/ml, treated with 100 µg/ml gentamycin for 30 min. and added at ~$2 \times 10^7$/well to 96-well plates containing NHBEs. After 3 hours, supernatants were removed and replaced with fresh growth medium with or without antibodies (0.08 to 50 µg/ml final concentration). After additional 24 hr incubation, presence of cytokines and chemokines in cell supernatants was assayed in triplicate with a Cytokine 25-plex AB bead kit, Human (including IL-1β, IL-1RA, IL-2, IL-2R, IL-4, IL-5, IL-6, IL-7, IL-8, IL-10, IL12p40p70, IL-13, IL-15, IL-17, TNF-α, IFN-α, IFN-γ, GM-CSF, MIP-1α, MIP-1β, IP-10, MIG, Eotaxin, RANTES and MCP-1) (Life Technologies, Carslbad, Calif.) in the Luminex 100IS multiplex fluorescence analyzer and reader system (Luminex Corporation, Austin, Tex.).

Rhinovirus Stimulation Assays

NHBE cells were seeded in Microtest 96-well tissue culture plates (BD Biosciences, Bedford, Mass.) at $1 \times 10^5$ cells/well. The next day, antibodies (0.08 to 50 µg/ml final concentration) were added to NHBE or BEAS-2B cells and incubated for 1 hr, followed by addition of 10 µl/well of rhinovirus. After additional 24 hr incubation, presence of cytokines and chemokines in cell supernatants was assayed by luminex assays as described above.

Figure 23:
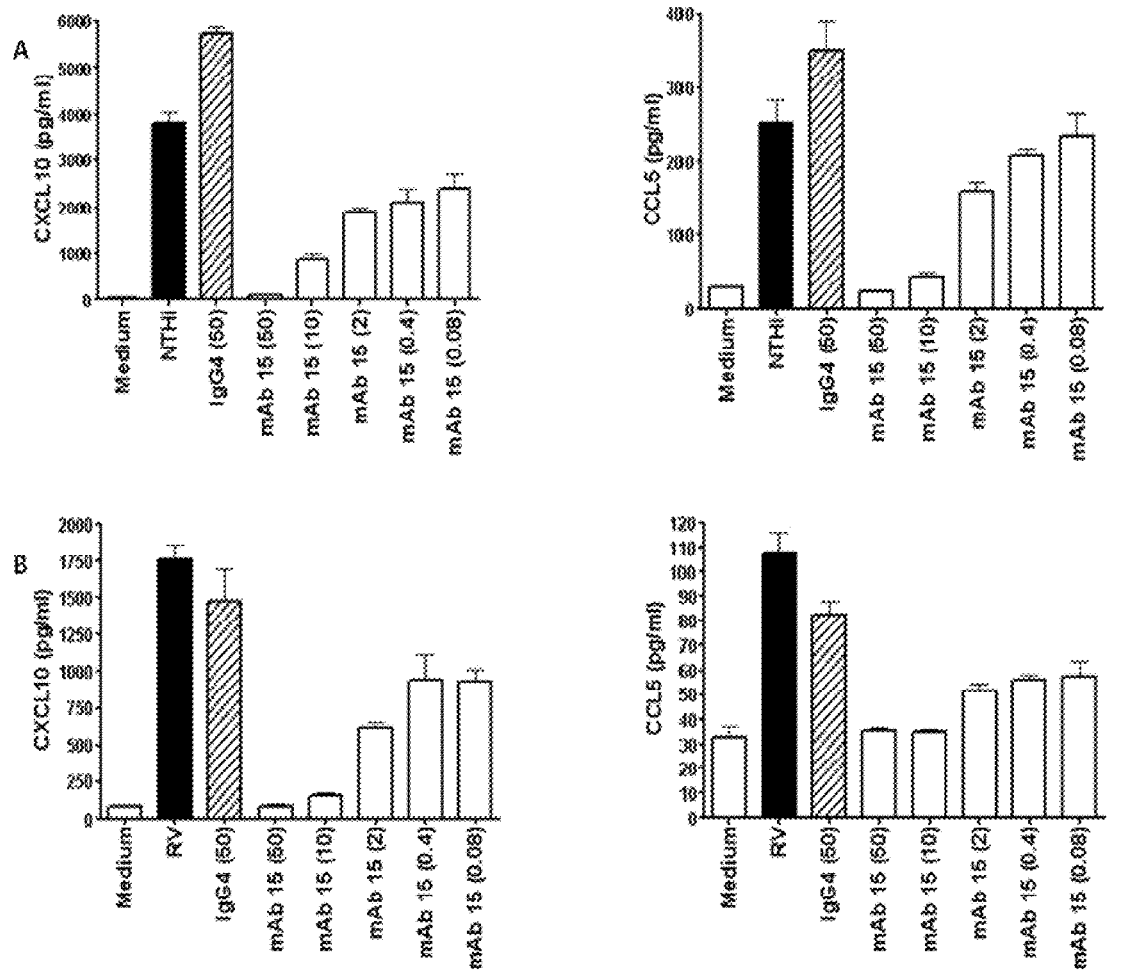
FIG. 23 shows effect of mAb 15EVQ on (A) NTHi and (B) rhinovirus induced CXCL10/IP-10 and CCL5/RANTES levels in NHBE cells.

Results mAb 15EVQ inhibited NTHi induced IP-10/CXCL10 and RANTES/CCL5 production in a dose-dependent manner, while the control antibody, human IgG4 (Sigma, St. Louis, Mo.), showed no inhibitory effect on NTHi stimulation (FIG. 23A). mAb 15EVQ also inhibited rhinovirus induced CXCL10/IP-10 and CCL5/RANTES production (FIG. 23B).

EXAMPLE 17

TLR3 Antibody Antagonists Suppress Inflammatory Responses in Astroctyes

Methods

Normal human astrocytes from 2 donors (Lonza, Walkersville, Md.) were plated in a 24 well plate at 75,000 cells/well and allowed to attach overnight. The next day, the astrocytes were treated with 200 ng/ml poly(I:C) and/or 10 µg/ml mAb 18 for 24 hours. Cytokines were measured by Luminex.

Results

Poly(I:C)—induced production of IL-6, IL-8, IL-12, IFN-α, IFN-γ, CXCL9/MIG, CCL3/MIP-1α, CCL4, CCL5/RANTES and CXCL10/IP-10 were inhibited by mAb 18, as shown in Table 10.

TABLE 10

|  | IL-6 | IL-8 | IL-12 | IFN-α | IFN-γ |
|---|---|---|---|---|---|
| Donor 1 | | | | | |
| untreated | 876.0 ± 36.8 | 539.7 ± 32.6 | 16.6 ± 0.5 | 28.8 ± 1.5 | 12.3 ± 0.3 |
| mAb 18 | 1011.9 ± 57.4 | 1401.9 ± 49.7 | 17.1 ± 0.5 | 31.6 ± 0.7 | 10.4 ± 0.2 |
| Poly(I:C) | ol* | ol | 30.3 ± 1.5 | 47.1 ± 3.1 | 35.9 ± 1.0 |
| Poly(I:C) + mAb 18 | 2225.0 ± 108.1 | 6104.4 ± 259.9 | 16.8 ± 0.9 | 30.5 ± 1.6 | 11.7 ± 0.6 |
| Donor 2 | | | | | |
| untreated | 729.1 ± 7.1 | 248.2 ± 4.7 | 14 ± 0.5 | 19.5 ± 1.8 | 10.5 ± 0.5 |
| mAb 18 | 779.0 ± 9.8 | 1132.6 ± 30.6 | 14.3 ± 0.6 | 20.8 ± 1.9 | 10.5 ± 0.1 |
| Poly(I:C) | ol | ol | 25.5 ± 0.4 | 36.3 ± 1.9 | 30.8 ± 0.9 |
| Poly(I:C) + mAb 18 | 3393.3 ± 107.5 | 8660.4 ± 354.3 | 16.2 ± 0.3 | 24.7 ± 1.2 | 12.6 ± 0.3 |

|  | CXCL9/MIG | CCL3/MIP-1a | CCL4 | CCL5/RANTES | CXCL10/IP-10 |
|---|---|---|---|---|---|
| Donor 1 | | | | | |
| untreated | 12.6 ± 0.7 | 21 ± 0.9 | 14.8 ± 0.7 | bl** | bl |
| mAb 18 | 14.8 ± 1.7 | 19.5 ± 1.5 | 14.8 ± 1.1 | bl | bl |
| Poly(I:C) | 78.3 ± 4.8 | 1569.3 ± 36.9 | 159.7 ± 12.7 | 788.2 ± 94.9 | 461.4 ± 10.3 |
| Poly(I:C) + mAb 18 | 18.5 ± 1.6 | 31.2 ± 1.9 | 13.2 ± 0.9 | bl | 6.9 ± 0.5 |
| Donor 2 | | | | | |
| untreated | 9.9 ± 1.6 | 12.3 ± 1.7 | 11.3 ± 0.3 | bl | bl |
| mAb 18 | 8.9 ± 0.7 | 13.2 ± 1.5 | 11.1 ± 0.7 | bl | bl |
| Poly(I:C) | 62 ± 3.8 | 1552.9 ± 41.1 | 140.7 ± 4.8 | 546.8 ± 21.7 | 533.2 ± 15 |
| Poly(I:C) + mAb 18 | 18.3 ± 2.7 | 66.6 ± 3.8 | 12.1 ± 0.8 | bl | 29.1 ± 6.2 |

*ol: over detection level
**bl: below detection level

EXAMPLE 18

TLR3 Antibody Antagonists Suppress Inflammatory Responses in Endothelial Cells Methods HUVEC cells (Lonza, Walkersville, Md.) were cultured in serum-containing growth medium recommended by Lonza. Cells were resuspended in serum-free media (Lonza, Walkersville, Md.), plated in 96-well plates at 3×10⁵ cells/ml, and incubated at 37° C., 5% CO2 for 24 hrs. Poly(I:C) (GE Healthcare, Piscataway, N.J.) was added at increasing concentrations (1.5 to 100 µg/ml) and incubated for another 24 hours at 37° C. For cytokine inhibition assays, mAb 15EVQ was added to the cells at various concentrations (0-50 µg/ml) and incubated for 30 min, after which 20 µg/ml poly(I:C) was added for 24 hours. Cell supernatants were collected and cytokine levels were measured using the human cytokine 30-plex kit and Luminex MAP technology (Invitrogen Corp., Carslbad, Calif.). To measure sICAM-1 expression, the HUVEC cells were treated with 20 µg/ml poly(I:C) and various concentrations of mAb 15EVQ (0.8-50 µg/ml). The cell supernatants were analyzed for sICAM-1 expression by ELISA (R&D systems). Cell viability was measured using the CellTiterGlo kit (Promega, Madison, Wis.).

Results

HUVEC cells produced the following cytokines in response to poly(I:C): IL-1RA, IL-2, IL-2R, IL-6, IL-7, CXCL8/IL-8, IL-12 (p40-p70), IL-15, IL-17, TNF-α, IFN-α, IFN-γ, GM-CSF, CCL3/MIP-1α, CCL4/MIP-1β, CXCL10/IP-10, CCL5/RANTES, CCL2/MCP-1, VEGF, G-CSF, FGF-basic, and HGF (Table 11). mAb 15EVQ dose-dependently reduced levels of all cytokines induced by poly(I:C) (Table 12). The ability of mAb 15EVQ to reduce poly(I:C)-induced production of TNF-α, CCL2/MCP-1, CCL5/RANTES, and CXCL10/IP-10 suggested that inhibition of TLR3-mediated activities may protect against leukocyte and T cell infiltration that can lead to atherosclerosis. Also, inhibition of VEGF by mAb 15EVQ suggested a potential benefit of TLR3 blockade in pathologies mediated by VEGF including angiogenesis in a variety of cancers and ocular diseases such as age-related macular degeneration.

TNF-α and IFN-γ function in leukocyte recruitment and increase the expression of adhesion molecules on the activated endothelium (Doukas et al., Am. J. Pathol. 145:137-47, 1994; Pober et al., Am. J. Pathol. 133:426-33, 1988). CCL2/MCP-1, CCL5/RANTES, and CXCL10/IP-10 have been implicated in monocyte and T cell recruitment and contribute to the development of atherosclerosis (Lundgerg et al., Clin. Immunol. 2009). The generation of VEGF by endothelial cells has been linked to abnormal tissue growth or tumors in a variety of cancers during angiogenesis (Livengood et al., Cell. Immunol. 249:55-62, 2007).

Soluble Intercellular Adhesion Molecule 1 (sICAM-1) is generated by proteolytic cleavage and is a marker for endothelial cell activation. ICAM-1 plays a key role in leukocyte migration and activation and is upregulated on endothelial cells and epithelial cells during inflammation where it mediates adhesion to leukocytes via integrin molecules LFA-1 and Mac-1. Poly(I:C) activated the endothelial cells to upregulate sICAM-1 expression and the unregulation was reduced by treatment with mAb 15EVQ (FIG. 24A).

TABLE 11

| Poly(I:C) µg/ml | IL-6 | CXCL8/IL-8 | CCL2/MCP-1 |
|---|---|---|---|
| 10 | 848.8 + 50.9 | 12876.0 + 2314.0 | 11813.4 + 1420.9 |
| 5 | 751.3 + 2.1 | 11363.7 + 108.2 | 11365.7 + 113.1 |
| 2.5 | 607.1 + 91.6 | 10961.5 + 2200.7 | 11607.3 + 2155.7 |
| 1.25 | 419.2 + 178.4 | 9631.5 + 3675.8 | 11690.9 + 3189.9 |
| 0.63 | 263.8 + 81.4 | 6231.9 + 1568.0 | 9075.6 + 1152.2 |
| 0.31 | 183.5 + 168.3 | 5257.9 + 1855.0 | 8106.8 + 1193.1 |
| 0.16 | 111.9 + 72.5 | 4057.6 + 1127.4 | 6619.8 + 1728.2 |
| no poly(I:C) | 0.00 | 1286.6 + 300.8 | 1360.1 + 245.4 |

| Poly(I:C) µg/ml | IL-2R | IL-15 | IL-17 |
|---|---|---|---|
| 100 | 784.4 + 45.4 | 61.3 + 12.5 | 43.8 + 5.3 |
| 50 | 718.6 + 56.8 | 61.3 + 12.5 | 47.6 + 0 |
| 25 | 735.7 + 23.4 | 56.7 + 18.9 | 58.3 + 4.9 |
| 12.5 | 650.5 + 29.8 | 38.8 + 6.5 | 39.8 + 10.9 |
| 6.25 | 643.4 + 39.9 | 34.2 + 0 | 32.1 + 0 |
| 3.13 | 681.8 + 24.3 | 38.8 + 6.5 | 43.8 + 5.3 |
| 1.56 | 578.6 + 10.5 | 29.4 + 6.7 | 36.1 + 5.6 |
| no poly(I:C) | 0.0 | 0.0 | 0.0 |

| Poly(I:C) µg/ml | IFNα | CXCL10/IP-10 | CCL4/MIP-1β |
|---|---|---|---|
| 100 | 50.7 + 0 | 3803.1 + 185.5 | 234.5 + 19.7 |
| 50 | 44.9 + 1.7 | 2235.9 + 184.6 | 291.6 + 41.8 |
| 25 | 46.1 + 0 | 2403.0 + 271.9 | 278.7 + 4.7 |
| 12.5 | 41.2 + 3.5 | 2185.4 + 64.9 | 243.8 + 63.4 |
| 6.25 | 36.1 + 0 | 2100.0 + 288.1 | 201.9 + 46.2 |
| 3.13 | 40.0 + 1.8 | 3553.2 + 197.1 | 191.5 + 20.8 |
| 1.56 | 42.5 + 1.7 | 2064.3 + 242.1 | 165.3 + 16.3 |
| no poly(I:C) | 0.0 | 0.0 | 0.0 |

| Poly(I:C) µg/ml | RANTES | TNFα | VEGF |
|---|---|---|---|
| 100 | 6266.9 + 1708.7 | 12.8 + 3.2 | 581.1 + 181.4 |
| 50 | 2919.7 + 119.4 | 11.5 + 3.2 | 637.9 + 47.7 |
| 25 | 2805.1 + 176.7 | 9.8 + 2.8 | 700.3 + 62.5 |
| 12.5 | 2598.6 + 68.6 | 7.3 + 0.9 | 513.2 + 73.5 |
| 6.25 | 2449.2 + 830.6 | 6.9 + 1.4 | 440.4 + 29.5 |
| 3.13 | 3117.1 + 795.7 | 7.3 + 0.9 | 393.9 + 40.2 |
| 1.56 | 2481.0 + 719.3 | 6.0 + 1.8 | 358.4 + 74.8 |
| no poly(I:C) | 4.9 + 4.5 | 1.9 + 0.4 | 32.1 + 8.8 | concentrations shown as pg/ml

TABLE 12

| mAb 15 (µg/ml) | 50.00 | 10.00 | 2.00 | 0.40 |
|---|---|---|---|---|
| PIC | + | + | + | + |
| IL-6 | 177.8 ± 5.6 * | 214.6 ± 3.6 * | 359.2 ± 57.6 * | 727.2 ± 50.5 * |
| CXCL8/IL-8 | 1040.7 ± 185.9 | 1765.9 ± 97.1 | 6460.3 ± 3684.4 | 57349.5 ± 6293.4 |
| CCL2/MCP-1 | 1187.7 ± 165.4 * | 1955.4 ± 72.7 * | 9054.4 ± 4110.9 * | 20000 ± 0.0 |
| IL-2R | 25.0 ± 35.3 * | 0.0 ± 0.0 * | 312.3 ± 137.6 * | 521.5 ± 5.5 |
| IL-15 | 0.0 ± 0.0 * | 0.0 ± 0.0 * | 0.0 ± 0.0 * | 4.1 ± 0.0 * |
| IL-17 | 1.3 ± 1.8 * | 11.8 ± 16.8 | 11.8 ± 16.8 | 27.9 ± 6.0 |
| IFNα | 0.9 ± 1.3 * | 0.9 ± 1.3 * | 19.0 ± 7.7 * | 36.1 ± 0.0 |
| CXCL10/IP-10 | 0.0 ± 0.0 * | 58.1 ± 2.6 * | 633.0 ± 471.6 * | 1441.4 ± 97.1 |
| CCL4/MIP-1β | 0.0 ± 0.0 * | 0.0 ± 0.0 * | 2.9 ± 4.1 * | 62.1 ± 7.2 * |
| RANTES | 3.0 ± 0.0 * | 15.4 ± 4.5 * | 201.1 ± 169.1 * | 952.4 ± 41.1 * |
| TNFα | 1.9 ± 0.4 * | 1.6 ± 0.0 * | 2.2 ± 0.0 * | 3.4 ± 0.0 |
| VEGF | 87.2 ± 8.7 * | 28.6 ± 8.7 * | 88.3 ± 52.1 * | 156.1 ± 6.4 * |

TABLE 12-continued

| mAb 15 (µg/ml) | 0.08 | 0.016 | 0.003 | 0 |
|---|---|---|---|---|
| PIC | + | + | + | − |
| IL-6 | 10000 ± 0 | 10000 ± 0 | 10000 ± 0 | 10000 ± 0 |
| CXCL8/IL-8 | 72422.8 ± 88279.2 | 47047.5 ± 52393.1 | 76066.5 ± 11354.1 | 96478.0 ± 122298.4 |
| CCL2/MCP-1 | 20000 ± 0.0 | 20000 ± 0.0 | 20000 ± 0.0 | 20000 ± 0.0 |
| IL-2R | 664.7 ± 9.8 | 661.2 ± 14.8 | 698.4 ± 57.6 | 654.2 ± 14.8 |
| IL-15 | 38.8 ± 6.5 | 43.4 ± 0.0 | 38.8 ± 6.5 | 43.4 ± 0.0 |
| IL-17 | 47.4 ± 10.4 | 54.3 ± 20.2 | 40.0 ± 0.0 | 51.2 ± 5.1 |
| IFNα | 44.9 ± 1.7 | 41.2 ± 3.5 | 47.3 ± 1.7 | 40.0 ± 1.8 |
| CXCL10/IP-10 | 3023.8 ± 166.1 | 2107.5 ± 372.6 | 2346.4 ± 226.1 | 2157.4 ± 282.7 |
| CCL4/MIP-1β | 176.6 ± 21.3 * | 227.5 ± 19.9 | 248.3 ± 19.4 | 281.7 ± 37.5 |
| RANTES | 2454.4 ± 98.5 * | 2698.1 ± 88.6 * | 2624.4 ± 129.8 * | 3459.7 ± 181.8 |
| TNFα | 6.3 ± 0.5 | 8.5 ± 0.0 | 7.6 ± 1.4 | 6.9 ± 2.3 |
| VEGF | 479.6 ± 14.1 | 544.6 ± 8.3 | 533.5 ± 70.2 | 607.3 ± 29.9 |

* indicates significant p-values (less than 0.05) comparing mAb15 concentration vs. poly(I:C) alone
Values are mean (pg/ml) ± SEM This suggested that TLR3 antibody antagonists can inhibit leukocyte trafficking and thus tissue damage caused by the influx of inflammatory cells.

For viability assays, HUVECs were cultured, plated and stimulated with poly(I:C) as described above. mAb 15EVQ dose-dependently restored poly(I:C)-induced reduction in HUVEC cell viability (FIG. 24B).

Down-modulation of endothelial cell activation can suppress excessive immune cell infiltration and reduce tissue damage caused by cytokines that are increased during inflammatory conditions. Inflammation and overexpression of cytokines and adhesion molecules on endothelial cells are key contributors to developing atherosclerosis and hypertension. These data provide rationale for exploring the potential benefit of TLR3 antagonists for use in diseases of the blood vessels including vasculitides, and those featuring endothelial dysfunction. Another disease that is affected by inflammation and overexpressed cytokines is Kaposi's sarcoma (KS) that is common in immunosuppressed and HIV infected individuals and is caused by Kaposi's sarcoma herpes virus (KSHV). VEGF and cytokine production contribute to the survival of KS cells (Livengood et al., Cell Immunol. 249:55-62, 2007). TLR3 antagonists could be beneficial at reducing angiogenic risks associated with KS and other tumors and at preventing cell viability loss and protecting endothelial barrier integrity to prevent vascular leakage, a potentially serious condition associated with organ failure and life-threatening inflammatory conditions such as sepsis. TLR3 antagonism may also be beneficial in viral infections involving endothelial cell pathology such as the viral hemorrhagic fevers caused by members of the families flaviviridae (e.g. Dengue, yellow fever), filoviridae (Ebola, Marburg), bunyaviridae (e.g. Hantavirus, Nairovirus, Phlebovirus), and arenaviridae (e.g. Lujo, Lassa, Argentine, Bolivian, Venezuelan hemorrhagic fevers (Sihibamiya et al., Blood 113:714-722, 2009).

EXAMPLE 19

Cross-Reactivity of TLR3 Antibody Antagonists with Cynomolgus and Murine TLR3

Activity against cynomolgus or murine TLR3 were assessed using the ISRE reporter gene assay as described in Example 2. The cynomolgus (SEQ ID NO: 217) and murine TLR3 cDNAs (SEQ ID NO: 161) were amplified from whole blood and cloned into the pCEP4 vector (Clontech), and expressed as described above. mAb 15EVQ had IC50s of 4.18 µg/ml and 1.74 µg/ml in the cyno NF-κB and ISRE assays, respectively, compared to IC50s of 0.44 and 0.65 µg/ml in the human TLR3 NF-kB and ISRE assays, respectively. Isotype control antibodies had no effect in these assays.

The invention claimed is:

1. An isolated antibody or fragment thereof that binds toll-like receptor 3 (TLR3), wherein the antibody binds at least one TLR3 amino acid residue selected from the group consisting of residues K467, R488 and R489 of SEQ ID NO: 2.

2. The isolated antibody or fragment of claim 1, wherein the TLR3 amino acid residues are selected from the group consisting of:
   a) residue K467 of SEQ ID NO: 2;
   b) residue R489 of SEQ ID NO: 2;
   c) residues K467 and R489 of SEQ ID NO: 2; and
   d) residues K467, R488, and R489 of SEQ ID NO: 2.

3. The isolated antibody or fragment of claim 1, wherein the antibody further binds at least one TLR3 amino acid residue selected from the group consisting of residues Y465, Y468, N517, D536, Q538, H539, N541, E570 and K619 of SEQ ID NO:2.

4. An isolated antibody or fragment thereof that binds toll-like receptor 3(TLR3), wherein the antibody has at least one of the following properties:
   a) reduces human TLR3 biological activity in an in vitro poly(I:C) NF-κB reporter gene assay >50% at <1 μg/ml;

b) inhibits >60% of IL-6 or CXCL10/IP-10 production from BEAS-2B cells stimulated with <100 ng/ml poly (I:C) at <10 μg/ml;

c) inhibits >50% of IL-6 or CXCL10/IP-10 production from BEAS-2B cells stimulated with <100 ng/ml poly (I:C) at <0.4 μg/ml;

d) inhibits >50% of IL-6 production from NHBE cells stimulated with 62.5 ng/ml poly(I:C) at <5 μg/ml;

e) inhibits >50% of IL-6 production from NHBE cells stimulated with 62.5 ng/ml poly(I:C)at <1 μg/ml;

f) inhibits >20% of poly(I:C)-induced IFN-γ, IL-6 or IL-12 production by PBMC at <1 μg/ml;

g) inhibits cynomologus TLR3 biological activity in an in vitro NF-κB reporter gene assay with IC50 <10 μg/ml; or h) inhibits cynomologus TLR3 biological activity in an in vitro ISRE reporter gene assay with IC50<5μg/ml.

5. An isolated monoclonal antibody or fragment reactive with TLR3 that competes for TLR3 binding with a monoclonal antibody comprising:

a) the heavy chain variable region of SEQ ID NO: 216 and the light chain variable region of SEQ ID NO: 41; or the heavy chain CDR 1, 2 and 3 amino acid sequences as shown in SEQ ID NOs: 82, 86 and 84 and the light chain CDR 1, 2 and 3 amino acid sequences as shown in SEQ ID NOs: 79, 80 and 87.

6. An isolated antibody or fragment reactive with TLR3 comprising both a heavy chain and a light chain variable region and wherein the antibody comprises:

a) the heavy chain CDR 1, 2 and 3 amino acid sequences as shown in SEQ ID NOs: 82, 196 and 84, wherein the HCDR2 of SEQ ID NO: 196 is further defined as shown in Formula (V):

$$Xaa_{24}\text{-I-D-P-S-D-S-Y-T-N-Y-}Xaa_{25}\text{-P-S-F-Q-G,} \quad (V)$$

wherein

Xaa$_{24}$ may be Phe or Arg; and

Xaa$_{25}$ may be Ala or Ser; and b) the light chain CDR 1, 2 and 3 amino acid sequences as shown in SEQ ID NOs: 79, 80 and 195, wherein the LCDR3 of SEQ ID NO: 195 is further defined as shown in Formula (VI):

$$Q\text{-}Q\text{-}Xaa_{18}\text{-}Xaa_{19}\text{-}Xaa_{20}\text{-}Xaa_{21}\text{-}Xaa_{22}\text{-}Xaa_{23}\text{-}T, \quad (VI)$$

wherein

Xaa$_{18}$ may be Tyr, Gly or Ala;

Xaa$_{19}$ may be Gly, Glu or Asn;

Xaa$_{20}$ may be Ser or Thr;

Xaa$_{21}$ may be Val, Ile or Leu;

Xaa$_{22}$ may be Ser or Leu; and

Xaa$_{23}$ may be Ile, Ser, Pro or Tyr.

7. An isolated antibody or fragment reactive with TLR3 comprising both a heavy chain and a light chain variable region and wherein the antibody comprises:

the heavy chain CDR 1, 2 and 3 amino acid sequences as shown in SEQ ID NOs: 82, 86 and 84 and the light chain CDR 1, 2 and 3 amino acid sequences as shown in SEQ ID NOs: 79, 80 and 87.

8. An isolated antibody or fragment reactive with TLR3 comprising both a heavy chain and a light chain variable region and wherein the antibody comprises:

a) the heavy chain variable region of SEQ ID NO: 216; or b) the light chain variable region of SEQ ID NO: 41; or c) the heavy chain variable region of SEQ ID NO: 216 and the light chain variable region of SEQ ID NO: 41; or d) the heavy chain of SEQ ID NO: 220; or e) the light chain of SEQ ID NO: 156; or f) the heavy chain of SEQ ID NO: 220 and the light chain of SEQ ID NO: 156.

9. The isolated antibody or fragment of claim 1, 4, 5 or 6, wherein the antibody is fully human or human-adapted.

10. The isolated antibody or fragment of claim 9, wherein the antibody is conjugated to polyethylene glycol.

11. The isolated antibody or fragment of claim 9, having an IgG4 isotype.

12. The isolated antibody or fragment of claim 9, wherein the Fc domain comprises S229P, P235A or L236A mutations.

13. A pharmaceutical composition comprising the isolated antibody or fragment of claim 9 and a pharmaceutically acceptable carrier.

14. An isolated antibody heavy chain comprising the amino acid sequence shown in SEQ ID NO: 216.

15. An isolated antibody light chain comprising the amino acid sequence shown in SEQ ID NO: 41.

16. An isolated antibody heavy chain comprising the amino acid sequence shown in SEQ ID NO: 220.

17. An isolated antibody light chain comprising the amino acid sequence shown in SEQ ID NO: 156.

* * * * *